US012257321B2

(12) United States Patent
Xiao et al.

(10) Patent No.: US 12,257,321 B2
(45) **Date of Patent: *Mar. 25, 2025**

(54) OPTIMIZED MINI-DYSTROPHIN GENES AND EXPRESSION CASSETTES AND THEIR USE

(71) Applicants: The University of North Carolina at Chapel Hill, Chapel Hill, NC (US); Bamboo Therapeutics, Inc., Chapel Hill, NC (US)

(72) Inventors: Xiao Xiao, Chapel Hill, NC (US); Juan Li, Chapel Hill, NC (US); Chunping Qiao, Chapel Hill, NC (US); Scott W. J. McPhee, Chapel Hill, NC (US); Richard J. Samulski, Hillsborough, NC (US); Maritza McIntyre, Rockville, MD (US)

(73) Assignees: The University of North Carolina at Chapel Hill, Chapel Hill, NC (US); Bamboo Therapeutics, Inc., Chapel Hill, NC (US)

( * ) Notice: Subject to any disclaimer, the term of this patent is extended or adjusted under 35 U.S.C. 154(b) by 54 days.

This patent is subject to a terminal disclaimer.

(21) Appl. No.: 18/150,377

(22) Filed: Jan. 5, 2023

(65) Prior Publication Data

US 2023/0398236 A1 Dec. 14, 2023

Related U.S. Application Data

(63) Continuation of application No. 16/787,938, filed on Feb. 11, 2020, now Pat. No. 11,547,765, which is a continuation of application No. 15/628,268, filed on Jun. 20, 2017, now abandoned.

(60) Provisional application No. 62/516,449, filed on Jun. 7, 2017, provisional application No. 62/352,675, filed on Jun. 21, 2016.

(51) Int. Cl.

| | |
|---|---|
| ***A61K 48/00*** | (2006.01) |
| ***A61K 38/17*** | (2006.01) |
| ***A61K 45/06*** | (2006.01) |
| ***C07K 14/47*** | (2006.01) |
| ***C07K 14/78*** | (2006.01) |
| ***C12N 15/86*** | (2006.01) |

(52) U.S. Cl.

CPC ...... *A61K 48/0058* (2013.01); *A61K 38/1709* (2013.01); *A61K 45/06* (2013.01); *C07K 14/4708* (2013.01); *C07K 14/78* (2013.01); *C12N 15/86* (2013.01); *A01K 2217/075* (2013.01); *A01K 2227/10* (2013.01); *A01K 2227/105* (2013.01); *A01K 2267/0306* (2013.01); *C12N 2750/14143* (2013.01); *C12N 2800/22* (2013.01); *C12N 2830/008* (2013.01)

(58) Field of Classification Search

CPC ........... A61K 48/0058; A61K 38/1709; A61K 45/06; C07K 14/4708; C07K 14/78; C12N 15/86; C12N 2750/14143; C12N 2800/22; C12N 2830/008; A01K 2217/075; A01K 2227/10; A01K 2227/105; A01K 2267/0306

See application file for complete search history.

(56) References Cited

U.S. PATENT DOCUMENTS

| | | | | |
|---|---|---|---|---|
| 6,057,158 | A | 5/2000 | Chamberlain et al. | |
| 6,063,622 | A | 5/2000 | Chamberlain et al. | |
| 6,083,750 | A | 7/2000 | Chamberlain et al. | |
| 6,812,339 | B1 | 11/2004 | Venter et al. | |
| 7,001,761 | B2 | 2/2006 | Xiao | |
| 7,112,668 | B2 | 9/2006 | Rastelli et al. | |
| 7,172,893 | B2 | 2/2007 | Rabinowitz et al. | |
| 7,510,867 | B2 | 3/2009 | Xiao | |
| 7,745,391 | B2 | 6/2010 | Mintz et al. | |
| 7,771,993 | B2 | 8/2010 | Stedman et al. | |
| 7,906,111 | B2 | 3/2011 | Wilson et al. | |
| 8,586,006 | B2 | 11/2013 | Hood et al. | |
| 9,061,059 | B2 | 6/2015 | Chakraborty et al. | |
| 9,089,604 | B2 | 7/2015 | Chakraborty et al. | |
| 9,220,755 | B2 | 12/2015 | Chakraborty et al. | |
| 11,547,765 | B2 * | 1/2023 | Xiao | A61P 21/00 |
| 2006/0073586 | A1 | 4/2006 | Xiao | |
| 2009/0004743 | A1 | 1/2009 | Ferrari et al. | |
| 2009/0181380 | A1 | 7/2009 | Belouchi et al. | |
| 2010/0120628 | A1 | 5/2010 | Belouchi et al. | |
| 2010/0144538 | A1 | 6/2010 | Belouchi et al. | |
| 2011/0097761 | A1 | 4/2011 | Chamberlain et al. | |
| 2011/0183924 | A1 | 7/2011 | Mintz et al. | |
| 2013/0136729 | A1 | 5/2013 | French et al. | |
| 2014/0010861 | A1 | 1/2014 | Bancel et al. | |

(Continued)

FOREIGN PATENT DOCUMENTS

| | | | |
|---|---|---|---|
| EP | 1287125 | A2 | 3/2003 |
| EP | 1303617 | A2 | 4/2003 |

(Continued)

OTHER PUBLICATIONS

"Office Action corresponding to Canadian Application No. 2,971,303 dated Jun. 5, 2023".
"Office Action corresponding to Indian Application No. 201817049231 dated Dec. 2, 2022".
"Office Action corresponding to Indonesian Application No. P00202106511 dated Mar. 29, 2023".
"Office Action corresponding to Malaysian Application No. PI2018002452 issued Mar. 15, 2023".
"Office Action corresponding to Mexican Application No. MX/a/2018/015921 issued Jan. 12, 2023".

(Continued)

*Primary Examiner* — Olga N Chernyshev
(74) *Attorney, Agent, or Firm* — Myers Bigel, P.A.

(57) ABSTRACT

This invention relates to polynucleotides encoding mini-dystrophin proteins, viral vectors comprising the same, and methods of using the same for delivery of mini-dystrophin to a cell or a subject.

14 Claims, 66 Drawing Sheets

Specification includes a Sequence Listing.

(56) References Cited

U.S. PATENT DOCUMENTS

| | | | |
|---|---|---|---|
| 2014/0171485 | A1 | 6/2014 | Bancel et al. |
| 2014/0200264 | A1 | 7/2014 | Bancel et al. |
| 2014/0206755 | A1 | 7/2014 | Bancel et al. |
| 2014/0234255 | A1 | 8/2014 | Lai et al. |
| 2014/0255467 | A1 | 9/2014 | Bancel et al. |
| 2014/0255468 | A1 | 9/2014 | Bancel et al. |
| 2014/0303093 | A1 | 10/2014 | Ervasti et al. |
| 2015/0044277 | A1 | 2/2015 | Bancel et al. |
| 2015/0246950 | A1 | 9/2015 | Sujata |
| 2018/0148488 | A1 | 5/2018 | Chamberlain et al. |

FOREIGN PATENT DOCUMENTS

| | | | |
|---|---|---|---|
| EP | 1366160 | A2 | 12/2003 |
| EP | 1668143 | A2 | 6/2006 |
| EP | 1716227 | A2 | 11/2006 |
| JP | 11318467 | | 11/1999 |
| JP | 2019525740 | A | 9/2019 |
| WO | 200028004 | | 5/2000 |
| WO | 200183695 | | 11/2001 |
| WO | 200206495 | | 1/2002 |
| WO | 200229056 | | 4/2002 |
| WO | 2002081517 | | 10/2002 |
| WO | 2005071059 | A2 | 8/2005 |
| WO | 2008088895 | A2 | 7/2008 |
| WO | 2013151665 | A2 | 10/2013 |
| WO | 2015197232 | A1 | 12/2015 |
| WO | 2015197869 | A1 | 12/2015 |

OTHER PUBLICATIONS

"Office Action corresponding to Peruvian Application No. 003282-2018/DIN issued Jan. 26, 2023".

"Office Action corresponding to Peruvian Application No. 003282-2018/DIN issued May 4, 2023".

Li, Hong-Hua , et al., "Adeno-associated virus vector carrying human minidystrophin gene SMCKA3999 effectively ameliorates dystrophic pathology in mdx model mice", Natl Med J China 83(17):1513-1516 (Sep. 10, 2003).

""Precision Genetic Medicine for Neuromuscular Diseases: 23rd International Congress of the World Muscle Society", Sarepta Therapeutics (2018) (27 pages)".

""Translarna: Assessment report for initial marketing authorization application", European Medicines Agency: Science Medicines Health (2014) (106 pages)".

""Translarna: Summary of Product Characteristics", European Medicines Agency (39 pages) (2014)".

"Anonymous: "The DMD mutations database The dystrophin gene", Dec. 24, 2015 (Dec. 24, 2015), XP055401365, Retrieved from the Internet: URL:https://web.archive.org/web/20151224134431/http://www.umd.be/DMD/W_DMD/gene.html (16 pages)".

"Duan "Muscle Gene Therapy: Methods and Protocols", Methods in Molecular Biology 709 (382 pages) (2011)".

"Duan "Systemic AAV micro-dystrophin gene therapy for Duchenne muscular dystrophy", Molecular Therapy 26(10):2337-2356 (2018)".

"Examination Report corresponding to Australian Application No. 2017281983 dated Apr. 8, 2021".

"GenBank Accession No. NM_004006.1, *Homo sapiens* dystrophin, Jun. 10, 1999 (10 pages)".

"Highlights of Prescribing Information Emflaza™ (deflazacort) tablets, for oral use EMFLAZA™ (deflazacort) oral suspension Initial U.S. Approval: 2017".

"Highlights of Prescribing Information: Dosage Forms and Strengths Exondys 51® safely and effectively. EXONDYS 51 (eteplirsen) injection, for intravenous use Initial U.S. Approval: 2016".

"International Preliminary Report on Patentability corresponding to International Application No. PCT/IB2017/053656 mailed Jan. 3, 2019".

"International Search Report corresponding to International Application No. PCT/IB2017/053656 mailed Sep. 29, 2017".

"Mendell "Safety Study of Mini-dystrophin Gene to Treat Duchenne Muscular Dystrophy", ClinicalTrials.gov NCT00428935, dated Feb. 5, 2013, (5 pages)".

"Office Action corresponding to Japanese Application No. 2020-187024 mailed Oct. 11, 2021".

"Office Action corresponding to Argentinian Application No. 20170101711 dated Nov. 11, 2021".

"Office Action corresponding to Australian Application No. 2017281983 dated Apr. 4, 2022".

"Office Action corresponding to Brazilian Application No. 112018076394-2 issued Nov. 16, 2022".

"Office Action corresponding to Chinese Application No. 201780050809.7 issued Oct. 22, 2021".

"Office Action corresponding to Colombian Application No. NC2019/0000395 issued Jun. 28, 2021".

"Office Action corresponding to Colombian Application No. NC2019/0000395 issued Nov. 25, 2021".

"Office Action corresponding to Indonesian Application No. PID201900102 issued Jun. 22, 2021".

"Office Action corresponding to Indonesian Application No. PID201900102 issued Nov. 25, 2020".

"Office Action corresponding to Israeli Application No. 263,199 dated Mar. 26, 2022".

"Office Action corresponding to Japanese Application No. 2020-187024 mailed Jul. 12, 2022".

"Office Action corresponding to Korean Application No. 10-2018-7037062 mailed Sep. 5, 2022".

"Office Action corresponding to Mexican Application No. MX/a/2018/015921 issued Mar. 16, 2022".

"Office Action corresponding to Russian Application No. 2019101208 issued Nov. 6, 2020".

"Office Action corresponding to Saudi Arabian Application No. 518400623 issued Mar. 10, 2022".

"Office Action corresponding to Saudia Arabian Application No. 518400623 issued Oct. 27, 2022".

"Office Action corresponding to Taiwanese Application No. 106120618 issued Oct. 7, 2019".

"Proudfoot "Ending the message: poly(A) signals then and now", Genes & Development 25:1770-1782 (2011)".

"Uniprot Accession No. GB5B864, naked mole rat dystrophin, Dec. 14, 2011 (2 pages)".

"Uniprot Accession No. P11532, human dystrophin, Oct. 1, 1989 (2 pages)".

"Written Opinion of the International Searching Authority corresponding to International Application No. PCT/IB2017/053656 mailed Sep. 29, 2017".

Aatsma-Rus , et al., ""Circulating Biomarkers for Duchenne Muscular Dystrophy", Journal of Neuromuscular Diseases 2:S49-S58 (2015)".

Anderson , et al., ""Deflazacort but Not Prednisone Improves Both Muscle Repair and Fiber Growth in Diaphragm and Limb Muscle in Vivo in the Mdx Dystrophic Mouse", Muscle & Nerve 19:1576-1585 (1996)".

Arnau, Jose , et al., "Reprint of: Current strategies for the use of affinity tags and tag removal for the purification of recombinant proteins", Protein Expression and Purification 48:1-13 (2005).

Athanasopoulos , et al., ""Codon Optimization of the Microdystrophin Gene for Duchenne Muscular Dystrophy Gene Therapy", Duan (ed.), Muscle Gene Therapy: Methods and Protocols, Methods in Molecular Biology, vol. 709:21-37 (2011)".

Beenakker, Ernesto A.C., et al., "Functional ability and muscle force in healthy children and ambulant Duchenne muscular dystrophy patients", European Journal of Paediatric Neurology, 9(6), 2005, 387-393.

Bello , et al., ""DMD genotypes and loss of ambulation in the CINRG Duchenne Natural History Study", Neurology 87:401-409 (2016)".

Berry, Marla J., et al., "Substitution of Cysteine for Selenocysteine in Type I lodothyronine Deiodinase Reduces the Catalytic Efficiency of the Protein but Enhances its Translation", Endocrinology 131(4):1848-1852 (1992).

Bhasin , et al., ""Molecular Extensibility of Mini-dystrophins and a Dystrophin Rod Construct", J. Mol. Biol. 352:795-806 (2005)".

(56) References Cited

OTHER PUBLICATIONS

Bowles , et al., ""Phase 1 Gene Therapy for Duchenne Muscular Dystrophy Using a Translational Optimized AAV Vector", Molecular Therapy 20(2):443-455 (2012)".
Burns, William R., et al., "A high molecular weight-melanoma associated antigen-specific chimeric antigen receptor redirects lymphocytes to target human melanomas", Cancer Res. 70(8):3027-3033 (Apr. 15, 2010).
Bushby , et al., ""Ataluren Treatment of Patients With Nonsense Mutation Dystrophinopathy", Muscle Nerve 50:477-487 (2014)".
Bushby , et al., ""Diagnosis and management of Duchenne muscular dystrophy, part 1: diagnosis, and pharmacological and psychosocial management", Lancet Neurol 9:77-93 (2010)".
Campbell , et al., ""Myostatin inhibitor in DMD", Muscle & Nerve pp. 1-20, 41-42 (22 pages) (2016)".
Cao , et al., ""Persistent Dystrophin Expression in the Skeletal Muscle of mdx Mice by Using a Tissue Specific Promoter", 53rd Annual Meeting of the Orthopaedic Research Society Poster No. 0424 (1 page) (2007)".
Chen , et al., "Functional Impairment of Circulating Angiogenic Cells for Treatment of Myocardial Infarction Is Differentially Driven by Both Advanced Age and Coronary Artery Disease, and Is Improved or Further Impaired by Modulating Nitric Oxide Synthase Expression", Molecular Therapy 21(1):S142 (2013).
Choi , et al., ""Optimization of AAV expression cassettes to improve packaging capacity and transgene expression in neurons", Molecular Brain 7:17 (2014) (10 pages)".
Cirak , et al., ""Exon skipping and dystrophin restoration in patients with Duchenne muscular dystrophy after systemic phosphorodiamidate morpholino oligomer treatment: an open-label, phase 2, dose-escalation study", Lancet 378:595-605 (2011)".
Dayton , et al., ""The advent of AAV9 expands applications for brain and spinal cord gene delivery", Expert Opin Biol Ther. 12(6):757-766 (2012)".
Finkel , et al., ""Phase 2a Study of Ataluren-Mediated Dystrophin Production in Patients with Nonsense Mutation Duchenne Muscular Dystrophy", PLOS One 8(12):e81302 (2013)".
Gao , et al., ""Clades of Adeno-Associated Viruses Are Widely Disseminated in Human Tissues", Journal of Virology 78(12):6381-6388 (2004)".
Gray , et al., ""Production of Recombinant Adeno-Associated Viral Vectors and Use in In Vitro and In Vivo Administration", Curr Protoc Neurosci. Oct. 2011 ; Chapter: Unit4.17. doi:10.1002/0471142301.ns0417s57 (36 pages)".
Griggs , et al., ""Prednisone in Duchenne Dystrophy", Arch Neurol 48:383-388 (1991)".
Guiraud , et al., ""Pharmacological advances for treatment in Duchenne muscular dystrophy", Current Opinion in Pharmacology 34:36-48 (2017)".
Harper , et al., ""Modular flexibility of dystrophin: Implications for gene therapy of Duchenne muscular dystrophy", Nature Medicine 8(3):253-261 (2002)".
Hauser , et al., ""Analysis of Muscle Creatine Kinase Regulatory Elements in Recombinant Adenoviral Vectors", Molecular Therapy 2(1):16-25 (2000)".
Henricson , et al., "The 6-Minute Walk Test and Person-Reported Outcomes in Boys with Duchenne Muscular Dystrophy and Typically Developing Controls: Longitudinal Comparisons and Clinically-Meaningful Changes Over One Year", PLOS Currents Muscular Dystrophy Jul. 8, 2013 . Edition 1. doi: 10.1371/currents.md.9e17658b007eb79fcd6f723089f79e06.
Hu, Peiqi , et al., "Prevention of Skeletal and Cardiac Dysfunction in Dystrophin/Utrophin Double KO Mice by Systemic Delivery of AAV9-Minidystrophin", Molecular Therapy 17(Supplement 1):S362 (May 2009).
Huchet , et al., ""Exhaustive characterization of the newly developed Duchenne muscular dystrophy rat model: a unique animal model for DMD which mimics the human disease at both the muscular and the cardiac levels", Abstracts 2017/Neuromuscular Disorders 27:S247 (2017)".
Jaynes , et al., ""The Muscle Creatine Kinase Gene Is Regulated by Multiple Upstream Elements, Including a Muscle-Specific Enhancer", Molecular and Cellular Biology 8(1):62-70 (1988)".
Kang, Robert , et al., "A Novel AAV Vector-based Combinatorial Gene Therapy Ameliorates Spine Abnormalities in a Severe DMD Murine Model", ORS 2015 Annual Meeting Poster No. 1573 (4 pages).
Kinali , et al., ""Local restoration of dystrophin expression with the morpholino oligomer AVI-4658 in Duchenne muscular dystrophy: a single-blind, placebo-controlled, dose-escalation, proof-of-concept study", Lancet Neurol 8:918-928 (2009)".
Koenig , et al., ""Detailed Analysis of the Repeat Domain of Dystrophin Reveals Four Potential Hinge Segments That May Confer Flexibility", The Journal of Biological Chemistry 265(8):4560-4566 (1990)".
Koenig , et al., ""The Complete Sequence of Dystrophin Predicts a Rod-Shaped Cytoskeletal Protein", Cell. 63:219-228 (1988)".
Koppanati, Bhanu Munil, ""In Utero Delivery of AAV Vectors for Efficient Treatment of Muscle Disorders", Doctoral Thesis, University of Pittsburgh (2009) (138 pages)".
Kornegay , et al., ""Pharmacologic Management of Duchenne Muscular Dystrophy: Target Identification and Preclinical Trials", ILAR Journal 55(1):119-149 (2014)".
Kornegay , et al., ""Widespread Muscle Expression of an AAV9 Human Mini-dystrophin Vector After Intravenous Injection in Neonatal Dystrophin-deficient Dogs", Molecular Therapy 18(8):1501-1508 (2010)".
Larcher , et al., ""Characterization of Dystrophin Deficient Rats: A New Model for Duchenne Muscular Dystrophy", PLOS One 9(10):e110371 (2014) (13 pages)".
Larkindale , et al., ""Duchenne Regulatory Science Consortium Meeting on Disease Progression Modeling for Duchenne Muscular Dystrophy", PLOS Currents Muscular Dystrophy Jan. 12, 2017 . Edition 1. doi: 10.1371/currents.md.83071bbd728982f-2f1073f4950e03586 (11 pages)".
Le Guiner , et al., ""Long-term microdystrophin gene therapy is effective in a canine model of Duchenne muscular dystrophy", Nature Communications | 8:16105 | DOI: 10.1038/ncomms 16105 | www.nature.com/naturecommunications (15 pages) (2017)".
Li , et al., ""Hydrodynamic Limb Vein Injection of AAV9 Results in Regional and Systemic Long-Term Expression of Minidystrophin in Young Adult GRMD Dogs", Molecular Therapy 17(1):S278 (2009)".
Li, Juan , et al., "Efficient Long-Term Bodywide Expression of an AAV9-Minidystrophin in the Muscle and Heart of Young Adult GRMD Dogs after Intravascular Injection without Immune Suppression", Molecular Therapy 19 (Supplement 1):S21 (May 2011) 1 page.
Li, Juan , et al., "Long-Term (2-8 years) Body-Wide Expression of AAV9-Minidystrophin Gene in Golden Retriever Muscular Dystrophy Dogs After Regional Limb Vein Injection", Molecular Therapy 24(Supplement 1):S284 (May 2016) 1 page.
Li, Juan , et al., "Muscle Force Improvement by Long-Term Systemic Expression of an AAV9 Minidystrophin after Delivery in Young Adult GRMD Dogs without Immune Suppression", Molecular Therapy 20(Supplement 1):S69 (May 2012) 1 page.
Lu , et al., ""Strength and Functional Measurement for Patients with Muscular Dystrophy", Muscular Dystrophy Chp. 17 pp. 321-330 (2012)".
Mann , et al., ""Antisense-induced exon skipping and synthesis of dystrophin in the mdx mouse", PNAS 98(1):42-47 (2001)".
Manning , et al., ""What has the mdx mouse model of duchenne muscular dystrophy contributed to our understanding of this disease?", J Muscle Res Cell Motil 36:155-167 (2015)".
McCourt , et al., ""In vitro stability of therapeutically relevant, internally truncated dystrophins", Skeletal Muscle (2015) (11 pages)".
McDonald , et al., ""The 6-Minute Walk Test and Other Endpoints in Duchenne Muscular Dystrophy: Longitudinal Natural History Observations Over 48 Weeks From a Multicenter Study", Muscle Nerve 48:343-356 (2013)".
McDonald , et al., ""The 6-Minute Walk Test as a New Outcome Measure in Duchenne Muscular Dystrophy", Muscle Nerve 41:500-510 (2010)".

(56) References Cited

OTHER PUBLICATIONS

Mendell , et al., ""Dystrophin Immunity in Duchenne's Muscular Dystrophy", N Engl J Med 363:1429-1437 (2010)".
Mendell , et al., ""Gene therapy for muscular dystrophy: Lessons learned and path forward", Neuroscience Letters 627:90-99 (2012)".
Mendell , et al., ""Longitudinal Effect of Eteplirsen versus Historical Control on Ambulation in Duchenne Muscular Dystrophy", Ann Neurol 79:257-271 (2016)".
Morris , et al., ""An Epitope Structure for the C-Terminal Domain of Dystrophin and Utrophin", Biochemistry 37:11117-11127 (1998)".
Nadarajah , et al., ""Serum matrix metalloproteinase-9 (MMP-9) as a biomarker for monitoring disease progression in Duchenne muscular dystrophy (DMD)", Neuromuscular Disorders 21:569-578 (2011)".
Nakamura , et al., ""Mammalian Models of Duchenne Muscular Dystrophy: Pathological Characteristics and Therapeutic Applications", Journal of Biomedicine and Biotechnology vol. 2011 (8 pages) (2011)".
Nguyen , et al., ""DOT1L regulates dystrophin expression and is critical for cardiac function", Genes & Development 25:263-274 (2011)".
Ogura , et al., ""Therapeutic potential of matrix metalloproteinases in Duchenne muscular dystrophy", Frontiers in Cell and Developmental Biology 2(11): 1-11 (2014)".
Peltz , et al., ""Ataluren as an agent for therapeutic nonsense suppression", Annu Rev Med. 64:407-425 (2013)".
Petkova , et al., ""In vivo analysis of dystrophin (re- ) expression in DmdEGFP and DmdEGFP-mdx reporter mice", Abstracts 2017/ Neuromuscular Disorders 27:S188 (2017)".
Porrua , et al., ""Transcription Termination: Variations on Common Themes", Trends in Genetics 32(8):508-522 (2016)".
Qiao , et al., ""Spliceosome-Mediated RNA Trans-Splicing for Muscular Dystrophies", Molecular Therapy 15(1):S55 (2007)".
Qiao, Chunping , et al., "Dobutamine Stress Enhances Echocardiography Detection in mdx Mouse Heart and Reveals Therapeutic Benefits by Minidystrophin Gene Therapy", Molecular Therapy 21(Supplement 1):S142 (May 2013) 1 page.
Reay , et al., ""Effect of Nuclear Factor ?B Inhibition on Serotype 9 Adeno-Associated Viral (AAV9) Minidystrophin Gene Transfer to the mdx Mouse", Mol Med 18:466-476 (2012)".
Richman, Sarah A., et al., "High-Affinity GD2-Specific CAR T Cells Induce Fatal Encephalitis in a Preclinical Neuroblastoma Model", Cancer Immunol. Res. 6(1):36-46 (Jan. 2018).
Rodrigues , et al., ""Current Translational Research and Murine Models For Duchenne Muscular Dystrophy", Journal of Neuromuscular Diseases 3:29-48 (2016)".
Salva , et al., ""Design of Tissue-specific Regulatory Cassettes for High-level rAAV-mediated Expression in Skeletal and Cardiac Muscle", Molecular Therapy 15(2):320-329 (2007)".
Shield , et al., ""E-Box Sites and a Proximal Regulatory Region of the Muscle Creatine Kinase Gene Differentially Regulate Expression in Diverse Skeletal Muscles and Cardiac Muscle of Transgenic Mice", Molecular and Cellular Biology 16(9):5058-5068 (1996)".
Sternberg , et al., ""Identification of Upstream and Intragenic Regulatory Elements That Confer Cell-Type-Restricted and Differentiation-Specific Expression on the Muscle Creatine Kinase Gene", Molecular and Cellular Biology 8(7):2896-2909 (1988)".
Tang , et al., ""AAV-directed muscular dystrophy gene therapy", Expert Opin. Biol. Ther. 10(3):395-408 (2010)".
Tang , et al., ""Gene Therapy Combined with NF-kappaB Inhibition for Duchenne Muscular Dystrophy", University of Pittsburgh (3 pages) ORS 2013 Annual Meeting, Poster No. 0626".
Tang, Ying , et al., "Gene Therapy Combined with NF-kappaB Inhibition for Duchenne Muscular Dystrophy", Molecular Therapy 21(Supplement 1):S111 (May 2013) 1 page.
Trollet , et al., ""Gene therapy for muscular dystrophy: current progress and future prospects", Expert Opin. Biol. Ther. 9(7): 849-866 (2009)".
Wang, B. , et al., "A canine minidystrophin is functional and therapeuticin mdx mice", Gene Therapy, 15, 2008, 1099-1106.
Wang, Bing , et al., "Adeno-associated virus vector carrying human minidystrophin genes effectively ameliorates muscular dystrophy in mdx mouse model", PNAS, 97(25), 2000, 13714-13719.
Wang, B. , et al., "Construction and analysis of compact muscle-specific promoters for AAV vectors", Gene Therapy, 15, 2008, 1489-1499.
Wang, Bing , et al., "Systemic human minidystrophin gene transfer improves functions and life span of dystrophin and dystrophin/ utrophin-deficient mice", Journal of Orthopaedic Research, 27(4), 2009, 421-426.
Watchko, Jon , et al., "Adeno-Associated Virus Vector-Mediated Minidystrophin Gene Therapy Improves Dystrophic Muscle Contractile Function in mdx Mice", Human Gene Therapy, 13(12), 2002, 1451-1460.
Wells, Dominic J., "Tracking progress: an update on animal models for Duchenne muscular dystrophy", Disease Models & Mechanisms, 11(6), Jan. 3, 2018.
Werling, Natalie Jayne, et al., "Systematic Comparison and Validation of QuantitativeReal-Time PCR Methods for the Quantitation of Adeno-Associated Viral Products", Human Gene Therapy Methods, 26, 2015, 82-92.
Willcocks, Rebecca J., et al., "Multicenter prospective longitudinal study of magnetic resonance biomarkers in a large duchenne muscular dystrophy cohort", Annals of Neurology, 79(4), 2016, 535-547.
Willmann, Raffaella , et al., "Mammalian animal models for Duchenne muscular dystrophy", Neuromuscular Disorders, 19(4), 2009, 241-249.
Wright, Melissa A., et al., "Consider Muscle Disease in Children with Elevated Transaminase", The Journal of the American Board of Family Medicine, 25(4), 2012, 536-540.
Xiao , et al., ", Production of High-Titer Recombinant Adena-Associated Virus Vectors in the Absence of Helper Adenovirus, (Mar. 1998), Journal of Virology 72(3) :2224-2232".
Yuan, Zhenhua , et al., "A Versatile Adeno-Associated Virus Vector Producer Cell Line Method for Scalable Vector Production of Different Serotypes", Human Gene Therapy 22:613-624 (May 2011).
Yuasa, K. , et al., "Injection of a recombinant AAV serotype 2 into canine skeletal muscles evokes strong immune responses against transgene products", Gene Therapy, 14, 2007, 1249-1260.
Yue, Yongping , et al., "Safe and bodywide muscle transduction in young adult Duchenne muscular dystrophy dogs with adeno-associated virus", Human Molecular Genetics, 24(20), 2015, 5880-5890.
Zhang , et al., ", Novel Mini-Dystrophin Gene Dual Adena-Associated Virus Vectors Restore Neuronal Nitric Oxide Synthase Expression at the Sarcolemma, (Jan. 2012), Human Gene Therapy 23:98-103".
Zhu , et al., ""Serum Enzyme Profiles Differentiate Five Types of Muscular Dystrophy", Hindawi Publishing Corporation: Disease Markers vol. 2015 (7 pages)".
"Office Action corresponding to Chinese Application No. 202210822937.1 issued Sep. 5, 2024".
"Office Action corresponding to Philippian Application No. 1/2018/ 502645 mailed Aug. 8, 2024".
"Office Action issued in New Zealand Application No. 748678 dated Dec. 16, 2024".
"Office Action corresponding to European Application No. 17740105.6 dated Jan. 15, 2025".

* cited by examiner

H&E STAINING OF CRYOSECTIONS (8μm) OF TIBIALIS ANTERIOR MUSCLES, 10X MAGNIFICATION.

LEFT HINDLIMB (NON-INJECTED SIDE) CRANIAL SARTORIUS MUSCLE

```
                1                                                          60
   Δ3990     (1) MVWWEEVEDCYEREDVQKKTFTKWVNAQFSKFGKQHIENLFSDLQDGRRLLDLLEGLTGQ
 Dys3978     (1) MLWWEEVEDCYEREDVQKKTFTKWVNAQFSKFGKQHIENLFSDLQDGRRLLDLLEGLTGQ
                61                                                        120
   Δ3990    (61) KLPKEKGSTRVHALNNVNKALRVLQNNNVDLVNIGSTDIVDGNHKLTLGLIWNIILHWQV
 Dys3978    (61) KLPKEKGSTRVHALNNVNKALRVLQNNNVDLVNIGSTDIVDGNHKLTLGLIWNIILHWQV
                121                                                       180
   Δ3990   (121) KNVMKNIMAGLQQTNSEKILLSWVRQSTRNYPQVNVINFTTSWSDGLALNALIHSHRPDL
 Dys3978   (121) KNVMKNIMAGLQQTNSEKILLSWVRQSTRNYPQVNVINFTTSWSDGLALNALIHSHRPDL
                181                                                       240
   Δ3990   (181) FDWNSVVCQQSATQRLEHAFNIARYQLGIEKLLDPEDVDTTYPDKKSILMYITSLFQVLP
 Dys3978   (181) FDWNSVVCQQSATQRLEHAFNIARYQLGIEKLLDPEDVDTTYPDKKSILMYITSLFQVLP
                241                                                       300
   Δ3990   (241) QQVSIEAIQEVEMLPRPPKVTKEEHFQLHHQMHYSQQITVSLAQGYERTSSPKPRFKSYA
 Dys3978   (241) QQVSIEAIQEVEMLPRPPKVTKEEHFQLHHQMHYSQQITVSLAQGYERTSSPKPRFKSYA
                301                                                       360
   Δ3990   (301) YTQAAYVTTSDPTRSPFPSQHLEAPEDKSFGSSLMESEVNLDRYQTALEEVLSWLLSAED
 Dys3978   (301) YTQAAYVTTSDPTRSPFPSQHLEAPEDKSFGSSLMESEVNLDRYQTALEEVLSWLLSAED
                361                                                       420
   Δ3990   (361) TLQAQGEISNDVEVVKDQFHTHEGYMMDLTAHQGRVGNILQLGSKLIGTGKLSEDEETEV
 Dys3978   (361) TLQAQGEISNDVEVVKDQFHTHEGYMMDLTAHQGRVGNILQLGSKLIGTGKLSEDEETEV
                421                                                       480
   Δ3990   (421) QEQMNLLNSRWECLRVASMEKQSNLHRVLMDLQNQKLKELNDWLTKTEERTRKMEEEPLG
 Dys3978   (421) QEQMNLLNSRWECLRVASMEKQSNLHRVLMDLQNQKLKELNDWLTKTEERTRKMEEEPLG
```

FIG. 55A

```
                481                                                        540
   Δ3990  (481) PDLEDLKRQVQQHKVLQEDLEQEQVRVNSLTHMVVVVDESSGDHATAALEEQLKVLGDRW
 Dys3978  (481) PDLEDLKRQVQQHKVLQEDLEQEQVRVNSLTHMVVVVDESSGDHATAALEEQLKVLGDRW
                541                                                        600
   Δ3990  (541) ANICRWTEDRWVLLQDQPDLAPGLTTIGASPTQTVTLVTQPVVTKETAISKLEMPSSLML
 Dys3978  (541) ANICRWTEDRWVLLQDQPDLAPGLTTIGASPTQTVTLVTQPVVTKETAISKLEMPSSLML
                601                                                        660
   Δ3990  (601) EVPTHRLLQQFPLDLEKFLAWLTEAETTANVLQDATRKERLLEDSKGVKELMKQWQDLQG
 Dys3978  (601) EVPTHRLLQQFPLDLEKFLAWLTEAETTANVLQDATRKERLLEDSKGVKELMKQWQDLQG
                661                                                        720
   Δ3990  (661) EIEAHTDVYHNLDENSQKILRSLEGSDDAVLLQRRLDNMNFKWSELRKKSLNIRSHLEAS
 Dys3978  (661) EIEAHTDVYHNLDENSQKILRSLEGSDDAVLLQRRLDNMNFKWSELRKKSLNIRSHLEAS
                721                                                        780
   Δ3990  (721) SDQWKRLHLSLQELLVWLQLKDDELSRQAPIGGDFPAVQKQNDVHRAFKRELKTKEPVIM
 Dys3978  (721) SDQWKRLHLSLQELLVWLQLKDDELSRQAPIGGDFPAVQKQNDVHRAFKRELKTKEPVIM
                781                                                        840
   Δ3990  (781) STLETVRIFLTEQPLEGLEKLYQEPRELPPEERAQNVTRLLRKQAEEVNTEWEKLNLHSA
 Dys3978  (781) STLETVRIFLTEQPLEGLEKLYQEPRELPPEERAQNVTRLLRKQAEEVNTEWEKLNLHSA
                841                                                        900
   Δ3990  (841) DWQRKIDETLERLQELQEATDELDLKLRQAEVIKGSWQPVGDLLIDSLQDHLEKVKALRG
 Dys3978  (841) DWQRKIDETLERLQELQEATDELDLKLRQAEVIKGSWQPVGDLLIDSLQDHLEKVKALRG
                901                                                        960
   Δ3990  (901) EIAPLKENVSHVNDLARQLTTLGIQLSPYNLSTLEDLNTRWKLLQVAVEDRVRQLHEAHR
 Dys3978  (901) EIAPLKENVSHVNDLARQLTTLGIQLSPYNLSTLEDLNTRWKLLQVAVEDRVRQLHEAHR
```

FIG. 55B

```
                    961                                                         1020
   Δ3990    (961)   DFGPASQHFLSTSVQGPWERAISPNKVPYYINHETQTTCWDHPKMTELYQSLADLNNVRF
 Dys3978    (961)   DFGPASQHFLSTSVQGPWERAISPNKVPYYINHETQTTCWDHPKMTELYQSLADLNNVRF

                    1021                                                        1080
   Δ3990   (1021)   SAYRTAMKLRRLQKALCLDLLSLSAACDALDQHNLKQNDQPMDILQIINCLTTIYDRLEQ
 Dys3978   (1021)   SAYRTAMKLRRLQKALCLDLLSLSAACDALDQHNLKQNDQPMDILQIINCLTTIYDRLEQ

                    1081                                                        1140
   Δ3990   (1081)   EHNNLVNVPLCVDMCLNWLLNVYDTGRTGRIRVLSFKTGIISLCKAHLEDKYRYLFKQVA
 Dys3978   (1081)   EHNNLVNVPLCVDMCLNWLLNVYDTGRTGRIRVLSFKTGIISLCKAHLEDKYRYLFKQVA

                    1141                                                        1200
   Δ3990   (1141)   SSTGFCDQRRLGLLLHDSIQIPRQLGEVASFGGSNIEPSVRSCFQFANNKPEIEAALFLD
 Dys3978   (1141)   SSTGFCDQRRLGLLLHDSIQIPRQLGEVASFGGSNIEPSVRSCFQFANNKPEIEAALFLD

                    1201                                                        1260
   Δ3990   (1201)   WMRLEPQSMVWLPVLHRVAAAETAKHQAKCNICKECPIIGFRYRSLKHFNYDICQSCFFS
 Dys3978   (1201)   WMRLEPQSMVWLPVLHRVAAAETAKHQAKCNICKECPIIGFRYRSLKHFNYDICQSCFFS

                    1261                                                        1320
   Δ3990   (1261)   GRVAKGHKMHYPMVEYCTPTTSGEDVRDFAKVLKNKFRTKRYFAKHPRMGYLPVQTVLEG
 Dys3978   (1261)   GRVAKGHKMHYPMVEYCTPTTSGEDVRDFAKVLKNKFRTKRYFAKHPRMGYLPVQTVLEG

                    1321
   Δ3990   (1321)   DNMETPDTM   SEQ ID NO:27
 Dys3978   (1321)   DNMET····   SEQ ID NO:7
```

FIG. 55C

```
                                 1                                                          60
Wildtype Δ3990         (1)  ATGGTTTGGTGGAAGAAGTAGAGGACTGTTATGAAAGAGAAGATGTTCAAAAGAAAACA
Hopti-Dys3978          (1)  ATGCTTTGGTGGGAGGAAGTGGAGGACTGCTACGAGAGAGAGGACGTGCAGAAGAAAACC

                                 61                                                        120
Wildtype Δ3990        (61)  TTCACAAAATGGGTAAATGCACAATTTTCTAAGTTTGGGAAGCAGCATATTGAGAACCTC
Hopti-Dys3978         (61)  TTCACCAAGTGGGTGAACGCCCAGTTCAGCAAGTTCGGCAAGCAGCACATCGAGAACCTG

                                 121                                                       180
Wildtype Δ3990       (121)  TTCAGTGACCTACAGGATGGGAGGCGCCTCCTAGACCTCCTCGAAGGCCTGACAGGGCAA
Hopti-Dys3978        (121)  TTCAGCGACCTGCAGGATGGCAGGAGACTGCTGGACCTGCTGGAGGGCCTGACCGGCCAG

                                 181                                                       240
Wildtype Δ3990       (181)  AAACTGCCAAAAGAAAAAGGATCCACAAGAGTTCATGCCCTGAACAATGTCAACAAGGCA
Hopti-Dys3978        (181)  AAGCTGCCCAAGGAGAAGGGCAGCACCAGAGTGCACGCCCTGAACAACGTGAACAAGGCC

                                 241                                                       300
Wildtype Δ3990       (241)  CTGCGGGTTTTGCAGAACAATAATGTTGATTTAGTGAATATTGGAAGTACTGACATCGTA
Hopti-Dys3978        (241)  CTGAGAGTGCTGCAGAACAACAACGTGGACCTGGTGAACATCGGCAGCACCGACATCGTG

                                 301                                                       360
Wildtype Δ3990       (301)  GATGGAAATCATAAACTGACTCTTGGTTTGATTTGGAATATAATCCTCCACTGGCAGGTC
Hopti-Dys3978        (301)  GACGGCAACCACAAGCTGACCCTGGGCCTGATCTGGAACATCATCCTGCACTGGCAGGTG

                                 361                                                       420
Wildtype Δ3990       (361)  AAAAATGTAATGAAAAATATCATGGCTGGATTGCAACAAACCAACAGTGAAAAGATTCTC
Hopti-Dys3978        (361)  AAGAACGTGATGAAGAACATCATGGCCGGCCTGCAGCAGACCAACAGCGAGAAGATCCTG

                                 421                                                       480
Wildtype Δ3990       (421)  CTGAGCTGGGTCCGACAATCAACTCGTAATTATCCACAGGTTAATGTAATCAACTTCACC
Hopti-Dys3978        (421)  CTGAGCTGGGTGAGGCAGAGCACCAGAAACTACCCCCAGGTGAACGTGATCAACTTCACC
```

FIG. 56A

```
                                481                                                        540
Wildtype Δ3990         (481) ACCAGCTGGTCTGATGGCCTGGCTTTGAATGCTCTCATCCATAGTCATAGGCCAGACCTA
Hopti-Dys3978          (481) ACCTCCTGGAGCGACGGCCTGGCCCTGAACGCCCTGATCCACAGCCACAGACCCGACCTG

                                541                                                        600
Wildtype Δ3990         (541) TTTGACTGGAATAGTGTGGTTTGCCAGCAGTCAGCCACACAACGACTGGAACATGCATTC
Hopti-Dys3978          (541) TTCGACTGGAACAGCGTGGTGTGTCAGCAGAGCGCCACCCAGAGACTGGAGCACGCCTTC

                                601                                                        660
Wildtype Δ3990         (601) AACATCGCCAGATATCAATTAGGCATAGAGAAACTACTCGATCCTGAAGATGTTGATACC
Hopti-Dys3978          (601) AACATCGCCAGATACCAGCTGGGCATCGAGAAGCTGCTGGACCCCGAGGACGTGGACACC

                                661                                                        720
Wildtype Δ3990         (661) ACCTATCCAGATAAGAAGTCCATCTTAATGTACATCACATCACTCTTCCAAGTTTTGCCT
Hopti-Dys3978          (661) ACCTACCCCGACAAGAAAAGCATCCTCATGTACATTACCAGCCTGTTCCAGGTGCTGCCC

                                721                                                        780
Wildtype Δ3990         (721) CAACAAGTGAGCATTGAAGCCATCCAGGAAGTGGAAATGTTGCCAAGGCCACCTAAAGTG
Hopti-Dys3978          (721) CAGCAGGTGTCCATCGAGGCCATCCAGGAAGTGGAAATGCTGCCCAGGCCCCCCAAAGTG

                                781                                                        840
Wildtype Δ3990         (781) ACTAAAGAAGAACATTTTCAGTTACATCATCAAATGCACTATTCTCAACAGATCACGGTC
Hopti-Dys3978          (781) ACCAAGGAGGAGCACTTCCAGCTGCACCACCAGATGCACTACAGCCAGCAGATCACAGTG

                                841                                                        900
Wildtype Δ3990         (841) AGTCTAGCACAGGGATATGAGAGAACTTCTTCCCCTAAGCCTCGATTCAAGAGCTATGCC
Hopti-Dys3978          (841) AGCCTGGCCCAGGGCTATGAGAGAACCAGCAGCCCCAAGCCCAGATTCAAGAGCTACGCC

                                901                                                        960
Wildtype Δ3990         (901) TACACACAGGCTGCTTATGTCACCACCTCTGACCCTACACGGAGCCCATTTCCTTCACAG
Hopti-Dys3978          (901) TACACCCAGGCCGCCTACGTGACCACCTCCGACCCCACCAGAAGCCCCTTCCCCAGCCAG
```

FIG. 56B

```
                             961                                                        1020
Wildtype Δ3990       (961)  CATTTGGAAGCTCCTGAAGACAAGTCATTTGGCAGTTCATTGATGGAGAGTGAAGTAAAC
Hopti-Dys3978        (961)  CACCTGGAGGCCCCCGAGGACAAGAGCTTCGGCAGCAGCCTGATGGAGAGCGAAGTGAAC

                             1021                                                       1080
Wildtype Δ3990      (1021)  CTGGACCGTTATCAAACAGCTTTAGAAGAAGTATTATCGTGGCTTCTTTCTGCTGAGGAC
Hopti-Dys3978       (1021)  CTGGACAGATACCAGACCGCCCTGGAGGAAGTGCTGTCCTGGCTGCTGAGCGCCGAGGAC

                             1081                                                       1140
Wildtype Δ3990      (1081)  ACATTGCAAGCACAAGGAGAGATTTCTAATGATGTGGAAGTGGTGAAAGACCAGTTTCAT
Hopti-Dys3978       (1081)  ACCCTGCAGGCCCAGGGCGAGATCAGCAACGACGTGGAAGTGGTGAAGGACCAGTTCCAC

                             1141                                                       1200
Wildtype Δ3990      (1141)  ACTCATGAGGGGTACATGATGGATTTGACAGCCCATCAGGGCCGGGTTGGTAATATTCTA
Hopti-Dys3978       (1141)  ACCCACGAGGGCTACATGATGGATCTGACCGCCCACCAGGGCAGAGTGGGCAATATCCTG

                             1201                                                       1260
Wildtype Δ3990      (1201)  CAATTGGGAAGTAAGCTGATTGGAACAGGAAAATTATCAGAAGATGAAGAAACTGAAGTA
Hopti-Dys3978       (1201)  CAGCTGGGCAGCAAGCTGATCGGCACCGGCAAGCTGAGCGAGGACGAGGAGACCGAAGTG

                             1261                                                       1320
Wildtype Δ3990      (1261)  CAAGAGCAGATGAATCTCCTAAATTCAAGATGGGAATGCCTCAGGGTAGCTAGCATGGAA
Hopti-Dys3978       (1261)  CAGGAGCAGATGAACCTGCTGAACAGCAGATGGGAGTGCCTGAGAGTGGCCAGCATGGAG

                             1321                                                       1380
Wildtype Δ3990      (1321)  AAACAAAGCAATTTACATAGAGTTTTAATGGATCTCCAGAATCAGAAACTGAAAGAGTTG
Hopti-Dys3978       (1321)  AAGCAGAGCAACCTGCACAGAGTGCTGATGGACCTGCAGAACCAGAAGCTGAAGGAGCTG

                             1381                                                       1440
Wildtype Δ3990      (1381)  AATGACTGGCTAACAAAAACAGAAGAAAGAACAAGGAAAATGGAGGAAGAGCCTCTTGGA
Hopti-Dys3978       (1381)  AACGACTGGCTGACCAAGACCGAGGAGCGGACCAGAAAGATGGAGGAGGAGCCCCTGGGC
```

FIG. 56C

```
                            1441                                                        1500
Wildtype Δ3990     (1441) CCTGATCTTGAAGACCTAAAACGCCAAGTACAACAACATAAGGTGCTTCAAGAAGATCTA
Hopti-Dys3978      (1441) CCCGACCTGGAGGACCTGAAGAGACAGGTGCAGCAGCACAAAGTGCTGCAGGAGGACCTG

                            1501                                                        1560
Wildtype Δ3990     (1501) GAACAAGAACAAGTCAGGGTCAATTCTCTCACTCACATGGTGGTGGTAGTTGATGAATCT
Hopti-Dys3978      (1501) GAGCAGGAGCAGGTGCGCGTGAACAGCCTGACCCACATGGTGGTGGTCGTGGACGAGAGC

                            1561                                                        1620
Wildtype Δ3990     (1561) AGTGGAGATCACGCAACTGCTGCTTTGGAAGAACAACTTAAGGTATTGGGAGATCGATGG
Hopti-Dys3978      (1561) AGCGGCGACCACGCCACAGCCGCCCTGGAAGAGCAGCTGAAAGTGCTGGGCGACAGATGG

                            1621                                                        1680
Wildtype Δ3990     (1621) GCAAACATCTGTAGATGGACAGAAGACCGCTGGGTTCTTTTACAAGACCAGCCTGACCTA
Hopti-Dys3978      (1621) GCCAATATTTGTAGGTGGACCGAGGACAGATGGGTGCTGCTGCAGGACCAGCCCGACCTG

                            1681                                                        1740
Wildtype Δ3990     (1681) GCTCCTGGACTGACCACTATTGGAGCCTCTCCTACTCAGACTGTTACTCTGGTGACACAA
Hopti-Dys3978      (1681) GCCCCTGGCCTGACCACCATCGGCGCCAGCCCCACCCAGACCGTGACCCTGGTGACCCAG

                            1741                                                        1800
Wildtype Δ3990     (1741) CCTGTGGTTACTAAGGAAACTGCCATCTCCAAACTAGAAATGCCATCTTCCTTGATGTTG
Hopti-Dys3978      (1741) CCCGTGGTGACAAAGGAGACCGCCATCAGCAAGCTGGAGATGCCCAGCTCCCTGATGCTG

                            1801                                                        1860
Wildtype Δ3990     (1801) GAGGTACCTACTCATAGATTACTGCAACAGTTCCCCCTGGACCTGGAAAAGTTTCTTGCC
Hopti-Dys3978      (1801) GAAGTGCCCACCCACCGCCTGCTCCAGCAGTTCCCCCTGGACCTGGAGAAGTTCCTGGCC

                            1861                                                        1920
Wildtype Δ3990     (1861) TGGCTTACAGAAGCTGAAACAACTGCCAATGTCCTACAGGATGCTACCCGTAAGGAAAGG
Hopti-Dys3978      (1861) TGGCTGACCGAGGCCGAAACCACCGCCAATGTGCTCCAGGACGCCACTAGAAAGGAGAGG
```

FIG. 56D

```
                           1921                                                       1980
Wildtype Δ3990    (1921) CTCCTAGAAGACTCCAAGGGAGTAAAAGAGCTGATGAAACAATGGCAAGACCTCCAAGGT
Hopti-Dys3978     (1921) CTGCTGGAGGACAGCAAGGGCGTGAAAGAGCTGATGAAGCAGTGGCAGGATCTGCAGGGC

                           1981                                                       2040
Wildtype Δ3990    (1981) GAAATTGAAGCTCACACAGATGTTTATCACAACCTGGATGAAAACAGCCAAAAAATCCTG
Hopti-Dys3978     (1981) GAAATCGAGGCCCACACCGACGTGTACCACAACCTGGACGAGAACAGCCAGAAGATTCTG

                           2041                                                       2100
Wildtype Δ3990    (2041) AGATCCCTGGAAGGTTCCGATGATGCAGTCCTGTTACAAAGACGTTTGGATAACATGAAC
Hopti-Dys3978     (2041) AGGAGCCTGGAGGGCAGCGACGACGCCGTCCTGCTCCAGAGGAGGCTGGACAACATGAAC

                           2101                                                       2160
Wildtype Δ3990    (2101) TTCAAGTGGAGTGAACTTCGGAAAAAGTCTCTCAACATTAGGTCCCATTTGGAAGCCAGT
Hopti-Dys3978     (2101) TTCAAGTGGAGCGAGCTGCGGAAGAAGAGCCTGAACATCCGGAGCCACCTGGAAGCCAGC

                           2161                                                       2220
Wildtype Δ3990    (2161) TCTGACCAGTGGAAGCGTCTGCACCTTTCTCTGCAGGAACTTCTGGTGTGGCTACAGCTG
Hopti-Dys3978     (2161) AGCGACCAGTGGAAGAGACTGCACCTGAGCCTGCAGGAGCTGCTGGTGTGGCTGCAGCTG

                           2221                                                       2280
Wildtype Δ3990    (2221) AAAGATGATGAATTAAGCCGGCAGGCACCTATTGGAGGCGACTTTCCAGCAGTTCAGAAG
Hopti-Dys3978     (2221) AAGGACGACGAGCTGAGCAGACAGGCCCCCATCGGCGGCGACTTCCCCGCCGTGCAGAAG

                           2281                                                       2340
Wildtype Δ3990    (2281) CAGAACGATGTACATAGGGCCTTCAAGAGGGAATTGAAAACTAAAGAACCTGTAATCATG
Hopti-Dys3978     (2281) CAGAACGACGTGCACCGGGCCTTCAAGAGGGAGCTGAAAACCAAGGAACCCGTGATCATG

                           2341                                                       2400
Wildtype Δ3990    (2341) AGTACTCTTGAGACTGTACGAATATTTCTGACAGAGCAGCCTTTGGAAGGACTAGAGAAA
Hopti-Dys3978     (2341) AGCACCCTGGAGACAGTGCGGATCTTCCTGACCGAGCAGCCCCTGGAGGGACTGGAGAAG
```

FIG. 56E

```
                                2401                                                        2460
Wildtype Δ3990     (2401) CTCTACCAGGAGCCCAGAGAGCTGCCTCCTGAGGAGAGAGCCCAGAATGTCACTCGGCTT
Hopti-Dys3978      (2401) CTGTACCAGGAGCCCAGAGAGCTGCCCCCCGAGGAGAGAGCCCAGAACGTGACCAGGCTG

                                2461                                                        2520
Wildtype Δ3990     (2461) CTACGAAAGCAGGCTGAGGAGGTCAATACTGAGTGGGAAAAATTGAACCTGCACTCCGCT
Hopti-Dys3978      (2461) CTGAGAAAGCAGGCCGAGGAAGTGAATACCGAGTGGGAGAAGCTGAATCTGCACAGCGCC

                                2521                                                        2580
Wildtype Δ3990     (2521) GACTGGCAGAGAAAAATAGATGAGACCCTTGAAAGACTCCAGGAACTTCAAGAGGCCACG
Hopti-Dys3978      (2521) GACTGGCAGAGAAAGATCGACGAGACCCTGGAGAGACTCCAGGAACTGCAGGAAGCCACC

                                2581                                                        2640
Wildtype Δ3990     (2581) GATGAGCTGGACCTCAAGCTGCGCCAAGCTGAGGTGATCAAGGGATCCTGGCAGCCCGTG
Hopti-Dys3978      (2581) GACGAGCTGGACCTGAAGCTGAGACAGGCCGAAGTGATCAAGGGCAGCTGGCAGCCTGTG

                                2641                                                        2700
Wildtype Δ3990     (2641) GGCGATCTCCTCATTGACTCTCTCCAAGATCACCTCGAGAAAGTCAAGGCACTTCGAGGA
Hopti-Dys3978      (2641) GGCGATCTGCTGATCGACTCCCTGCAGGATCACCTGGAGAAAGTGAAGGCCCTGCGGGGC

                                2701                                                        2760
Wildtype Δ3990     (2701) GAAATTGCGCCTCTGAAAGAGAACGTGAGCCACGTCAATGACCTTGCTCGCCAGCTTACC
Hopti-Dys3978      (2701) GAGATCGCCCCCCTGAAGGAGAATGTGAGCCACGTGAACGACCTGGCCAGACAGCTGACC

                                2761                                                        2820
Wildtype Δ3990     (2761) ACTTTGGGCATTCAGCTCTCACCGTATAACCTCAGCACTCTGGAAGACCTGAACACCAGA
Hopti-Dys3978      (2761) ACCCTGGGCATCCAGCTGAGCCCCTACAACCTGAGCACACTGGAGGATCTGAACACCCGG

                                2821                                                        2880
Wildtype Δ3990     (2821) TGGAAGCTTCTGCAGGTGGCCGTCGAGGACCGAGTCAGGCAGCTGCATGAAGCCCACAGG
Hopti-Dys3978      (2821) TGGAAACTGCTGCAGGTGGCCGTGGAGGATAGAGTGAGGCAGCTGCACGAAGCCCACAGA
```

FIG. 56F

```
                                     2881                                                       2940
Wildtype Δ3990    (2881) GACTTTGGTCCAGCATCTCAGCACTTTCTTTCCACGTCTGTCCAGGGTCCCTGGGAGAGA
Hopti-Dys3978     (2881) GACTTCGGCCCTGCCTCCCAGCACTTCCTGAGCACCAGCGTGCAGGGCCCCTGGGAGAGA

                                     2941                                                       3000
Wildtype Δ3990    (2941) GCCATCTCGCCAAACAAAGTGCCCTACTATATCAACCACGAGACTCAAACAACTTGCTGG
Hopti-Dys3978     (2941) GCCATCTCCCCCAACAAAGTGCCCTACTACATCAACCACGAGACCCAGACCACCTGCTGG

                                     3001                                                       3060
Wildtype Δ3990    (3001) GACCATCCCAAAATGACAGAGCTCTACCAGTCTTTAGCTGACCTGAATAATGTCAGATTC
Hopti-Dys3978     (3001) GACCACCCTAAGATGACCGAGCTGTATCAGAGCCTGGCCGACCTGAACAATGTGCGGTTC

                                     3061                                                       3120
Wildtype Δ3990    (3061) TCAGCTTATAGGACTGCCATGAAACTCCGAAGACTGCAGAAGGCCCTTTGCTTGGATCTC
Hopti-Dys3978     (3061) AGCGCCTACAGAACCGCCATGAAGCTGCGGAGACTGCAGAAGGCCCTGTGCCTGGATCTG

                                     3121                                                       3180
Wildtype Δ3990    (3121) TTGAGCCTGTCAGCTGCATGTGATGCCTTGGACCAGCACAACCTCAAGCAAAATGACCAG
Hopti-Dys3978     (3121) CTGAGCCTGAGCGCCGCCTGCGACGCCCTGGACCAGCACAACCTGAAGCAGAATGACCAG

                                     3181                                                       3240
Wildtype Δ3990    (3181) CCCATGGATATCCTGCAGATTATTAATTGTTTGACCACTATTTATGACCGCCTGGAGCAA
Hopti-Dys3978     (3181) CCCATGGACATCCTGCAGATCATCAACTGCCTGACCACAATCTACGACCGGCTGGAACAG

                                     3241                                                       3300
Wildtype Δ3990    (3241) GAGCACAACAATTTGGTCAACGTCCCTCTCTGCGTGGATATGTGTCTGAACTGGCTGCTG
Hopti-Dys3978     (3241) GAGCACAACAACCTGGTGAATGTGCCCCTGTGCGTGGACATGTGCCTGAATTGGCTGCTG

                                     3301                                                       3360
Wildtype Δ3990    (3301) AATGTTTATGATACGGGACGAACAGGGAGGATCCGTGTCCTGTCTTTAAAACTGGCATC
Hopti-Dys3978     (3301) AACGTGTACGACACCGGCAGGACCGGCAGAATCCGCGTGCTGAGCTTCAAGACCGGCATC
```

FIG. 56G

```
                                   3361                                                       3420
Wildtype Δ3990     (3361) ATTTCCCTGTGTAAAGCACATTTGGAAGACAAGTACAGATACCTTTTCAAGCAAGTGGCA
Hopti-Dys3978      (3361) ATCAGCCTGTGCAAGGCCCACCTGGAGGATAAGTACCGCTACCTGTTCAAGCAGGTGGCC

                                   3421                                                       3480
Wildtype Δ3990     (3421) AGTTCAACAGGATTTTGTGACCAGCGCAGGCTGGGCCTCCTTCTGCATGATTCTATCCAA
Hopti-Dys3978      (3421) AGCAGCACCGGCTTCTGCGATCAGAGGAGACTGGGCCTGCTGCTGCACGATAGCATCCAG

                                   3481                                                       3540
Wildtype Δ3990     (3481) ATTCCAAGACAGTTGGGTGAAGTTGCATCCTTTGGGGGCAGTAACATTGAGCCAAGTGTC
Hopti-Dys3978      (3481) ATCCCTAGGCAGCTGGGCGAAGTGGCCAGCTTTGGCGGCAGCAACATCGAGCCCTCTGTG

                                   3541                                                       3600
Wildtype Δ3990     (3541) CGGAGCTGCTTCCAATTTGCTAATAATAAGCCAGAGATCGAAGCGGCCCTCTTCCTAGAC
Hopti-Dys3978      (3541) AGGAGCTGCTTCCAGTTCGCCAACAACAAGCCCGAGATCGAGGCCGCCCTGTTCCTGGAC

                                   3601                                                       3660
Wildtype Δ3990     (3601) TGGATGAGACTGGAACCCCAGTCCATGGTGTGGCTGCCCGTCCTGCACAGAGTGGCTGCT
Hopti-Dys3978      (3601) TGGATGAGGCTGGAGCCTCAGAGCATGGTGTGGCTGCCTGTGCTGCACAGAGTGGCCGCC

                                   3661                                                       3720
Wildtype Δ3990     (3661) GCAGAAACTGCCAAGCATCAGGCCAAATGTAACATCTGCAAAGAGTGTCCAATCATTGGA
Hopti-Dys3978      (3661) GCCGAGACCGCCAAGCACCAGGCCAAGTGCAATATCTGCAAGGAGTGCCCCATCATCGGC

                                   3721                                                       3780
Wildtype Δ3990     (3721) TTCAGGTACAGGAGTCTAAAGCACTTTAATTATGACATCTGCCAAAGCTGCTTTTTTTCT
Hopti-Dys3978      (3721) TTCCGGTACAGGAGCCTGAAGCACTTCAACTACGACATCTGCCAGAGCTGCTTTTTCAGC

                                   3781                                                       3840
Wildtype Δ3990     (3781) GGTCGAGTTGCAAAAGGCCATAAAATGCACTATCCCATGGTGGAATATTGCACTCCGACT
Hopti-Dys3978      (3781) GGCAGAGTGGCCAAGGGCCACAAAATGCACTACCCCATGGTGGAGTACTGCACCCCCACC
```

FIG. 56H

```
                          3841                                                         3900
Wildtype Δ3990   (3841) ACATCAGGAGAAGATGTTCGAGACTTTGCCAAGGTACTAAAAAACAAATTTCGAACCAAA
Hopti-Dys3978    (3841) ACCTCCGGCGAGGATGTGAGAGACTTCGCCAAAGTGCTGAAGAATAAGTTCCGGACCAAG

                          3901                                                         3960
Wildtype Δ3990   (3901) AGGTATTTTGCGAAGCATCCCCGAATGGGCTACCTGCCAGTGCAGACTGTCTTAGAGGGG
Hopti-Dys3978    (3901) CGGTACTTTGCCAAGCACCCCAGGATGGGCTACCTGCCCGTGCAGACCGTGCTGGAAGGC

                          3961
Wildtype Δ3990   (3961) GACAACATGGAAACTCCCGACACAATGTAG   SEQ ID NO:28
Hopti-Dys3978    (3961) GACAACATGGAGACC············TGA   SEQ ID NO:1
```

FIG. 56I

OPTIMIZED MINI-DYSTROPHIN GENES AND EXPRESSION CASSETTES AND THEIR USE

STATEMENT OF PRIORITY

This application is a continuation of and claims priority to U.S. patent application Ser. No. 16/787,938, filed on Feb. 11, 2020, now U.S. Pat. No. 11,547,765, which is a continuation of and claims priority to U.S. patent application Ser. No. 15/628,268, filed on Jun. 20, 2017, now abandoned, which claims the benefit of U.S. Provisional Application Ser. No. 62/352,675, filed on Jun. 21, 2016, and U.S. Provisional Application Ser. No. 62/516,449, filed on Jun. 7, 2017, the contents of each of which are incorporated herein by reference in their entirety.

STATEMENT REGARDING FEDERALLY SPONSORED RESEARCH OR DEVELOPMENT

This invention was made with government support under Grant Nos. AR050595, AR056394, and AR056953 awarded by the National Institutes of Health. The government has certain rights in the invention.

STATEMENT REGARDING ELECTRONIC FILING OF A SEQUENCE LISTING

A Sequence Listing in XML format, submitted under 37 C.F.R. § 1.831-1.834, entitled 5470-784CT2_ST26.xml, 80,246 bytes in size, generated on Jan. 4, 2023 and filed electronically, is provided in lieu of a paper copy. This Sequence Listing is hereby incorporated by reference into the specification for its disclosures.

FIELD OF THE INVENTION

This invention relates to polynucleotides encoding mini-dystrophin proteins, viral vectors comprising the same, and methods of using the same for delivery of mini-dystrophin to a cell or a subject.

BACKGROUND OF THE INVENTION

Duchenne muscular dystrophy (DMD) is a severe, x-linked, progressive neuromuscular disease affecting approximately one in 3,600 to 9200 live male births. The disorder is caused by frame shift mutations in the dystrophin gene abolishing the expression of the dystrophin protein. Due to the lack of the dystrophin protein, skeletal muscle, and ultimately heart and respiratory muscles (e.g., intercostal muscles and diaphragm), degenerate causing premature death. Progressive weakness and muscle atrophy begins in childhood, starting in the lower legs and pelvis before spreading into the upper arms. Other symptoms include loss of certain reflexes, waddling gait, frequent falls, difficulty rising from a sitting or lying position, difficulty climbing stairs, changes to overall posture, impaired breathing, and cardiomyopathy. Many children are unable to run rapidly or jump. The atrophied muscles, in particular the calf muscles (and, less commonly, muscles in the buttocks, shoulders, and arms), may be enlarged by an accumulation of fat and connective tissue, causing them to look larger and healthier than they actually are (called pseudohypertrophy). Bone thinning and scoliosis are common. Ultimately, independent ambulation is lost, and a wheelchair becomes necessary, in most cases between 12 to 15 years of age. As the disease progresses, the muscles in the diaphragm that assist in breathing and coughing become weaker. Affected individuals experience breathing difficulties, respiratory infections, and swallowing problems. Almost all DMD patients will develop cardiomyopathy. Pneumonia compounded by cardiac involvement is the most frequent cause of death, which frequently occurs before the third decade.

Becker muscular dystrophy (BMD) has less severe symptoms than DMD, but still leads to premature death. Compared to DMD, BMD is characterized by later-onset skeletal muscle weakness. Whereas DMD patients are wheelchair dependent before age 13, those with BMD lose ambulation and require a wheelchair after age 16. BMD patients also exhibit preservation of neck flexor muscle strength, unlike their counterparts with DMD. Despite milder skeletal muscle involvement, heart failure from DMD-associated dilated cardiomyopathy (DCM) is a common cause of morbidity and the most common cause of death in BMD, which occurs on average in the mid-40s.

Dystrophin is a cytoplasmic protein encoded by the dmd gene, and functions to link cytoskeletal actin filaments to membrane proteins. Normally, the dystrophin protein, located primarily in skeletal and cardiac muscles, with smaller amounts expressed in the brain, acts as a shock absorber during muscle fiber contraction by linking the actin of the contractile apparatus to the layer of connective tissue that surrounds each muscle fiber. In muscle, dystrophin is localized at the cytoplasmic face of the sarcolemma membrane.

First identified in 1987, the dmd gene is the largest known human gene at approximately 2.5 Mb. The gene is located on the X chromosome at position Xp21 and contains 79 exons. The most common mutations that cause DMD or BMD are large deletion mutations of one or more exons (60-70%), but duplication mutations (5-10%), and single nucleotide variants, (including small deletions or insertions, single-base changes, and splice site changes accounting for approximately 25%-35% of pathogenic variants in males with DMD and about 10%-20% of males with BMD) can also cause pathogenic dystrophin variants.

In DMD, mutations often lead to a frame shift resulting in a premature stop codon and a truncated, non-functional or unstable protein. Nonsense point mutations can also result in premature termination codons with the same result. While mutations causing DMD can affect any exon, exons 2-20 and 45-55 are common hotspots for large deletion and duplication mutations. In frame deletions result in the less severe Becker muscular dystrophy (BMD), in which patients express a truncated, partially functional dystrophin.

Full-length dystrophin is a large (427 kDa) protein comprising a number of subdomains that contribute to its function. These subdomains include, in order from the amino-terminus toward the carboxy-terminus, the N-terminal actin-binding domain, a central so-called "rod" domain, a cysteine-rich domain and lastly a carboxy-terminal domain or region. The rod domain is comprised of 4 proline-rich hinge domains (abbreviated H), and 24 spectrin-like repeats (abbreviated R) in the following order: a first hinge domain (H1), 3 spectrin-like repeats (R1, R2, R3), a second hinge domain (H2), 16 more spectrin-like repeats (R4, R5, R6, R7, R8, R9, R10, R11, R12, R13, R14, R15, R16, R17, R18, R19), a third hinge domain (H3), 5 more spectrin-like repeats (R20, R21, R22, R23, R24), and finally a fourth hinge domain (H4). Subdomains toward the carboxy-terminus of the protein are involved in connecting to the dystrophin-associated glycoprotein complex (DGC), a large protein complex that forms a critical link between the cytoskeleton and the extra-cellular matrix.

No treatment definitively halts or reverses progression of DMD. Treatment with corticosteroids is the current standard of care, but this merely slows progression by a year or two. A number of new drugs for DMD have recently been approved by regulators. These include ataluren, which causes read-through of premature stop codons, and eteplirsen, which causes skipping of exon 51, generating an internally deleted partially functional dystrophin. However, the mechanism of action of these drugs is not expected to help all DMD patients, and further evidence is required to definitively demonstrate their clinical efficacy in DMD.

With advances over the last 10-15 years in use of adeno-associated virus (AAV) mediated gene therapy to potentially treat a variety of rare diseases, there has been renewed hope and interest that AAV could be used to treat DMD and less severe dystrophinopathies (i.e., other muscle diseases associated with mutations in the dmd gene). Due to limits on payload size of AAV vectors, attention has focused on creating micro- or mini-dystrophins, smaller versions of dystrophin that eliminate non-essential subdomains while maintaining at least some function of the full-length protein. AAV-mediated mini-dystrophin gene therapy has shown promise in mdx mice, an animal model for DMD, with widespread expression in muscle and evidence of improved muscle function (See, e.g., Wang et al., *J. Orthop. Res.* 27:421 (2009)). When related experiments using a micro-dystrophin vector were attempted in the GRMD DMD dog model, however, powerful immunosuppressant drugs were required to achieve significant transduction of muscle cells (Yuasa et al., *Gene Ther.* 14:1249 (2007)). Similarly, when human DMD patients were treated with AAV vectors designed to express a mini-dystrophin, minimal protein was detected in only two of the six patients, whereas a T-cell response against the mini-dystrophin protein was stimulated in three (Bowles, et al., Mol Ther. 20(2):443-455 (2012)).

Thus, there exists a need in the art for AAV vectors encoding mini-dystrophins that can be expressed at high levels in transduced cells of subjects with DMD while minimizing immune responses to the mini-dystrophin protein.

SUMMARY OF THE INVENTION

Disclosed and exemplified herein are mini-dystrophin proteins, codon-optimized genes for expressing such mini-dystrophin proteins, AAV vectors for transducing cells with such genes, and methods of prevention and treatment using such AAV vectors, in particular for preventing and treating dystrophinopathies in subjects in need thereof. In some of these embodiments, AAV vectors of the disclosure are capable of guiding production of significant levels of mini-dystrophin in transduced cells while causing no or only muted immune response against the mini-dystrophin protein.

Certain non-limiting embodiments (E) of the inventions of the disclosure are set forth below. These and related embodiments are described in further detail in the Detailed Description, including the Examples and Drawings.

E1. A mini-dystrophin protein comprising, consisting essentially of, or consisting of the N-terminus, the Actin Binding Domain (ABD), hinge H1, rods R1 and R2, hinge H3, rods R22, R23, and R24, hinge H4, the cysteine-rich (CR) domain, and a portion of the carboxy-terminal (CT) domain of wildtype human muscle dystrophin protein (SEQ ID NO:25), wherein the CT domain does not comprise the last three amino acid residues at the carboxy-terminus of wildtype dystrophin protein.

E2. The mini-dystrophin protein of E1, wherein the N-terminus and Actin Binding Domain (ABD) together comprise, consist essentially of, or consist of amino acid numbers 1-240 from SEQ ID NO:25; hinge H1 comprises, consists essentially of, or consists of amino acid numbers 253-327 from SEQ ID NO:25; rod R1 comprises, consists essentially of, or consists of amino acid numbers 337-447 from SEQ ID NO:25; rod R2 comprises, consists essentially of, or consists of amino acid numbers 448-556 from SEQ ID NO:25; hinge H3 comprises, consists essentially of, or consists of amino acid numbers 2424-2470 from SEQ ID NO:25; rod R22 comprises, consists essentially of, or consists of amino acid numbers 2687-2802 from SEQ ID NO:25; rod R23 comprises, consists essentially of, or consists of amino acid numbers 2803-2931 from SEQ ID NO:25; rod R24 comprises, consists essentially of, or consists of amino acid numbers 2932-3040 from SEQ ID NO:25; hinge H4 comprises, consists essentially of, or consists of amino acid numbers 3041-3112 from SEQ ID NO:25; the CR domain comprises, consists essentially of, or consists of amino acid numbers 3113-3299 from SEQ ID NO:25; and the portion of the CT domain comprises, consists essentially of, or consists of amino acid numbers 3300-3408 from SEQ ID NO:25.

E3. The mini-dystrophin protein of any one of E1 and E2, wherein the mini-dystrophin protein comprises, consists essentially of, or consists of the amino acid sequence of SEQ ID NO:7.

E4. A mini-dystrophin protein comprising, consisting essentially of, or consisting of the N-terminus, the Actin Binding Domain (ABD), hinge H1, rods R1, R2, R22, R23, and R24, hinge H4, the cysteine-rich (CR) domain, and a portion of the carboxy-terminal (CT) domain of wildtype human muscle dystrophin protein (SEQ ID NO:25), wherein the CT domain does not comprise the last three amino acid residues at the carboxy-terminus of wildtype dystrophin protein.

E5. The mini-dystrophin protein of E4 wherein the N-terminus and Actin Binding Domain (ABD) together comprise, consist essentially of, or consist of amino acid numbers 1-240 from SEQ ID NO:25; hinge H1 comprises, consists essentially of, or consists of amino acid numbers 253-327 from SEQ ID NO:25; rod R1 comprises, consists essentially of, or consists of amino acid numbers 337-447 from SEQ ID NO:25; rod R2 comprises, consists essentially of, or consists of amino acid numbers 448-556 from SEQ ID NO:25; rod R22 comprises, consists essentially of, or consists of amino acid numbers 2687-2802 from SEQ ID NO:25; rod R23 comprises, consists essentially of, or consists of amino acid numbers 2803-2931 from SEQ ID NO:25; rod R24 comprises, consists essentially of, or consists of amino acid numbers 2932-3040 from SEQ ID NO:25; hinge H4 comprises, consists essentially of, or consists of amino acid numbers 3041-3112 from SEQ ID NO:25; the CR domain comprises, consists essentially of, or consists of amino acid numbers 3113-3299 from SEQ ID NO:25; and the portion of the CT domain comprises, consists essentially of, or consists of amino acid numbers 3300-3408 from SEQ ID NO:25.

E6. The mini-dystrophin protein of any one of E4 and E5, wherein the mini-dystrophin protein comprises, consists essentially of, or consists of the amino acid sequence of SEQ ID NO:8.

E7. A polynucleotide encoding the mini-dystrophin protein of E1-E3.

E8. A polynucleotide encoding the mini-dystrophin protein of E4-E6.

E9. The polynucleotide of any one of E7 and E8, wherein the nucleobase sequence thereof is assembled from the coding sequence of the native wildtype gene encoding full-length human muscle dystrophin, an example of which is provided by NCBI Reference Sequence NM_004006.2.

E10. The polynucleotide of E9, wherein the nucleobase sequence thereof is provided by SEQ ID NO:26.

E11. The polynucleotide of any one of E7-E10, wherein the nucleobase sequence is codon-optimized.

E12. The polynucleotide of E11, wherein the codon-optimization decreases or increases the GC content compared to the wildtype sequence.

E13. The polynucleotide of E11, wherein the codon-optimization decreases or increases the number of CpG dinucleotides compared to the wildtype sequence.

E14. The polynucleotide of E11, wherein the codon-optimization eliminates one or more cryptic splice sites.

E15. The polynucleotide of E11, wherein the codon-optimization eliminates one or more ribosome entry sites other than the one at the start of the coding sequence for the mini-dystrophin protein.

E16. The polynucleotide of E11, wherein the codon-optimization substitutes one or more rare codons for codons that occur with higher frequency in the type and/or species of cell in which the mini-dystrophin gene is intended to be expressed.

E17. The polynucleotide of E12, wherein the codon-optimization increases the GC content compared to wildtype and increases the level of gene expression by at least 50%, 100%, 150%, 200%, 250%, 300%, 350%, 400%, 450%, 500%, 550%, 600%, 650%, 700%, 750%, 800%, 900%, 1000%, or more.

E18. The polynucleotide of E12, wherein the codon-optimization increases the GC content compared to wildtype at least 5%, 10%, 15%, 20%, 25%, 30%, 35%, 40%, 45%, 50%, 55%, 60%, 65%, 70%, 75%, 80%, 85%, 90%, 95%, 100%, or more.

E19. The polynucleotide of E12, wherein the GC content is about or at least 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, or more.

E20. The polynucleotide of E13, wherein the codon-optimization decreases or increases the number of CpG dinucleotides compared to the wildtype by about or at least 5%, 10%, 15%, 20%, 25%, 30%, 35%, 40%, 45%, 50%, 55%, 60%, or more.

E21. The polynucleotide of E20, wherein the number of CpG dinucleotides, if reduced, is reduced in an amount sufficient to fully or partially suppress the silencing of gene expression due to the methylation of CpG motifs.

E22. The polynucleotide of E11, wherein the codon-optimization increases the codon adaptation index (CAI) of the mini-dystrophin gene in reference to highly expressed human genes to a value that is at least 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99.

E23. The polynucleotide of any one of E11-E22, wherein the nucleobase sequence is human codon-optimized.

E24. The polynucleotide of any one of E11-E22, wherein the nucleobase sequence is canine codon-optimized.

E25. The polynucleotide of E23, wherein the human codon-optimized sequence is provided by SEQ ID NO:1, or a nucleobase sequence at least 90%, 91%, 92%, 93%, 94%, 95%, 96%, 97%, 98%, 99%, or 99.5% identical thereto.

E26. The polynucleotide of E23, wherein the human codon-optimized sequence is provided by SEQ ID NO:2, or a nucleobase sequence at least 90%, 91%, 92%, 93%, 94%, 95%, 96%, 97%, 98%, 99%, or 99.5% identical thereto.

E27. The polynucleotide of E24, wherein the canine codon-optimized sequence is provided by SEQ ID NO:3, or a nucleobase sequence at least 90%, 91%, 92%, 93%, 94%, 95%, 96%, 97%, 98%, 99%, or 99.5% identical thereto.

E28. A vector comprising the polynucleotide of any of any one of E7-E27.

E29. The vector of E28, wherein the polynucleotide is operably linked to a genetic control region.

E30. The vector of E29, wherein the genetic control region is a promoter.

E31. The vector of E30, wherein the promoter is muscle-specific in being more active in muscle cells compared to other types of cells, such as liver cells.

E32. The vector of any one of E30-E31, wherein the genetic control region further includes an enhancer.

E33. The vector of any one of E30-E32, wherein the promoter, and enhancer if present, is from a muscle creatine kinase (CK) gene.

E34. The vector of E33, wherein the CK gene is from mouse or human.

E35. The vector of E33, wherein the genetic control region is the mouse CK7 enhancer and promoter.

E36. The vector of any one of E29-E36, wherein the genetic control region comprises the nucleobase sequence selected from the group SEQ ID NO:4, SEQ ID NO:5, and SEQ ID NO:16.

E37. The vector of any one of E28-E36, wherein the polynucleotide is operably linked to a transcription terminator region.

E38. The vector of E37, wherein the transcription terminator region comprises the nucleobase sequence of SEQ ID NO:6 or SEQ ID NO:17.

E39. The vector of any one of E28-E38, wherein the vector is an AAV viral vector genome and comprises flanking AAV inverted terminal repeats (ITRs).

E40. The vector of E39, wherein the ITRs are both AAV2 ITRs.

E41. The vector of any one of E39 and E40, wherein the nucleobase sequence of the vector is provided by a nucleobase sequence selected from the group SEQ ID NO:9, SEQ ID NO:10, SEQ ID NO:11, SEQ ID NO:12, and SEQ ID NO:18.

E42. A recombinant AAV (rAAV) particle comprising an AAV capsid and the vector of any one of E39-E41.

E43. The rAAV particle of E42, wherein the AAV capsid is the AAV9 capsid.

E44. A rAAV particle, comprising an AAV capsid having tropism for striated muscle and a vector genome for expressing a human mini-dystrophin protein.

E45. The rAAV particle of E44, wherein the AAV capsid is from the AAV9 serotype.

E46. The rAAV particle of any one of E44 and E45, wherein the vector genome comprises a human codon-optimized nucleic acid sequence encoding the human mini-dystrophin protein.

E47. The rAAV particle of any one of E44-E46, wherein the human mini-dystrophin protein comprises the following subdomains or portions thereof from full-length human muscle dystrophin protein in order from N-terminus to C-terminus: N-terminal domain, Actin-Binding Domain (ABD), hinge H1, rod R1, rod R2, hinge H3, rod R22, rod R23, rod R24, hinge H4, the Cysteine-Rich (CR) Domain, and a portion of the carboxy-terminal (CT) domain, wherein the portion of the CT domain does not include the last 3 amino acids from dystrophin.

E48. The rAAV particle of any one of E44-E47, wherein the human mini-dystrophin protein comprises the amino acid sequence of SEQ ID NO:7.

E49. The rAAV particle of any one of E44-E46, wherein the human mini-dystrophin protein comprises the following subdomains or portions thereof from full-length human muscle dystrophin protein in order from N-terminus to C-terminus: N-terminal domain, Actin-Binding Domain (ABD), hinge H1, rod R1, rod R2, rod R22, rod R23, rod R24, hinge H4, the Cysteine-Rich (CR) Domain, and a portion of the carboxy-terminal (CT) domain, wherein the portion of the CT domain does not include the last 3 amino acids from dystrophin.

E50. The rAAV particle of any one of E44-E46, and E49, wherein the human mini-dystrophin protein comprises the amino acid sequence of SEQ ID NO:8.

E51. The rAAV particle of any one of E44-E47, wherein the human codon-optimized nucleic acid sequence encoding the human mini-dystrophin protein comprises the nucleic acid sequence of SEQ ID NO:1.

E52. The rAAV particle of any one of E44-E46, E49, and E50, wherein the human codon-optimized nucleic acid sequence encoding the human mini-dystrophin protein comprises the nucleic acid sequence of SEQ ID NO:3.

E53. The rAAV particle of any one of E44-E52, wherein the vector genome further comprises AAV inverted terminal repeats (ITRs) flanking the codon-optimized nucleic acid sequence.

E54. The rAAV particle of E53, wherein the AAV ITRs are AAV2 ITRs.

E55. The rAAV particle of any one of E44-E54, wherein the vector genome further comprises a muscle-specific transcriptional regulatory element operably linked with the human codon optimized nucleic acid sequence.

E56. The rAAV particle of E55, wherein the muscle-specific transcriptional regulatory element is positioned between the 5' AAV2 ITR and the human codon-optimized nucleic acid sequence.

E57. The rAAV particle of any one of E55 and E56, wherein the muscle-specific transcriptional regulatory element is derived from the human or mouse creatine kinase (CK) gene.

E58. The rAAV particle of any one of E55-E57, wherein the muscle-specific transcriptional regulatory element comprises an enhancer and a promoter.

E59. The rAAV particle of any one of E55-E58, wherein the muscle-specific transcriptional regulatory element is the mouse CK7 enhancer and promoter.

E60. The rAAV particle of any one of E55-E59, wherein the muscle-specific transcriptional regulatory element comprises the nucleic acid sequence of SEQ ID NO:16.

E61. The rAAV particle of any one of E44-E60, wherein the vector genome further comprises a transcription termination sequence positioned between the codon-optimized nucleic acid sequence and the 3' AAV2 ITR.

E62. The rAAV particle of E61, wherein the transcription termination sequence comprises a polyadenylation signal.

E63. The rAAV particle of any one of E44-E62, wherein the vector genome comprises in 5' to 3' order: a first AAV2 ITR, a muscle-specific transcriptional regulatory element operably linked to a human codon-optimized nucleic acid sequence encoding a human mini-dystrophin protein, a transcription termination sequence, and a second AAV2 ITR.

E64. The rAAV particle of E63, wherein the muscle-specific transcriptional regulatory element comprises the nucleic acid sequence of SEQ ID NO:16.

E65. The rAAV particle of embodiments E63 or E64, wherein the human codon-optimized nucleic acid sequence comprises the nucleic acid sequence of SEQ ID NO:1.

E66. The rAAV particle of embodiments E63-E65, wherein the transcription termination sequence comprises the nucleic acid sequence of SEQ ID NO:17.

E67. The rAAV particle of any one of E44-E48, E51, and E53-E66, wherein the vector genome comprises the nucleic acid sequence of SEQ ID NO:18 or the reverse-complement thereof.

E68. The rAAV particle of any one of E44-E48, E51, and E53-E66, wherein the vector genome consists essentially of the nucleic acid sequence of SEQ ID NO:18 or the reverse-complement thereof.

E69. The rAAV particle of any one of E44-E48, E51, and E53-E66, wherein the vector genome consists of the nucleic acid sequence of SEQ ID NO:18 or the reverse-complement thereof.

E70. A recombinant AAV particle, comprising an AAV9 capsid and a vector genome comprising the nucleic acid sequence of SEQ ID NO:18 or the reverse complement thereof.

E71. A recombinant AAV particle, comprising an AAV9 capsid and a vector genome consisting essentially of the nucleic acid sequence of SEQ ID NO:18 or the reverse complement thereof.

E72. A recombinant AAV particle, comprising an AAV9 capsid and a vector genome consisting of the nucleic acid sequence of SEQ ID NO:18 or the reverse complement thereof.

E73. A pharmaceutical composition comprising the rAAV particle of any one of E42-E72 and a pharmaceutically acceptable carrier.

E74. A method for treating a dystrophinopathy comprising administering to a subject in need of treatment for a dystrophinopathy a therapeutically effective amount of the composition of E73.

E75. Use of the recombinant AAV (rAAV) particle of any one of E42-E72 or use of the composition of E73 in the preparation of a medicament for treating a subject with a dystrophinopathy.

E76. The rAAV particle of any one of E42-E72 or the composition of E73 for use in the treatment of a subject having a dystrophinopathy.

E77. The method, use, rAAV particle, or composition for use of any one of E74-E76, wherein the dystrophinopathy is Duchenne muscular dystrophy (DMD), Becker muscular dystrophy (BMD), or DMD-associated dilated cardiomyopathy.

E78. The method, use, rAAV particle, or composition for use of any one of E74-E77, wherein the subject is a male or female human subject.

E79. The method, use, rAAV particle, or composition for use of any one of E74-E78, wherein the subject is ambulatory when first treated with or administered the composition.

E80. The method, use, rAAV particle, or composition for use of any one of E74-E79, wherein the subject is about or at least 4, 5, 6, 7, 8, 9, 10, 11, 12, 13, 14, 15, or 16 years of age when first treated with or administered the composition.

E81. The method, use, rAAV particle, or composition for use of any one of E74-E79, wherein the method, use, rAAV particle, or composition for use is effective to restore dystrophin associated protein complex at the sarcolemma of muscle cells compared to untreated controls.

E82. The method, use, rAAV particle, or composition for use of any one of E74-E79, wherein the method, use, rAAV particle, or composition for use is effective to improve the dystrophic histopathology in the heart compared to untreated controls.

E83. The method, use, rAAV particle, or composition for use of any one of E74-E79, wherein the method, use, rAAV particle, or composition for use is effective to inhibit fibrosis in limb muscle and diaphragm compared to untreated controls.

E84. The method, use, rAAV particle, or composition for use of any one of E74-E79, wherein the method, use, rAAV particle, or composition for use is effective to reduce muscle lesion score compared to untreated controls.

E85. The method, use, rAAV particle, or composition for use of any one of E74-E79, wherein the method, use, rAAV particle, or composition for use is effective to reduce muscle fatigue compared to untreated controls.

E86. The method, use, rAAV particle, or composition for use of any one of E74-E79, wherein the method, use, rAAV particle, or composition for use is effective to increase the maximum absolute or relative forelimb grip strength of $Dmd^{mdx}$ rats compared to untreated controls.

E87. The method, use, rAAV particle, or composition for use of any one of E74-E79, wherein the method, use, rAAV particle, or composition for use is effective to increase the detectable level of mini-dystrophin mRNA or protein in skeletal muscle, heart muscle or diaphragm.

E88. The method, use, rAAV particle, or composition for use of any one of E74-E79, wherein the method, use, rAAV particle, or composition for use is effective to reduce average MMP-9 levels in blood of subjects to within about 15-, 14-, 13-, 12-, 11-, 10-, 9-, 8-, 7-, 6-, 5-, 4-, 3-, or 2-fold greater than that in healthy controls.

E89. The method, use, rAAV particle, or composition for use of any one of E74-E79, wherein the method, use, rAAV particle, or composition for use is effective to reduce average ALT, AST, or LDH levels in blood of subjects to within about 7-, 6-, 5-, 4-, 3-, or 2-fold greater than that in healthy controls.

E90. The method, use, rAAV particle, or composition for use of any one of E74-E79, wherein the method, use, rAAV particle, or composition for use is effective to reduce average total CK levels in blood of subjects to within about 50-, 48-, 46-, 44-, 42-, 40-, 38-, 36-, 34-, 32-, 30-, 28-, 26-, 24-, 22-, 20-, 18-, 16-, 14-, 12-, 10-, 9-, 8-, 7-, 6-, 5-, 4-, 3-, or 2-fold greater than that in healthy controls.

E91. The method, use, rAAV particle, or composition for use of any one of E74-E79, wherein the method, use, rAAV particle, or composition for use is effective to increase the average 6 minute walk distance (6MWD) of subjects by at least 5, 10, 15, 20, 25, 30, 35, 40, 45, 50, 55, 60, 65, 70, 75, 80, 85, 90, 95, or 100 meters compared to the average 6MWD of untreated controls 3, 6, 9, 12, 15, 18, 21, 24, 27, 30, 33, or 36 months after administration of the vector.

E92. The method, use, rAAV particle, or composition for use of any one of E74-E79, wherein the method, use, rAAV particle, or composition for use is effective to reduce the average time required to perform the 4 stair climb test by at least 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, or 4.0 seconds compared to the average time of untreated controls 3, 6, 9, 12, 15, 18, 21, 24, 27, 30, 33, or 36 months after administration of the vector.

E93. The method, use, rAAV particle, or composition for use of any one of E74-E79, wherein the method, use, rAAV particle, or composition for use is effective to reduce the average proportion of subjects that have lost ambulation by at least 5%, 10%, 15%, 20%, 25%, 30%, 35%, 40%, 45%, 50%, 55%, 60% or 65% compared to the average proportion of untreated controls that have lost ambulation 3, 6, 9, 12, 15, 18, 21, 24, 27, 30, 33, or 36 months after administration of the vector.

E94. The method, use, rAAV particle, or composition for use of any one of E74-E79, wherein the method, use, rAAV particle, or composition for use is effective to reduce the average fat fraction in the lower extremities of subjects by at least 5%, 10%, 15%, 20%, 25%, 30%, 35%, 40%, 45%, 50%, 55%, 60%, 65%, 70% or 75% compared to the average fat fraction in the lower extremities of untreated controls 3, 6, 9, 12, 15, 18, 21, 24, 27, 30, 33, or 36 months after administration of the vector.

E95. The method, use, rAAV particle, or composition for use of any one of E88-E94, wherein the controls are age and sex matched to the subjects.

E96. The method, use, rAAV particle, or composition for use of any one of E91-E94, wherein the subjects and untreated controls are stratified according to age, prior corticosteroid treatment, and/or baseline performance on the 6MWT.

E97. The method, use, rAAV particle, or composition for use of any one of E74-E79, wherein the method, use, rAAV particle, or composition for use is effective to cause at least 5%, 10%, 15%, 20%, 25%, 30%, 35%, 40%, 45%, 50%, 55%, 60%, 65%, 70%, 75%, 80%, 85% or 90% of skeletal muscle fibers of a subject to express the mini-dystrophin protein 3, 6, 9, 12, 15, 18, 21, 24, 27, 30, 33, or 36 months after administration of the vector.

E98. The method, use, rAAV particle, or composition for use of any one of E97, wherein the skeletal muscle fibers are present in a biopsy obtained from the bicep, deltoid or quadriceps muscle of the subject.

E99. The method, use, rAAV particle, or composition for use of any one of E74-E98, wherein the method, use, rAAV particle, or composition for use causes a cellular immune response against the mini-dystrophin protein or muscle inflammation in less than or equal to about 0%, 1%, 2%, 3%, 4%, 5%, 6%, 7%, 8%, 9%, 10%, 11%, 12%, 13, 14%, 15%, 16%, 17%, 18%, 19% or 20% of subjects 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 months after administration of the vector.

E100. The method, use, rAAV particle, or composition for use of any one of E74-E99, wherein the method, use, rAAV particle, or composition for use is effective without need for concomitant immune suppression in treated subjects.

E101. The method, use, rAAV particle, or composition for use of any one of E74-E76, wherein the subject is a $Dmd^{mdx}$ rat and the method, use, rAAV particle, or composition for use is effective to result in a reduction in serum AST, ALT, LDH, or total creatine kinase levels at 3 months or 6 months post-injection compared to age matched controls administered only vehicle.

E102. The method, use, rAAV particle, or composition for use of any one of E74-E76, wherein the subject is a $Dmd^{mdx}$ rat and the method, use, rAAV particle, or composition for use is effective to result in a reduction in fibrosis in biceps femoris, diaphragm, or heart muscle at 3 months or 6 months post-injection compared to age matched controls administered only vehicle.

E103. The method, use, rAAV particle, or composition for use of any one of E74-E76, wherein the subject is a $Dmd^{mdx}$ rat and the method, use, rAAV particle, or composition for use is effective to result in an increase in forelimb grip force at 3 months or 6 months post-injection compared to age matched controls administered only vehicle.

E104. The method, use, rAAV particle, or composition for use of any one of E74-E76, wherein the subject is a $Dmd^{mdx}$ rat and the method, use, rAAV particle, or composition for use is effective to result in a reduction in muscle fatigue as measured over 5 closely spaced trials testing forelimb grip force at 3 months or 6 months post-injection compared to age matched controls administered only vehicle.

E105. The method, use, rAAV particle, or composition for use of any one of E74-E76, wherein the subject is a $Dmd^{mdx}$ rat and the method, use, rAAV particle, or composition for use is effective to result in an increase in left ventricular ejection fraction as measured using echocardiography at 6 months post-injection compared to age matched controls administered only vehicle.

E106. The method, use, rAAV particle, or composition for use of any one of E74-E76, wherein the subject is a $Dmd^{mdx}$ rat and the method, use, rAAV particle, or composition for use is effective to result in an increase in the ratio of the velocity of early to late left ventricular filling (i.e., E/A ratio) as measured using echocardiography at 3 months or 6 months post-injection compared to age matched controls administered only vehicle.

E107. The method, use, rAAV particle, or composition for use of any one of E74-E76, wherein the subject is a $Dmd^{mdx}$ rat and the method, use, rAAV particle, or composition for use is effective to result in a decrease in the isovolumetric relaxation time (IVRT) or the time in milliseconds between peak E velocity and its return to baseline, wherein the E wave deceleration time (DT) is measured using echocardiography at 3 months or 6 months post-injection compared to age matched controls administered only vehicle.

E108. The method, use, rAAV particle, or composition for use of E74-E76, wherein the subject is a $Dmd^{mdx}$ rat and the method, use, rAAV particle, or composition for use is effective to transduce biceps femoris, diaphragm, heart muscle, or other striated muscles, and express the mini-dystrophin protein encoded by the opti-Dys3978 gene without inducing a cellular immune response against the mini-dystrophin protein by 3 months or 6 months post-injection.

E109. The method, use, rAAV particle, or composition for use of any one of E74-E76, wherein the subject is a $Dmd^{mdx}$ rat and the method, use, rAAV particle, or composition for use is effective to partially or completely reverse the increase in left ventricular end-diastolic diameter at 6 months post-injection compared to age matched controls administered only vehicle.

E110. The method, use, rAAV particle, or composition for use of any one of E74-E100, wherein the subject is also treated with, or the composition also comprises, at least a second agent effective for treating dystrophinopathy, examples of which include an antisense oligonucleotide that causes exon skipping of the DMD gene, an anti-myostatin antibody, an agent that promotes ribosomal read-through of nonsense mutations, an agent that suppresses premature stop codons, an anabolic steroid, or a corticosteroid (such as, without limitation, prednisone, deflazacort, or prednisolone).

E111. The method, use, rAAV particle, or composition for use of any one of E74-E110, wherein the composition is administered systemically, such as by intravenous injection, or locally, such as directly into a muscle.

E112. The method, use, rAAV particle, or composition for use of any one of E74-E111, wherein the dose of rAAV particles used in the method, use, rAAV particle, or composition for use is selected from the group of doses consisting of: $1\times10^{12}$ vg/kg, $2\times10^{12}$ vg/kg, $3\times10^{12}$ vg/kg, $4\times10^{12}$ vg/kg, $5\times10^{12}$ vg/kg, $6\times10^{12}$ vg/kg, $7\times10^{12}$ vg/kg, $8\times10^{12}$ vg/kg, $9\times10^{12}$ vg/kg, $1\times10^{13}$ vg/kg, $2\times10^{13}$ vg/kg, $3\times10^{13}$ vg/kg, $4\times10^{13}$ vg/kg, $5\times10^{13}$ vg/kg, $6\times10^{13}$ vg/kg, $7\times10^{13}$ vg/kg, $8\times10^{13}$ vg/kg, $9\times10^{13}$ vg/kg, $1\times10^{14}$ vg/kg, $1.5\times10^{14}$ vg/kg, $2\times10^{14}$ vg/kg, $2.5\times10^{14}$ vg/kg, $3\times10^{14}$ vg/kg, $3.5\times10^{14}$ vg/kg, $4\times10^{14}$ vg/kg, $5\times10^{14}$ vg/kg, $6\times10^{14}$ vg/kg, $7\times10^{14}$ vg/kg, $8\times10^{14}$ vg/kg, and $9\times10^{14}$ vg/kg, where vg/kg stands for vector genomes per kilogram of subject body weight.

E113. The composition of E73, further comprising empty capsids of the same AAV serotype as the rAAV particle, wherein the concentration ratio of empty capsids to rAAV particles is about or at least 0.5:1, 1:1, 2:1, 3:1, 4:1, 5:1, 6:1, 7:1, 8:1, 9:1, 10:1, or more.

E114. A method of expressing a mini-dystrophin protein in a cell, comprising contacting the cell with the rAAV particle of any one of E42-E72.

E115. The method of E114, wherein the cell is a muscle cell.

E116. The method of E115, wherein the muscle cell is from skeletal muscle, diaphragm, or heart.

E117. A method of making the rAAV particle of any one of E42-E72, comprising introducing into a producer cell the vector of any one of E39-E41, an AAV rep gene, an AAV cap gene, and genes for helper functions, incubating the cells, and purifying the rAAV particles produced by the cells.

E118. The method of E117, wherein the producer cells are adherent.

E119. The method of E117, wherein the producer cells are non-adherent.

E120. The method of any one of E117-E119, wherein the vector is contained in one plasmid, the AAV rep and cap genes are contained in a second plasmid, and the helper function genes are contained in a third plasmid, where all three plasmids are introduced into the packaging cells.

E121. The method of any one of E117-E120, wherein the step of introducing is effected by transfection.

E122. The method of any one of E117-E121, wherein the producer cells are HEK 293 cells.

E123. The method of any one of E117-E122, wherein the producer cells are grown in serum free medium.

E124. The method of any one of E117-E123, wherein the AAV cap gene encodes the AAV9 VP1, VP2 and VP3 proteins.

E125. The method of any one of E117-E124, wherein the rAAV particles are purified using density gradient ultracentrifugation, or column chromatography.

E126. An rAAV particle produced by the method of any one of E117-E125.

BRIEF DESCRIPTION OF THE DRAWINGS

(FIG. 6A) Cryosections (8 μm) of tibialis anterior muscles from wild-type control C57BL/10 mice, untreated dKO mice, and vector-treated dKO (T-dKO) mice were subjected to hematoxylin and eosin (H&E) staining for histopathology (10× magnification). (FIG. 6B) Quantitative analyses of muscle mass, heart mass, percentage of centrally localized nuclei and serum creatine kinase activities.

(FIG. 9A) The PR interval of the ECG was improved in vector-treated dKO mice. (FIG. 9B) Quantitative data of the analysis. The experiment was done to carefully monitor the heart rate of the three groups so that the ECG was not affected by the variation in heart rate. $^{*}p<0.05$.

"n" refers to sample size; "D" refers to number days since dosing; "W" refers to number of weeks since dosing; "E" is notation for the specified coefficient times ten raised to the power of the specified exponent (thus, "1E13" stands for $1\times10^{13}$, "3E13" stands for $3\times10^{13}$, "1E14" stands for $1\times10^{14}$, and "3E14" stands for $3\times10^{14}$); "vg/kg" stands for vector genomes per kilogram body weight; and "w/o HAS" refers to a treatment arm where the vector was administered in PBS without human serum albumin. On the right side of the graph, at 25 weeks, the order of average body weight data from top to bottom is the same as the top to bottom order of the treatment arms listed in the legend (except for treatment of $Dmd^{mdx}$ rats with $1\times10^{14}$ vg/kg vector administered in vehicle without HSA, for which data collection ended at 13 weeks from the study start). These same abbreviations are used in other figures herein.

Figure 38A:
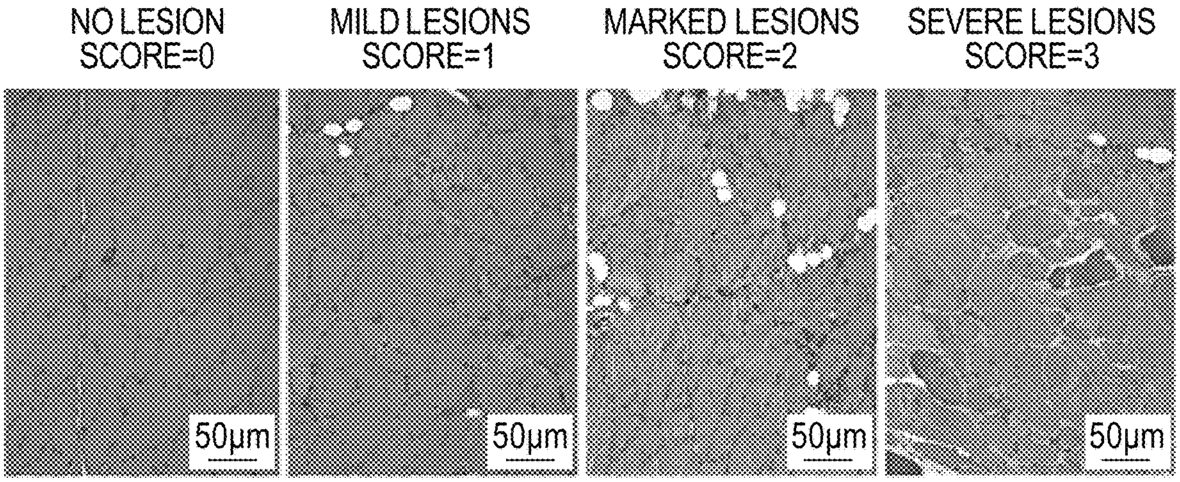

FIG. 38A provides exemplary photomicrographs of skeletal muscle from $Dmd^{mdx}$ rats stained for histological examination illustrating a semi-quantitative scoring scheme used to estimate the degree of severity of muscle lesions caused by the absence of dystrophin. In skeletal muscle, such as that illustrated, a score of 0 corresponded to the absence of lesions; 1 corresponded to the presence of some regenerative activity as evidenced by centronucleated fibers and small foci of regeneration; 2 corresponded to the presence of degenerated fibers, isolated or in small clusters; and 3 corresponded to tissue remodeling and fiber replacement by fibrotic or adipose tissue. Scoring for heart used different criteria as explained in the text.

Figure 38B:
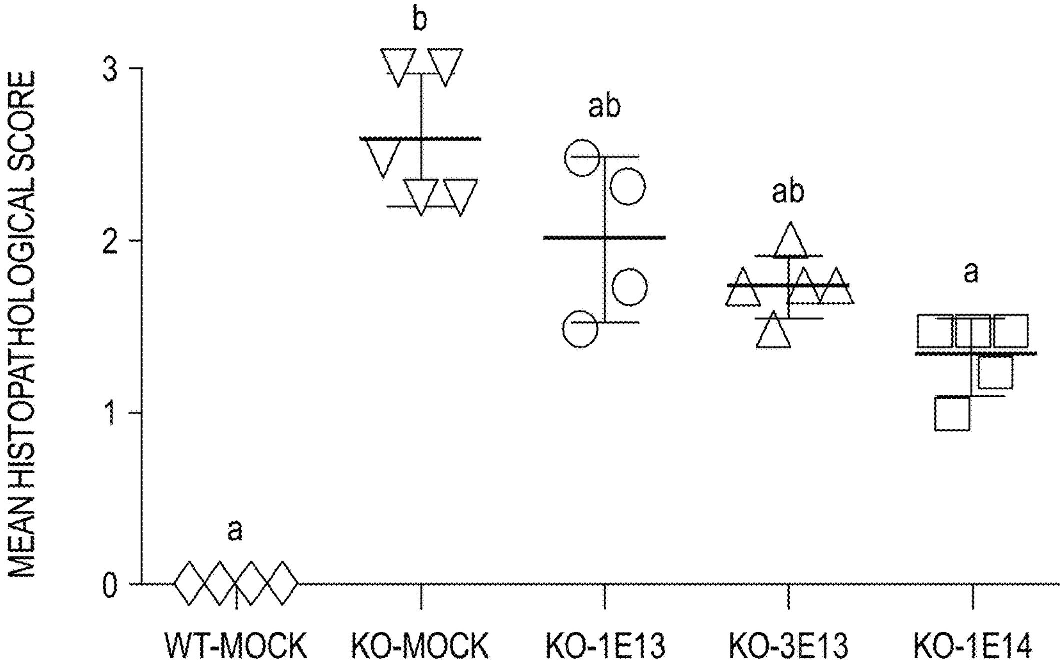

FIG. 38B shows total DMD lesion scores for rats (that is, average of lesion subscores for biceps femoris, pectoralis, diaphragm and cardiac muscles) at 3 months post-injection are shown, individually as well as the mean among all rats in each treatment arm, and compared to show a vector dose-responsive reduction in lesion score. "WT mock" refers to WT rats treated with vehicle, "KO mock" refers to $Dmd^{mdx}$ rats treated with vehicle, "KO 1E13", "3E13", and "1E14", refer to $Dmd^{mdx}$ rats treated with the indicated doses of AAV9.hCK.Hopti-Dys3978.spA vector in vg/kg. Letters above bars indicate that the underlying data is not statistically different from other bars over which the same letters appear. Conversely, bars over which different letters appear are statistically different from each other. Statistics were calculated using the Kruskal-Wallis and Dunn's tests.

Figure 39A:
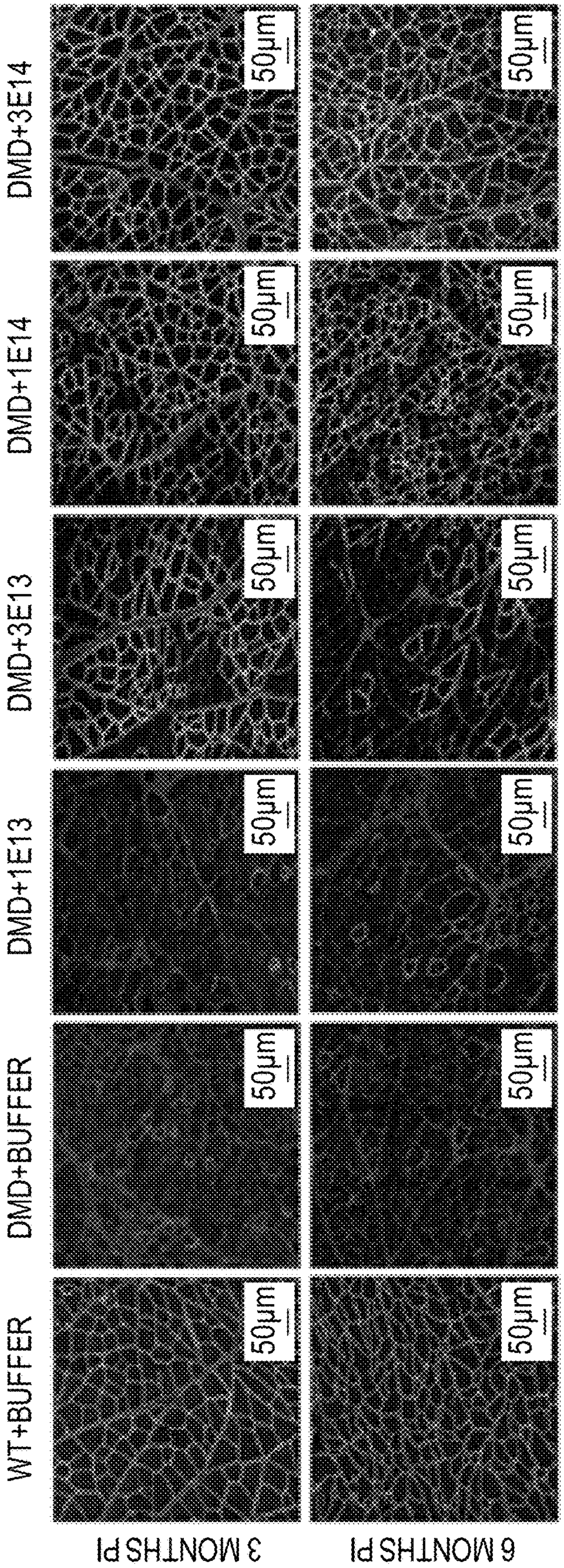

FIG. 39A provides representative sections from biceps femoris muscle samples from $Dmd^{mdx}$ rats treated with increasing doses of AAV9.hCK.Hopti-Dys3978.spA vector, and negative controls. Samples were dual labeled with an antibody that specifically binds to full length rat dystrophin and human mini-dystrophin, and wheat germ agglutinin conjugate which stains connective tissue. Top panel are micrographs from animals sacrificed at 3 months post-injection. Bottom panel are micrographs from animals sacrificed at 6 months post-injection.

Figure 39B:
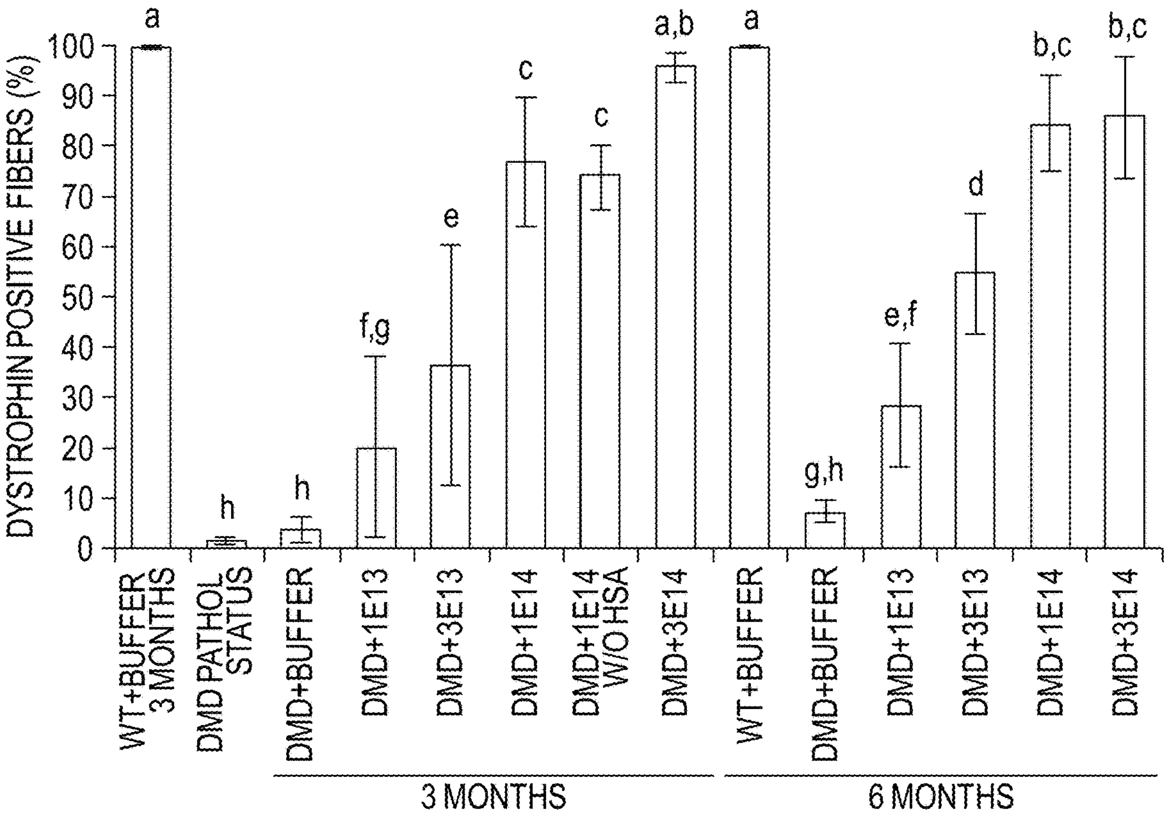

FIG. 39B provides percent fibers in random sections from biceps femoris muscle samples from $Dmd^{mdx}$ rats treated with increasing doses of AAV9.hCK.Hopti-Dys3978.spA vector, and negative controls, that stained positive for presence of dystrophin protein. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.

Figure 39C:
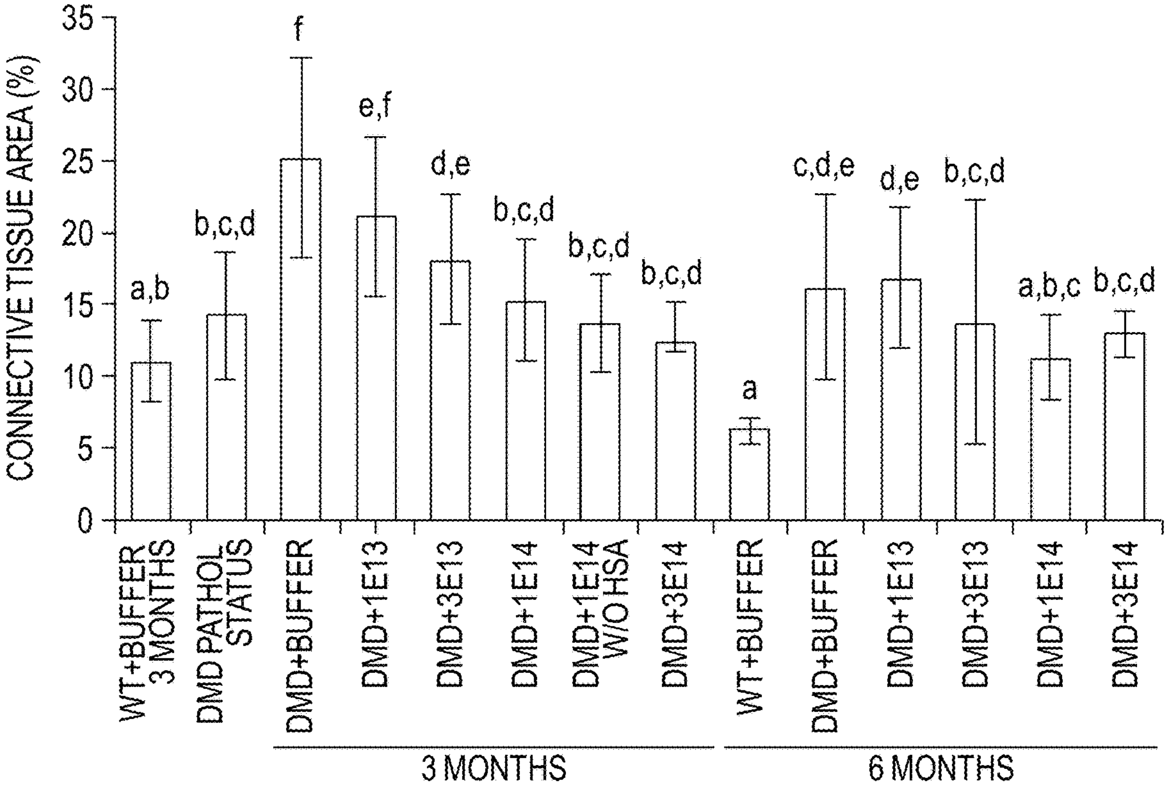

FIG. 39C provides percent area in random sections of biceps femoris muscle samples from $Dmd^{mdx}$ rats treated with increasing doses of AAV9.hCK.Hopti-Dys3978.spA vector, and negative controls, that stained positive for presence of connective tissue. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.

Figure 40A:
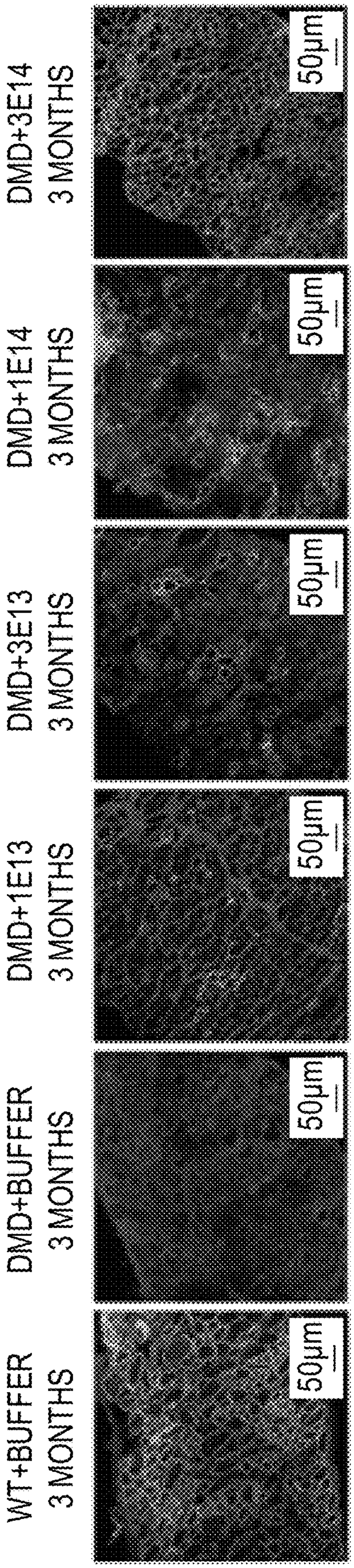

FIG. 40A provides representative sections from diaphragm muscle samples from $Dmd^{mdx}$ rats treated with increasing doses of AAV9.hCK.Hopti-Dys3978.spA vector, and negative controls, sacrificed at 3 months post-injection. Samples were dual labeled with an antibody that specifically binds to full length rat dystrophin and human mini-dystrophin, and wheat germ agglutinin conjugate which stains connective tissue.

Figure 40B:
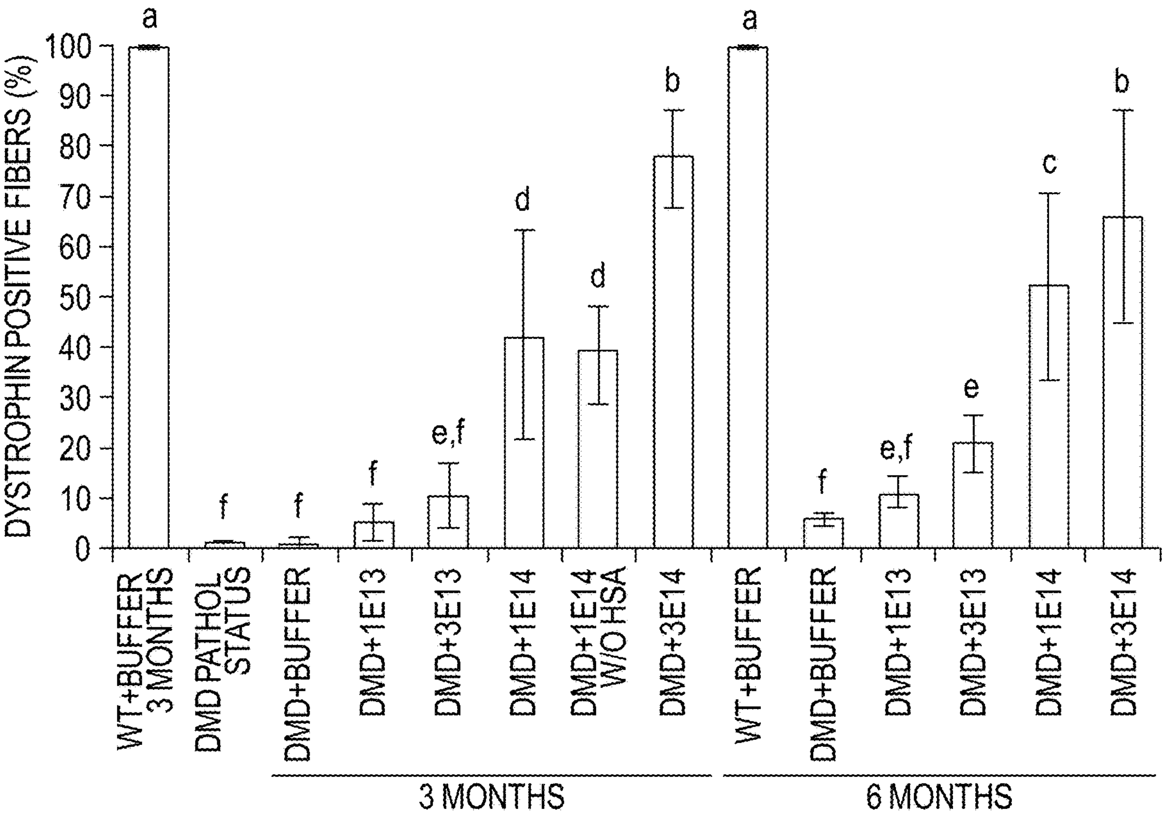

FIG. 40B provides percent fibers in random sections from diaphragm muscle samples from $Dmd^{mdx}$ rats treated with increasing doses of AAV9.hCK.Hopti-Dys3978.spA vector, and negative controls, that stained positive for presence of dystrophin. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.

Figure 40C:
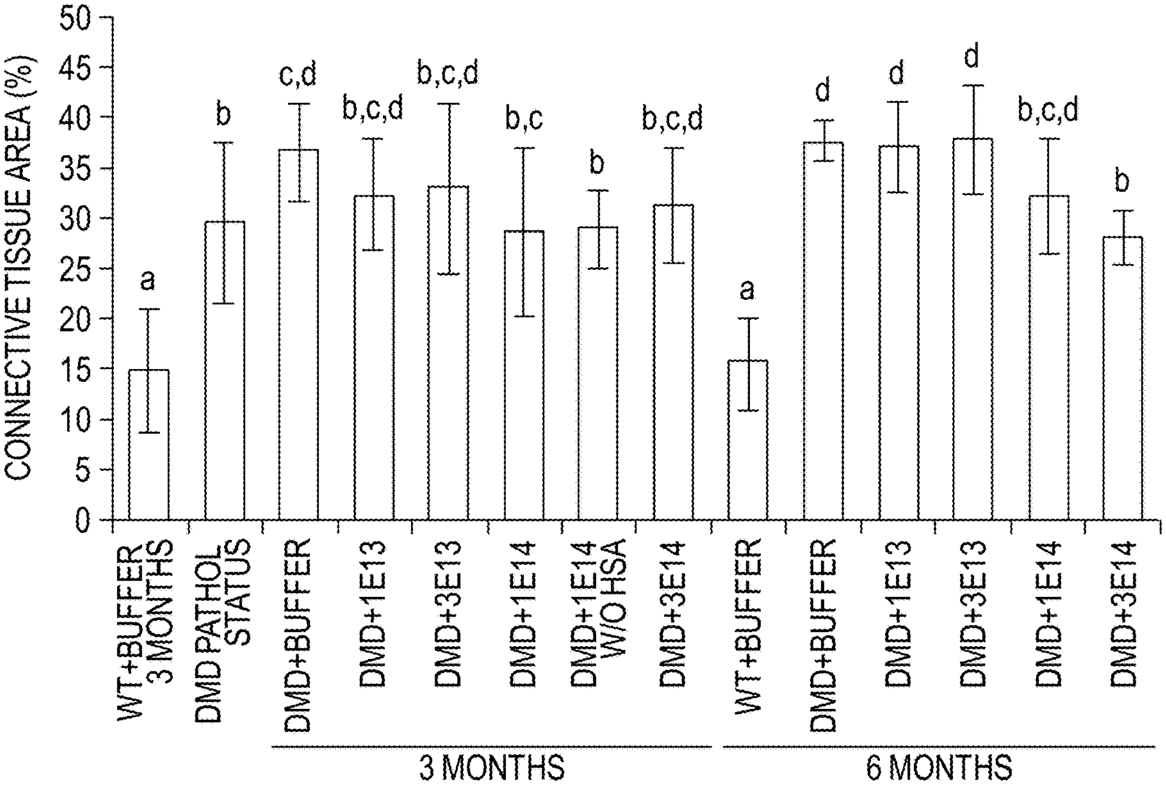

FIG. 40C provides percent area in random sections of diaphragm muscle samples from $Dmd^{mdx}$ rats treated with increasing doses of AAV9.hCK.Hopti-Dys3978.spA vector, and negative controls, that stained positive for presence of connective tissue. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.

Figure 41A:
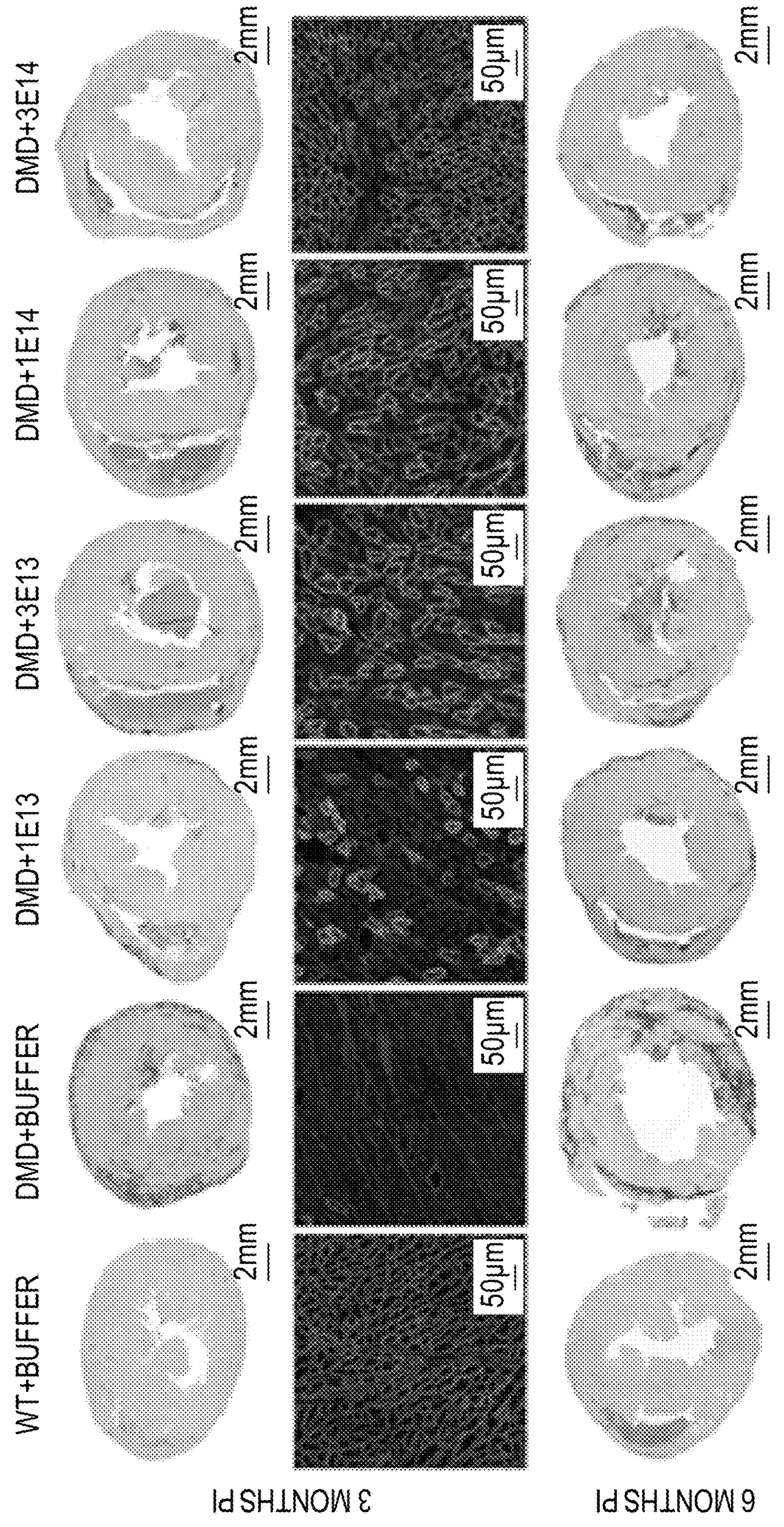

FIG. 41A shows representative transverse sections of heart at one-third from the apex taken from $Dmd^{mdx}$ rats treated with increasing doses of AAV9.hCK.Hopti-Dys3978.spA vector (top panel), and negative controls (bottom panel), sacrificed at 3 months and 6 months post-injection. Histology sections were stained with picrosirius red to permit visualization of connective tissue. The middle panel contains representative sections of heart muscle taken from vector and vehicle treated $Dmd^{mdx}$ rats dual labeled with an antibody that specifically binds to full length rat dystrophin and human mini-dystrophin, and wheat germ agglutinin conjugate which stains connective tissue.

Figure 41B:
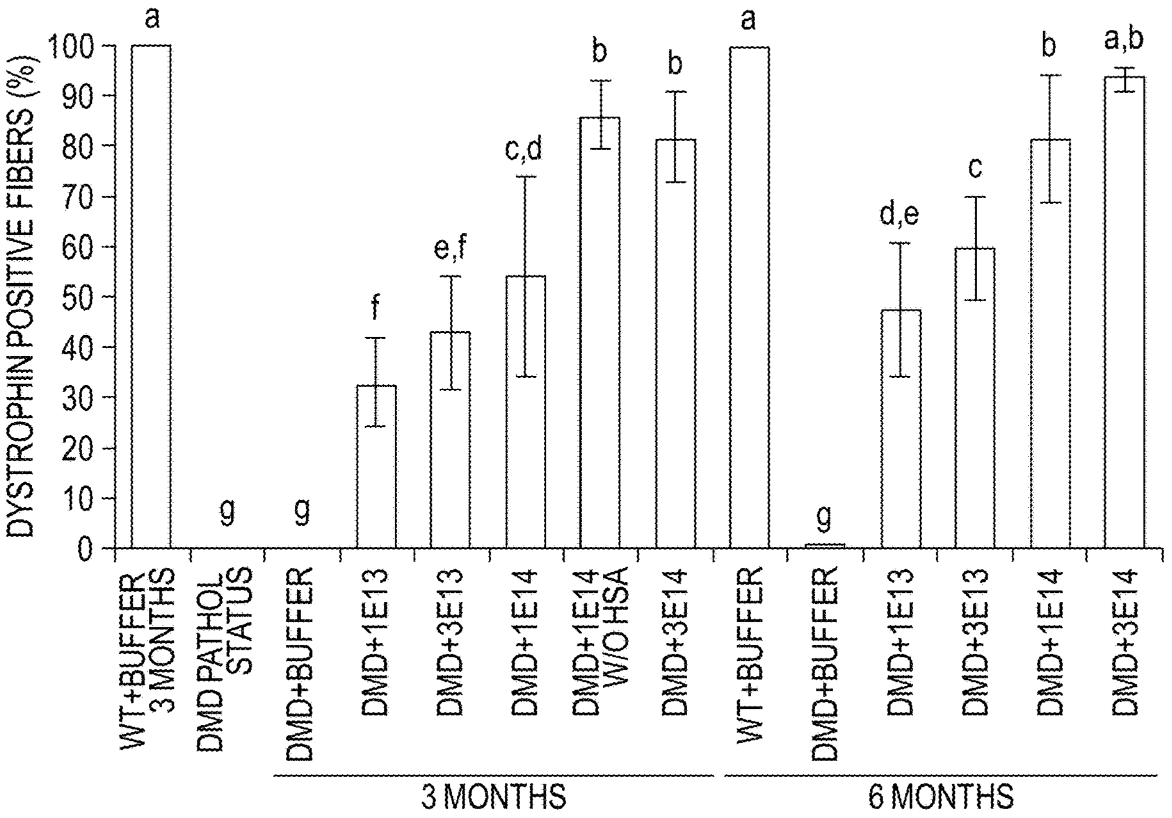

FIG. 41B provides percent fibers in random sections from heart muscle samples from $Dmd^{mdx}$ rats treated with increasing doses of AAV9.hCK.Hopti-Dys3978.spA vector, and negative controls, stained for presence of dystrophin protein. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.

Figure 41C:
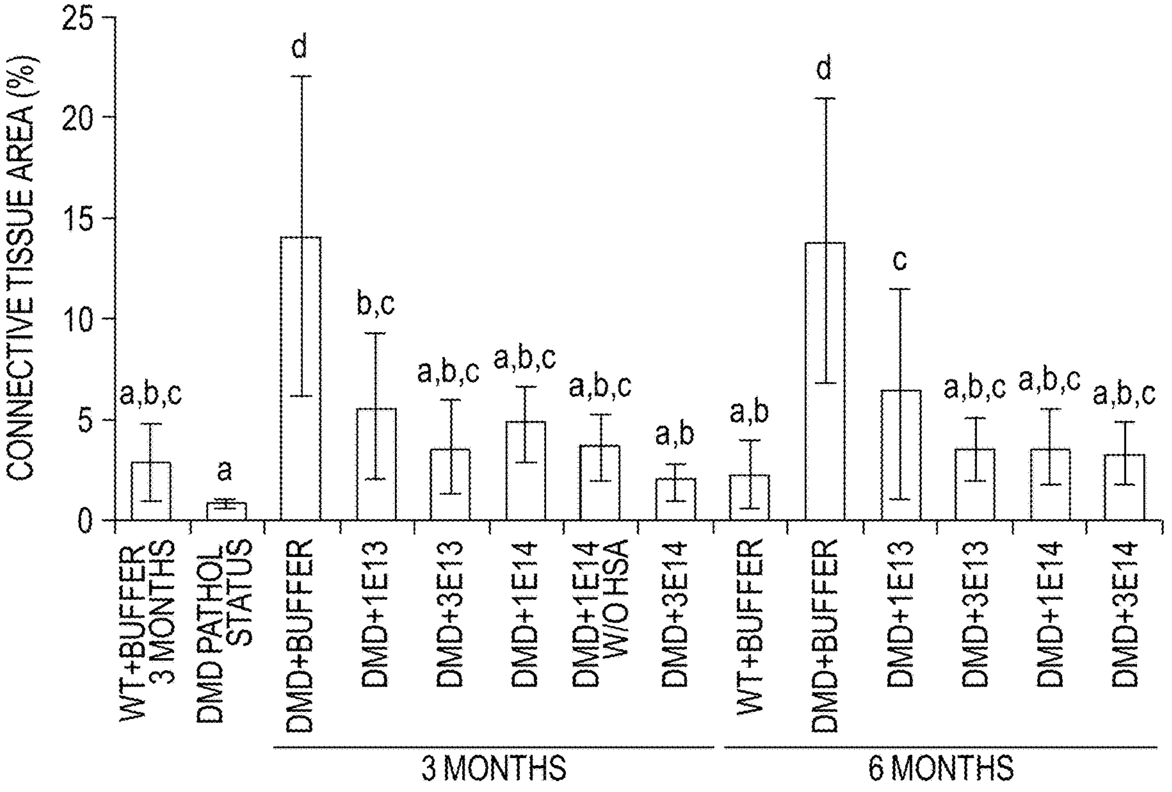

FIG. 41C provides percent area in random sections of heart muscle samples from $Dmd^{mdx}$ rats treated with increasing doses of AAV9.hCK.Hopti-Dys3978.spA vector, and negative controls, stained for presence of connective tissue. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.

Figure 42A:
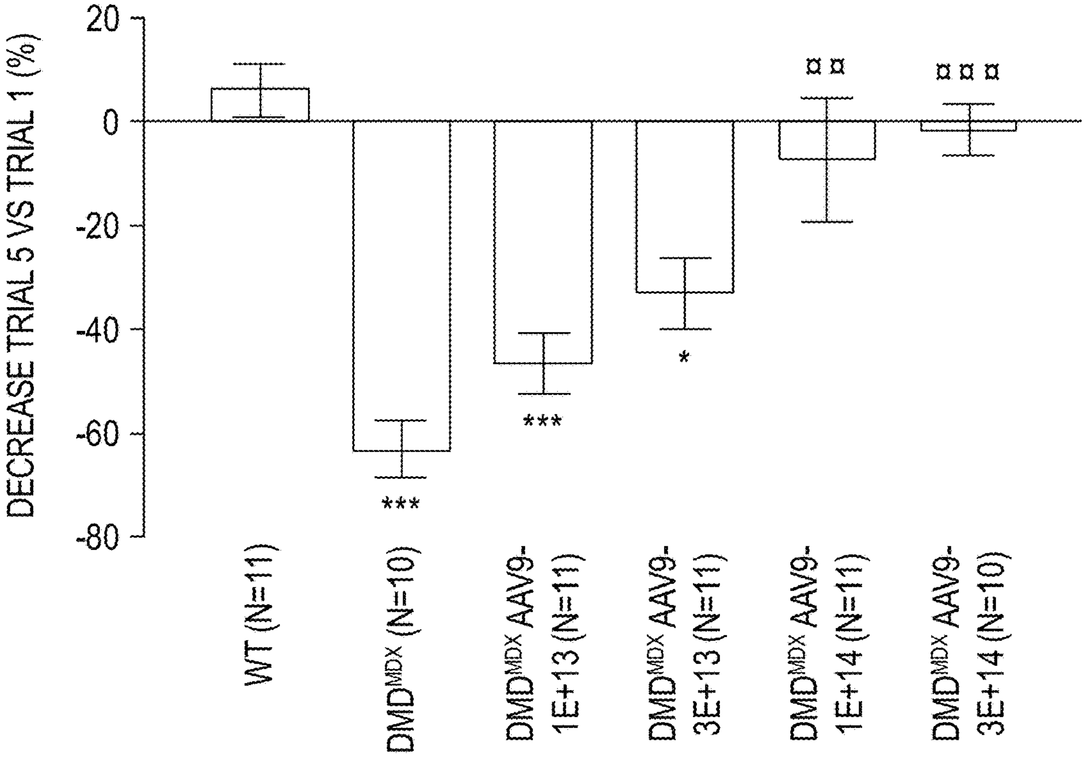

FIG. 42A provides data regarding muscle fatigue in Dmd$^{mdx}$ rats treated with increasing doses of AAV9.hCK.Hopti-Dys3978.spA vector compared to Dmd$^{mdx}$ and WT rats treated with vehicle measured by repeating five closely spaced grip strength tests. Tests were conducted 3 months post-injection in rats injected at 7-9 weeks of age, or when the rats were approximately 4.5 months old. Graph shows the decrease in forelimb grip force measured between trials 1 and 5 (expressed as percentage of trial 1 force). Results are represented as mean±SEM. Statistics compare Dmd$^{mdx}$ rats treated with vector against WT rats receiving vehicle (*p<0.05; ***p<0.001), and Dmd$^{mdx}$ rats receiving vehicle (¤¤<0.01; ¤¤¤p<0.001), both as negative controls.

Figure 42B:
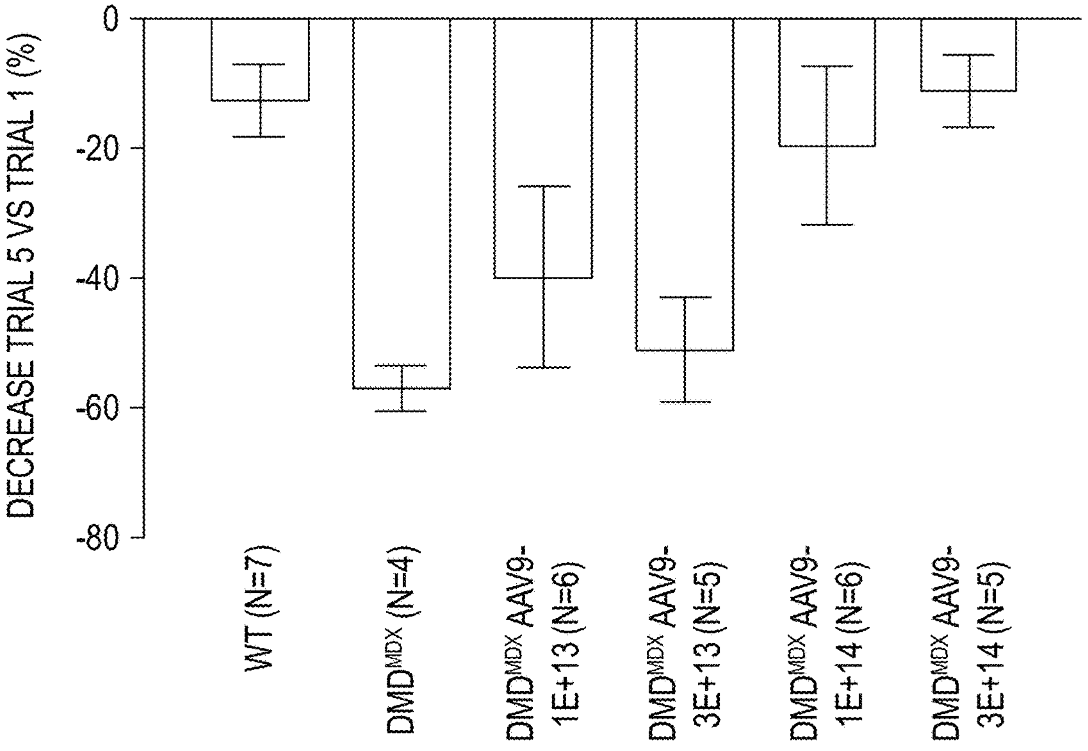

FIG. 42B provides data regarding muscle fatigue in Dmd$^{mdx}$ rats treated with increasing doses of AAV9.hCK.Hopti-Dys3978.spA vector compared to Dmd$^{mdx}$ and WT rats treated with vehicle measured by repeating five closely spaced grip strength tests. Tests were conducted 6 months post-injection in rats injected at 7-9 weeks of age, or when the rats were approximately 7.5 months old. Graph shows the decrease in forelimb grip force measured between trials 1 and 5 (expressed as percentage of trial 1 force). Results are represented as mean±SEM.

Figure 43:
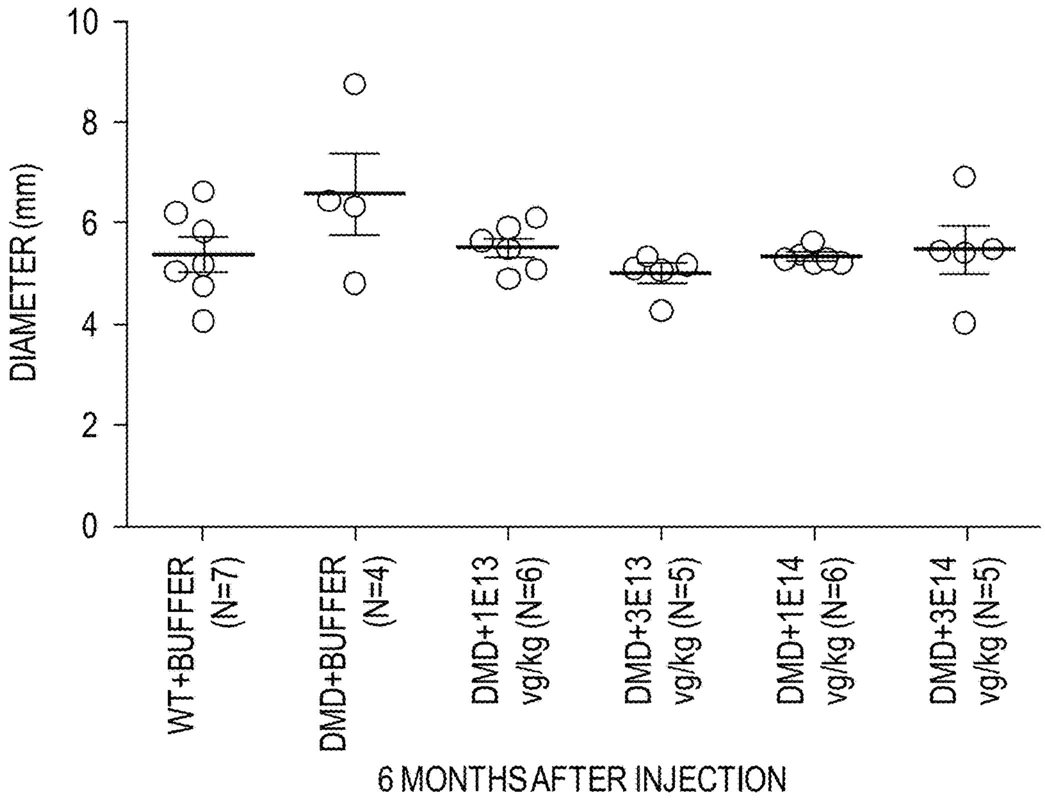

FIG. 43 provides left ventricular (LV) end-diastolic diameter measured during diastole from long-axis images obtained by M-mode echocardiography 6 months post-injection in WT and Dmd$^{mdx}$ rats administered vehicle or AAV9.hCK.Hopti-Dys3978.spA vector. Descriptive statistics shown are mean±SEM.

Figure 44:
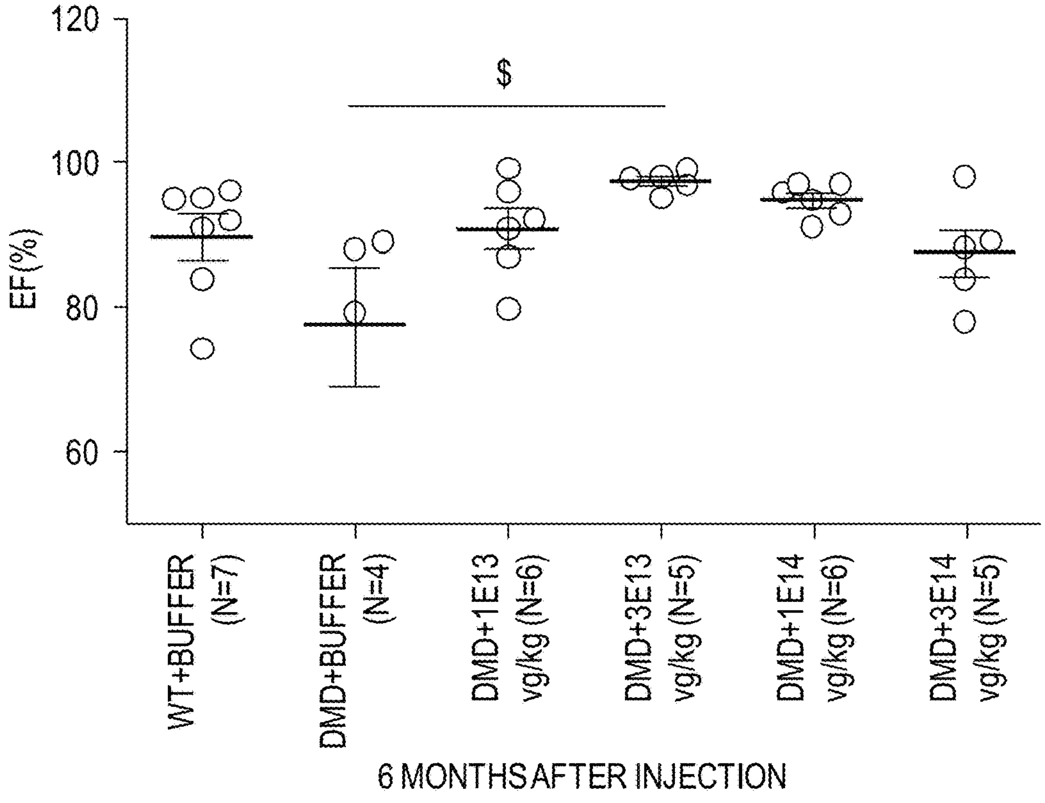

FIG. 44 provides ejection fractions measured during diastole from long-axis images obtained by M-mode echocardiography 6 months post-injection in WT and Dmd$^{mdx}$ rats administered vehicle or AAV9.hCK.Hopti-Dys3978.spA vector. Descriptive statistics shown are mean±SEM, and the "$" symbol indicates a statistically significant difference between the data over which it is placed and the data for Dmd$^{mdx}$ rats treated with vehicle (buffer) (p<0.05).

Figure 45A:
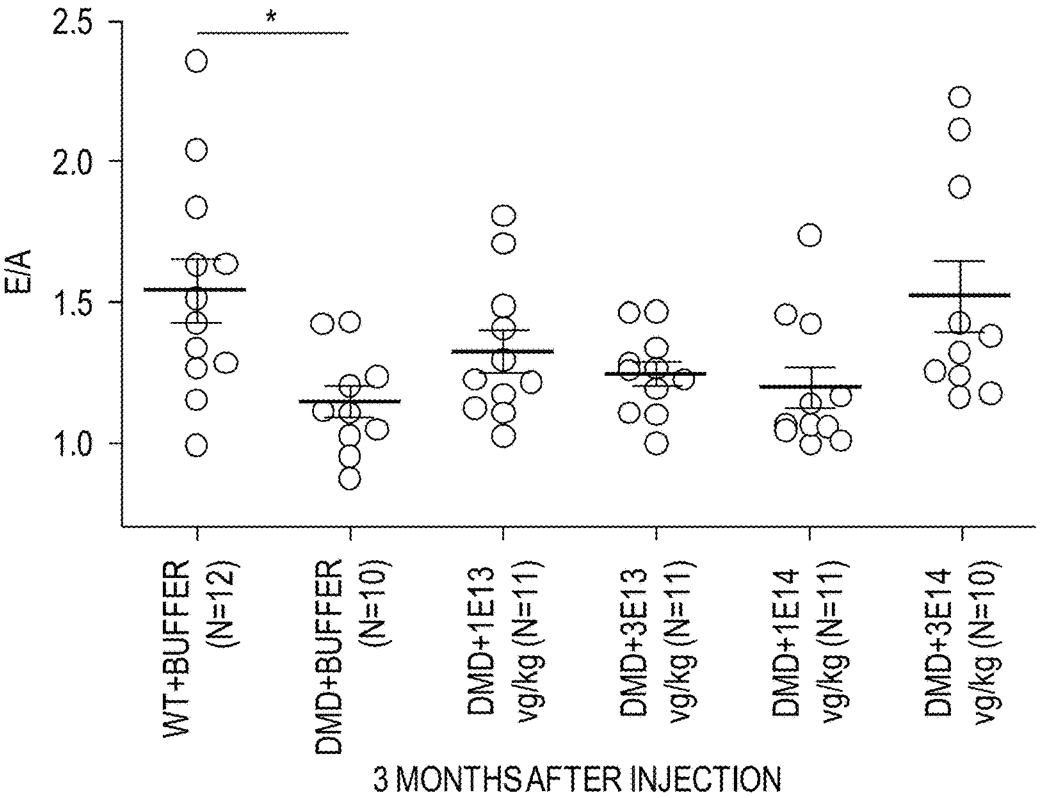

FIG. 45A provides E/A ratios measured using pulsed Doppler with an apical four-chamber orientation 3 months post-injection in WT and Dmd$^{mdx}$ rats administered vehicle or AAV9.hCK.Hopti-Dys3978.spA vector. Descriptive statistics shown are mean±SEM, and the "*" symbol indicates a statistically significant difference between the data over which it is placed and the data for WT rats treated with vehicle (buffer) (p<0.05).

Figure 45B:
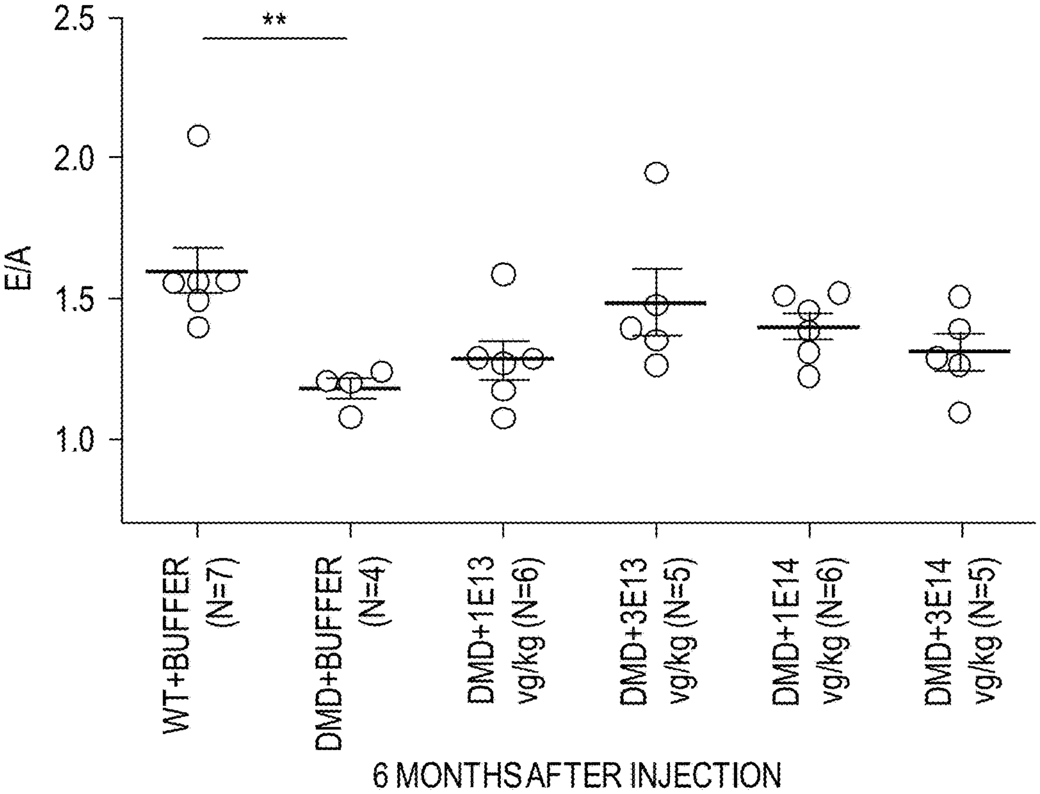

FIG. 45B provides E/A ratios measured using pulsed Doppler with an apical four-chamber orientation 6 months post-injection in WT and Dmd$^{mdx}$ rats administered vehicle or AAV9.hCK.Hopti-Dys3978.spA vector. Descriptive statistics shown are mean SEM, and the "**" symbol indicates a statistically significant difference between the data over which it is placed and the data for WT rats treated with vehicle (buffer) (p<0.01).

Figure 46A:
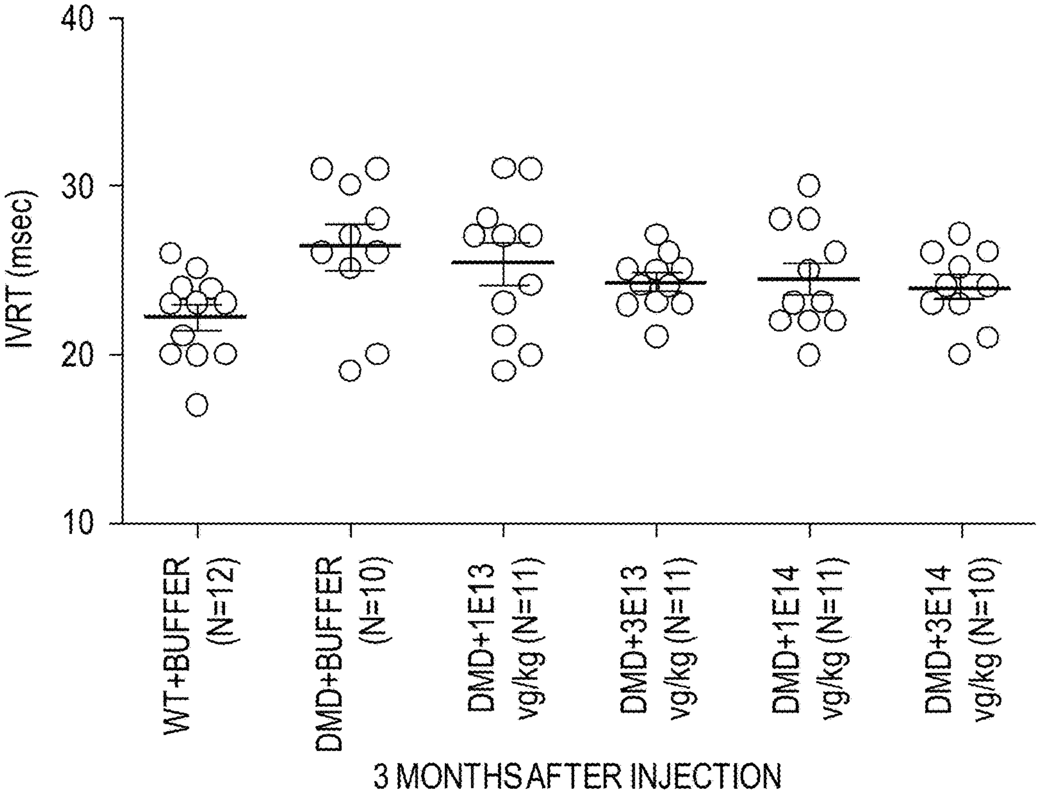

FIG. 46A provides isovolumetric relaxation time measured using pulsed Doppler with an apical four-chamber orientation 3 months post-injection in WT and Dmd$^{mdx}$ rats administered vehicle or AAV9.hCK.Hopti-Dys3978.spA vector. Descriptive statistics shown are mean±SEM.

Figure 46B:
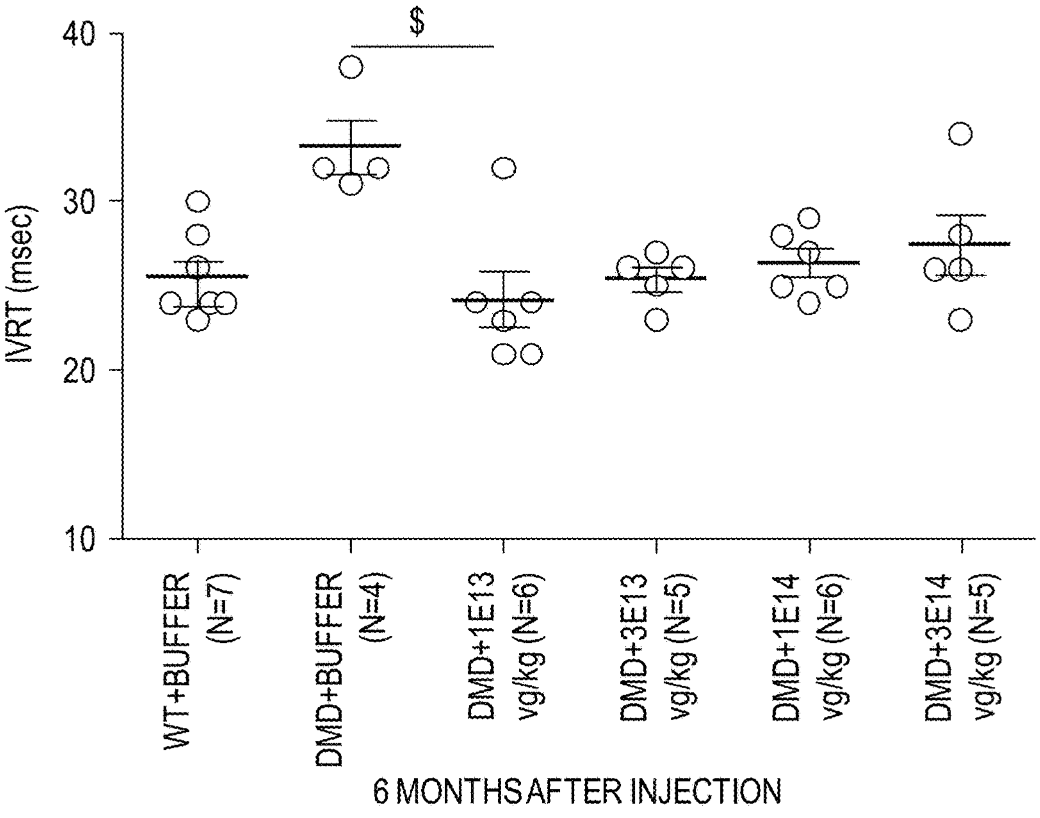

FIG. 46B provides isovolumetric relaxation time measured using pulsed Doppler with an apical four-chamber orientation 6 months post-injection in WT and Dmd$^{mdx}$ rats administered vehicle or AAV9.hCK.Hopti-Dys3978.spA vector. Descriptive statistics shown are mean±SEM, and the "$" symbol indicates a statistically significant difference between the data over which it is placed and the data for Dmd$^{mdx}$ rats treated with vehicle (buffer) (p<0.05).

Figure 47:
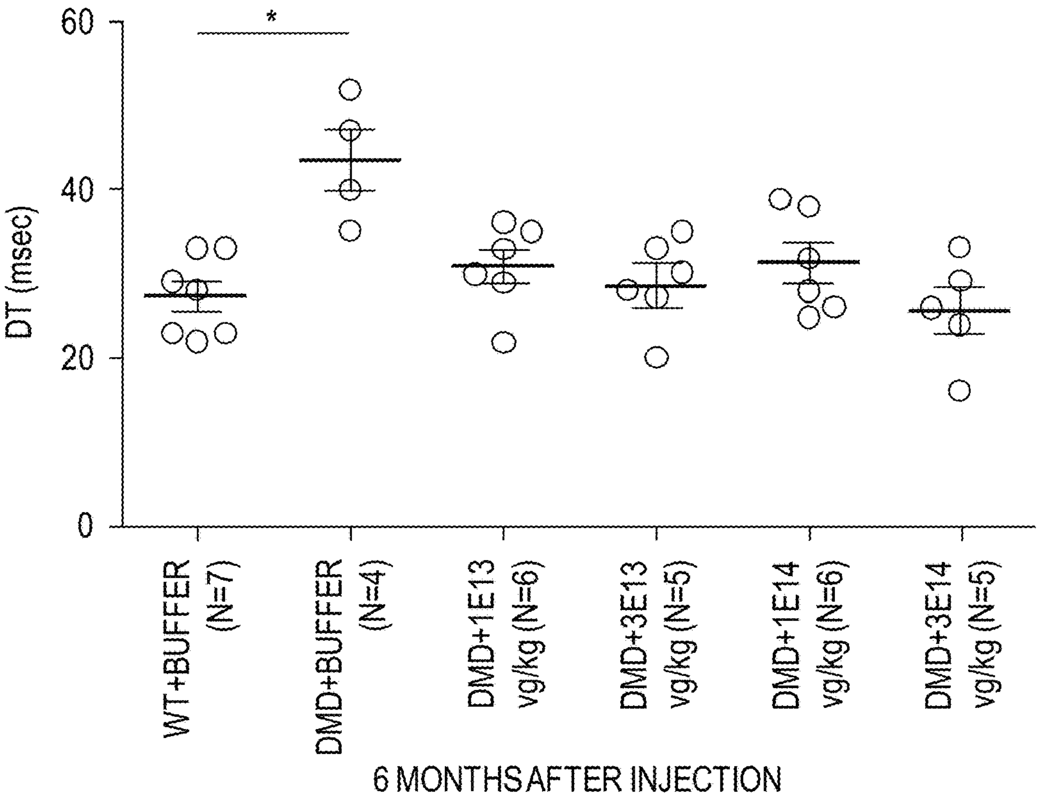

FIG. 47 provides deceleration time measured using pulsed Doppler with an apical four-chamber orientation 6 months post-injection in WT and Dmd$^{mdx}$ rats administered vehicle or AAV9.hCK.Hopti-Dys3978.spA vector. Descriptive statistics shown are mean±SEM, and the "*" symbol indicates a statistically significant difference between the data over which it is placed and the data for WT rats treated with vehicle (buffer) (p<0.05).

Figure 48A:
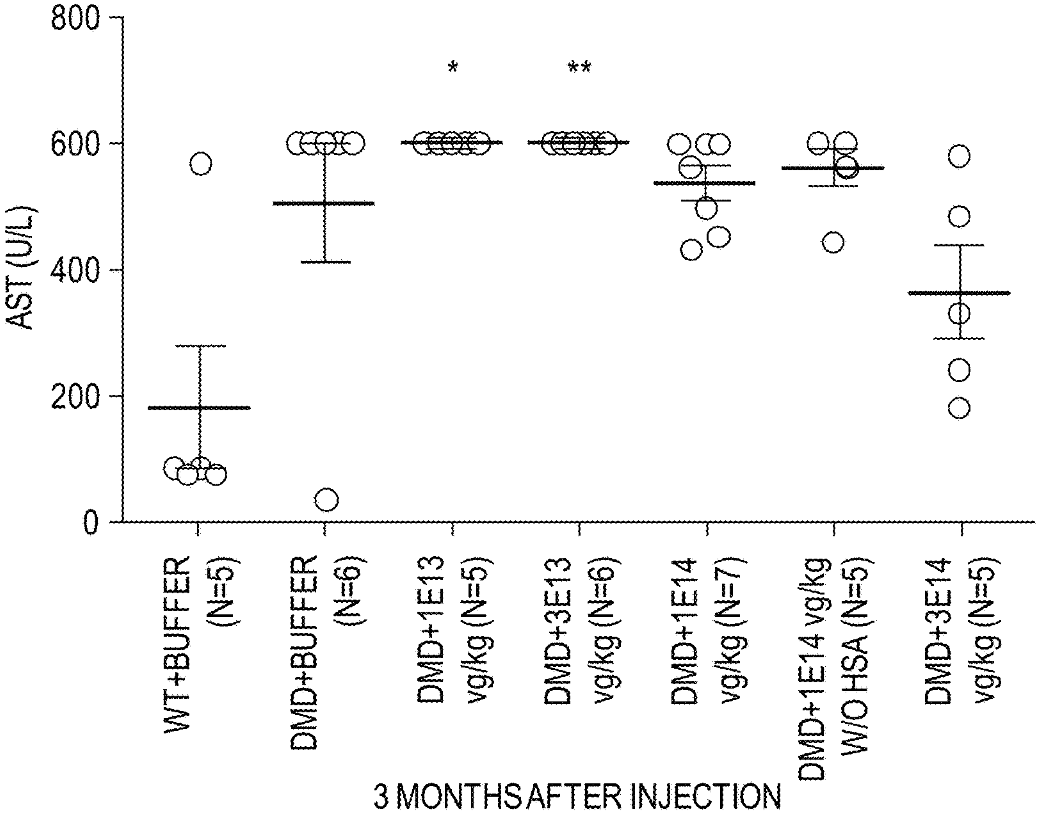

FIG. 48A shows effect in Dmd$^{mdx}$ rats of increasing doses of AAV9.hCK.Hopti-Dys3978.spA vector on blood AST levels 3 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) as a negative control (**p<0.01, *p<0.05).

Figure 48B:
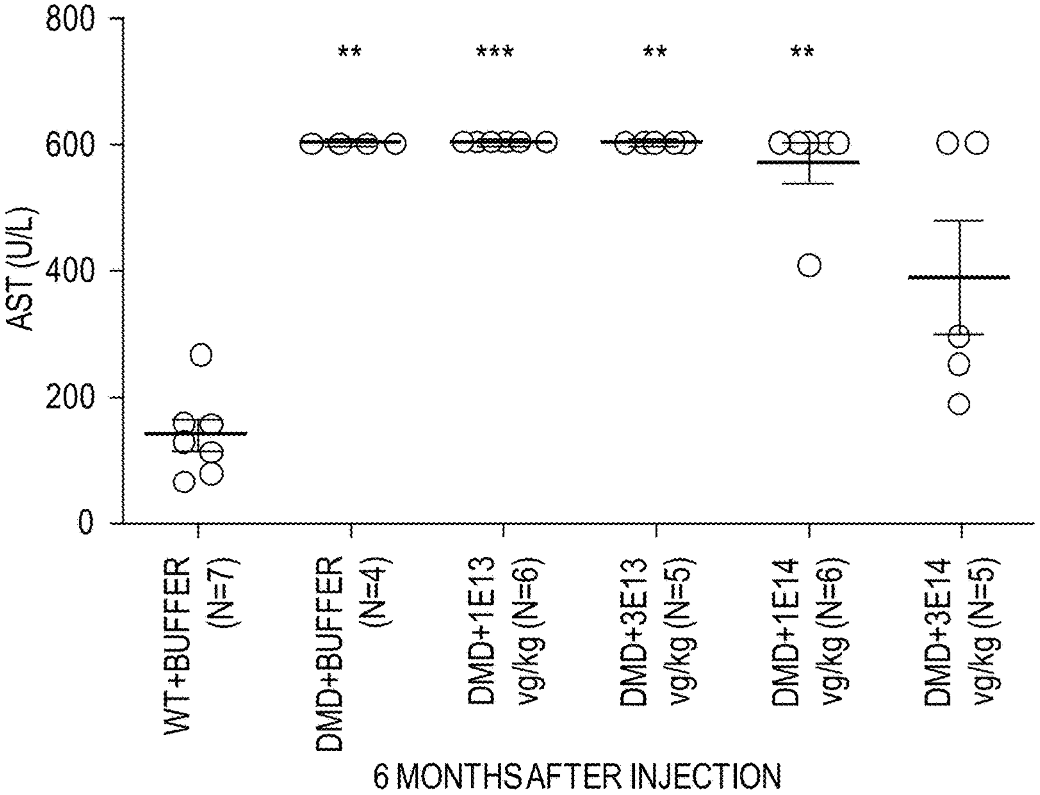

FIG. 48B shows effect in Dmd$^{mdx}$ rats of different doses of AAV9.hCK.Hopti-Dys3978.spA vector on blood AST levels 6 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) as a negative control (*p<0.001, p<0.01).

Figure 49A:
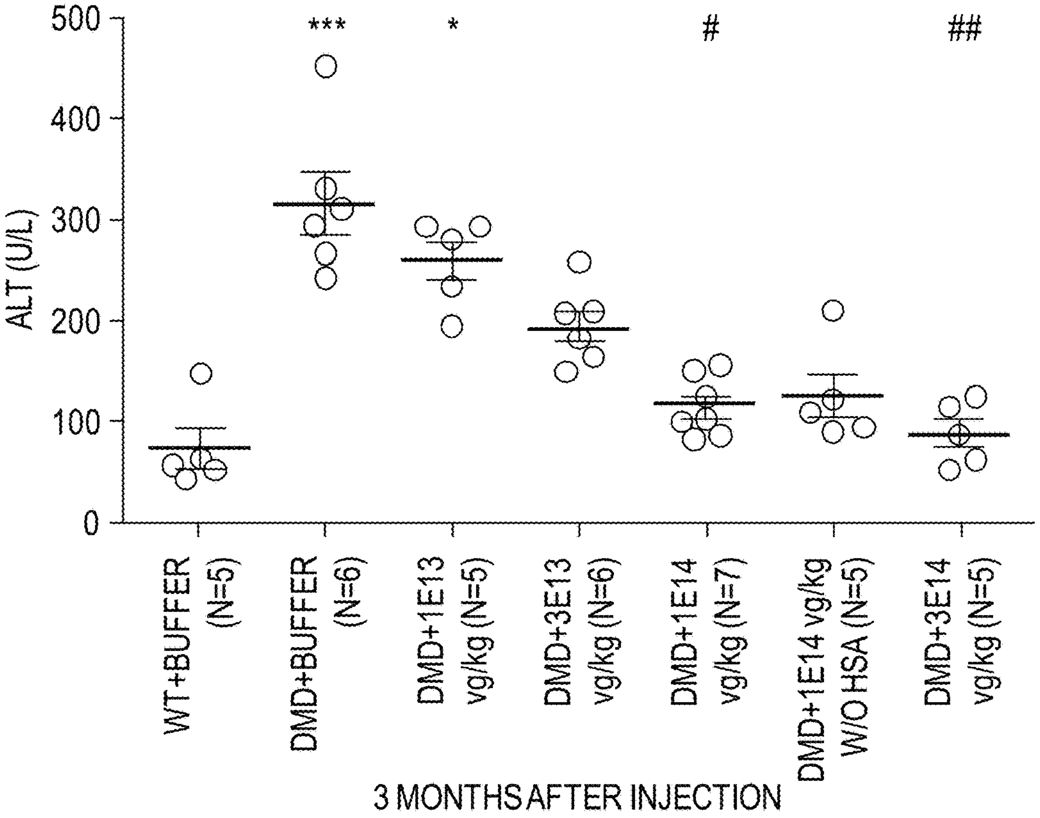

FIG. 49A shows effect in Dmd$^{mdx}$ rats of different doses of AAV9.hCK.Hopti-Dys3978.spA vector on blood ALT levels 3 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) (***p<0.001, *p<0.05), or against Dmd$^{mdx}$ rats that received buffer (##p<0.01, #p<0.05), as negative controls.

Figure 49B:
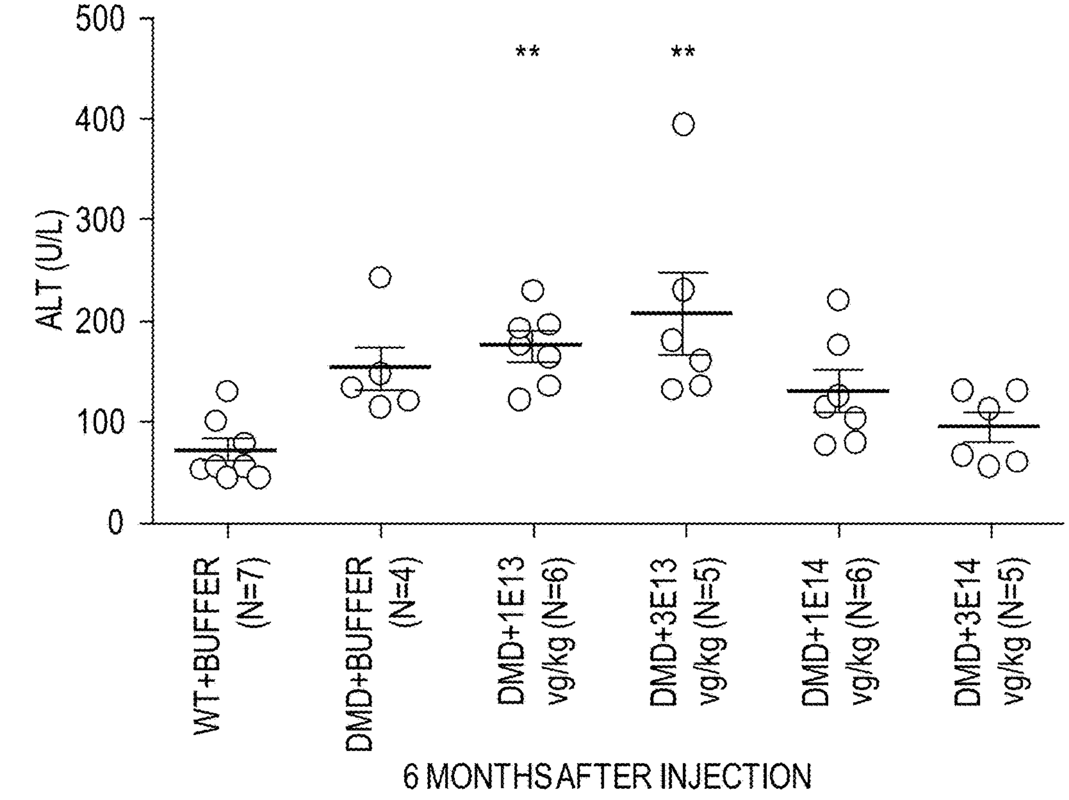

FIG. 49B shows effect in Dmd$^{mdx}$ rats of different doses of AAV9.hCK.Hopti-Dys3978.spA vector on blood ALT levels 6 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) as a negative control (**p<0.01).

Figure 50A:
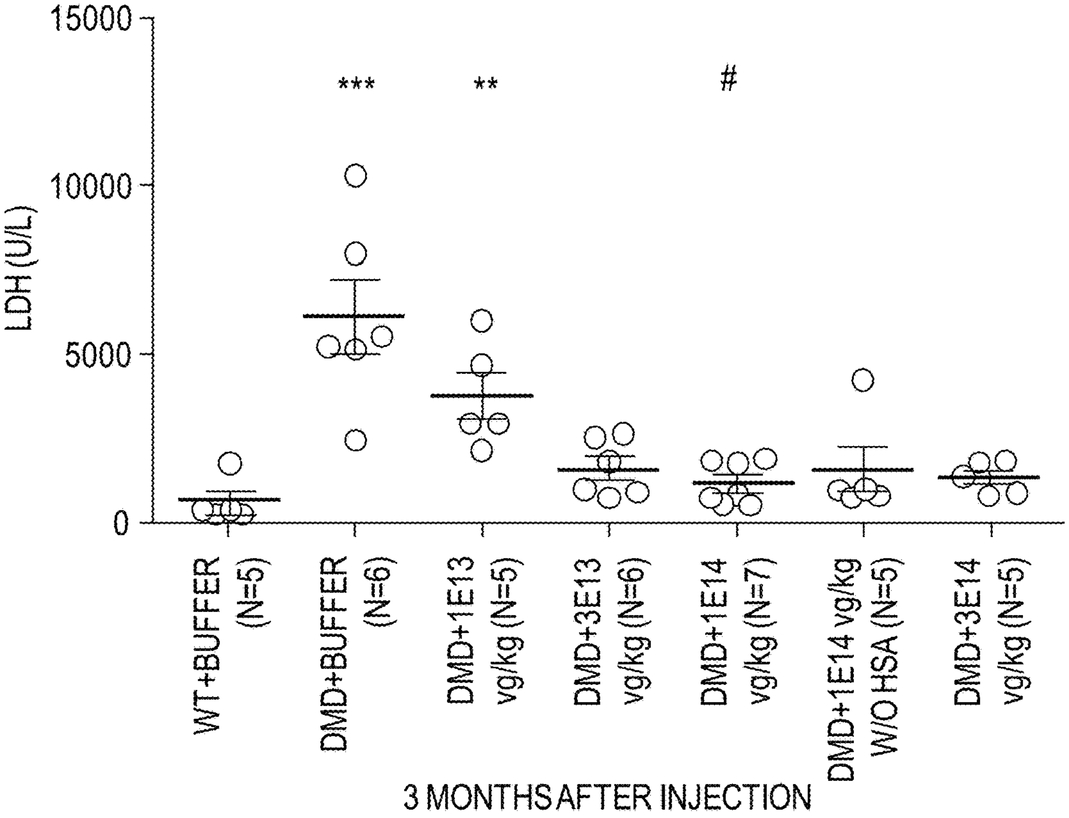

FIG. 50A shows effect in Dmd$^{mdx}$ rats of different doses of AAV9.hCK.Hopti-Dys3978.spA vector on blood LDH levels 3 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) (*p<0.001, p<0.01), or against Dmd$^{mdx}$ rats that received buffer (#p<0.05), as negative controls.

Figure 50B:
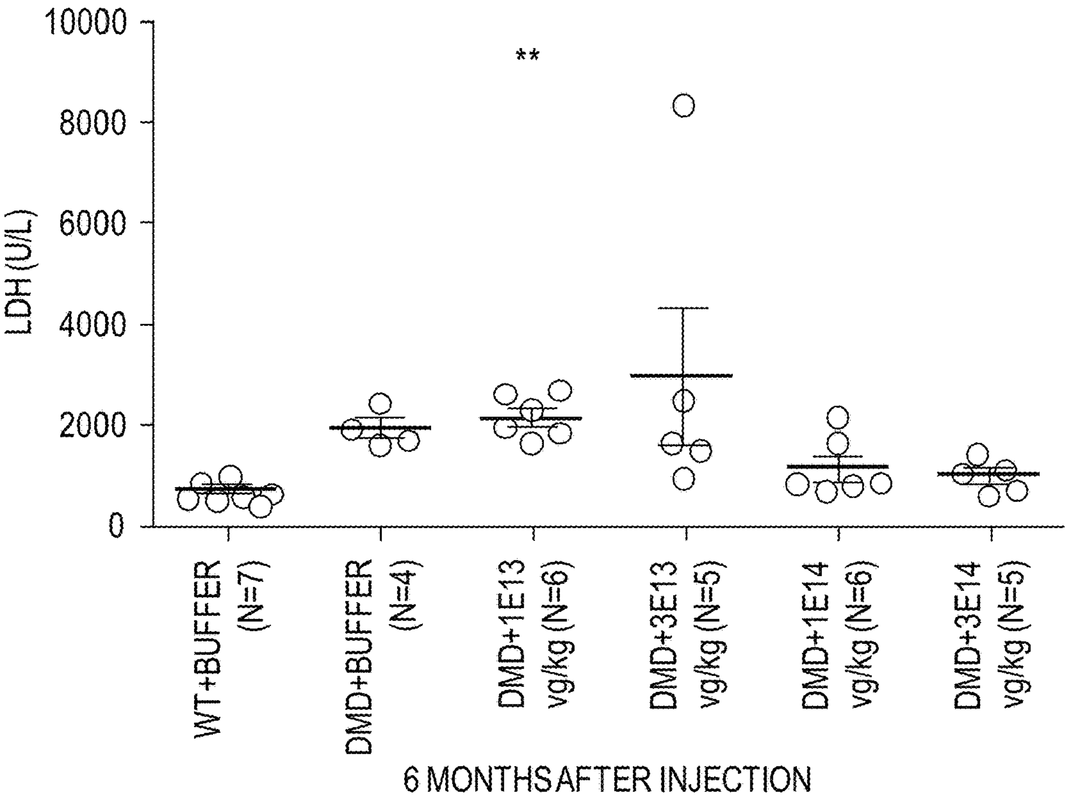

FIG. 50B shows effect in Dmd$^{mdx}$ rats of different doses of AAV9.hCK.Hopti-Dys3978.spA vector on blood LDH levels 6 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) as a negative control (**p<0.01).

Figure 51A:
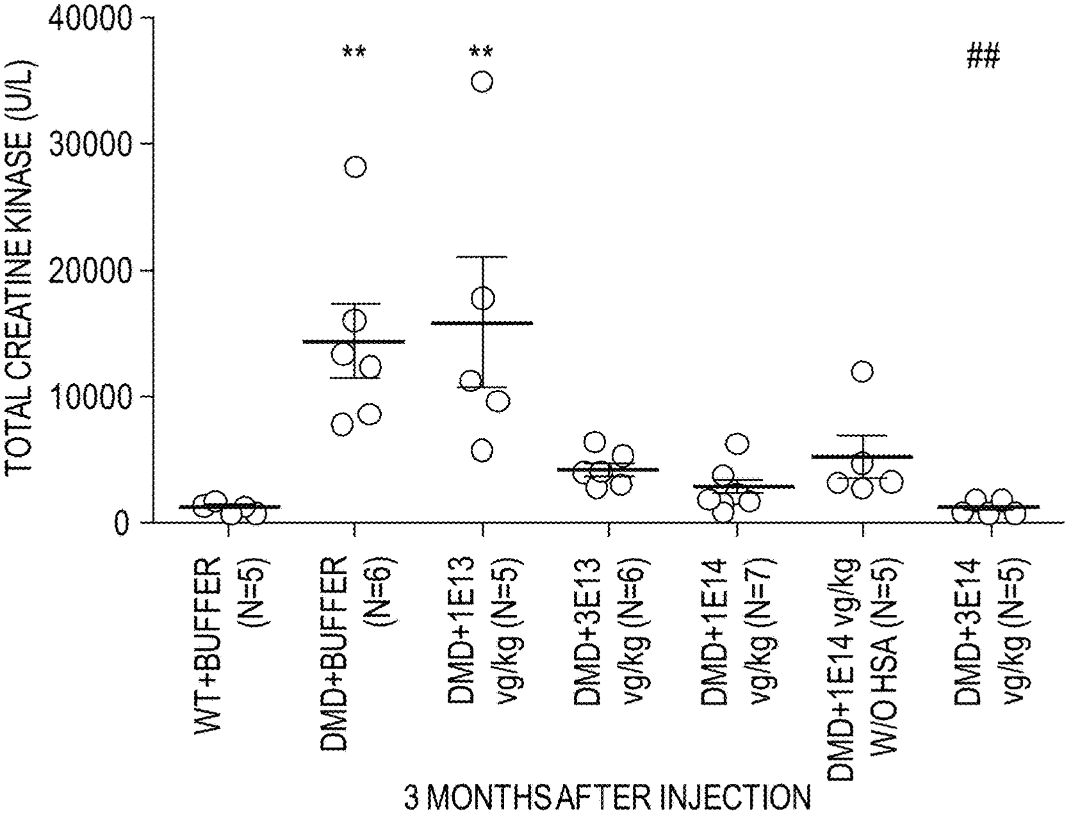

FIG. 51A shows effect in $Dmd^{mdx}$ rats of different doses of AAV9.hCK.Hopti-Dys3978.spA vector on blood total creatine kinase (CK) levels 3 months post-injection. Results are represented as mean±SEM. Statistical analyses were performed using the non-parametric Kruskal Wallis test and a post-hoc Dunn's multiple comparison test. Statistics compare $Dmd^{mdx}$ rats treated with vector against WT rats that received buffer (vehicle) (**p<0.01), or compare $Dmd^{mdx}$ rats dosed with $3\times10^{14}$ vg/kg vector against $Dmd^{mdx}$ rats that received buffer or $1\times10^{13}$ vg/kg vector (##p<0.01).

Figure 51B:
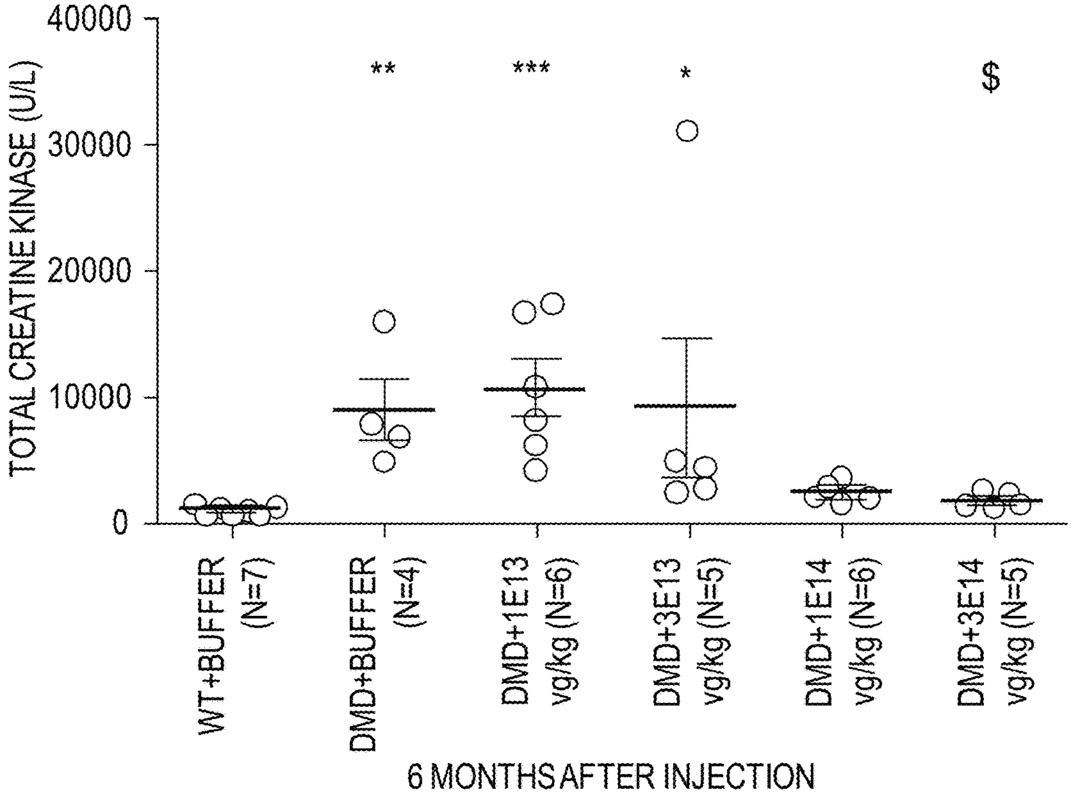

FIG. 51B shows effect in $Dmd^{mdx}$ rats of different doses of AAV9.hCK.Hopti-Dys3978.spA vector on blood total creatine kinase (CK) levels 6 months post-injection. Results are represented as mean±SEM. Statistical analyses were performed using the non-parametric Kruskal Wallis test and a post-hoc Dunn's multiple comparison test. Statistics compare $Dmd^{mdx}$ rats treated with vector against WT rats that received buffer (vehicle) as a negative control (*p<0.001, p<0.01, *p<0.05), or compare $Dmd^{mdx}$ rats dosed with $3\times10^{14}$ vg/kg vector against $Dmd^{mdx}$ rats that received $1\times10^{13}$ vg/kg vector ($p<0.05).

Figure 52A:
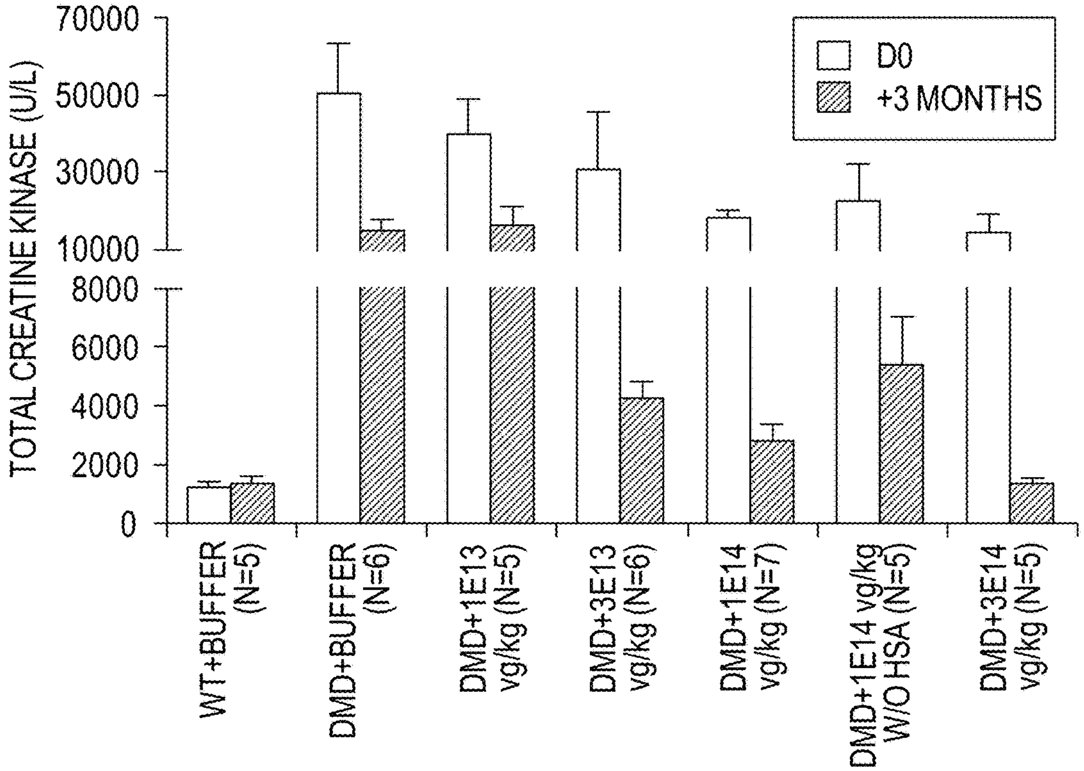

FIG. 52A provides total creatine kinase (CK) evolution between day of injection (D0) of vehicle of vector and sacrifice 3 months post-injection. Solid bars indicate data from D0, whereas hatched bars indicate data at 3 months. Results are represented as mean±SEM.

Figure 52B:
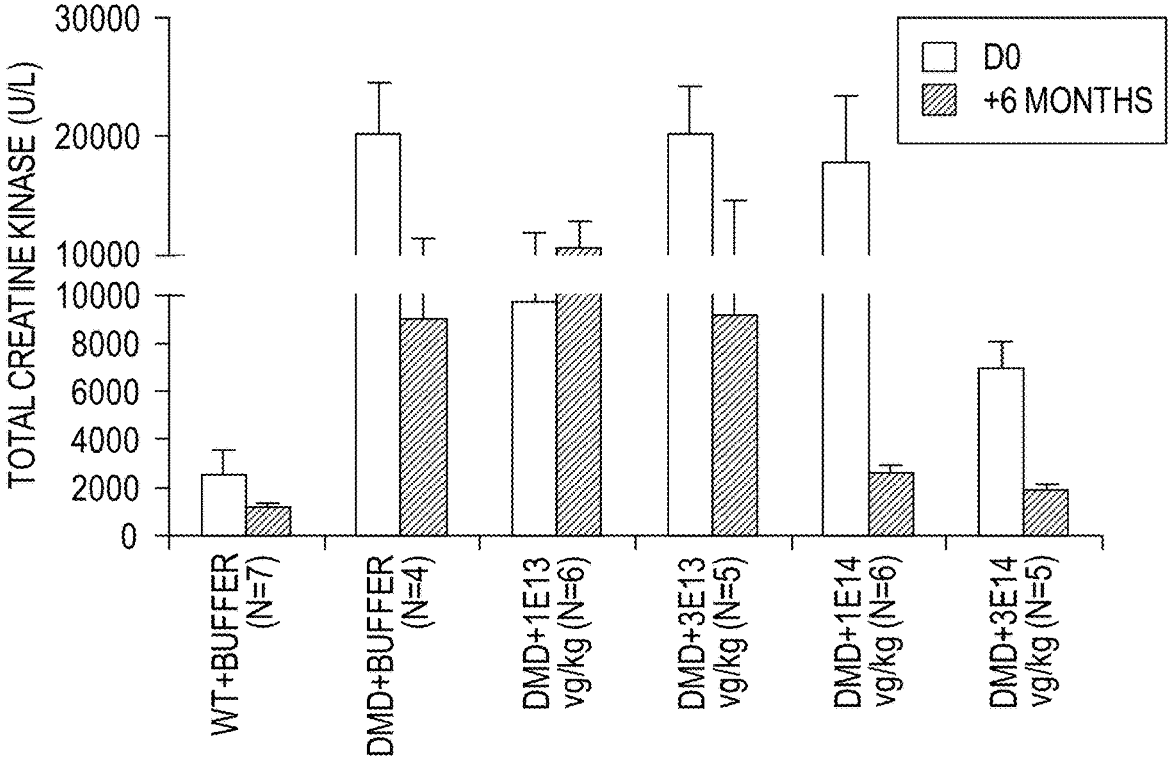

FIG. 52B provides total creatine kinase (CK) evolution between day of injection (D0) of vehicle of vector and sacrifice 6 months post-injection. Solid bars indicate data from D0, whereas hatched bars indicate data at 6 months. Results are represented as mean±SEM.

Figure 53A:
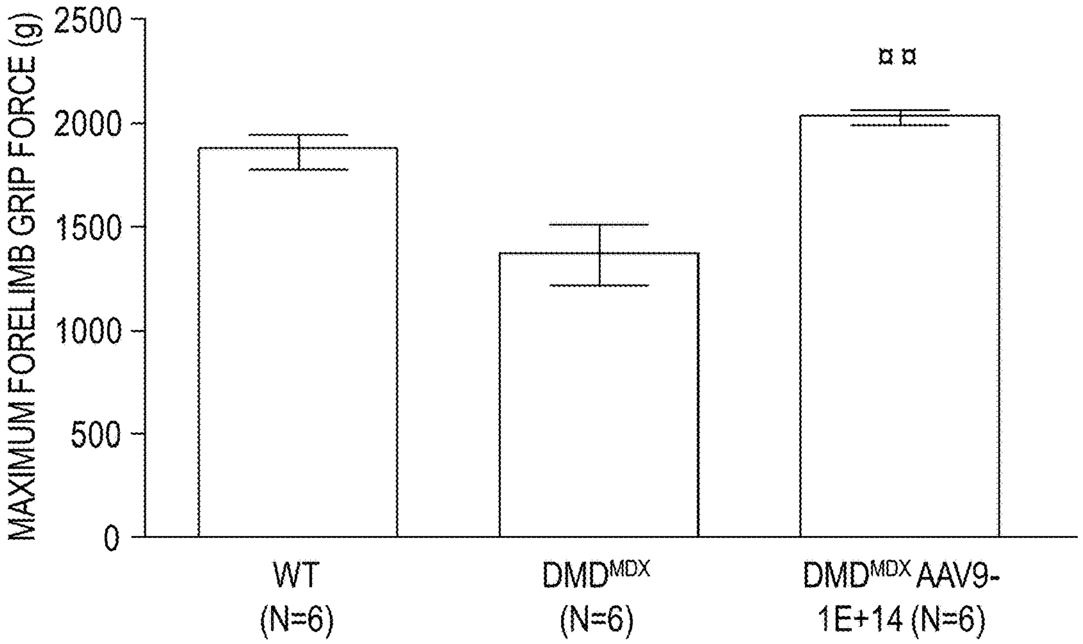

FIG. 53A provides average absolute maximum forelimb grip strength of older $Dmd^{mdx}$ rats treated with $1\times10^{14}$ vg/kg AAV9.hCK.Hopti-Dys3978.spA vector compared to $Dmd^{mdx}$ and WT rats treated with vehicle. Tests were conducted 3 months post-injection in rats injected at 4 months of age, or when the rats were approximately 7 months old. Results are represented as mean±SEM. Statistics compare $Dmd^{mdx}$ rats treated with vector against $Dmd^{mdx}$ rats treated with vehicle (*p<0.01).

Figure 53B:
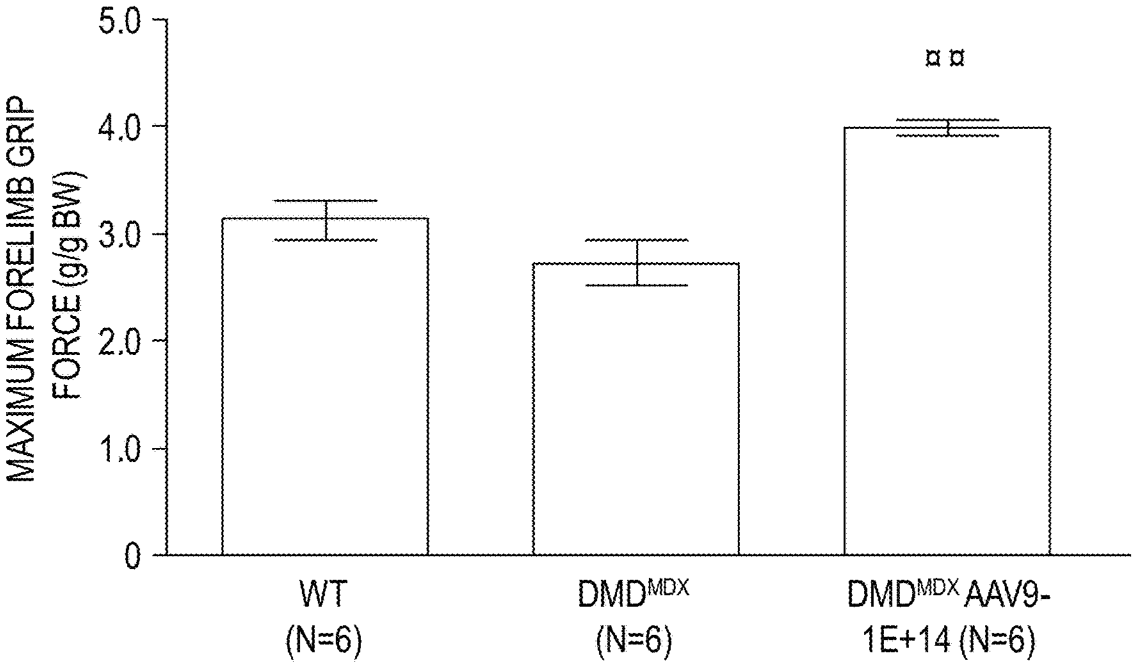

FIG. 53B provides average maximum forelimb grip strength relative to body weight of older $Dmd^{mdx}$ rats treated with $1\times10^{14}$ vg/kg AAV9.hCK.Hopti-Dys3978.spA vector compared to $Dmd^{mdx}$ and WT rats treated with vehicle. Tests were conducted 3 months post-injection in rats injected at 4 months of age, or when the rats were approximately 7 months old. Results are represented as mean±SEM. Statistics compare $Dmd^{mdx}$ rats treated with vector against $Dmd^{mdx}$ rats treated with vehicle (*p<0.01).

Figure 53C:
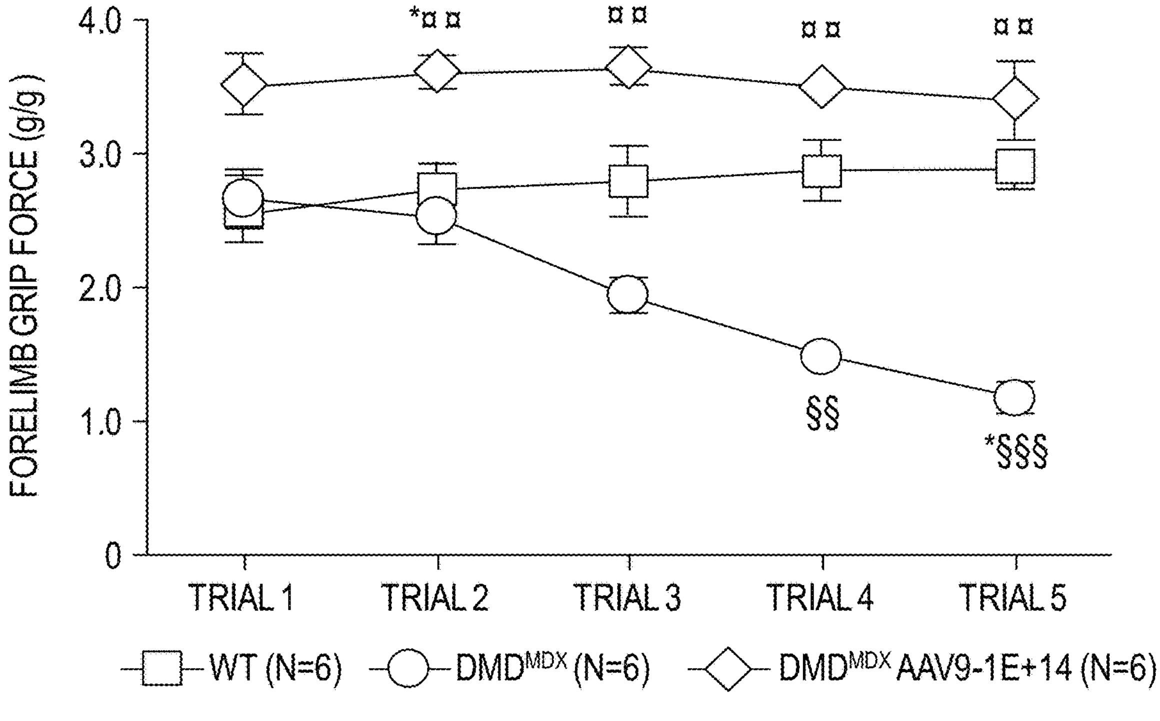

FIG. 53C shows evolution of forelimb grip force as a measure of muscle fatigue in older $Dmd^{mdx}$ rats treated with $1\times10^{14}$ vg/kg AAV9.hCK.Hopti-Dys3978.spA vector compared to $Dmd^{mdx}$ and WT rats treated with vehicle. Test was conducted by measuring average maximum grip force 5 times with short intervals between each trial. Tests were conducted 3 months post-injection in rats injected at 4 months of age, or when the rats were approximately 7 months old. Results are provided relative to body weight and as the mean±SEM. Statistics compare $Dmd^{mdx}$ rats treated with vector against WT rats receiving vehicle (*p<0.05) and $Dmd^{mdx}$ rats receiving vehicle (¤ ¤ p<0.01), and compare later trials against trial 1 in vehicle treated $Dmd^{mdx}$ rats (§§ p<0.01, §§§ p<0.001).

Figure 54A:
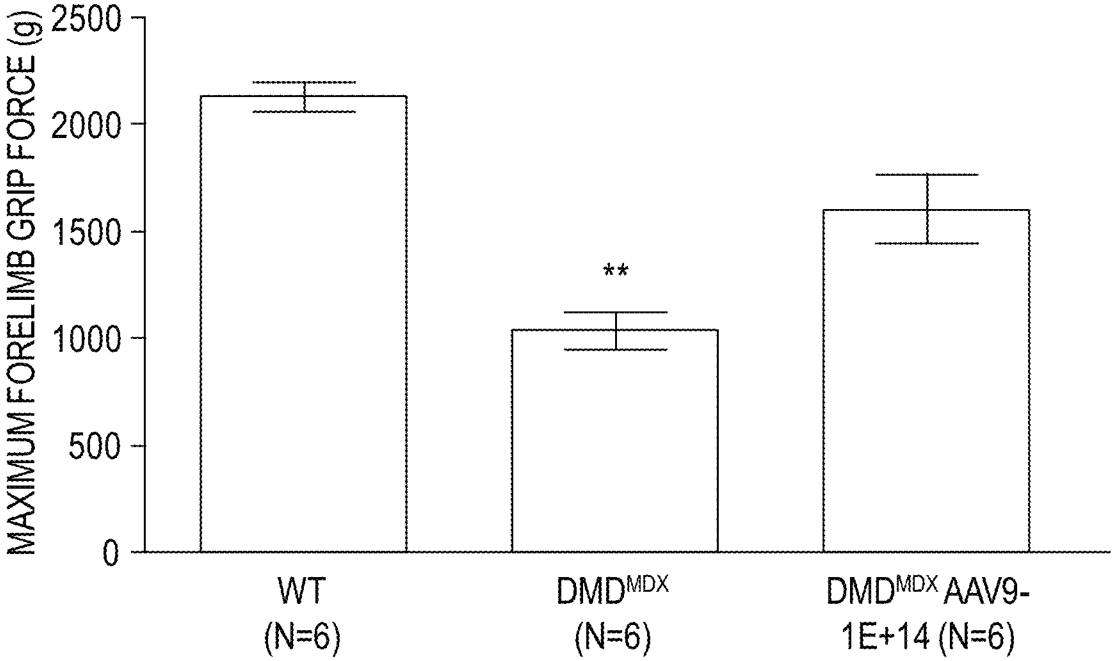

FIG. 54A provides average absolute maximum forelimb grip strength of older $Dmd^{mdx}$ rats treated with $1\times10^{14}$ vg/kg AAV9.hCK.Hopti-Dys3978.spA vector compared to $Dmd^{mdx}$ and WT rats treated with vehicle. Tests were conducted 3 months post-injection in rats injected at 6 months of age, or when the rats were approximately 9 months old. Results are represented as mean±SEM. Statistics compare $Dmd^{mdx}$ rats treated with vehicle against WT rats treated with vehicle (**p<0.01).

Figure 54B:
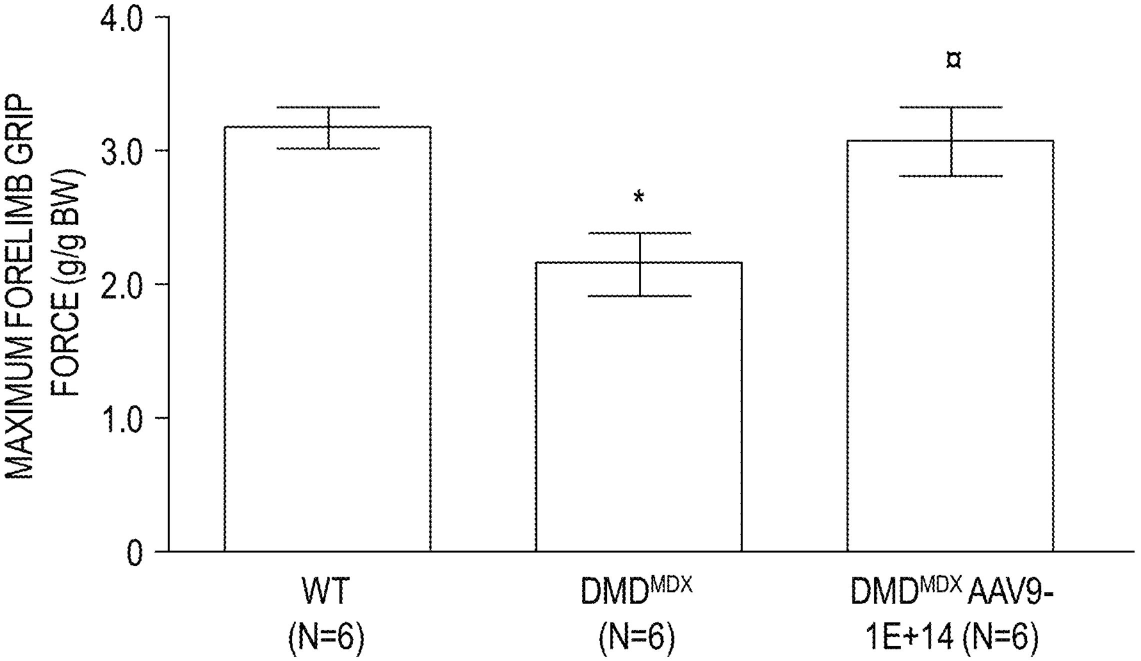

FIG. 54B provides average maximum forelimb grip strength relative to body weight of older $Dmd^{mdx}$ rats treated with $1\times10^{14}$ vg/kg AAV9.hCK.Hopti-Dys3978.spA vector compared to $Dmd^{mdx}$ and WT rats treated with vehicle. Tests were conducted 3 months post-injection in rats injected at 6 months of age, or when the rats were approximately 9 months old. Results are represented as mean±SEM. Statistics compare $Dmd^{mdx}$ rats treated with vehicle against WT rats treated with vehicle (*p<0.05) or $Dmd^{mdx}$ rats treated with vector against $Dmd^{mdx}$ rats treated with vehicle (¤ p<0.05).

Figure 54C:
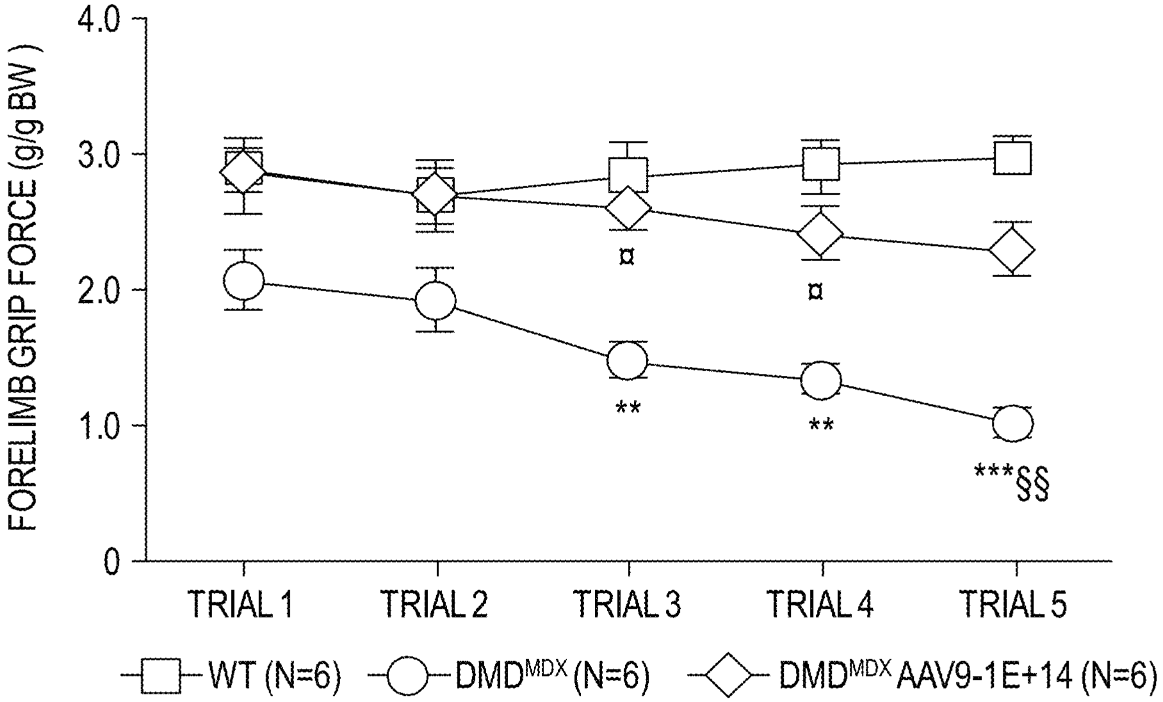

FIG. 54C shows evolution of forelimb grip force as a measure of muscle fatigue in older $Dmd^{mdx}$ rats treated with $1\times10^{14}$ vg/kg AAV9.hCK.Hopti-Dys3978.spA vector compared to $Dmd^{mdx}$ and WT rats treated with vehicle. Test was conducted by measuring average maximum grip force 5 times with short intervals between each trial. Tests were conducted 3 months post-injection in rats injected at 6 months of age, or when the rats were approximately 9 months old. Results are provided relative to body weight and as the mean±SEM. Statistics compare $Dmd^{mdx}$ rats treated with vector against $Dmd^{mdx}$ rats receiving vehicle (¤ p<0.05), $Dmd^{mdx}$ rats treated with vehicle against WT rats receiving vehicle (p<0.01, *p<0.001), and trial 5 against trial 1 in vehicle treated $Dmd^{mdx}$ rats (§§ p<0.01).

FIGS. 55A-55C provide an alignment between the amino acid sequences of the mini-dystrophin protein Δ3990 (SEQ ID NO:27) and the mini-dystrophin protein Dys3978 (SEQ ID NO:7).

FIGS. 56A-56I provide an alignment between the nucleic acid sequence encoding mini-dystrophin Δ3990 (SEQ ID NO:28), which is derived from the wildtype nucleic acid sequence encoding human dystrophin protein, and the human codon-optimized nucleic acid sequence encoding mini-dystrophin Dys3978 (called Hopti-Dys3978; SEQ ID NO:1).

DETAILED DESCRIPTION OF THE INVENTION

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *PatentIn User Manual,* 99-102 (November 1990) (U.S. Patent and Trademark Office).

Except as otherwise indicated, standard methods known to those skilled in the art may be used for the construction of recombinant parvovirus and AAV (rAAV) constructs, packaging vectors expressing the parvovirus Rep and/or Cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, N Y, 1989); AUSUBEL et al., CURRENT PROTOCOLS IN MOLECULAR BIOLOGY (Green Publishing Associates, Inc. and John Wiley & Sons, Inc., New York).

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

Definitions

The following terms are used in the description herein and the appended claims.

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the term "adeno-associated virus" (AAV), includes but is not limited to, AAV type 1 (AAV1), AAV type 2 (AAV2), AAV type 3 (AAV3, including types 3A and 3B), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10), AAV type 11 (AAV 11), AAV type 12 (AAV12), AAV type 13 (AAV13), Avian AAV ATCC VR-865, Avian AAV strain DA-1, Bb1, Bb2, Ch5, Cy2, Cy3, Cy4, Cy5, Cy6, Hu1, Hu10, Hu11, Hu13, Hu15, Hu16, Hu17, Hu18, Hu19, Hu2, Hu20, Hu21, Hu22, Hu23, Hu24, Hu25, Hu26, Hu27, Hu28, Hu29, Hu3, Hu31, Hu32, Hu34, Hu35, Hu37, Hu39, Hu4, Hu40, Hu41, Hu42, Hu43, Hu44, Hu45, Hu46, Hu47, Hu48, Hu49, Hu51, Hu52, Hu53, Hu54, Hu55, Hu56, Hu57, Hu58, Hu6, Hu60, Hu61, Hu63, Hu64, Hu66, Hu67, Hu7, Hu9, HuLG15, HuS17, HuT17, HuT32, HuT40, HuT41, HuT70, HuT71, HuT88, Pi1, Pi2, Pi3, Rh1, Rh10, Rh13, Rh2, Rh25, Rh32, Rh33, Rh34, Rh35, Rh36, Rh37, Rh38, Rh40, Rh43, Rh48, Rh49, Rh50, Rh51, Rh52, Rh53, Rh54, Rh55, Rh57, Rh58, Rh61, Rh62, Rh64, Rh74, Rh8, snake AAV, avian AAV, bovine AAV, canine AAV, equine AAV, ovine AAV, goat AAV, shrimp AAV, AAV1.1, AAV2.5, AAV6.1, AAV6.3.1, AAV9.45, RHM4-1 (SEQ ID NO:5 of WO 2015/013313), AAV2-TT, AAV2-TT-S312N, AAV3B-S312N, AAV-LK03, and any other AAV now known or later discovered. see, e.g., Fields et al., VIROLOGY, volume 2, chapter 69 (4th ed., Lippincott-Raven Publishers). Capsids may be derived from a number of AAV serotypes disclosed in U.S. Pat. No. 7,906,111; Gao et al., 2004, J. Virol. 78:6381; Moris et al., 2004, Virol. 33:375; WO 2013/063379; WO 2014/194132; and include true type AAV (AAV-TT) variants disclosed in WO 2015/121501, and RHM4-1, RHM15-1 through RHM15-6, and variants thereof, disclosed in WO 2015/013313, and one skilled in the art would know there are likely other variants not yet identified that perform the same or similar function, or may include components from two or more AAV capsids. A full complement of AAV cap proteins includes VP1, VP2, and VP3. The open reading frame comprising nucleotide sequences encoding AAV capsid proteins may comprise less than a full complement AAV cap proteins or the full complement of AAV cap proteins may be provided.

and any other AAV now known or later discovered. See, e.g., FIELDS et al., VIROLOGY, volume 2, chapter 69 (4th ed., Lippincott-Raven Publishers). A number of relatively new AAV serotypes and clades have been identified (See, e.g., Gao et al., (2004) J. Virol. 78:6381; Moris et al., (2004) Virol. 33-:375).

AAV is a small non-enveloped virus with an icosahedral capsid about 20-30 nm in diameter. AAV are not able to replicate without the contribution of so-called helper proteins from other viruses (e.g., adenovirus, herpes simplex virus, vaccinia virus and human papillomavirus), and so were placed into a special genus, called dependovirus (because they depend on other viruses for replication) within the family of parvoviridae. Although many different serotypes of AAV have been discovered, and many humans produce antibodies against one or more AAV serotypes (suggesting widespread history of AAV infection), no diseases are known to be caused by AAV suggesting AAV is non-pathogenic in humans.

Although many different AAV serotypes have been discovered, one of the best characterized is AAV2, and the following discussion of AAV biology focuses on some of what has been learned regarding AAV2. The life cycle of other AAV serotypes is believed to be similar, although the details may differ. The particular details by which AAV2 or any other AAV serotype infect and replicate inside cells are provided merely to aid in the understanding of the inventions disclosed herein, and are not intended to limit their scope in any way. Even if some of this information is later found to be incorrect or incomplete, it should not be construed as detracting from the utility or enablement of the inventions disclosed and claimed herein. Further information about AAV lifecycle can be found in M. Goncalves, Virol J 2:43 (2005), M D Weitzman and R M Linden, Adeno-Associated Virus Biology, Ch. 1, pp. 1-23, Adeno-Associated Virus Methods and Protocols, Ed. R O Snyder and P Moullier, Humana Press (2011), GE Berry and A Asokan, Curr Opin Virol 21:54-60 (2016), and references cited therein.

The wild type genome of AAV2 is linear DNA approximately 4.7 kilobases in length. Although mostly single-stranded, the 5' and 3' ends of the genome consist of so-called inverted terminal repeats (ITR), each 145 base-pairs long and containing palindromic sequences that self-anneal through classic Watson-Crick base-pairing to form T-shaped hairpin structures. One of these structures contains a free 3' hydroxyl group that, relying on cellular DNA polymerases, permits initiation of viral DNA replication through a self-priming strand-displacement mechanism. See, for example, M. Goncalves, Adeno-associated virus: from defective virus to effective vector, Virology J 2:43 (2005). Due to the mechanism by which the single-stranded viral genomes are replicated and then packaged into capsids in infected cells, plus (sense or coding) and minus (antisense or non-coding) strands are packaged with equal efficiency into separate particles.

In addition to the flanking ITRs, the wild type AAV2 genome contains two genes, rep and cap, that code respectively for four replication proteins (Rep 78, Rep 68, Rep 52, and Rep 40) and three capsid proteins (VP1, VP2, and VP3) through efficient use of alternative promoters and splicing. The large replication proteins, Rep 78 and 68, are multifunctional and play a role in AAV transcription, viral DNA replication, and site-specific integration of the viral genome into human chromosome 19. The smaller Rep proteins have been implicated in packing the viral genome into the viral capsids in infected cell nuclei. The three capsid proteins are produced through a combination of alternative splicing and use of alternative translational start sites, so that all three proteins share sequence towards their carboxy-termini, but VP2 includes additional amino-terminal sequence absent from VP3, and VP1 includes additional amino-terminal sequence absent from both VP2 and VP3. It is estimated that capsids contain a total of 60 capsid proteins in an approximate VP1:VP2:VP3 stoichiometry of 1:1:10, although these ratios can apparently vary.

Despite its relatively small size, and therefore capacity to carry heterologous genes, AAV has been identified as a leading viral vector for gene therapy. Advantages of using AAV compared to other viruses that have been proposed as gene therapy vectors include the ability of AAV to support long term gene expression in transduced cells, to transduce both dividing and nondividing cells, to transduce a wide variety of different types of cells depending on serotype, the inability to replicate without a helper virus, and an apparent lack of pathogenicity associated with wild type infections.

Because of their small size, AAV capsids can physically accommodate a single stranded DNA genome that is at most about 4.7-5.0 kilobases in length. Without modifying the genome, there would not be enough room to include a heterologous gene, such as coding sequence for a therapeutic protein, and gene regulatory elements, such as a promoter and optionally an enhancer. To create more room, the rep and cap genes can be removed and replaced with desired heterologous sequences, as long as the flanking ITRs are retained. The functions of the rep and cap genes can be provided in trans on a different piece of DNA. By contrast, the ITRs are the only AAV viral elements that must remain in cis with the heterologous sequence. Combining the ITRs with a heterologous gene and removing the rep and cap genes to a different plasmid lacking ITRs also prevents production of infectious wild type AAV at the same time that AAV vector for gene therapy is being produced. Removing rep and cap also means that AAV vectors for gene therapy cannot replicate in the cells they transduce.

In some embodiments, the genome of AAV vectors is linear single-stranded DNA flanked by AAV ITRs. Before it can support transcription and translation of the heterologous gene, the single stranded DNA genome must be converted to double-stranded form by cellular DNA polymerases that utilize the free 3'-OH of one of the self-priming ITRs to initiate second-strand synthesis. In alternative embodiments, full length-single stranded genomes of opposite polarity can anneal to generate a full length double-stranded genome, and can result when a plurality of AAV vectors carrying genomes of opposite polarity simultaneously transduce the same cell. After double-stranded vector genomes form, by whatever mechanism, the cellular gene transcription machinery can act on the double-stranded DNA to express the heterologous gene.

In other embodiments, the vector genome can be designed to be self-complementary (scAAV), having a wild type ITR at each end and a mutated ITR in the middle. See, for example, McCarty, D M, et al., Adeno-associated virus terminal repeat (TR) mutant generates self-complementary vectors to overcome the rate-limiting step to transduction in vivo. Gene Ther. 10:2112-18 (2003). It has been proposed that after entering a cell, self-complementary AAV genomes can self-anneal starting with the ITR in the middle to form a double-stranded genome without need for de novo DNA replication. This approach was shown to result in more efficient transduction and faster expression of heterologous gene, but reduces the size of the heterologous gene that may be used by about half.

Different strategies for producing AAV vectors for gene therapy have been developed, but one of the most common is the triple transfection technique, in which three different plasmids are transfected into producer cells. See, for example, N. Clement and J. Grieger, Mol Ther Methds Clin Dev, 3:16002 (2016), Grieger, J C, et al., Mol Ther 24(2): 287-97 (2016), and the references cited therein. In this technique, a plasmid is created that includes the sequence of the vector genome including, for example a heterologous promoter and optionally an enhancer, and a heterologous gene to express a desired RNA or protein, flanked by the left and right ITRs. The vector plasmid would be co-transfected into producer cells, such as HEK293 cells, with a second plasmid containing the rep and cap genes, and a third plasmid containing adenovirus (or other virus) helper genes required to replicate and package the vector genome into AAV capsids. In alternative embodiments of the technique, rep, cap and adenovirus helper genes all reside on the same plasmid, and two plasmids are co-transfected into producer cells. Examples of adenovirus helper genes include E1a, E1b, E2a, E4orf6, and VA RNA genes. For many AAV serotypes, the AAV2 ITRs can be substituted for native ITRs without significantly impairing the ability of the vector genome to be replicated and packaged into non-AAV2 capsids. This approach, known as pseudo-typing, merely requires using a rep/cap plasmid that contains the rep and cap genes from the other serotype. Thus, for example, an AAV gene therapy vector could use an AAV9 capsid and a vector genome containing AAV2 ITRs flanking a heterologous gene (which can be designated "AAV2/9"), such as a mini-dystrophin. After the AAV particles are produced by the cell, they can be collected and purified using standard techniques known in the art, such as ultracentrifugation in a CsCl gradient, or using chromatography columns of various types.

The parvovirus particles and genomes of the present invention can be from, but are not limited to AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73: 939; Chiorini et al., (1997) *J. Virol.* 71:6823; Chiorini et al., (1999) *J. Virol.* 73:1309; Gao et al., (2002) *Proc. Nat. Acad. Sci. USA* 99:11854; Moris et al., (2004) Virol. 33-:375-383; Mori et al., (2004) *Virol.* 330: 375; Muramatsu et al., (1996) *Virol.* 221:208; Ruffing et al., (1994) *J. Gen. Virol.* 75:3385; Rutledge et al., (1998) *J. Virol.* 72:309; Schmidt et al., (2008) *J. Virol.* 82:8911; Shade et al., (1986) *J. Virol.* 58:921; Srivastava et al., (1983) *J Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. ITR sequences from AAV1, AAV2 and AAV3 are provided by Xiao, X., (1996), "Characterization of Adeno-associated virus (AAV) DNA replication and integration," Ph.D. Dissertation, University of Pittsburgh, Pittsburgh, PA (incorporated herein it its entirety).

As used herein, "transduction" of a cell by AAV refers to AAV-mediated transfer of genetic material into the cell. See, e.g., FIELDS et al., VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide" is a linear sequence of nucleotides in which the 3'-position of each monomeric unit is linked to the 5'-position of the neighboring monomeric unit via a phosphate group. Polynucleotides may be RNA (containing RNA nucleotides only), DNA (containing DNA nucleotides only), RNA and DNA hybrids (containing RNA and DNA nucleotides), as well as other hybrids containing naturally occurring and/or non-naturally occurring nucleotides. The linear order of bases of the nucleotides in a polynucleotide is called the "nucleotide sequence," "nucleic acid sequence," "nucleobase sequence," or sometimes, just "sequence" of the polynucleotide. Typically, the order of bases is provided starting from the 5' end of the polynucleotide and ending at the 3' end of the polynucleotide. As known in the art, polynucleotides can adopt secondary structures, such as regions of self-complementarity. Polynucleotides can also hybridize with fully or partially complementary polynucleotides through classic Watson-Crick base pairing, or other mechanisms familiar to those of ordinary skill.

As used herein, a "gene" is a section of a polynucleotide, typically but not necessarily of DNA, that encodes a polypeptide or protein. In some embodiments, genes can be interrupted by introns. In some embodiments a polynucleotide can encode more than one polypeptide or protein due to mechanisms such as alternative splicing, use of alternate start codons, or other biological mechanisms familiar to those of ordinary skill in the art. The term "open reading frame," abbreviated "ORF," refers to a portion of a polynucleotide that encodes a polypeptide or protein.

The term "codon-optimized," as used herein, refers to a gene coding sequence that has been optimized to increase expression by substituting one or more codons normally present in a coding sequence (for example, in a wildtype sequence, including, e.g., a coding sequence for dystrophin or a mini-dystrophin) with a codon for the same (synonymous) amino acid. In this manner, the protein encoded by the gene is identical, but the underlying nucleobase sequence of the gene or corresponding mRNA is different. In some embodiments, the optimization substitutes one or more rare codons (that is, codons for tRNA that occur relatively infrequently in cells from a particular species) with synonymous codons that occur more frequently to improve the efficiency of translation. For example, in human codon-optimization one or more codons in a coding sequence are replaced by codons that occur more frequently in human cells for the same amino acid. Codon optimization can also increase gene expression through other mechanisms that can improve efficiency of transcription and/or translation. Strategies include, without limitation, increasing total GC content (that is, the percent of guanines and cytosines in the entire coding sequence), decreasing CpG content (that is, the number of CG or GC dinucleotides in the coding sequence), removing cryptic splice donor or acceptor sites, and/or adding or removing ribosomal entry sites, such as Kozak sequences. Desirably, a codon-optimized gene exhibits improved protein expression, for example, the protein encoded thereby is expressed at a detectably greater level in a cell compared with the level of expression of the protein provided by the wildtype gene in an otherwise similar cell.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al.,

*Meth. Enzymol.,* 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

"Substantial homology" or "substantial similarity," means, when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the sequence.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous" or "exogenous" nucleotide or nucleic acid sequence are used interchangeably herein and refer to a nucleic acid sequence that is not naturally occurring in the virus or a cell. In some embodiments, the heterologous nucleic acid comprises an open reading frame that encodes a polypeptide or nontranslated RNA of interest (e.g., for delivery to a cell or subject).

As used herein, the terms "virus vector," "viral vector," "gene delivery vector," or sometimes just "vector," refer to a virion or virus particle that functions as a nucleic acid delivery vehicle and which comprises a vector genome packaged within the virion or virus particle. Vectors can be infectious or non-infectious. Non-infectious vectors cannot replicate themselves without exogenously added factors. Vectors may be AAV particles or virions comprising an AAV capsid within which is packaged an AAV vector genome.

These vectors may also be referred to herein as "recombinant AAV" (abbreviated "rAAV") vectors, particles or virions.

A vector genome is a polynucleotide for packaging within a vector particle or virion for delivery into a cell (which cell may be referred to as a "target cell"). Typically, a vector genome is engineered to contain a heterologous nucleic acid sequence, such as a gene, for delivery into the target cell. A vector genome may also contain one or more nucleic acid sequences that function as regulatory elements to control expression of the heterologous gene in the target cell. A vector genome may also contain wildtype or modified viral nucleic acid sequence(s) required for the production and/or function of the vector, such as, without limitation, replication of the vector genome in a host and packaging into vector particles. In some embodiments, the vector genome is an "AAV vector genome," which is capable of being packaged into an AAV capsid. In some embodiments, an AAV vector genome includes one or two inverted terminal repeats (ITRs) in cis with the heterologous gene to support replication and packaging. All other structural and non-structural protein coding sequences required for AAV vector production may be provided in trans (e.g., from a plasmid, or by stably integrating the sequences into a host cell). In certain embodiments, an AAV vector genome comprises at least one ITR (e.g., an AAV ITR), optionally two ITRs (e.g., two AAV ITRs), which typically will be at the 5' and 3' ends of the vector genome and flank the heterologous nucleic acid sequence, but need not be contiguous thereto. The ITRs can be the same or different from each other, and from the same or different AAV serotypes.

The terms "host cell," "host cell line," and "host cell culture" are used interchangeably and refer to cells into which exogenous nucleic acid has been introduced, including the progeny of such cells. Host cells include "transformants," "transformed cells," and "transduced cells," which include the primary transformed cell and progeny derived therefrom without regard to the number of passages. For purposes of producing AAV vectors, certain host cells may be used as "producer" or "packaging" cells that contain all the genes required to assemble functional virus particles including a capsid and vector genome. As understood by those of ordinary skill in the art, different host cells can usefully serve as producer cells, such as HEK293 cells, or the Pro10 cell line, but others are possible. The required genes for virion assembly include the vector genome as described elsewhere herein, AAV rep and cap genes, and certain helper genes from other viruses, including without limitation adenovirus. As appreciated by those ordinarily skilled, the requisite genes for AAV production can be introduced into producer cells in various ways, including without limitation transfection of one or more plasmids, however, certain of the genes can already be present in the producer cells, either integrated into the genome or carried on an episome.

The term "inverted terminal repeat" or "ITR" includes any palindromic viral terminal repeat or synthetic sequence that forms a hairpin structure and functions as an inverted terminal repeat (i.e., mediates certain viral functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al. See also FIELDS et al., VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered. An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, persistence, and/or provirus rescue, and the like. The sequence of the AAV2 ITRs are 145 basepairs long, and are provided herein as SEQ ID NO:14 and SEQ ID NO:15.

"Cis-motifs" includes conserved sequences such as found at or close to the termini of the genomic sequence and recognized for initiation of replication; cryptic promoters or sequences at internal positions likely used for transcription initiation, splicing or termination.

"Flanked," with respect to a sequence that is flanked by other elements, indicates the presence of one or more the flanking elements upstream and/or downstream, i.e., 5' and/or 3', relative to the sequence. The term "flanked" is not intended to indicate that the sequences are necessarily contiguous. For example, there may be intervening sequences between the nucleic acid encoding the transgene and a flanking element. A sequence (e.g., a transgene) that is "flanked" by two other elements (e.g., TRs), indicates that one element is located 5' to the sequence and the other is located 3' to the sequence; however, there may be intervening sequences there between.

"Transfection" of a cell means that genetic material is introduced into a cell for the purpose of genetically modifying the cell. Transfection can be accomplished by a variety of means known in the art, such as calcium phosphate, polyethyleneimine, electroporation, and the like.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g. episomes), or integration of transferred genetic material into the genomic DNA of host cells.

"Transgene" is used to mean any heterologous nucleotide sequence incorporated in a vector, including a viral vector, for delivery to and including expression in a target cell (also referred to herein as a "host cell"), and associated expression control sequences, such as promoters. It is appreciated by those of skill in the art that expression control sequences will be selected based on ability to promote expression of the transgene in the target cell. An example of a transgene is a nucleic acid encoding a therapeutic polypeptide.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., Fields et al., Virology, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral or vector genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered. A synthetic large Rep protein may be altered by insertion, deletion, truncation and/or missense mutations.

In the native AAV genome, the different Rep proteins are encoded by a single gene through use of two different promoters and alternative splicing. For purposes of AAV vector production, however, Rep proteins can be expressed in producer cells from a single gene, or from distinct polynucleotides, one sequence for each Rep protein to be expressed. Thus, for example, a Rep encoding gene can be engineered to inactivate the p5 or p19 promoter so that only small or only large Rep proteins are expressed the respective modified genes. Expression of the large and small Rep proteins from different genes can be advantageous when one of the viral promoters is inactive in a host cell, in which case a constitutively active promoter can be used instead, or where it is desired to express the Rep proteins at different levels under the control of separate transcriptional and/or translational control elements. For example, in some embodiments, it may be advantageous to down-regulate expression of the large Rep protein relative to small Rep protein (e.g., Rep78/68) to avoid toxicity to the host cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

A "micro-dystrophin" or a "mini-dystrophin" is an engineered protein comprising certain subdomains or portions of subdomains present in full length muscle dystrophin or isoforms thereof that possess at least some of the functionality of dystrophin when expressed in a muscle cell. Micro-dystrophins and mini-dystrophins are smaller than full length muscle dystrophin (Dp427m). Relative to full length muscle dystrophin, micro-dystrophins and mini-dystrophins may contain deletions at the N-terminus, the C-terminus, internally, or any combination thereof.

As used herein, a "dystrophinopathy" is a muscle disease caused by pathogenic variants in DMD, the gene encoding the protein dystrophin. Dystrophinopathies manifest as a spectrum of phenotypes depending on the nature of the underlying genetic lesion. The mild end of the spectrum includes without limitation the phenotypes of asymptomatic increase in serum concentration of creatine phosphokinase (CK) and muscle cramps with myoglobinuria. The severe end of the spectrum includes without limitation the progressive muscle diseases Duchenne muscular dystrophy (DMD) and Becker muscular dystrophy (BMD), in which skeletal muscle is primarily affected and heart to a lesser degree, and DMD-associated dilated cardiomyopathy (DCM), in which the heart is primarily affected.

Mini-Dystrophin Polynucleotides, Expression Cassettes and Vectors

The present disclosure provides codon-optimized mini-dystrophin gene sequences and expression cassettes containing the same. Such genes and expression cassettes are useful for, among other applications, gene therapy to prevent or treat dystrophinopathies, such as DMD, in subjects in need thereof. Expression of mini-dystrophin proteins in transduced muscle cells is able to replicate and replace at least some of the function normally attributable to full-length dystrophin, such as supporting a mechanically strong link between the extra-cellular matrix and the cytoskeleton.

The codon-optimized sequences are designed to fit within the size limitations of parvovirus vectors, e.g., AAV vectors, as well as provide enhanced expression of mini-dystrophin compared to non-optimized sequences. In some embodiments, the optimized mini-dystrophin sequences provide increased expression of mini-dystrophin protein in muscle cells or in muscle in animals that is at least about 5% greater than the expression of non-codon-optimized dystrophin sequences, e.g., at least about 5, 10, 20, 30, 40, 50, 75, 100, 200, 300, 400, or 500% or more, where the non-codon-optimized sequence is based on the mRNA encoding wild-type human full-length muscle dystrophin, as exemplified by NCBI Reference Sequence NM_004006.2, which is incorporated by reference.

Thus, one aspect of the invention relates to a polynucleotide encoding a mini-dystrophin protein, the polynucleotide comprising, consisting essentially of, or consisting of: (a) the nucleotide sequence of SEQ ID NO:1 or a sequence at least about 90% identical thereto; (b) the nucleotide sequence of SEQ ID NO:2 or a sequence at least about 90% identical thereto; or (c) the nucleotide sequence of SEQ ID NO:3 or a sequence at least about 90% identical thereto. In some embodiments, the polynucleotide is at least about 90%, 91%, 92%, 93%, 94%, 95%, 96%, 97%, 98%, or 99% identical to the nucleotide sequence of one of SEQ ID NOS: 1-3. In certain embodiments, the polynucleotide has a length that is within the capacity of a viral vector, e.g., a parvovirus vector, e.g., an AAV vector. In some embodiments, the polynucleotide is about 5000, 4900, 4800, 4700, 4600, 4500, 4400, 4300, 4200, 4100, or about 4000 nucleotides, or fewer.

In some embodiments, the mini-dystrophin protein encoded by the polynucleotide comprises, consists essentially of, or consists of the N-terminus, hinge H1, rods R1 and R2, hinge H3, rods R22, R23, and R24, hinge H4, the cysteine-rich domain (CR domain), and in some embodiments, all or a portion of the carboxy-terminal domain (CT domain) of wild-type dystrophin protein. In other embodiments, the mini-dystrophin protein encoded by the polynucleotide comprises, consists essentially of, or consists of the N-terminus, Actin-Binding Domain (ABD), hinge H1, rods R1 and R2, rods R22, R23, and R24, hinge H4, the CR domain, and in some embodiments, all or a portion of the CT domain of wild-type dystrophin protein. In further embodiments, the mini-dystrophin protein does not comprise the last three amino acids at the C-terminus of the wild-type dystrophin protein (SEQ ID NO:25). In certain embodiments, the polynucleotide encodes a mini-dystrophin protein comprising, consisting essentially of, or consisting of the amino acid sequence of SEQ ID NO:7 or SEQ ID NO:8 or a sequence at least about 90%, 91%, 92%, 93%, 94%, 95%, 96%, 97%, 98%, or 99% identical to the nucleotide sequence of SEQ ID NO:7 or SEQ ID NO:8.

The nucleotide sequence of dystrophin is well known in the art and may be found in sequence databases such as GenBank. For example, the human dystrophin mRNA sequence may be found at GenBank Accession No. M18533 or NCBI Reference Sequence NM_004006.2, which are incorporated by reference herein in their entirety.

In some embodiments, the polynucleotide is part of an expression cassette for production of dystrophin protein. The expression cassette may further comprise expression elements useful for increasing expression of dystrophin.

In some embodiments, the polynucleotide of the invention is operably linked to a promoter. The promoter may be a constitutive promoter or a tissue-specific or tissue-preferred promoter such as a muscle-specific or muscle-preferred promoter. In some embodiments, the promoter is a creatinine kinase promoter, e.g., a promoter comprising, consisting essentially of, or consisting of the nucleotide sequence of SEQ ID NO: 4 or SEQ ID NO: 5.

In some embodiments, the polynucleotide of the invention is operably linked to a polyadenylation element. In some embodiments, the polyadenylation element comprises the nucleotide sequence of SEQ ID NO: 6.

In some embodiments, the polynucleotide is part of an expression cassette comprising, consisting essentially of, or consisting or the polynucleotide operably linked to a promoter and a polyadenylation element. In certain embodiments, the gene expression cassette comprises, consists essentially or, or consists of the nucleotide sequence of any one of SEQ ID NOS: 9-12 or a sequence at least about 90% identical thereto, e.g., at least about 90%, 91%, 92%, 93%, 94%, 95%, 96%, 97%, 98%, or 99% identical.

Another aspect of the invention relates to a vector comprising the polynucleotides of the invention. Suitable vectors include, but are not limited to, a plasmid, phage, phagemid, viral vector (e.g., AAV vector, an adenovirus vector, a herpesvirus vector, an alphavirus, or a baculovirus vector), bacterial artificial chromosome (BAC), or yeast artificial chromosome (YAC). For example, the nucleic acid can comprise, consist of, or consist essentially of an AAV vector comprising a 5' and/or 3' terminal repeat (e.g., 5' and/or 3' AAV terminal repeat). In some embodiments, the vector is a viral vector, e.g., a parvovirus vector, e.g., an AAV vector, e.g., an AAV9 vector. The viral vector may further comprise a nucleic acid comprising a recombinant viral template, wherein the nucleic acid is encapsidated by the parvovirus capsid. The invention further provides a recombinant parvovirus particle (e.g., a recombinant AAV particle) comprising the polynucleotides of the invention. Viral vectors and viral particles are discussed further below.

In certain embodiments, the viral vector exhibits modified tissue tropism compared to vectors from which the modified vector is derived. In one embodiment, the parvovirus vector exhibits systemic tropism for skeletal, cardiac, and/or diaphragm muscle. In other embodiments, the parvovirus vector has reduced tropism for liver compared to a virus vector comprising a wild-type capsid protein. Tissue tropism can be modified by altering certain viral capsid amino acids, for example, those present in AAV capsid VP1, VP2, and/or VP3 proteins, according to the knowledge of those ordinarily skilled in the art.

In some embodiments, the vector genome is self-complementary or duplexed, and AAV virions containing such vector genomes are known as scAAV vectors. scAAV vectors are described in international patent publication WO 01/92551 (the disclosure of which is incorporated herein by reference in its entirety). Use of scAAV to express a mini-dystrophin may provide an increase in the number of cells transduced, the copy number per transduced cell, or both.

An additional aspect of the invention relates to a transformed cell comprising the polynucleotide and/or vector of the invention. The cell may be an in vitro, ex vivo, or in vivo cell.

A further aspect of the invention relates to a non-human transgenic animal comprising the polynucleotide and/or vector and/or transformed cell of the invention. In some embodiments, the transgenic animal is a laboratory animal, e.g., an animal model of a disease, e.g., an animal model of muscular dystrophy.

Another aspect of the invention relates to a mini-dystrophin protein encoded by the polynucleotides of the invention. The mini-dystrophin protein contains all of the sequences necessary for a functional dystrophin protein. The domains of dystrophin are well known in the art and sequences may be found in sequence databases such as GenBank. For example, the human dystrophin amino acid sequence may be found at NCBI Reference Sequence: NP_003997.1 and GenBank Accession No. AAA53189, which are incorporated by reference herein in their entirety.

In some embodiments, the mini-dystrophin protein comprises, consists essentially of, or consists of the N-terminus, hinge H1, rods R1 and R2, hinge H3, rods R22, R23, and R24, hinge H4, the CR domain, and in some embodiments, all or a portion of the CT domain, wherein the mini-dystrophin protein does not comprise the last three amino acids at the C-terminus of wild-type dystrophin protein (SEQ ID NO:25). According to some of these embodiments, the N-terminal actin binding domain comprises, consists essentially of, or consists of amino acid numbers 1-240 from SEQ ID NO:25, the amino acid sequence of full length human dystrophin protein; H1 comprises, consists essentially of, or consists of amino acid numbers 253-327 from SEQ ID NO:25; R1 comprises, consists essentially of, or consists of amino acid numbers 337-447 from SEQ ID NO:25; R2 comprises, consists essentially of, or consists of amino acid numbers 448-556 from SEQ ID NO:25; H3 comprises, consists essentially of, or consists of amino acid numbers 2424-2470 from SEQ ID NO:25; R22 comprises, consists essentially of, or consists of amino acid numbers 2687-2802 from SEQ ID NO:25; R23 comprises, consists essentially of, or consists of amino acid numbers 2803-2931 from SEQ ID NO:25; R24 comprises, consists essentially of, or consists of amino acid numbers 2932-3040 from SEQ ID NO:25; H4 comprises, consists essentially of, or consists of amino acid numbers 3041-3112 from SEQ ID NO:25; the CR domain comprises, consists essentially of, or consists of amino acid numbers 3113-3299 from SEQ ID NO:25; and the CT domain comprises, consists essentially of, or consists of amino acid numbers 3300-3408 from SEQ ID NO:25. In certain embodiments, the mini-dystrophin protein comprises, consists essentially of, or consists of the amino acid sequence of SEQ ID NO: 7. Further description of this and related constructs is included in Example 1 herein.

In some embodiments, the mini-dystrophin protein comprises, consists essentially of, or consists of the N-terminus, hinge H1, rods R1 and R2, rods R22, R23, and R24, hinge H4, the CR domain, and in some embodiments, all or a portion of the CT domain. In certain embodiments, the mini-dystrophin protein does not comprise the last three amino acids at the C-terminus of wild-type dystrophin protein. According to some of these embodiments, the N-terminal actin binding domain comprises, consists essentially of, or consists of amino acid numbers 1-240 from SEQ ID NO:25, the amino acid sequence of full length human dystrophin protein; H1 comprises, consists essentially of, or consists of amino acid numbers 253-327 from SEQ ID NO:25; R1 comprises, consists essentially of, or consists of amino acid numbers 337-447 from SEQ ID NO:25; R2 comprises, consists essentially of, or consists of amino acid numbers 448-556 from SEQ ID NO:25; R22 comprises, consists essentially of, or consists of amino acid numbers 2687-2802 from SEQ ID NO:25; R23 comprises, consists essentially of, or consists of amino acid numbers 2803-2931 from SEQ ID NO:25; R24 comprises, consists essentially of, or consists of amino acid numbers 2932-3040 from SEQ ID NO:25; H4 comprises, consists essentially of, or consists of amino acid numbers 3041-3112 from SEQ ID NO:25; cysteine rich domain comprises, consists essentially of, or consists of amino acid numbers 3113-3299 from SEQ ID NO:25; and carboxy-terminal domain comprises, consists essentially of, or consists of amino acid numbers 3300-3408 from SEQ ID NO:25. In certain embodiments, the mini-dystrophin protein comprises, consists essentially of, or consists of the amino acid sequence of SEQ ID NO: 8.

A further aspect of the invention relates to a method of producing a mini-dystrophin protein in a cell, comprising contacting the cell with the polynucleotide or vector of the invention, thereby producing the mini-dystrophin in the cell. The cell may be an in vitro, ex vivo, or in vivo cell, e.g., a cell line or a primary cell. Methods of producing a protein in a cell by introduction of a polynucleotide encoding the protein are well known in the art.

Another aspect of the invention relates to a method of producing a mini-dystrophin protein in a subject, comprising delivering to the subject the polynucleotide, vector and/or transformed cell of the invention, thereby producing the mini-dystrophin protein in the subject.

An additional aspect of the invention relates to a method of treating muscular dystrophy in a subject in need thereof, comprising delivering to the subject a therapeutically effective amount of the polynucleotide, vector, and/or transformed cell of the invention, thereby treating muscular dystrophy in the subject. The muscular dystrophy may be any form of muscular dystrophy, e.g., Duchenne muscular dystrophy or Becker muscular dystrophy.

Recombinant Virus Vectors

The virus vectors of the present invention are useful for the delivery of polynucleotides encoding mini-dystrophin to cells in vitro, ex vivo, and in vivo. In particular, the virus vectors can be advantageously employed to deliver or transfer polynucleotides encoding mini-dystrophin to animal, including mammalian, cells.

The virus vector may also comprise a heterologous nucleic acid that shares homology with and recombines with a locus on a host chromosome. This approach can be utilized, for example, to correct a genetic defect in the host cell.

As a further alternative, the polynucleotides encoding mini-dystrophin can be used to produce mini-dystrophin protein in a cell in vitro, ex vivo, or in vivo. For example, the virus vectors may be introduced into cultured cells and the expressed mini-dystrophin protein isolated therefrom.

It will be understood by those skilled in the art that the polynucleotide encoding mini-dystrophin can be operably associated with appropriate control sequences. For example, the polynucleotide can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter and optionally enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced. An enhancer, if employed, can be chosen from the same gene and species as the promoter, from the orthologous gene in a different species as the promoter, from a different gene in the same species as the promoter, or from a different gene in a different species as the promoter.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred) promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the polynucleotide encoding mini-dystrophin is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering polynucleotide encoding mini-dystrophin into a broad range of cells, including dividing and non-dividing cells. The virus vectors can be employed to deliver the polynucleotide to a cell in vitro, e.g., to produce mini-dystrophin in vitro or for ex vivo gene therapy. The virus vectors are additionally useful in a method of delivering the polynucleotide to a subject in need thereof, e.g., to express mini-dystrophin. In this manner, the protein can be produced in vivo in the subject. The subject can be in need of mini-dystrophin because the subject has a deficiency of functional dystrophin. Further, the method can be practiced because the production of mini-dystrophin in the subject may impart some beneficial effect.

The virus vectors can also be used to produce mini-dystrophin in cultured cells or in a subject (e.g., using the subject as a bioreactor to produce the protein or to observe the effects of the protein on the subject, for example, in connection with screening methods).

In general, the virus vectors of the present invention can be employed to deliver the polynucleotide encoding mini-dystrophin to treat and/or prevent any disease state for which it is beneficial to deliver mini-dystrophin. Illustrative disease states include, but are not limited to muscular dystrophies including Duchenne and Becker.

Virus vectors according to the instant invention find use in diagnostic and screening methods, whereby a polynucleotide encoding mini-dystrophin is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

According to certain embodiments of the disclosure of AAV vectors or particles for treating dystrophinopathy, such as DMD, the disclosure provides AAV vectors or particles including AAV capsids from an AAV serotype that has tropism for striated muscle, including without limitation, skeletal muscle, including the diaphragm, and cardiac muscle. Non-limiting examples of naturally occurring AAV capsids having tropism for striated muscle are AAV1, AAV6, AAV7, AAV8, and AAV9. However, other embodiments include AAV capsids that are not known to occur naturally, but rather have been engineered for the express purpose of creating novel AAV capsids that preferentially transduce striated muscle compared to other tissues. Such engineered capsids are known in the art, but the disclosure encompasses new muscle-specific AAV capsids yet to be developed. Non-limiting examples of muscle-specific engineered AAV capsids were reported in Yu, C Y, et al., Gene Ther 16(8): 953-62 (2009), Asokan, A, et al., Nat Biotech 28(1):79-82 (2010 (describing AAV2i8), Bowles, D E, et al., Mol Therapy 20(2):443-455 (2012) (describing AAV 2.5), and Asokan, A, et al., Mol Ther 20(4):699-708 (2012). The amino acid sequences of the capsid proteins, including VP1, VP2, and VP3 proteins, for many naturally and non-naturally occurring AAV serotypes are known in the art. In one non-limiting example, the amino acid sequence for the AAV9 serotype is provided as the amino acid sequence of SEQ ID NO:13.

The AAV particles of the disclosure for treating dystrophinopathy, such as DMD, include a vector genome for expressing a mini-dystrophin protein with dystrophin subdomains selected to at least partially restore in transduced muscle cells the function supplied by the missing full length dystrophin protein. According to some embodiments, the mini-dystrophin protein is constructed from subdomains from the full length wild type human dystrophin protein. In some embodiments, the mini-dystrophin protein includes the following subdomains from the human dystrophin protein in the following order from N-terminus to C-terminus: N-terminal actin binding domain (ABD); H1 hinge domain; R1 and R2 spectrin-like repeat domains; H3 hinge domain; R22, R23 and R24 spectrin-like repeat domains; H4 hinge domain; cysteine rich (CR) domain; and carboxy-terminal (CT) domain. According to some of these embodiments, the N-terminal actin binding domain comprises, consists essentially of, or consists of amino acid numbers 1-240 from SEQ ID NO:25, the amino acid sequence of full length human dystrophin protein; H1 comprises, consists essentially of, or consists of amino acid numbers 253-327 from SEQ ID NO:25; R1 comprises, consists essentially of, or consists of amino acid numbers 337-447 from SEQ ID NO:25; R2 comprises, consists essentially of, or consists of amino acid numbers 448-556 from SEQ ID NO:25; H3 comprises, consists essentially of, or consists of amino acid numbers 2424-2470 from SEQ ID NO:25; R22 comprises, consists essentially of, or consists of amino acid numbers 2687-2802 from SEQ ID NO:25; R23 comprises, consists essentially of, or consists of amino acid numbers 2803-2931 from SEQ ID NO:25; R24 comprises, consists essentially of, or consists of amino acid numbers 2932-3040 from SEQ ID NO:25; H4 comprises, consists essentially of, or consists of amino acid numbers 3041-3112 from SEQ ID NO:25; the CR domain comprises, consists essentially of, or consists of amino acid numbers 3113-3299 from SEQ ID NO:25; and the CT domain comprises, consists essentially of, or consists of amino acid numbers 3300-3408 from SEQ ID NO:25. According to certain embodiments, the mini-dystrophin protein has the amino acid sequence of SEQ ID NO:7.

The vector genome of the AAV particles of the disclosure for treating dystrophinopathy, such as DMD, includes a gene for expressing a mini-dystrophin. Typically, the vector genome will lack the rep and cap genes normally present in wild type AAV to provide room for the gene expressing the mini-dystrophin. In some embodiments, the gene encodes a mini-dystrophin protein with the following subdomains from full length human dystrophin protein: ABD-H1-R1-R2-H3-R22-R23-R24-H4-CRD-CTD. In some embodiments, the CTD is only a portion of the CTD found in wildtype muscle dystrophin, and in some embodiments does not include the last three amino acids present in wildtype muscle dystrophin (SEQ ID NO:25). In certain embodiments, the gene encodes for a human mini-dystrophin protein having the amino acid sequence of SEQ ID NO:7.

According to some embodiments, the gene encoding the human mini-dystrophin protein is codon-optimized with respect to the species of the subject to which the AAV particles of the disclosure will be administered to effect gene therapy. Without wishing to be bound by theory, it is believed that codon-optimization improves the efficiency with which transduced cells are able to transcribe the gene into mRNA and/or translate the mRNA into protein, thereby increasing the amount of mini-dystrophin protein produced compared to expression of a mini-dystrophin encoding gene that is non-codon-optimized. In some non-limiting embodiments, the codon-optimization is human codon-optimization, but codon-optimization can be performed with respect to other species, including canine.

In some embodiments, codon-optimization substitutes one or more codons that pair with relatively rare tRNAs present in a species, such as human, with synonymous codons that pair with more prevalent tRNAs for the same amino acid. This approach can increase the efficiency of translation. In other embodiments, codon-optimization eliminates certain cis-acting motifs that can influence the efficiency of transcription or translation. Non-limiting examples of codon-optimization include adding a strong Kozak sequence at the intended start of the coding sequence, or eliminating internal ribosome entry sites downstream of the intended start codon. Other cis-acting motifs that may be eliminated through codon-optimization include internal TATA-boxes; chi-sites; ARE, INS, and/or CRS sequence elements; repeat sequences and/or RNA secondary structures; cryptic splice donor and/or acceptor sites, branch points; and SalI sites.

In certain embodiments, codon-optimization increases the GC content (that is, the number of G and C nucleobases present in a nucleic acid sequence, usually expressed as a percentage) relative to the wildtype sequence from which the mini-dystrophin gene was assembled. In some embodiments, the GC content is at least 5%, 10%, 15%, 20%, 25%, 30%, 35%, 40%, 45%, 50%, 55%, 60%, 65%, 70%, 75%, 80%, 85%, 90%, 95%, 100%, or greater than the GC content of the corresponding wildtype gene. In related embodiments, the GC content of a codon-optimized gene is about or at least 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, or greater.

In some embodiments, codon-optimization increases the codon adaptation index (CAI) of the gene encoding the mini-dystrophin protein. The CAI is a measure of synonymous codon usage bias in a particular species. The CAI value (which ranges from 0 to 1) in a particular species is positively correlated with gene expression levels. See, for example, Sharp, P M and W-H Lie, Nuc Acids Res 15(3): 1281-95 (1987). According to certain embodiments, codon-optimization increases the CAI of the mini-dystrophin gene in reference to highly expressed human genes to a value that is at least 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99.

In other embodiments, codon-optimization reduces the number of CpG dinucleotides in the coding sequence of a mini-dystrophin. Without wishing to be bound by any particular theory of operation, it is believed that methylation at CpG dinucleotides can silence gene transcription, such that reducing the number of CpG dinucleotides in a gene sequence can reduce the level of methylation, thereby resulting in enhanced transcription efficiency. Thus, in some embodiments of the codon-optimized mini-dystrophin genes, the number of CpG dinucleotides is reduced by about or at least 5%, 10%, 15%, 20%, 25%, 30%, 35%, 40%, 45%, 50%, 55%, 60%, or more compared to the wildtype sequence from which the mini-dystrophin gene was assembled.

A non-limiting example of a human codon-optimized human mini-dystrophin gene is provided by the DNA sequence of SEQ ID NO:1. This DNA sequence, which is 3978 nucleobases long (including a stop codon) is referred to herein as Hopti-Dys3978, although the particular terminology is merely used for convenience and is not intended to be limiting. The mini-dystrophin protein sequence encoded by SEQ ID NO:1, which is called Dys3978, is provided by SEQ ID NO:7. An example of a canine codon-optimized human mini-dystrophin gene is provided by SEQ ID NO:3, which also encodes Dys3978. As described in additional detail herein, the coding sequence for the mini-dystrophin of SEQ ID NO:7 was assembled from subsequences of the wildtype full-length human muscle dystrophin gene (as exemplified by NCBI Reference Sequence NM_004006.2, which is incorporated by reference) corresponding to certain subdomains present in the dystrophin protein (SEQ ID NO:25). The resulting gene sequence is provided herein as SEQ ID NO:26, which was then human codon-optimized, resulting in the DNA sequence of SEQ ID NO:1. Without limitation, the codon-optimization increased the GC content, decreased the use of infrequent codons (that is, increased the codon-adaptation index (CAI)), and included a strong translation initiation site (Kozak consensus sequence or similar), compared to the gene sequence before codon-optimization.

The vector genome of the AAV particles of the disclosure for treating dystrophinopathy, such as DMD, further include AAV inverted terminal repeats (ITR) flanking the codon-optimized gene encoding mini-dystrophin protein. In some embodiments, the ITRs are from the same AAV serotype as the capsid (for example, without limitation AAV9 ITRs used with AAV9 capsid), but in other embodiments, AAV ITRs from a different serotype may be used. For example, ITRs from the AAV2 serotype may be used in a vector genome in combination with an AAV capsid from a different, non-AAV2 serotype. Non-limiting examples include use of AAV2 ITRs with a capsid from the AAV1, AAV6, AAV7, AAV8, or AAV9 serotypes, or a different naturally or non-naturally occurring AAV serotype. In a particular non-limiting example, AAV2 ITRs may be used in combination with the capsid from the AAV9 serotype. From the perspective of the plus or sense DNA strand of the vector genome, the sequence of the left, 5', or upstream AAV2 ITR is provided as the DNA sequence of SEQ ID NO:14, and the sequence of the right, 3', or downstream AAV2 ITR is provided as the DNA sequence of SEQ ID NO:15.

The vector genome of the AAV vectors of the disclosure for treating dystrophinopathy, such as DMD, further includes a transcriptional regulatory element operably linked with the gene encoding the mini-dystrophin protein so that the vector genome, once converted into its double stranded form can express the mini-dystrophin gene in transduced cells. Transcriptional regulatory elements typically include a promoter, but optionally one or more enhancer elements that can act to augment the rate of transcription initiation from the promoter.

Operable linkage of a transcriptional regulatory element with respect to the mini-dystrophin coding sequence means that the transcriptional regulatory element can function to control transcription and expression of the gene, but does not necessarily require any particular structural or spatial relationship. Because vector genomes of the disclosure are typically packaged into AAV capsids as single-stranded DNA molecules, it should be understood that the operable linkage may not be functional until the vector genome is converted into double-stranded form. Usually, a promoter will be positioned 5' or upstream of a gene sequence encoding the mini-dystrophin protein, but other transcriptional regulatory elements, such as enhancers, may be positioned 5' or elsewhere, such as 3', of the gene.

In some embodiments, the transcriptional regulatory element can be a strong constitutively active promoter, such those found in certain viruses that infect eukaryotic cells. A well-known example from the art include the promoter from the cytomegalovirus (CMV), but others are known as well such at the promoter from the Rous sarcoma virus (RSV). Strong viral promoters such as CMV or RSV are typically not tissue specific, so that if used the mini-dystrophin protein would be expressed not only in muscle cells, but any other cell type, such as liver, transduced by the AAV particles of the disclosure. Hence, in other embodiments, a muscle-specific transcriptional regulatory element can be used to reduce the amount of mini-dystrophin protein expressed in non-muscle cells, such as liver cells, that may also be transduced by the AAV particles of the disclosure.

Muscle-specific transcriptional regulatory elements can be derived from muscle-specific genes from any species, including mammalian species, such as without limitation, human or mouse muscle genes. Muscle-specific transcriptional regulatory elements will typically include at minimum a promoter from a muscle-specific gene as well as one or more enhancers from the same or a different muscle specific gene. Such enhancers can originate from many parts of the native gene, such as enhancers positioned 5' or 3' of the gene, or even reside in introns. Muscle-specific transcriptional regulatory elements can be removed en bloc from a muscle-specific gene and inserted into a plasmid for producing the AAV vector genomes of the disclosure, or can be engineered to tailor their activity and reduce their size as much as possible.

Non-limiting examples of muscle-specific genes from which muscle-specific transcriptional regulatory elements can be derived include the muscle creatine kinase gene, myosin heavy chain gene, or myosin light chain gene, or the alpha 1 actin gene from skeletal muscle, though others are possible as well. These genes can be from human, mouse, or other species.

Muscle-specific transcriptional regulatory elements that have been created for use in gene therapy applications are described in the art, and may be used in the AAV vectors of the disclosure for treating muscular dystrophy. In non-limiting examples, Hauser described muscle-specific transcriptional regulatory elements known as CK4, CK5, and CK6 derived from the mouse creatine kinase (MCK) gene (Hauser, M A, et al., Mol Therapy 2(1):16-25 (2000)), Salva described muscle-specific transcriptional regulatory elements known as CK1 and CK7, derived from the MCK gene, and MHCK1 and MHCK7, which additionally include enhancers from the mouse α-MHC gene (Salva, M Z, et al., Mol Therapy 15(2):320-9 (2007)), and Wang described muscle-specific transcriptional regulatory elements known as enh358MCK, dMCK and tMCK (Wang, B, et al., Gene Therapy 15:1489-9 (2008)). Use of other muscle-specific transcriptional regulatory elements in the AAV vectors of the disclosure for treating muscular dystrophy are also possible.

Non-limiting examples of muscle-specific transcriptional regulatory elements that may be used in the AAV vectors of the disclosure for treating muscular dystrophy include CK4, CK5, CK6, CK1, CK7, MHCK1, MHCK7, enh358MCK, dMCK and tMCK, each as described in the art, or those disclosed herein as having the DNA sequences of SEQ ID NO:4, SEQ ID NO:5, and SEQ ID NO:16. Other muscle-specific transcriptional regulatory elements may be used as well.

The vector genome of the AAV vectors of the disclosure for treating dystrophinopathy, such as DMD, further includes a transcription termination sequence positioned 3' of the coding sequence for the mini-dystrophin gene. Inclusion of transcription termination sequence ensures that the mRNA transcript encoding the mini-dystrophin protein will be appropriately polyadenylated by the transduced cell thereby ensuring efficient translation of the message into protein. Without intending to be limited by any particular theory of operation, research into mammalian transcription termination sequences identified a consensus sequence in the 3' UTR of genes that serves to terminate transcription and signal polyadenylation of the growing transcript. Specifically, these sequences typically include the motif AATAAA, followed by 15-30 nucleotides, and then CA. See, for example, N. Proudfoot, Genes Dev 25:1770-82 (2011). Other motifs, such as an upstream element (USE) and downstream element (DSE) may contribute to transcription termination in some genes. Many transcription termination sequences are known in the art and can be used in the AAV vectors of the disclosure. Non-limiting examples include the polyadenylation signal from the SV40 virus early or late genes (SV40 early or late polyA) or the polyadenylation signal from the bovine growth hormone gene (bGH polyA). Transcription termination sequences from other genes of any species may be used in the AAV vectors of the disclosure. Alternatively, synthetic transcription termination sequences may be designed and used to signal transcription termination and polyadenylation. Additional non-limiting examples of transcription termination sequences that may be used in the AAV vectors of the disclosure include those disclosed herein as having the DNA sequences of SEQ ID NO:6 and SEQ ID NO:17.

According to certain non-limiting embodiments, the disclosure provides an AAV viral particle or vector for treating dystrophinopathy, such as DMD, comprising an AAV capsid and a vector genome encoding a mini-dystrophin protein. In some embodiments, the mini-dystrophin protein includes the following subdomains from full length human dystrophin protein: ABD-H1-R1-R2-H3-R22-R23-R24-H4-CRD-CTD. In some embodiments, the CTD is only a portion of the CTD found in wildtype muscle dystrophin, and in some embodiments does not include the last three amino acids present in wildtype muscle dystrophin (SEQ ID NO:25). According to certain embodiments, the gene encoding the mini-dystrophin protein of SEQ ID NO:7 is human codon-optimized and has the DNA sequence of SEQ ID NO:1. In some embodiments, the AAV capsid is from the AAV9 serotype.

As noted elsewhere herein, single-stranded AAV vector genomes are packaged into capsids as the plus strand or minus strand in about equal proportions. Consequently, embodiments of the vector or particle include AAV particles in which the vector genome is in the plus strand polarity (that is, has the nucleobase sequence of the sense or coding DNA strand), as well as AAV particles in which the vector genome is in the minus strand polarity (that is, has the nucleobase sequence of the antisense or template DNA strand). Given the nucleobase sequence of the plus strand in its regular 5' to 3' order, the nucleobase sequence of the minus strand in its 5' to 3' order can be determined as the reverse-complement of the nucleobase sequence of the plus strand.

In some embodiments of the vector, the vector genome, when in plus polarity, comprises a muscle-specific transcriptional regulatory element derived from the creatine kinase gene having the DNA sequence of SEQ ID NO:16 positioned 5' of and operably linked with SEQ ID NO:1, the DNA sequence of the human codon-optimized gene encoding mini-dystrophin protein. Particles comprising the corresponding minus strand are also possible, where the sequence of nucleobases from its 5' end would be the reverse complement of the sequence of the aforementioned plus strand. In other embodiments, the vector genome, when in plus polarity comprises a first AAV2 ITR followed by the DNA sequence of SEQ ID NO:16 positioned 5' of and operably linked with the DNA sequence of SEQ ID NO:1, and a transcription termination sequence comprising the DNA sequence of SEQ ID NO:17 positioned 3' of the mini-dystrophin gene, followed by a second AAV2 ITR. Particles comprising the corresponding minus strand are also possible, where the sequence of nucleobases from its 5' end would be the reverse complement of the sequence of the aforementioned plus strand.

In certain other embodiments of the vector, the vector genome, when in plus polarity, comprises in 5' to 3' order a first AAV2 ITR, a transcriptional regulatory element sequence defined by the DNA sequence of SEQ ID NO:16, a human codon optimized gene sequence for expressing a mini-dystrophin, the gene sequence defined by the DNA sequence of SEQ ID NO:1 in operable linkage with the transcriptional regulatory element, a transcription termination sequence defined by the DNA sequence of SEQ ID NO:17, and a second AAV2 ITR. Particles comprising the corresponding minus strand are also possible, where the sequence of nucleobases from its 5' end would be the reverse complement of the sequence of the aforementioned plus strand.

According to a particular non-limiting embodiment, an AAV vector for treating dystrophinopathy, such as DMD, which may be referred to herein as AAV9.hCK.Hopti-Dys3978.spA, comprises a capsid from the AAV9 serotype and a vector genome, which vector genome may be referred to herein as hCK.Hopti-Dys3978.spA, comprising, consisting essentially of, or consisting of, when the genome is in plus polarity, the DNA sequence of SEQ ID NO:18 or, when the genome is in the minus polarity, the reverse-complement of the DNA sequence of SEQ ID NO:18 (that is, when the vector genome sequence is read 5' to 3').

Methods of Producing Virus Vectors

The present disclosure further provides methods of producing AAV vectors. In one particular embodiment, the present disclosure provides a method of producing a recombinant parvovirus particle, comprising providing to a cell permissive for AAV replication and packaging a recombinant AAV vector genome, comprising a mini-dystrophin gene, associated genetic control elements and flanking AAV ITRs, and AAV replication and packaging functions, such as those provided by the AAV rep and cap genes, under conditions sufficient for the replication and packaging of the recombinant AAV particles, whereby rAAV particles are produced by the cell. Conditions sufficient for the replication and packaging of the rAAV particles include without limitation helper functions, such as those from adenovirus and/or herpesvirus. Cells permissive for AAV replication and packaging are known herein as packaging cells or producer cells, terms encompassed by the broader term host cells. The rAAV particle vector genome, replication and packaging functions and, where required, helper functions can be provided via viral or non-viral vectors, such as plasmids, and can exist within the packaging cells stably or transiently, either integrated into the cell's genome or in an episome.

Recombinant AAV vectors of the disclosure can be made by several methods known to skilled artisans (see, e.g., WO 2013/063379). An exemplary method is described in Grieger, et al. 2015, Molecular Therapy 24(2):287-297, the contents of which are incorporated by reference. Briefly, efficient transfection of HEK293 cells is used as a starting point, wherein an adherent HEK293 cell line from a qualified clinical master cell bank is used to grow in animal component-free suspension conditions in shaker flasks and WAVE bioreactors that allow for rapid and scalable rAAV particle production. Using the triple transfection method (e.g., WO 96/40240), the suspension HEK293 cell line is capable of generating, in some embodiments, greater than $1\times10^5$ vector genome (vg) containing particles per cell, or greater than $1\times10^{14}$ vg/L of cell culture when harvested 48 hours post-transfection. Triple transfection refers to the fact that the packaging cell is transfected with three plasmids: one plasmid encodes the AAV rep and cap genes, another plasmid encodes various helper functions (e.g., adenovirus or HSV proteins such as Ela, E1b, E2a, E4, and VA RNA, and another plasmid encodes the vector genome, i.e., the mini-dystrophin gene and its various control elements flanked by AAV ITRs. To achieve the desired yields, a number of variables can be optimized such as selection of a compatible serum-free suspension media that supports both growth and transfection, selection of a transfection reagent, transfection conditions and cell density. Vectors can be collected from the medium and/or by lysing the cells, and then purified using the classic density gradient ultracentrifugation technique, or using column chromatographic or other techniques.

The packaging functions include genes for viral vector replication and packaging. Thus, for example, the packaging functions may include, as needed, functions necessary for viral gene expression, viral vector replication, rescue of the viral vector from the integrated state, viral gene expression, and packaging of the viral vector into a viral particle. The packaging functions may be supplied together or separately to the packaging cell using a genetic construct such as a plasmid or an amplicon, a Baculovirus, or HSV helper construct. The packaging functions may exist extrachromosomally within the packaging cell, but may also be integrated into the cell's chromosomal DNA. Examples include genes encoding AAV Rep and Cap proteins. Rep and cap genes can be provided to packaging cell together as part of the same viral or non-viral vector. For example, the rep and cap sequences may be provided by a hybrid adenovirus vector (e.g., inserted into the Ela or E3 regions of a deleted adenovirus vector) or herpesvirus vector, such as an EBV vector. Alternatively, AAV rep and cap genes can be provided separately. Rep and cap genes can also be stably integrated into the genome of a packaging cell, or exist on an episome. Typically, rep and cap genes will not be flanked by ITRs to avoid packaging of these sequences into rAAV vector particles.

The helper functions include helper virus elements needed for establishing active infection of the packaging cell which is required to initiate packaging of the viral vector. Examples include functions derived from adenovirus, baculovirus and/or herpes virus sufficient to result in packaging of the viral vector. For example, adenovirus helper functions will typically include adenovirus components Ela, E1b, E2a, E4, and VA RNA. The packaging functions may be supplied by infection of the packaging cell with the required virus. Alternatively, use of infectious virus can be avoided, whereby the packaging functions may be supplied together or separately to the packaging cell using a non-viral vector such as a plasmid or an amplicon. See, e.g., pXR helper plasmids as described in Rabinowitz et al., 2002, J. Virol. 76:791, and pDG plasmids described in Grimm et al., 1998, Human Gene Therapy 9:2745-2760. The packaging functions may exist extrachromosomally within the packaging cell, but may also be integrated into the cell's chromosomal DNA (e.g., E1 or E3 in HEK 293 cells).

Any method of introducing the nucleotide sequence carrying the helper functions into a cellular host for replication and packaging may be employed, including but not limited to electroporation, calcium phosphate precipitation, microinjection, cationic or anionic liposomes, and liposomes in combination with a nuclear localization signal. In embodiments wherein the helper functions are provided by transfection using a virus vector or infection using a helper virus; standard methods for producing viral infection may be used.

Any suitable permissive or packaging cell known in the art may be employed in the production of the packaged viral vector. Mammalian cells or insect cells are preferred. Examples of cells useful for the production of packaging cells in the practice of the invention include, for example, human cell lines, such as VERO, WI38, MRC5, A549, HEK 293 cells (which express functional adenoviral E1 under the control of a constitutive promoter), B-50 or any other HeLa cells, HepG2, Saos-2, HuH7, and HT1080 cell lines. In one aspect, the packaging cell is capable of growing in suspension culture, especially in serum-free growth media. In one embodiment, the packaging cell is a HEK293 that grows in suspension in serum free medium. In another embodiment, the packaging cell is the HEK293 cell described in U.S. Pat. No. 9,441,206 and deposited as ATCC No. PTA 13274. Numerous rAAV particle packaging cell lines are known in the art, including, but not limited to, those disclosed in WO 2002/46359.

Cell lines for use as packaging cells include insect cell lines, particularly when baculoviral vectors are used to introduce the genes required for rAAV particle production as described herein. Any insect cell that allows for replication of AAV and that can be maintained in culture can be used in accordance with the present disclosure. Examples include Spodoptera frugiperda, such as the Sf9 or Sf21 cell lines, *Drosophila* spp. cell lines, or mosquito cell lines, e.g., *Aedes albopictus*-derived cell lines.

After AAV vector particles of the disclosure have been produced and purified, they can be titered to prepare compositions for administration to subjects, such as human subjects with muscular dystrophy. AAV vector titering can be accomplished using methods known in the art. In certain embodiments, AAV vector particles can be titered using quantitative PCR (qPCR) using primers against sequences in the vector genome, for example, AAV2 ITR sequences if present, or other sequences in the vector genome. By performing qPCR in parallel on dilutions of a standard of known concentration, such as a plasmid containing the sequence of the vector genome, a standard curve can be generated permitting the concentration of the AAV vector to be calculated as the number of vector genomes (vg) per unit volume, such as microliters or milliliters. Alternatively, the number of AAV vector particles containing genomes can be determined using dot blot using a suitable probe for the vector genome. These techniques are described further in Gray, S J, et al., Production of recombinant adeno-associated viral vectors and use in in vitro and in vivo administration, Curr Protoc Neurosci (2011) and Werling N J, et al., Gene Ther Meth 26:82-92 (2015). Once the concentration of AAV vector genomes in the stock is determined, it can be diluted into or dialyzed against suitable buffers for use in preparing a composition for administration to subjects.

Methods of Treatment

The disclosure provides methods for treating a dystrophinopathy by administering to a subject in need of treatment for dystrophinopathy a therapeutically effective dose or amount of an AAV vector of the disclosure, such as, without limitation, the vector known as AAV9.hCK.Hopti-Dys3978.spA. In some embodiments, the dystrophinopathy is a muscular dystrophy, including without limitation Duchenne muscular dystrophy (DMD), Becker muscular dystrophy (BMD), DMD-associated dilated cardiomyopathy (DCM), and symptomatic carrier states in females. Thus, in some embodiments, the disclosure provides methods for treating muscular dystrophy by administering to a subject in need of treatment for muscular dystrophy a therapeutically effective dose or amount of an AAV vector of the disclosure, such as, without limitation, the vector known as AAV9.hCK.Hopti-Dys3978.spA. In related embodiments, the disclosure provides methods for treating Duchenne muscular dystrophy (DMD), Becker muscular dystrophy (BMD), DMD-associated dilated cardiomyopathy (DCM), and symptomatic carrier states in females, in subjects in need of treatment therefore.

Also provided is the use of an AAV vector or pharmaceutical composition of the disclosure in the manufacture of a medicament for use in the methods of treatment disclosed herein. In addition, there is provided an AAV vector or pharmaceutical composition of the disclosure for use in a method of treatment disclosed herein.

Treatment of subjects with a dystrophinopathy, such as DMD, need not result in a cure to be considered effective, where cure is defined as either halting disease progression, or partially or completely restoring the subject's muscle function. Rather a therapeutically effective dose or amount of an AAV vector of the disclosure is one that serves to reduce or ameliorate the symptoms of, slow the progression of, or improve the quality of life of a subject with the dystrophinopathy, such as DMD. According to certain non-limiting embodiments, treatment of subjects with a dystrophinopathy can improve their mobility, delay the time to their loss of ambulation or other mobility, and in the cases of severe dystrophinopathy, such as DMD, extend the life of subjects with the disorder.

The methods of treatment of the disclosure can be used to treat male or female subjects with a dystrophinopathy, such as DMD. In the case of females, treatment can be provided to symptomatic carriers, or to the rare female subject with full blown disease. The methods of the disclosure can also be used to treat subjects of any age with a dystrophinopathy, including subjects less than 1 year old, or about or at least 1 year old, or about or at least 2, 3, 4, 5, 6, 7, 8, 9, 10, 11, 12, 13, 14, 15, 16, 17, 18, 19, 20, 21, 22, 23, 24, 25, 26, 27, 28, 29, 30 years old or older. Subjects, when treated, may be ambulatory, or non-ambulatory.

The methods of treatment of the disclosure can be used to treat subjects with a dystrophinopathy regardless of the underlying genetic lesion (for example, deletions, duplications, splice site variants, or nonsense mutations in the dystrophin gene), so long as the lesion results in a reduction or loss in the function of the native human dystrophin gene.

In certain embodiments of the disclosure, treating a subject with a therapeutically effective dose or amount of an AAV mini-dystrophin vector will reduce tissue concentrations of one or more biomarkers that are associated with the existence or progression of muscular dystrophy.

According to certain embodiments, the biomarkers are certain enzymes released from damaged skeletal muscle or cardiac muscle cells into the blood (including serum or plasma). Non-limiting examples include creatinine kinase (CK), the transaminases alanine aminotransferase (ALT) and aspartate aminotransferase (AST), and lactic acid dehydrogenase (LDH), the average levels of which are all known to be elevated in subjects with DMD.

In some embodiments, a therapeutically effective dose or amount of an AAV mini-dystrophin vector of the disclosure is effective to reduce elevated ALT levels in blood of DMD patients to within about 7-, 6-, 5-, 4-, 3-, or 2-fold greater than that typically found in healthy subjects of similar age and sex. In other embodiments, a therapeutically effective dose or amount of an AAV mini-dystrophin vector of the disclosure is effective to reduce elevated AST levels in blood of DMD patients to within about 7-, 6-, 5-, 4-, 3-, or 2-fold greater than that typically found in healthy subjects of similar age and sex. In some embodiments, a therapeutically effective dose or amount of an AAV mini-dystrophin vector of the disclosure is effective to reduce elevated LDH levels in blood of DMD patients to within about 7-, 6-, 5-, 4-, 3-, or 2-fold greater than that typically found in healthy subjects of similar age and sex. And in some other embodiments, a therapeutically effective dose or amount of an AAV mini-dystrophin vector of the disclosure is effective to reduce elevated total CK levels in blood of DMD patients to within about 50-, 48-, 46-, 44-, 42-, 40-, 38-, 36-, 34-, 32-, 30-, 28-, 26-, 24-, 22-, 20-, 18-, 16-, 14-, 12-, 10-, 9-, 8-, 7-, 6-, 5-, 4-, 3-, or 2-fold greater than that typically found in healthy subjects of similar age and sex. It has also been found that matrix metalloproteinase-9 (MMP-9), an enzyme associated with degradation or remodeling of the extracellular matrix, is elevated in the blood of DMD patients. See, for example, Nadaraja, V D, et al., Neuromusc. Disorders 21:569-578 (2011). Thus, in some embodiments, a therapeutically effective dose or amount of an AAV mini-dystrophin vector of the disclosure is effective to reduce elevated MMP-9 levels in blood of DMD patients to within about 15-, 14-, 13-, 12-, 11-, 10-, 9-, 8-, 7-, 6-, 5-, 4-, 3-, or 2-fold greater than that typically found in healthy subjects of similar age and sex.

In other embodiments, a therapeutically effective dose or amount of an AAV mini-dystrophin vector of the disclosure is effective to alter the levels of ALT, AST, LDH, CK and MMP-9 as indicated above alone or in combination with one or more of these same or other biomarkers. Thus, in an exemplary non-limiting embodiment, a therapeutically effective dose or amount of an AAV mini-dystrophin vector of the disclosure is effective to reduce ALT and AST, ALT and LDH, AST and CK, or AST and MMP-9, etc.

In some methods of treatment of the disclosure, an effective dose or amount of an AAV vector is one that improves average subject performance in the 6 minute walk-test (6MWT). The 6MWT has been established as a reproducible and valid measure of muscle function and mobility of human subjects with muscular dystrophy, in particular, DMD. See, for example, McDonald, C M, et al., Muscle Nerve 41(4):500-10 (2010); Henricson, E, et al., PLOS Currents Musc Dys, 8 Jul. 2013; McDonald, C M, et al., Muscle Nerve 48:343-56 (2013). In the test, the distance in meters that a subject can, starting from rest, walk continually and unaided during a 6 minute period is recorded. This distance is also known as the 6 minute walk distance (6MWD). In some applications of the test, an individual subject may be tested more than once over a period of days, and the results averaged. Due to its advantages, the 6MWT has been adopted as a primary clinical endpoint in drug trials involving ambulatory DMD patients. See, for example, Bushby, K, et al., Muscle Nerve 50:477-87 (2014); Mendell, J R, et al., Ann Neurol 79:257-71 (2016); Campbell, C, et al., Muscle Nerve 55(4):458-64 (2017). Usually, in these trials, each subject in the treatment group has his ambulation tested using the 6MWT over a period of months or years to determine if a treatment effect exists.

According to some embodiments of the methods of treatment of the disclosure, therapeutic efficacy is determined statistically by comparing the treatment effect of AAV vectors of the disclosure on the average 6MWT performance of treated subjects, such as those with DMD, in comparison with the average 6MWT performance of untreated control subjects with the same type of dystrophinopathy, such as DMD. Such controls can have been included in the same studies used to evaluate the therapeutic efficacy of AAV vectors of the disclosure, or can be similar subjects drawn from natural history studies of the progression of DMD or other dystrophinopathies. Controls can be age matched (or stratified, for example and without limitation, into those subjects younger than or older than some threshold age, such as 6, 7, 8, 9, or 10 years), matched for status of prior corticosteroid treatment (that is, yes or no, or length of time of previous treatment), matched for baseline performance in the 6MWT before any treatment (except perhaps with corticosteroids) (or stratified, for example and without limitation, into those subjects whose baseline performance is below and above some threshold, such as 200 m, 250 m, 300 m, 350 m, 400 m, 450 m, or 500 m), or some other attribute determined to be clinically relevant.

According to certain embodiments of the methods of treatment of the disclosure, a therapeutically effective dose or amount of an AAV vector of the disclosure is effective to increase the average 6MWD of subjects with dystrophinopathy, such as DMD, by about or at least 5, 10, 15, 20, 25, 30, 35, 40, 45, 50, 55, 60, 65, 70, 75, 80, 85, 90, 95, or 100 meters or more compared to similar matched or stratified controls 3, 6, 9, 12, 15, 18, 21, 24, 27, 30, 33, or 36 months after administration of the vector. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

According to certain embodiments of the methods of treatment of the disclosure, a therapeutically effective dose or amount of an AAV vector of the disclosure is effective to increase the average 6MWD of subjects with dystrophinopathy, such as DMD, by about or at least 5, 10, 15, 20, 25, 30, 35, 40, 45, 50, 55, 60, 65, 70, 75, 80, 85, 90, 95, or 100 meters or more compared to similar matched or stratified controls 30, 60, 90, 120, 150, 180, 210, 240, 270, 300, 330, 360, 390, 420, 450, 480, 510, 540, 570, 600, 630, 660, 690 or 720 days after administration of the vector. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

As an alternative to the 6MWT, therapeutic efficacy can be expressed as reduction in the time it takes a subject to ascend 4 standard sized stairs, a test known as the 4 stair climb test. This test has been used to assess the effectiveness of corticosteroid treatment in DMD patients. Griggs, R C, et al., Arch Neurol 48(4):383-8 (1991). Thus, according to certain embodiments of the methods of treatment of the disclosure, a therapeutically effective dose or amount of an AAV vector of the disclosure is effective to reduce the average time it takes for subjects with dystrophinopathy, such as DMD, to perform the 4 stair climb test by about or at least 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, or 4.0 seconds or more compared to similar matched or stratified controls 3, 6, 9, 12, 15, 18, 21, 24, 27, 30, 33, or 36 months after administration of the vector. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

In related embodiments of the methods of treatment of the disclosure, a therapeutically effective dose or amount of an AAV vector of the disclosure is effective to reduce the average time it takes for subjects with dystrophinopathy, such as DMD, to perform the 4 stair climb test by about or at least 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, or 4.0 seconds or more compared to similar matched or stratified controls 30, 60, 90, 120, 150, 180, 210, 240, 270, 300, 330, 360, 390, 420, 450, 480, 510, 540, 570, 600, 630, 660, 690 or 720 days after administration of the vector. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

Therapeutic efficacy can also be expressed as a reduction over time in the percentage of subjects that experience loss of ambulation a specified time after treatment compared to controls. Loss of ambulation is defined as start of continuous reliance on wheelchair use. Thus, according to yet other embodiments of the methods of treatment of the disclosure, a therapeutically effective dose or amount of an AAV vector of the disclosure reduces, 3, 6, 9, 12, 15, 18, 21, 24, 27, 30, 33, or 36 months after administration to subjects with dystrophinopathy, such as DMD, the average number of subjects that have lost ambulation by at least 5%, 10%, 15%, 20%, 25%, 30%, 35%, 40%, 45%, 50%, 55%, 60%, 65% or more compared to similar matched or stratified controls. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

In some embodiments of the methods of treatment of the disclosure, a therapeutically effective dose or amount of an AAV vector of the disclosure is effective to delay the onset of one or more symptoms in a subject having a dystrophinopathy, such as DMD. Diagnosis before onset of symptoms can be accomplished through prenatal, perinatal or postnatal genetic testing for mutations in the DMD gene. According to certain embodiments, treatment with an AAV vector of the disclosure is effective to delay onset of one or more symptoms of DMD by at least or about 3, 4, 5, 6, 7, 8, 9, 10, 12, 14, 15, 16, 18, 20, 22, 24, 25, 26, 28, 30, 32, 34, 35, 36, 38, 40, 42, 44, 45, 46, 48, 50, 52, 54, 55, 56, 28, 60, 62, 64, 65, 66, 68, 70, 72, 74, 75, 76, 78, or 80 months, or more compared to similar matched or stratified controls. As appreciated by those of ordinary skill, early symptoms of DMD include without limitation delay in walking ability (to an average age of about 18 months, compared to an average of 12-15 months in babies without DMD); difficulty jumping, running or climbing stairs; proneness to falling; proximal muscle weakness, evidenced, for example, by exhibiting the Gowers' maneuver when rising from the floor; enlarged calves, due to pseudohypertrophy; waddling gait due to subjects' walking on toes and/or balls of feet; tendency to maintain balance by sticking out bellies and pulling back shoulders; and cognitive impairments, such as diminished receptive language, expressive language, visuospatial ability, fine motor skills, attention, and memory skills. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

Therapeutic efficacy can also be expressed as a reduction over time in the percentage of vector treated subjects that experience an increase in the amount of adipose tissue that replaces lean muscle tissue compared to untreated controls. In some embodiments, this progression toward increased adiposity can be determined using MRI analysis of the leg muscles of DMD patients and expressed as the fat fraction (FF), as explained further in Willcocks, R J, et al., Multicenter prospective longitudinal study of magnetic resonance biomarkers in a large Duchenne muscular dystrophy cohort, Ann Neurol 79:535-47 (2016). In related embodiments, treatment of DMD subjects with an AAV vector of the disclosure is effective to reduce the average FF in their lower extremities as determined by MRI by about or at least 5%, 10%, 15%, 20%, 25%, 30%, 35%, 40%, 45%, 50%, 55%, 60%, 65%, 70%, 75%, or more 3, 6, 9, 12, 15, 18, 21, 24, 27, 30, 33, or 36 months after treatment compared to matched controls. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

In some embodiments, a therapeutically effective dose or amount of an AAV vector of the disclosure is one that results in at least 5%, 10%, 15%, 20%, 25%, 30%, 35%, 40%, 45%, 50%, 55%, 60%, 65%, 70%, 75%, 80%, 85%, 90%, or more of skeletal muscle fibers expressing the mini-dystrophin protein 3, 6, 9, 12, 15, 18, 21, 24, 27, 30, 33, or 36 months after treatment. The percentage of muscle fibers that are positive for mini-dystrophin protein expression may be determined by immunolabeling sections of biopsied muscle from treated subjects with an anti-dystrophin antibody capable of specifically binding the mini-dystrophin protein. Suitable immunolabeling techniques are described in the Examples, and are familiar to those of ordinary skill in the art. Exemplary muscles of treated subjects from which biopsies may be taken include bicep, deltoid, and quadriceps, although other muscles may be biopsied as well. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

In some embodiments, a dose or amount of an AAV vector of the disclosure for treating dystrophinopathy, such as muscular dystrophy, such as DMD, is determined to be therapeutically effective and at the same time causes either no cellular (T cell) immune response specific for the mini-dystrophin protein in treated subjects, or in only a low percentage of such subjects. Existence or extent of a T cell response against the mini-dystrophin protein can be determined using the ELISPOT assay to detect peripheral blood mononuclear cells (PBMCs) isolated from subject blood that produce gamma interferon (IFNγ) in response to exposure to an overlapping peptide library covering the mini-dystrophin protein amino acid sequence. In certain embodiments, the threshold for a positive IFNγ response can be set as greater than 50 spot-forming cells per million PBMCs tested. Use of other assays to detect a T cell response against the mini-dystrophin protein are also possible including without limitation detection of T cell infiltrates in biopsies of muscle or other tissues expressing mini-dystrophin protein obtained from vector treated subjects. Subjects can be human subjects or animal subjects, such as animal models of DMD, such as the mdx mouse, mdx rat, or GRMD dog models. In other embodiments, a dose or amount of an AAV vector of the disclosure for treating dystrophinopathy, such as muscular dystrophy, such as DMD, is determined to be therapeutically effective and at the same time causes either no inflammatory response against the capsid, vector genome (or any component thereof), or mini-dystrophin protein expressed by transduced cells, or in only a low percentage of such subjects. Without wishing to be bound by any particular theory of operation, inflammation in response to an AAV vector may be caused by an innate immune response. Inflammation, if any exists, in the muscles of vector treated subjects can be detected using magnetic resonance imaging. See, for example, J Garcia, Skeletal Radiol 29:425-38 (2000) and Schulze, M, et al., Am J Radiol 192:1708-16 (2009). Subjects can be human subjects or animal subjects, such as animal models of DMD, such as the mdx mouse, mdx rat, or GRMD dog models. In some of the embodiments described above, existence or absence of cellular immune response or inflammation is determined 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months after treatment, or some other time after treatment. In related embodiments, a low percentage of subjects exhibiting a cellular immune response to the mini-dystrophin protein would be less than or equal to about 0%, 1%, 2%, 3%, 4%, 5%, 6%, 7%, 8%, 9%, 10%, 11%, 12%, 13%, 14%, 15%, 16%, 17%, 18%, 19% or 20% of subjects administered vector. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

In related embodiments, a dose or amount of an AAV vector of the disclosure for treating dystrophinopathy, such as muscular dystrophy, such as DMD, is therapeutically effective without need for concomitant immune suppression in treated subjects. Thus, in certain embodiments, treatment of a subject with dystrophinopathy, such as DMD, is effective without need to administer to the subject before, during or after treatment with AAV vector one or more immune-suppressing drugs (apart from steroid treatment, which is the current standard of care). Exemplary immune-suppressing drugs include but are not limited to calcineurin inhibitors, such as tacrolimus and cyclosporin, antiproliferative agents, such as mycophenolate, leflunomide, and azathioprine, or mTOR inhibitors, such as sirolimus and everolimus.

As explored in greater detail in the Examples, efficacy of the AAV vectors of the disclosure, including without limitation the vector designated as AAV9.hCK.Hopti-Dys3978.spA, can be tested in animal models of Duchenne muscular dystrophy, and results used to predict efficacious doses of such vectors in human DMD patients. Various animal models are known in the art, including the mdx mouse model, the Golden Retriever muscular dystrophy model, and more recently, the $Dmd^{mdx}$ rat model, which is described in greater detail in the Examples.

Based on the $Dmd^{mdx}$ rat model, effective doses of AAV vectors of the disclosure, including the vector designated as AAV9.hCK.Hopti-Dys3978.spA, can be established with respect to various biological parameters and aspects of the disease course in the rats.

Thus, according to certain embodiments of the disclosure, treatment of $Dmd^{mdx}$ rats with a dose of AAV9.hCK.Hopti-Dys3978.spA of at least $1\times10^{14}$ vg/kg or $3\times10^{14}$ vg/kg is effective to reduce serum AST, ALT, LDH, or total creatine kinase levels at 3 months or 6 months post-injection compared to controls.

In other embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to reduce fibrosis in biceps femoris, diaphragm, or heart muscle at 3 months or 6 months post-injection compared to controls.

In yet other embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to increase forelimb grip force at 3 months or 6 months post-injection compared to controls.

According to other embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to reduce muscle fatigue as measured over 5 closely spaced trials testing forelimb grip force at 3 months or 6 months post-injection compared to controls.

In some other embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to increase the left ventricular ejection fraction as measured using echocardiography at 6 months post-injection compared to controls.

In other embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to increase the ratio of the velocity of early to late left ventricular filling (i.e., E/A ratio) as measured using echocardiography at 3 months or 6 months post-injection compared to controls.

According to some embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to decrease the isovolumetric relaxation time (IVRT) or the time in milliseconds between peak E velocity and its return to baseline (i.e., the E wave deceleration time (DT)) as measured using echocardiography at 3 months or 6 months post-injection compared to controls.

In each of the foregoing embodiments, the increase or decrease of the physiologic measurement in vector-treated animals compared to control animals can, in some embodiments, be tested for statistical significance. The choice of which statistical test to apply is within the knowledge of those ordinarily skilled in the art. Where a p-value is adopted as the way in which to assess statistical significance, such p-values, once calculated, can be compared to a predefined significance level, and if the p-value is smaller than the significance level, the treatment effect can be determined to be statistically significant. In some embodiments, the significance level can be predefined as 0.25, 0.20, 0.15, 0.10, 0.05, 0.04, 0.03, 0.02, 0.01, 0.005, or some other significance level. Thus, in an exemplary non-limiting embodiment, where the significance level is predefined as 0.05, then calculation of a $p\text{-value}<0.05$ would be interpreted to represent a statistically significant difference between vector-treated and control groups.

In each of the foregoing embodiments, the controls can be age matched animals of the same sex and genetic background that are untreated, or treated only with vehicle and not vector. Other controls are also possible, however.

In some other embodiments, treatment of $Dmd^{mdx}$ rats with a dose of AAV9.hCK.Hopti-Dys3978.spA of at least $3\times10^{14}$ vg/kg is effective to transduce biceps femoris, diaphragm, heart muscle, or other striated muscles, and express the mini-dystrophin protein encoded by the opti-Dys3978 gene without inducing a cellular immune response against the mini-dystrophin protein by 3 months or 6 months post-injection. Cellular immune response against the mini-dystrophin protein can be assessed by isolating splenocytes, or blood lymphocytes, such as peripheral blood mononuclear cells (PBMCs), from test animals, incubating the cells with peptides from an overlapping peptide library covering the mini-dystrophin protein amino acid sequence (for example, peptides 15 amino acids long overlapping by 10 amino acids each) in pools (for example, 5 pools), and determining whether the cells produce gamma interferon (IFNγ) in response to being exposed to the peptides. Production of IFNγ can be determined using the ELISPOT assay according to the knowledge of those ordinarily skilled in the art. See, for example, Smith, J G, et al., Clin Vaccine Immunol 8(5):871-9 (2001), Schmittel A, et al., J Immunol Methods 247:17-24 (2001), and Marino, A T, et al., Measuring immune responses to recombinant AAV gene transfer, Ch. 11, pp. 259-72, Adeno-Associated Virus Methods and Protocols, Ed. R O Snyder and P Moullier, Humana Press (2011). In certain embodiments, the threshold for a positive IFNγ response can be set as greater than 50 spot-forming cells per million cells tested, or in other embodiments, as at least 3-times the number of spot-forming cells detected using a negative control (for example, medium only without added peptides), so that a negative response would be considered below these thresholds.

In some embodiments of the methods of treatment of the present disclosure, an AAV vector for treating dystrophinopathy, such as DMD, is administered to a subject in need of treatment for dystrophinopathy, such as DMD, jointly with at least a second agent established or believed to be effective for treating dystrophinopathy, such as DMD. Joint administration of the AAV vector means treating a subject before, contemporaneously with, or after treatment of the second agent. According to certain embodiments, the AAV vector is jointly administered with an antisense oligonucleotide that causes exon skipping of the DMD gene, for example of exon 51 of the dystrophin gene, or some other exon of the dystrophin gene. Agents that cause skipping of exon 51 of the dystrophin gene include drisapersen and eteplirsen, but others are possible. In other embodiments, the AAV vector is jointly administered with an agent that inhibits myostatin function in the subject, such as an anti-myostatin antibody, examples of which are provided in U.S. Pat. Nos. 7,888,486, 8,992,913, and 8,415,459. In other embodiments, where the dystrophinopathy of the subject can be attributed to a nonsense mutation in the dystrophin gene, the AAV vector is jointly administered with an agent that promote ribosomal read-through of nonsense mutations, such as ataluren, or with an agent that suppresses premature stop codons, such as an aminoglycoside, such as gentamicin. In other embodiments, the AAV vector is jointly administered with an anabolic steroid, such as oxandrolone. And in yet other embodiments, the AAV vector is jointly administered with a corticosteroid, such as without limitation prednisone, deflazacort, or prednisolone. In some embodiments of these methods, the AAV vector is an AAV9 vector comprising a genome including a human codon-optimized gene encoding a mini-dystrophin protein, such as, without limitation, the vector designated as AAV9.hCK.Hopti-Dys3978.spA.

Pharmaceutical Formulations and Modes of Administration

Virus vectors and capsids according to the present invention find use in both veterinary and human medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults. Optionally, the subject is "in need of" the methods of the present invention, e.g., because the subject has or is believed at risk for a disorder including those described herein or that would benefit from the delivery of a polynucleotide including those described herein. As a further option, the subject can be a laboratory animal and/or an animal model of disease.

In particular embodiments, the present invention provides a pharmaceutical composition comprising a virus vector (such as an rAAV particle) and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a polynucleotide encoding mini-dystrophin to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about 105 infectious units are introduced to the cell.

The cell(s) into which the virus vector is introduced can be of any type, including but not limited to muscle cells (e.g., skeletal muscle cells, cardiac muscle cells, smooth muscle cells and/or diaphragm muscle cells), stem cells, germ cells, and the like. In representative embodiments, the cell can be any progenitor cell. As a further possibility, the cell can be a stem cell (e.g., muscle stem cell). Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

A further aspect of the invention is a method of administering the virus vector to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

In certain embodiments, an AAV vector or particle of the disclosure can be administered to a subject in compositions comprising empty AAV capsids of the same or a different serotype. Empty capsids are AAV capsids comprising the typical arrangement and ratios of VP1, VP2 and VP3 capsid proteins, but do not contain a vector genome. Without wishing to be bound by any particular theory of operation, it is hypothesized that the presence of empty capsids can reduce the immune response against the capsid of the AAV vector, and thereby increase transduction efficiency. Empty capsids can occur naturally in a preparation of AAV vector, or be added in known quantities to achieve known ratios of empty capsids to AAV vector (that is, capsids containing vector genomes). Preparation, purification and quantitation of empty capsids is within the knowledge of those ordinarily skilled in the art. Compositions comprising AAV vectors of the disclosure and empty capsids can be formulated with an excess of empty capsids relative to AAV vectors, or an excess of genome containing AAV vectors relative to empty capsids. Thus, in some embodiments, compositions of the disclosure comprise AAV vectors of the disclosure and empty capsids of the same or a different serotype, wherein the ratio of empty capsids to AAV vectors is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10 to 1, or some other ratio.

In other embodiments, the disclosure provides exemplary efficacious doses of AAV vector particles for treating dystrophinopathy, such as muscular dystrophy, such as DMD, quantified as vector genomes (vg) per kilogram of subject body weight (kg), abbreviated vg/kg. According to certain embodiments, an efficacious dose of an AAV vector of the disclosure, including those comprising an AAV9 capsid and a genome including a human codon-optimized gene encoding a mini-dystrophin protein, such as, without limitation, the vector designated as AAV9.hCK.Hopti-Dys3978.spA, is about $1\times10^{12}$ vg/kg, $2\times10^{12}$ vg/kg, $3\times10^{12}$ vg/kg, $4\times10^{12}$ vg/kg, $5\times10^{12}$ vg/kg, $6\times10^{12}$ vg/kg, $7\times10^{12}$ vg/kg, $8\times10^{12}$ vg/kg, $9\times10^{12}$ vg/kg, $1\times10^{13}$ vg/kg, $2\times10^{13}$ vg/kg, $3\times10^{13}$ vg/kg, $4\times10^{13}$ vg/kg, $5\times10^{13}$ vg/kg, $6\times10^{13}$ vg/kg, $7\times10^{13}$ vg/kg, $8\times10^{13}$ vg/kg, $9\times10^{13}$ vg/kg, $1\times10^{14}$ vg/kg, $1.5\times10^{14}$ vg/kg, $2\times10^{14}$ vg/kg, $2.5\times10^{14}$ vg/kg, $3\times10^{14}$ vg/kg, $3.5\times10^{14}$ vg/kg, $4\times10^{14}$ vg/kg, $5\times10^{14}$ vg/kg, $6\times10^{14}$ vg/kg, $7\times10^{14}$ vg/kg, $8\times10^{14}$ vg/kg, or $9\times10^{14}$ vg/kg, or some other dose. In any of these embodiments, the AAV vector may be administered to a subject in a pharmaceutically acceptable composition alone, or with empty capsids of the same capsid serotype at an empty capsid to vector ratio of about 0.5:1, 1:1, 2:1, 3:1, 4:1, 5:1, 6:1, 7:1, 8:1, 9:1, 10:1, or some other ratio.

Exemplary modes of administration include oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular (including administration to skeletal, diaphragm and/or cardiac muscle), intrapleural, intracerebral, and intra-articular), topical (e.g., to both skin and mucosal surfaces, including airway surfaces, and transdermal administration), intra-lymphatic, and the like, as well as direct tissue or organ injection (e.g., to skeletal muscle, cardiac muscle, or diaphragm muscle).

Administration can be to any site in a subject, including, without limitation, a site selected from the group consisting of a skeletal muscle, a smooth muscle, the heart, and the diaphragm.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* $10^5$: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration. In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Administration to smooth muscle can be by any suitable method including intravenous administration, intra-arterial administration, and/or intra-peritoneal administration. In one embodiment, administration can be to endothelial cells present in, near, and/or on smooth muscle.

Delivery to a target tissue can also be achieved by delivering a depot comprising the virus vector and/or capsid. In representative embodiments, a depot comprising the virus vector and/or capsid is implanted into skeletal, smooth, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector according to the present invention is administered to skeletal muscle, diaphragm muscle and/or cardiac muscle (e.g., to treat and/or prevent muscular dystrophy).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, or a micro-dystrophin. In particular embodiments, the virus vector can be administered to skeletal, diaphragm and/or cardiac muscle as described elsewhere herein.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. 2004-0013645).

Having described the present invention, the same will be explained in greater detail in the following examples, which are included herein for illustration purposes only, and which are not intended to be limiting to the invention.

EXAMPLE 1

Synthesis of Codon-Optimized Human Mini-Dystrophin Genes

Previously we generated a number of miniature versions of human dystrophin gene by PCR cloning of human muscle dystrophin cDNA, generating mini-dystrophin genes that have large deletions in the central rod domain and nearly complete deletion of the C-terminal region of the dystrophin coding sequence (Wang et al., *Proc. Natl. Acad. Sci., USA* 97:13714 (2000); U.S. Pat. Nos. 7,001,761 and 7,510,867). These mini-dystrophin genes were tested to be highly functional in vivo in DMD mdx mouse models (Watchko et al., *Human Gene Therapy* 13:1451 (2002)). One of these mini-dystrophin proteins, named Δ3990, was described in U.S. Pat. No. 7,510,867 under SEQ ID NO:6. The protein sequence of Δ3990 and the DNA encoding it are provided herein by SEQ ID NO:27 and SEQ ID NO:28, respectively.

Figure 1:
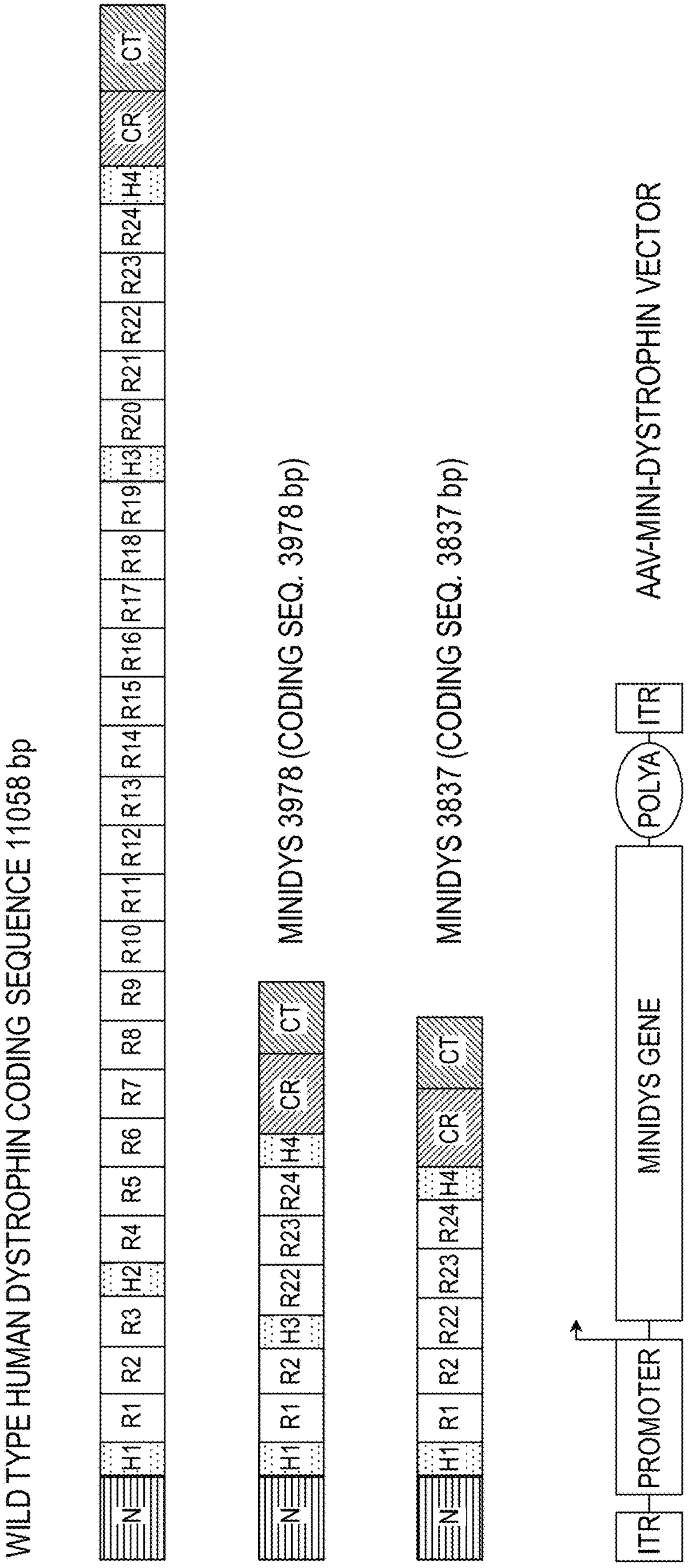
FIG. 1 shows construction of highly truncated mini-dystrophin genes. Wild-type muscle dystrophin has four major domains: the N-terminal domain (N); the central rod domain, which contains 24 rod repeats (R) and four hinges (H); a cysteine-rich (CR) domain, and the carboxy-terminal (CT) domain. The mini-dystrophin genes were constructed by deleting a large portion of the central rods and hinges and most of the CT domain. The mini-dystrophin genes were codon-optimized, fully synthesized and subsequently cloned between a CMV promoter or a muscle-specific synthetic hybrid promoter at the 5' end of the gene, and a small poly(A) sequence at the 3' end of the gene. This gene segment, containing promoter, codon-optimized mini-dystrophin gene, and polyA signal, was then cloned into a plasmid containing left and right AAV inverted terminal repeats (ITRs) so that the gene segment was flanked by the ITRs.

A modification of the Δ3990 mini-dystrophin was also designed, codon-optimized, and tested for activity. This new human mini-dystrophin, called Dys3978, is 1325 amino acids in length, and includes the following portions or subdomains from wildtype full-length human muscle dystrophin (SEQ ID NO:25): the N-terminus and actin-binding domain (ABD), hinge H1, rods R1 and R2, hinge H3, rods R22, R23 and R24, hinge H4, the cysteine-rich domain (CR domain) and part of the carboxy-terminal domain (CT domain). The amino acid sequence of this protein is provided by SEQ ID NO:7 and is illustrated schematically in FIG. 1. To reduce potential immunogenicity, the last four amino acids at the C-terminus of the Δ3990 protein were deleted. In creating Δ3990, this sequence had been formed by joining part of the amino-terminal end of the dystrophin carboxy-terminal domain (ending at P3409) with the last three amino acids of dystrophin (3683-3685, or DTM). This stretch of four amino acids has no known function and could function as a new epitope because the sequence does not occur in wildtype dystrophin. In addition, a valine at amino acid position 2 in Δ3990, not present in wildtype dystrophin, but which resulted from creation of a consensus Kozak initiation sequence around the start codon of Δ3990 was changed to the leucine ordinarily present in dystrophin. Thus there are 5 amino acid differences between Δ3990 and Dys3978. An amino acid sequence alignment between Δ3990 and Dys3978 is provided in FIGS. 55A-55C.

The gene encoding Dys3978 was constructed by combining subsequences from the wildtype dystrophin coding sequence corresponding to the protein subdomains described above. The resulting gene is provided by SEQ ID NO:26. To increase the expression of Dys3978, the gene sequence was codon-optimized using human codon algorithms. The resulting human codon-optimized gene, called Hopti-Dys3978, is provided as SEQ ID NO:1. A canine codon-optimized gene encoding Dys3978, called Copti-Dys3978, was also generated, the sequence of which is provided as SEQ ID NO:3. An alignment comparing the DNA sequences of Hopti-Dys3978 and the non-codon-optimized gene encoding Δ3990 is provided in FIGS. 56A-56I.

Among other changes, codon-optimization of the gene encoding Dys3978 increased total GC content from about 46% in the non-codon-optimized gene to about 61% in the human codon-optimized gene (i.e., Hopti-Dys3978). Increasing GC content can result in increased mRNA levels in mammalian cells. See, for example, Grzegorz, K, et al., PLoS Biol, 4(6):e180 (2006); and Newman, Z R, et al., PNAS, E1362-71 (2016). Codon-optimization also increased the codon adaptation index (CAI) and included addition of a Kozak consensus transcription initiation recognition site at the beginning of the coding sequence.

Figure 2:
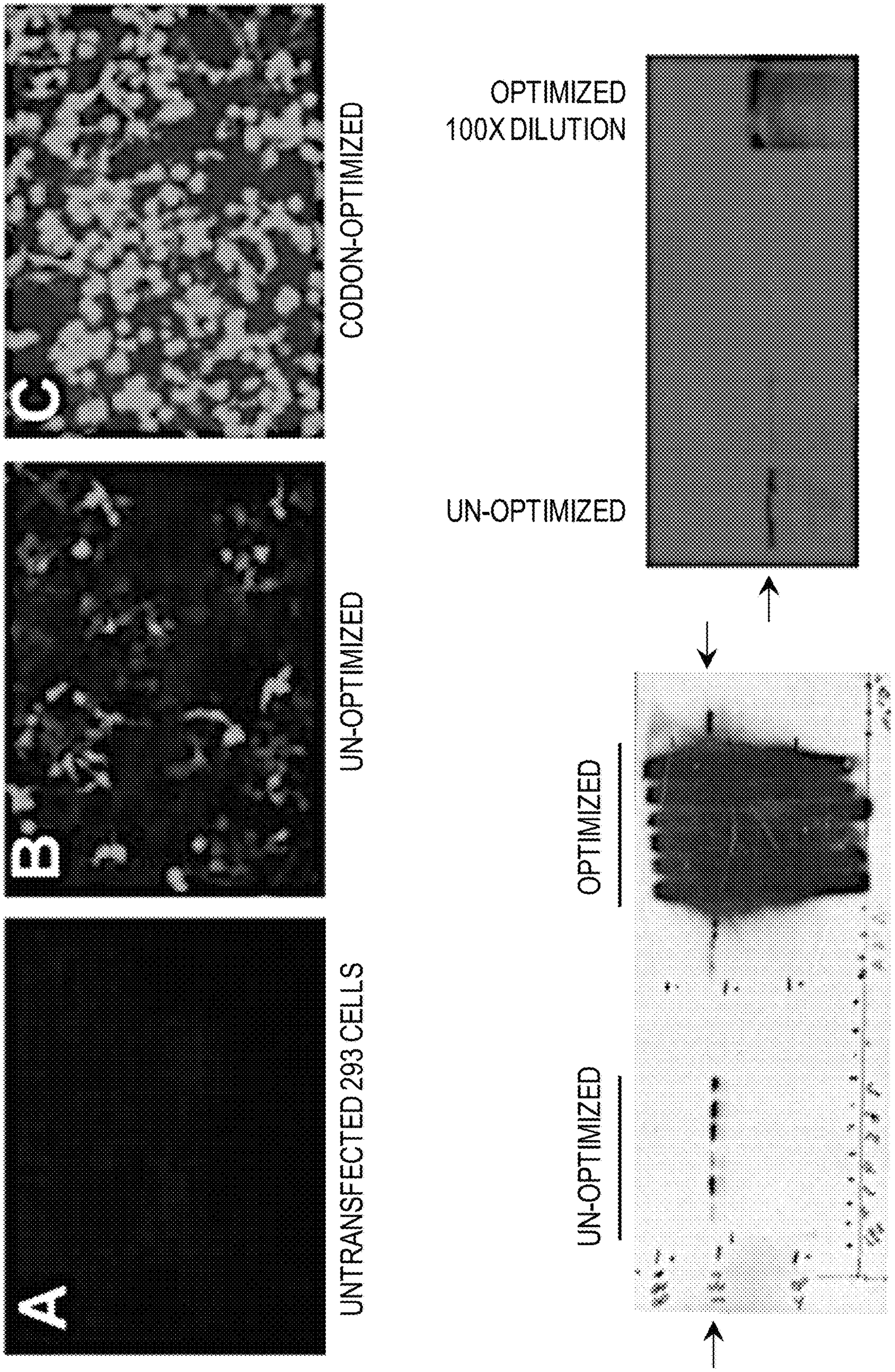
FIG. 2 shows codon-optimization effectively enhances mini-dystrophin gene expression. The top panels show immunofluorescence (IF) staining of mini-dystrophin protein in (A) untransfected 293 cells or after transfection of original un-optimized (B), or optimized (C) mini-dystrophin Dys3978 vector plasmids. The bottom panels show Western blots of the mini-dystrophin in the transfected 293 cells. Blot on the left used an equal amount of cell lysates and shows overwhelming expression by the optimized cDNA. Blot on the right used a 100× dilution of the cell lysate from 293 cells transfected with optimized mini-dystrophin cDNA, while the non-optimized sample was not diluted. Note that the signal of the optimized one is still stronger after 100× dilution.

To examine if human codon optimization could enhance gene expression, the Hopti-Dys3978 gene was cloned into an AAV vector expression cassette containing the constitutively active CMV promoter and a small synthetic polyadenylation (polyA) signal sequence (SEQ ID NO: 6). After transfection into human HEK 293 cells, the vector plasmid containing the Hopti-Dys3978 gene showed surprisingly greater protein expression than the non-optimized gene encoding Dys3978, as determined qualitatively using immunofluorescent staining and Western blot against dystrophin protein (FIG. 2).

A gene encoding a human mini-dystrophin similar in structure to Dys3978, except that hinge H3 is absent, was also generated and codon-optimized. This gene, called Hopti-Dys3837 (SEQ ID NO: 2) encodes a human mini-dystrophin protein of 1278 amino acids called Dys3837 (SEQ ID NO: 8), which is also illustrated schematically in FIG. 1.

For other experiments described herein, the human and canine codon-optimized Dys3978 genes were placed under the control of one of two different synthetic muscle-specific promoter and enhancer combinations derived from the muscle creatine kinase gene identified below:

1) Synthetic hybrid muscle-specific promoter (hCK) (SEQ ID NO: 4); and
2) Synthetic hybrid muscle-specific promoter plus (hCK-plus) (SEQ ID NO: 5);

For use in the experiments, the following vectors were constructed using standard molecular cloning techniques. The gene expression cassettes of the specified promoter, mini-dystrophin gene and polyA sequence were cloned into an AAV vector plasmid backbone containing AAV2 inverted terminal repeats (ITRs) flanking the expression cassette.

```
1) AAV-CMV-Hopti-Dys3978
                                        (SEQ ID NO: 9)
2) AAV-hCK-Hopti-Dys3978
                                       (SEQ ID NO: 10)
3) AAV-hCK-Hopti-Dys3837
                                       (SEQ ID NO: 11)
4) AAV-hCKplus-Hopti-Dys3837
                                       (SEQ ID NO: 12)
5) AAV-hCK-Copti-Dys3978
```

EXAMPLE 2

CMV-Hopti-Dys3978 in Dystrophin/Utrophin Double Knockout Mice

Figure 3:
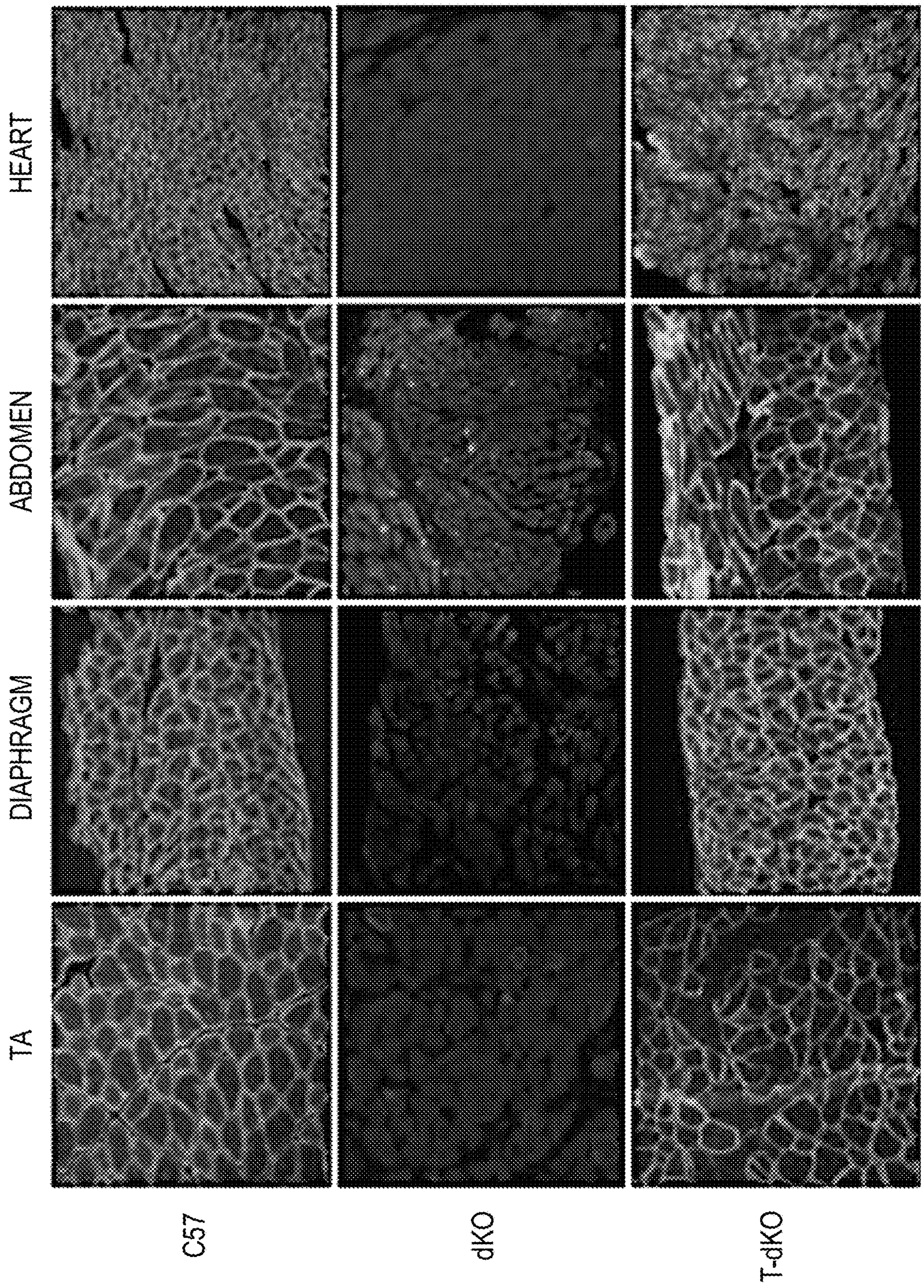
FIG. 3 shows IF staining of human mini-dystrophin expression in dystrophin/utrophin double knockout (dKO) mice treated with AAV9 vector. Muscle and heart samples from wild-type control mice C57BL/10 (C57), untreated dKO mice, and AAV9-CMV-Hopti-Dys3978 treated dKO mice (T-dKO) were thin-sectioned and stained with an antibody that also recognizes both the mouse wild-type dystrophin and human mini-dystrophin protein. Highly efficient expression was achieved in all samples examined.
Figure 4:
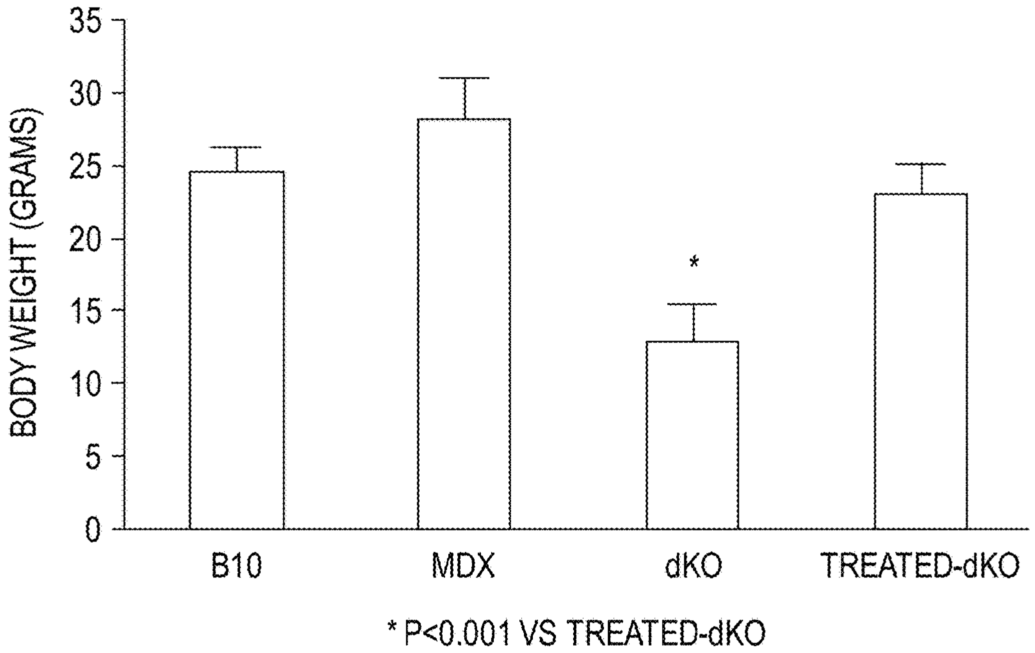
FIG. 4 shows normalization of body weight of dKO mice as a result of AAV9-CMV-Hopti-Dys3978 treatment. Data were obtained at 4 months of age from wild-type control B10 mice (C57BL/10), untreated mdx mice, untreated dKO mice, and vector-treated dKO mice.
Figure 6A:
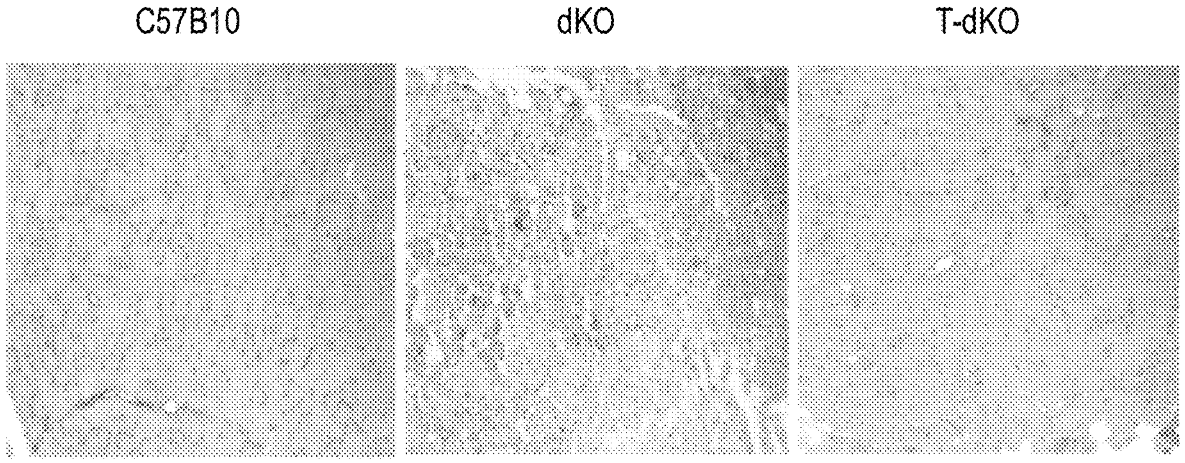
FIGS. 6A-6B show amelioration of dystrophic pathology of dKO mice as a result of AAV9-CMV-Hopti-Dys3978 treatment.
Figure 5:
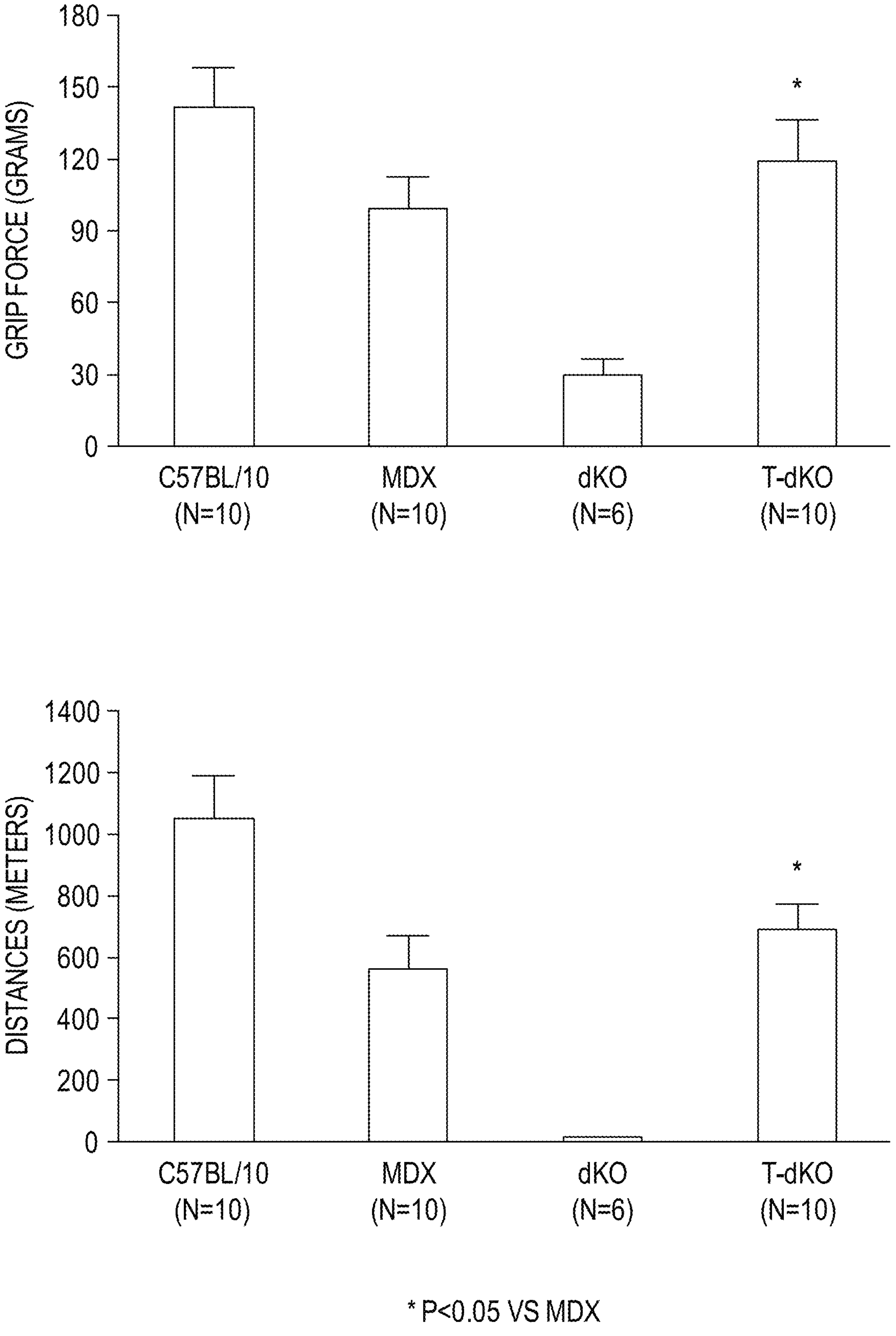
FIG. 5 shows improvement of grip force and treadmill running of dKO mice as a result of AAV9-CMV-Hopti-Dys3978 treatment. Data were obtained at 3 months of age from wild-type control B10 mice (C57BL/10), untreated mdx mice, untreated dKO mice, and vector-treated dKO mice (T-dKO).
Figure 6B:
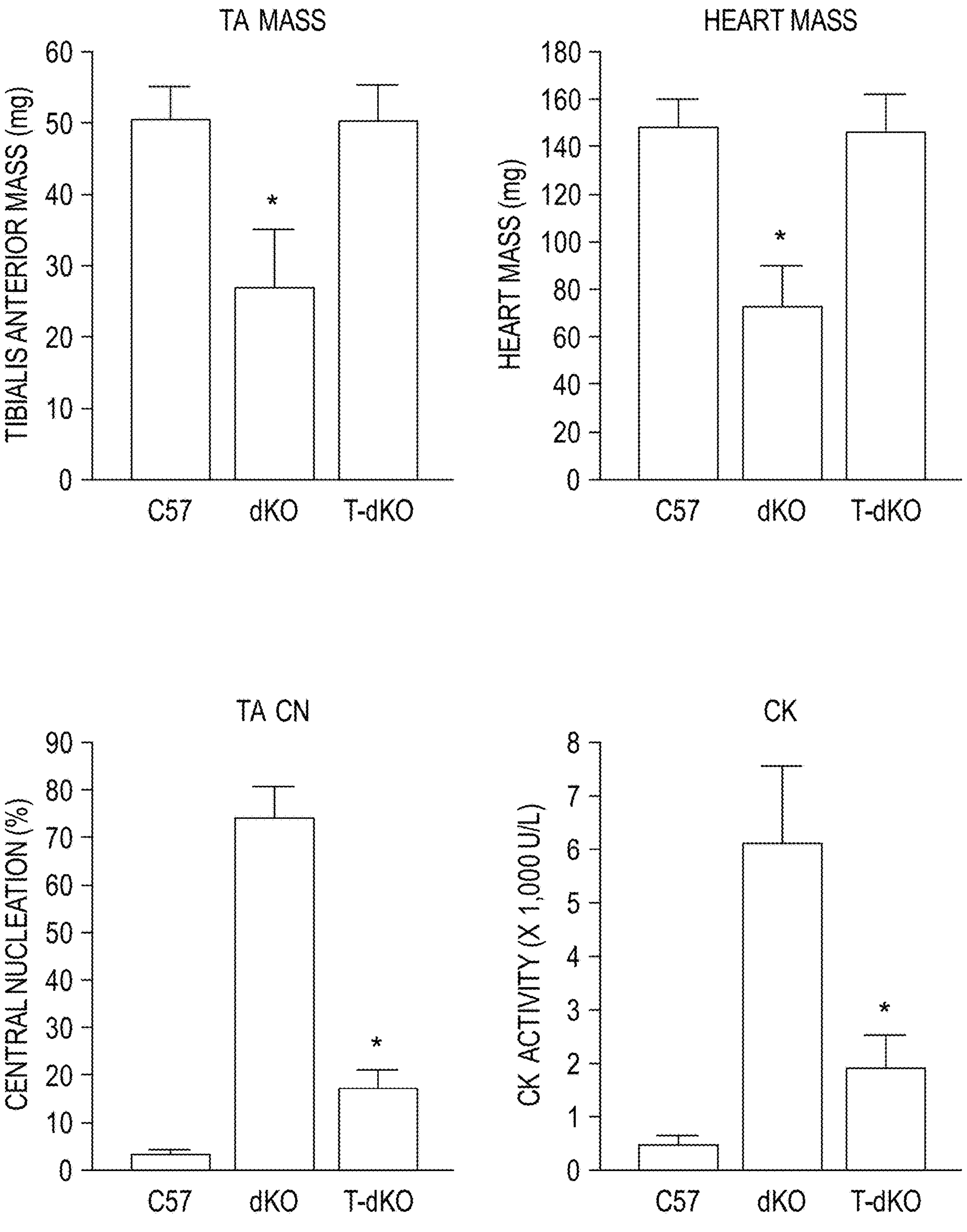
Figure 7:
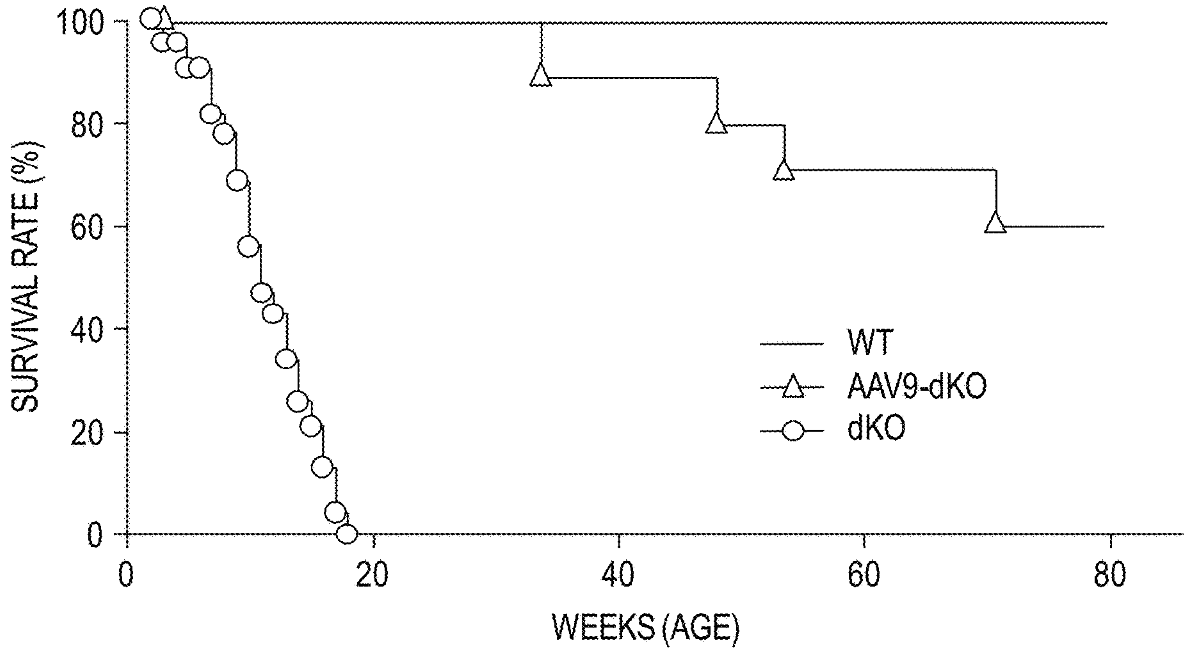
FIG. 7 shows survival curves of dKO mice treated with human codon-optimized mini-dystrophin Dys3978 vector (AAV9-CMV-Hopti-Dys3978) compared to untreated dKO mice and wildtype mice. Greater than 50% of the treated dKO mice survived longer than 80 weeks (duration of the experiment).

The loss of dystrophin in the patients of Duchenne muscular dystrophy (DMD) results in devastating skeletal muscle degeneration and cardiomyopathy. Mdx mice lacking only dystrophin have a much milder phenotype, whereas double knockout (dKO) mice lacking both dystrophin and its homolog utrophin exhibit the similarly severe dystrophic clinical signs seen in DMD patients. It was previously demonstrated that intraperitoneal injection in neonatal homozygous dKO mice with $3\times10^{11}$ vg/mouse of AAV1-CMV-Δ3990 (not codon-optimized) was able to partially restore growth, functions and prolong life-span for a few months (50% survival rate at 22 weeks) (see FIG. 6B from Wang et al., *J. Orthop. Res,* 27:421 (2009)). Here, the therapeutic effects of systemic delivery of human codon-optimized Hopti-Dys3978 gene were evaluated using AAV9 as the capsid. The results demonstrate that a single systemic administration (IP) of AAV9-CMV-Hopti-Dys3978 at about $2\times10^{13}$ vg/kg into 1-week-old neonatal dKO mice led to widespread expression of the mini-dystrophin gene in skeletal muscles and in the entire heart muscle (FIG. 3). The AAV9-treated dKO mice showed near normal growth curve and body weight (FIG. 4) and significantly improved muscle function as evaluated by the grip force and treadmill running tests (FIG. 5). The treated dKO mice also showed amelioration of dystrophic pathology (FIGS. 6A-6B) and great improvement of overall health. When compared to the dKO mice treated with an AAV1 vector expressing non-codon-optimized Δ3990, the dKO mice treated with Hopti-Dys3978 gene showed a much prolonged life-span (50% survival rate: 22 weeks vs. more than 80 weeks) (FIG. 7). Unexpectedly, the fertility of both male and female dKO mice were restored (Table 1), suggesting overall function improvement and possibly improvement in smooth muscle function as well.

TABLE 1

| Mini-dystrophin restores fertility of dKO mice | | |
|---|---|---|
| Breeding pairs: | | |
| Pair #1: | T-dKO male X T-dKO female | 5 pups |
| Pair #2: | T-dKO male X T-dKO female | 4 pups |
| Pair #3: | T-dKO male X T-dKO female | 0 pups |
| Pair #4: | mdx male X T-dKO female | 5 pups |
| Pair #5: | mdx male X T-dKO female | 6 pups |

The untreated dKO mice are completely infertile. However fertility was restored by AAV-CMV-Hopti-Dys3978 in both males and females of treated dKO (T-dKO) mice.

The results described above demonstrate that systemic delivery of codon-optimized Hopti-Dys3978 gene was more efficacious than the non-codon optimized Δ3990 gene.

Figure 8:
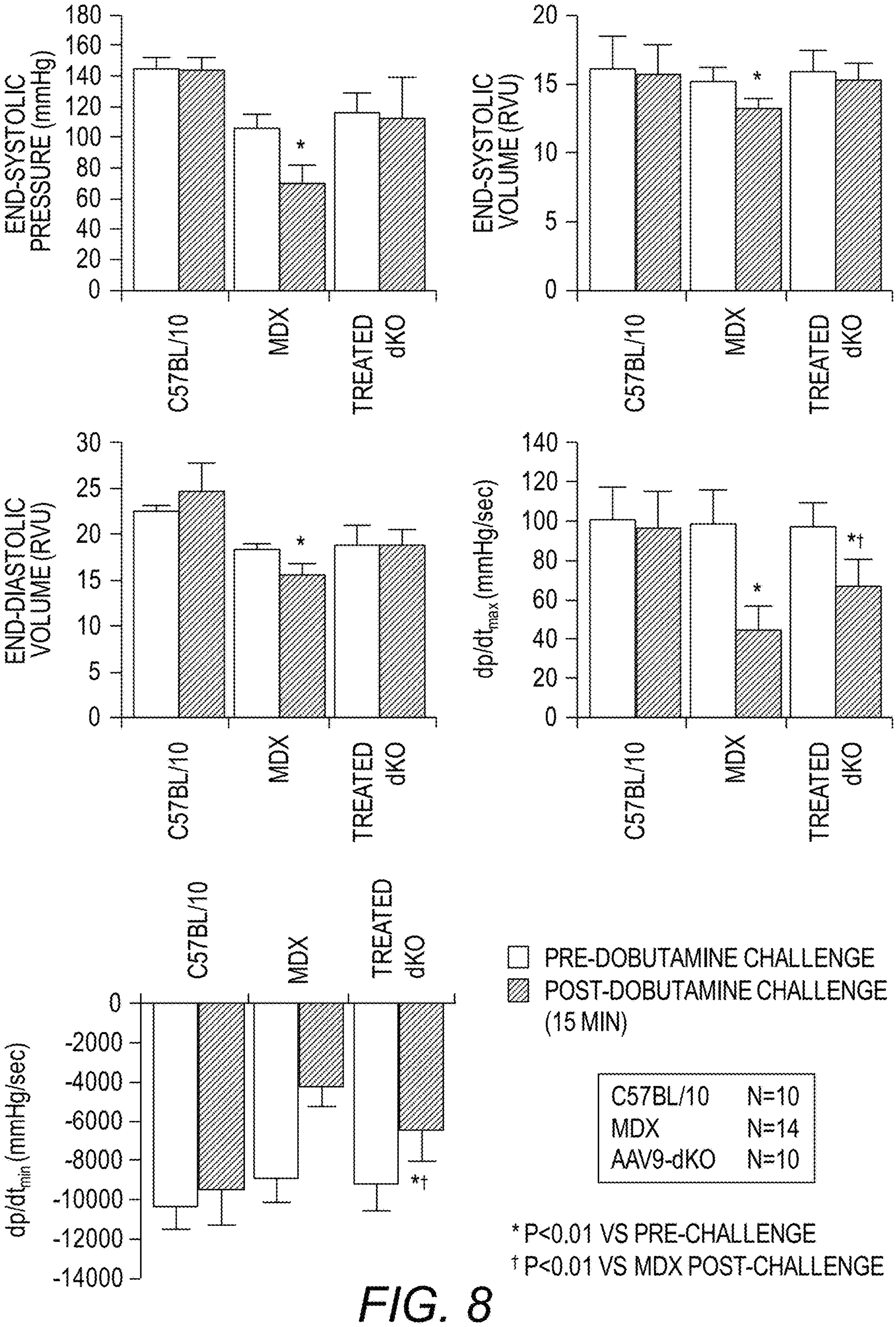
FIG. 8 shows improvement in cardiac functions of dKO mice as a result of AAV9-CMV-Hopti-Dys3978 treatment. Hemodynamic analysis was performed on wild-type control C57BL/10 mice, untreated mdx mice, and AAV9 vector-treated dKO mice. The untreated dKO mice were too sick to sustain the procedure. Data were collected from the three groups of mice without or with dobutamine challenge.
Figure 9A:
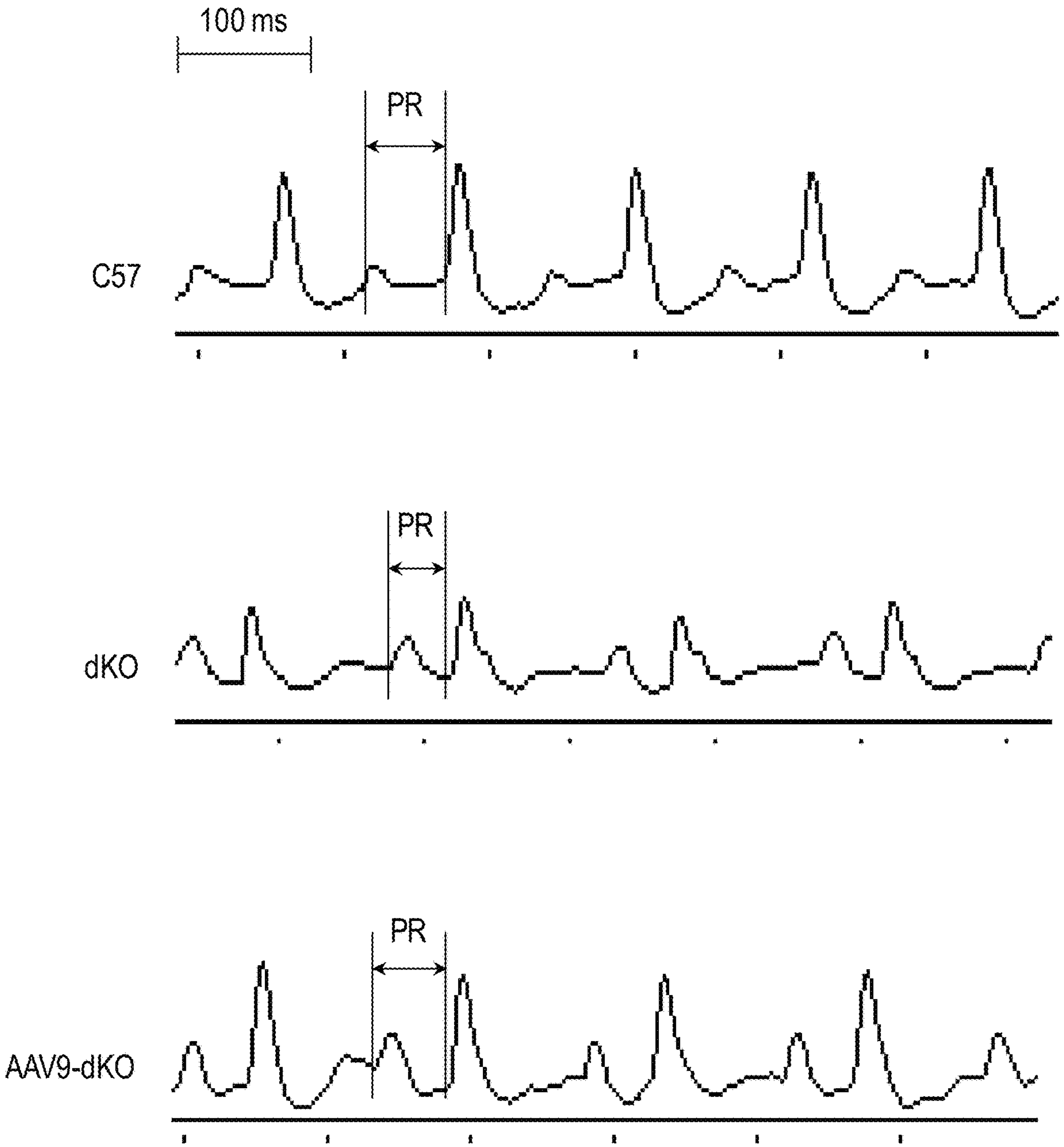
FIGS. 9A-9B show improvement in electrocardiography (ECG) of dKO mice as a result of AAV9-CMV-Hopti-Dys3978 treatment.
Figure 9B:
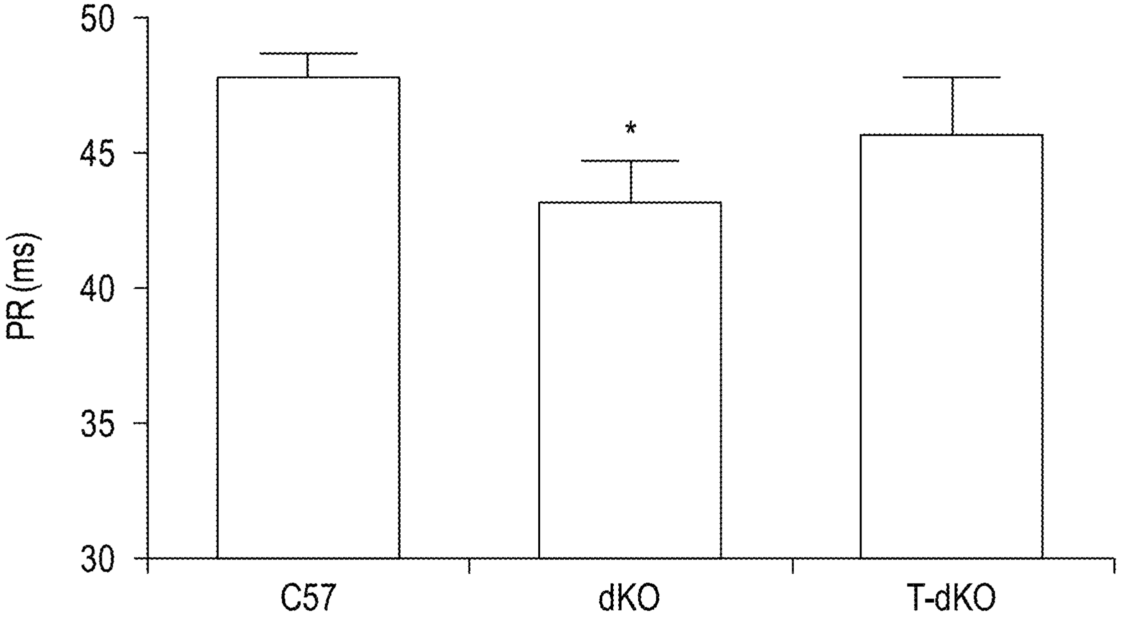
Figure 9B:
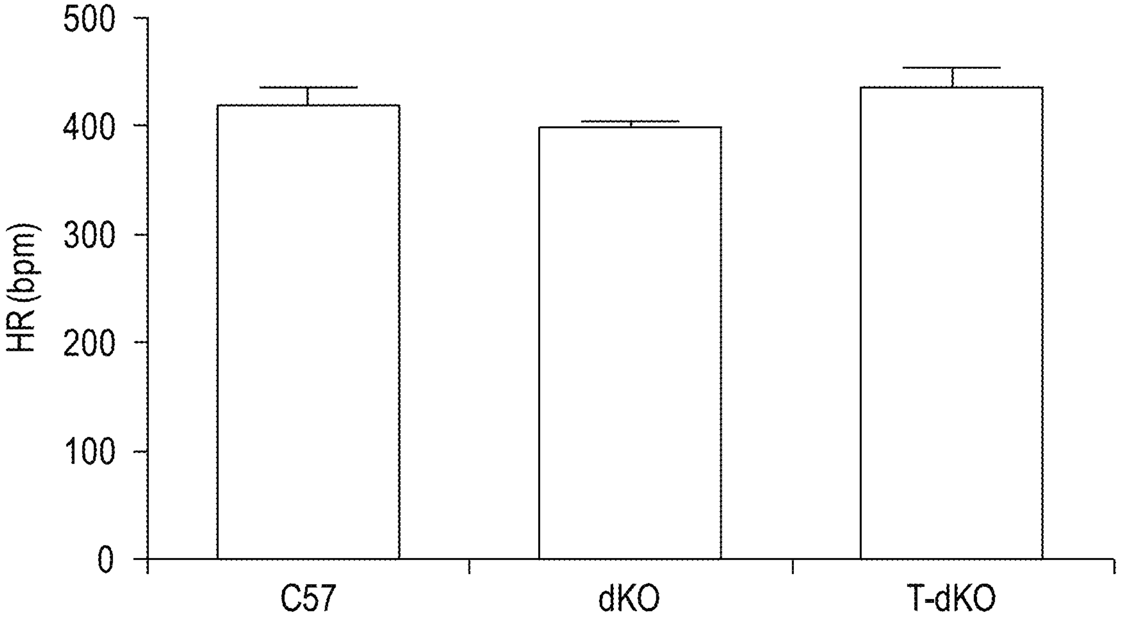

Importantly, great improvement in cardiac functions was also observed. Therapeutic effects in the heart were evaluated at 4 months of age by hemodynamic analysis using the Millar Pressure-volume system. Untreated dKO mice barely survived over 4 months. The very small body size, kyphosis and severe muscle and cardiac dysfunctions made dKO mice too sick to tolerate the hemodynamic analysis procedure. Therefore, the AAV9-treated dKO mice were compared with untreated, age-matched mdx mice which had much milder phenotypes due to an intact utrophin gene, which is known to compensate for lack of dystrophin in this model. While measurement by echocardiography showed mdx mice had no apparent cardiac deficit under baseline condition when compared with C57/B10 wildtype mice, they did show apparent deficits as measured by hemodynamics at the baseline (FIG. 8, open bars). The results herein show that the AAV9-treated dKO mice displayed similar baseline cardiac hemodynamics to that of the mdx mice, including end-systolic pressure, end-diastolic volume, maximal rate of isovolumic contraction ($dp/dt_{max}$) and maximal rate of isovolumic relaxation (dp/dt min). However, after challenge with dobutamine, treated dKO mice displayed similar baseline cardiac hemodynamics to that of the mdx mice, including end-systolic pressure, end-diastolic volume, maximal rate of isovolumic contraction ($dp/dt_{max}$ and $dp/dt_{min}$), whereas the AAV9-treated dKO mice performed significantly better than mdx mice in every parameter examined (FIG. 8, filled bars). Furthermore, greater than 50% of the mdx mice died within the 30-min dobutamine challenge window, consistent with our previous report (Wu et al., *Proc. Natl. Acad. Sci. USA* $10^5$:14814 (2008)). In striking contrast, due to cardiac expression of the mini-dystrophin transgene in the AAV9-treated dKO mice, dobutamine-induced heart failure was largely prevented. Greater than 90% of the AAV9-treated dKO mice survived the dobutamine stress test in the 30 min window. Finally, the commonly seen PR interval deficit shown in electrocardiograms (ECG) was also improved (FIGS. 9A-9B). The PR interval is time from the onset of the P wave to the start of the QRS complex. Taken together, these results demonstrate the effectiveness of AAV9-CMV-Hopti-Dys3978 gene therapy for cardiomyopathy in a severe DMD mouse model.

EXAMPLE 3 hCK-Hopti-Dys3978 in Mdx Mice

Figure 10:
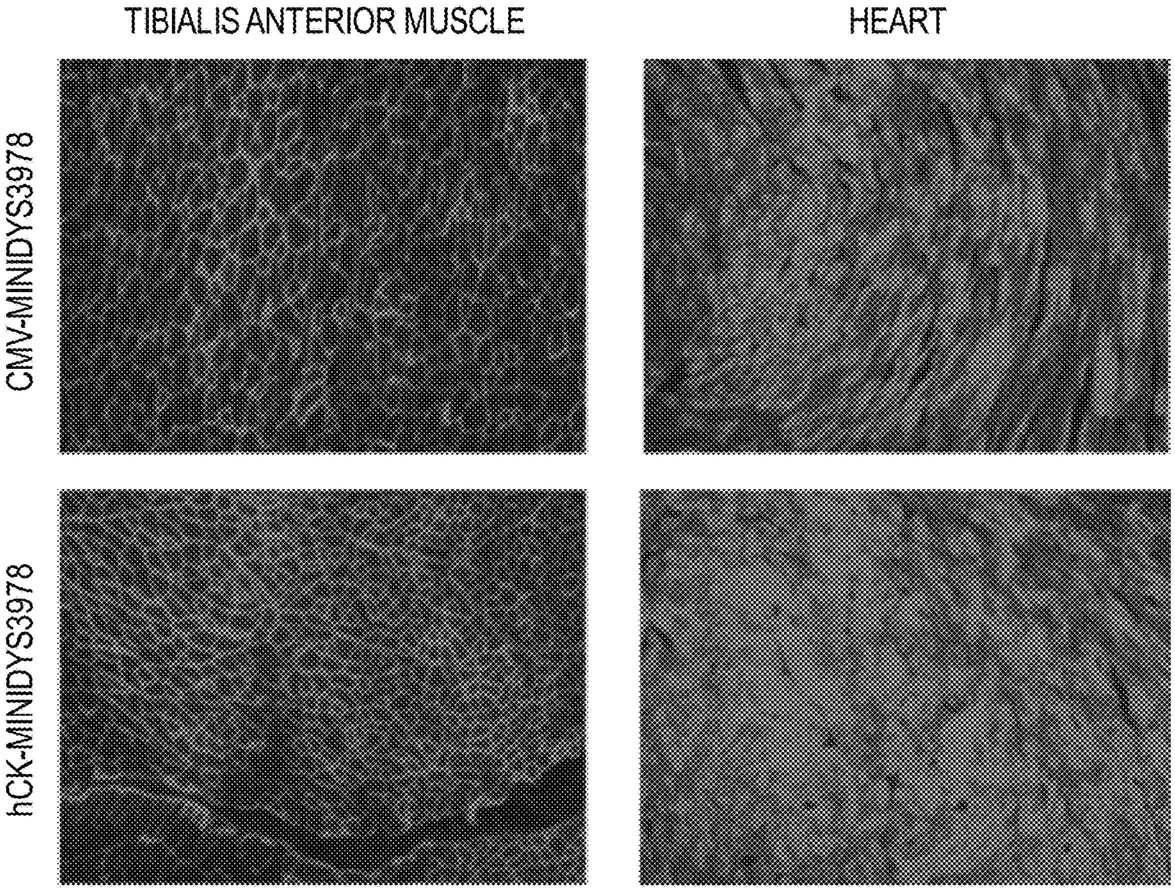
FIG. 10 shows a comparison of the non-tissue specific CMV promoter and the muscle-specific hCK promoter in driving human codon-optimized mini-dystrophin Dys3978 in mdx mice after tail vein injection of AAV9-Hopti-Dys3978 vectors containing CMV or hCK promoter. Using IF staining, the human mini-dystrophin Dys3978 showed robust expression in limb muscle and heart muscle as well. It appeared that the hCK promoter was more effective over the CMV promoter.

To examine if the hybrid synthetic muscle-specific promoter hCK was able to effectively drive Dys3978 gene expression, it was compared with the same construct driven by the strong non-specific CMV promoter. Immunofluorescent staining of mini-dystrophin expression in mdx mice following tail vein injection of the respective vectors showed that the two promoters, i.e., hCK and CMV, delivered equivalent expression levels in muscle and heart (FIG. 10).

EXAMPLE 4

CMV-Hopti-Dys3978 in DMD Canine Model Gold Retriever Muscular Dystrophy (GRMD) Dogs Based on studies in the mdx mice and dystrophin/utrophin double KO (dKO) mice, the same vector, AAV9-CMV-Hopti-Dys3978 was tested in the golden retriever muscular dystrophy (GRMD) dog, a large animal DMD model. Specifically, the vector was administered to a 2.5-month-old GRMD dog, "Jelly," and then followed for more than 8 years post injection.

Figure 11:
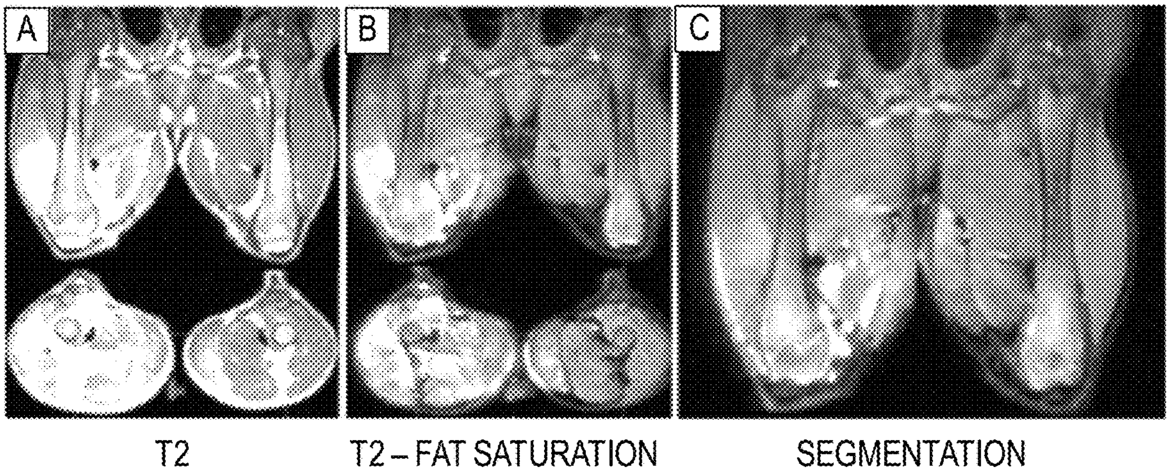
FIG. 11 shows magnetic resonance imaging (MRI) images of the hind limb of GRMD dog "Jelly" after isolated limb vein perfusion of the AAV9-CMV-Hopti-Dys3978 vector. The vector was infused with pressure in the right hind leg which had a tight tourniquet placed at the groin area. The whitish signals indicated vector solution retention in the perfused limb.

Experimental procedures: GRMD dog "Jelly" (2.5 months old female; 6.3 kg; serum CK: 20262 units/L before treatment) was injected with AAV9-CMV-Hopti-Dys3978 vector at a dose of $1\times10^{13}$ vg/kg via the right hind limb. Under general anesthesia, a rubber tourniquet was positioned at the proximal pelvic extremity (the groin area) to cover a majority of muscles in the right hind limb. The AAV9 vector was injected via the great saphenous vein using a Harvard pump set at injection speed 1 ml/sec. The vector volume was 20 ml/kg body weight (130 ml total). The tourniquet was released after 10 minutes accounting from the start of injection. Muscles in the injected limb became harder as revealed by palpation. MRI images on the hind limbs were collected at about 1 hour post injection and confirmed vector fluid in the injected limb (FIG. 11). No immuno-suppressant such as steroid was used at any time point throughout the more than 8 years of observation. Muscle biopsy procedures were performed at 5 time points up to 4 years post vector injection. Final necropsy was done at the age of 8 years, 4 months, at which time "Jelly" was still ambulant but much less active than before.

Figure 12:
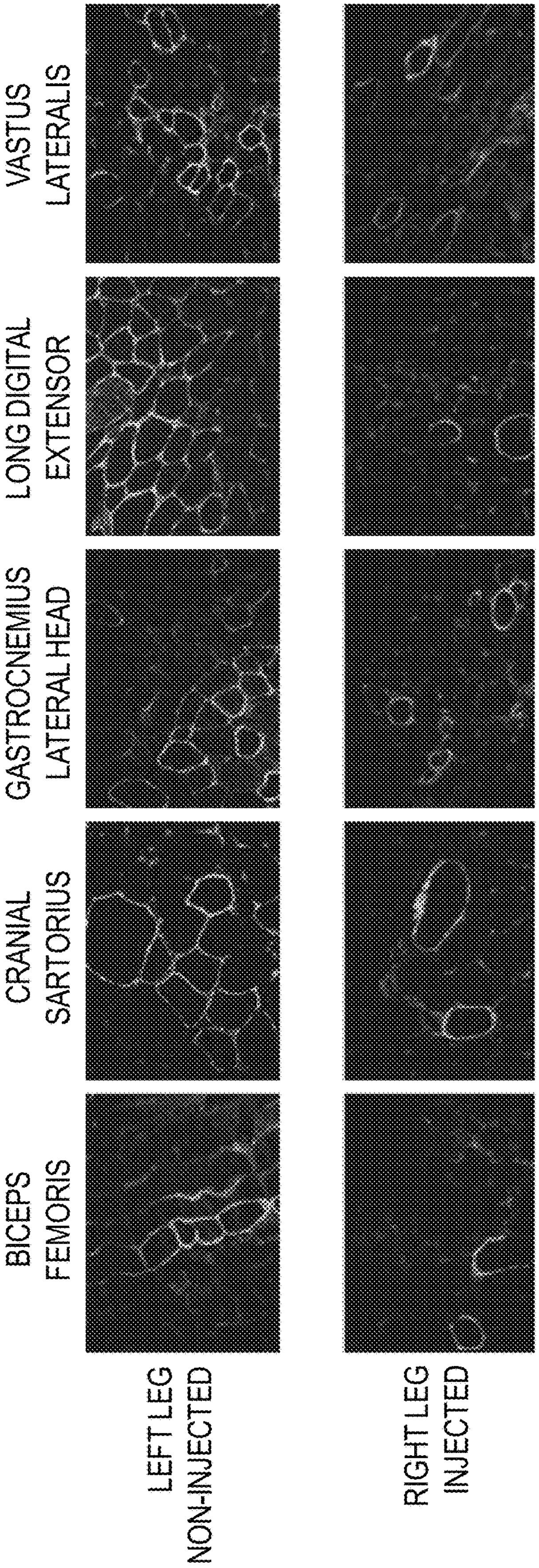
FIG. 12 shows IF staining of human mini-dystrophin Dys3978 expression at 2 months post vector injection in GRMD dog "Jelly." Biopsy samples of 5 different muscle groups in both right and left hind legs were examined. The non-injected left leg also had detectable dys3978, suggesting that the AAV9 vector had traveled from the site of injection to the contralateral leg.
Figure 13:
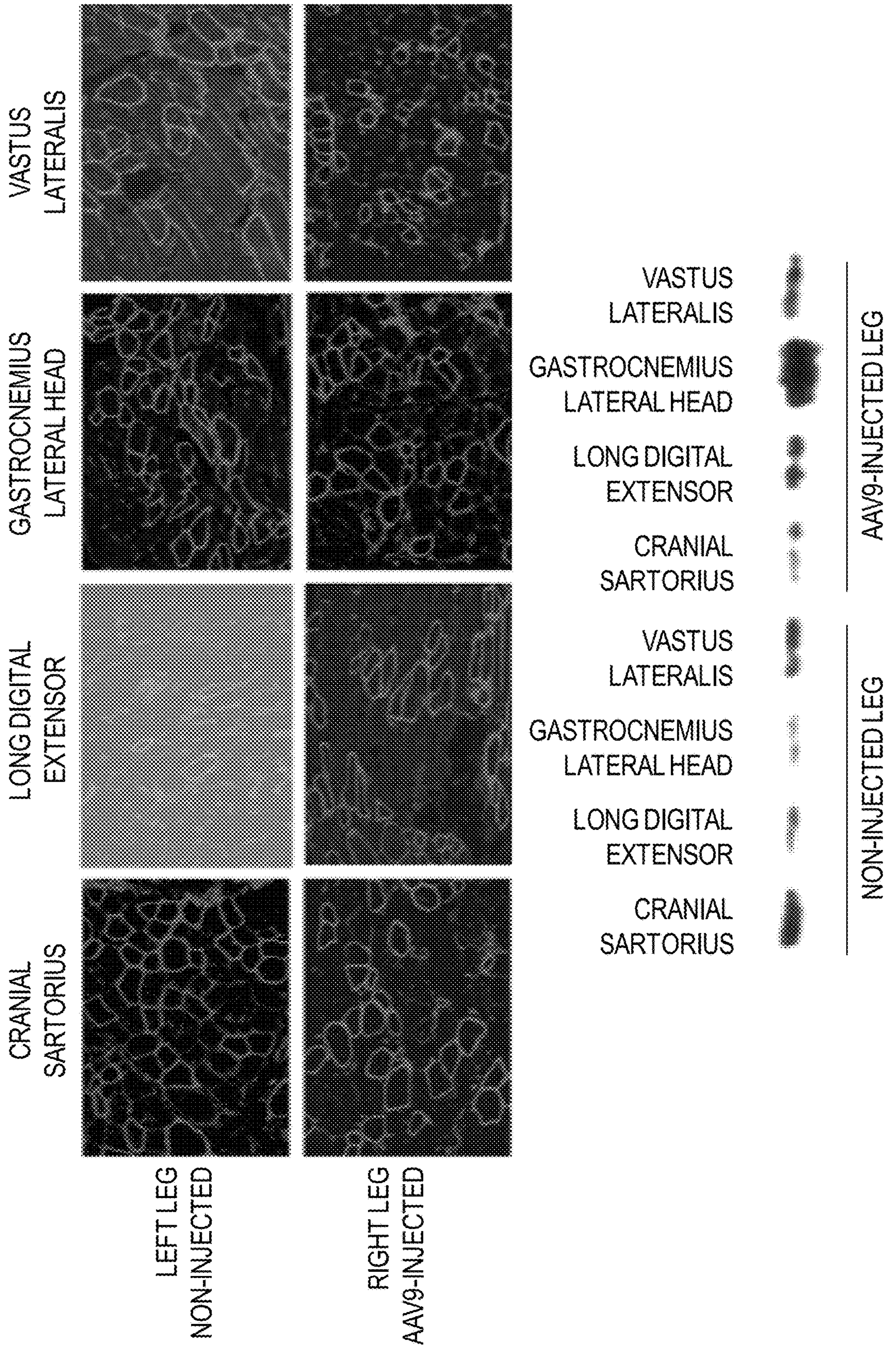
FIG. 13 shows IF staining of human mini-dystrophin Dys3978 expression at 7 months post vector injection in GRMD dog "Jelly." Biopsy samples of 4 different muscle groups in both right and left hind legs were examined. The non-injected left leg also had detectable Dys3978, suggesting that the AAV9 vector had traveled from the site of injection to the contralateral leg. Western blot analysis of Dys3978 was done on the same samples.
Figure 14:
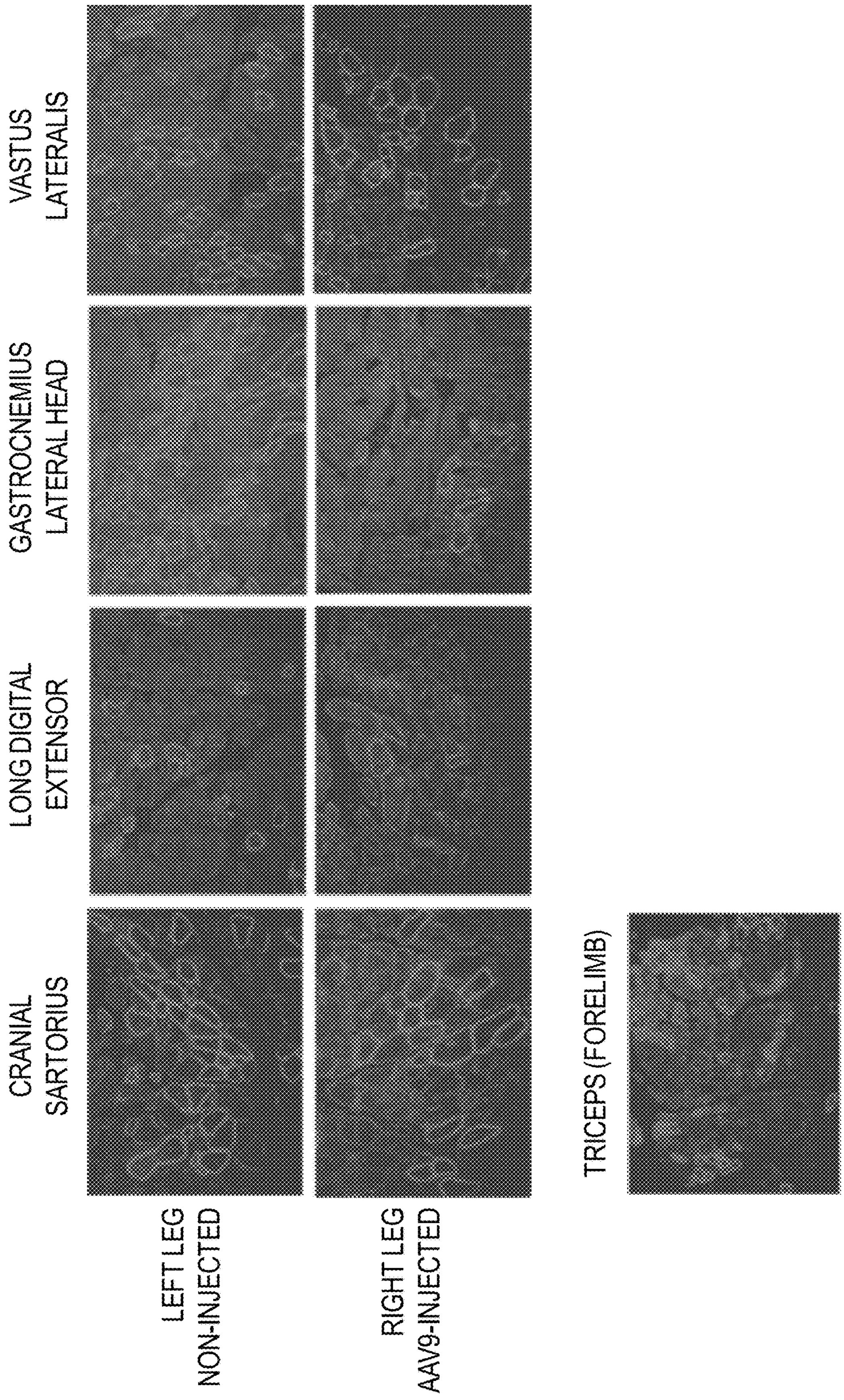
FIG. 14 shows IF staining of human mini-dystrophin Dys3978 expression at 12 months post vector injection in GRMD dog "Jelly." Biopsy samples of 4 different muscle groups in both right and left hind legs and 1 sample in the forelimb were examined. The non-injected left leg also had detectable Dys3978, suggesting that the AAV9 vector had traveled from the site of injection to the contralateral leg.
Figure 15:
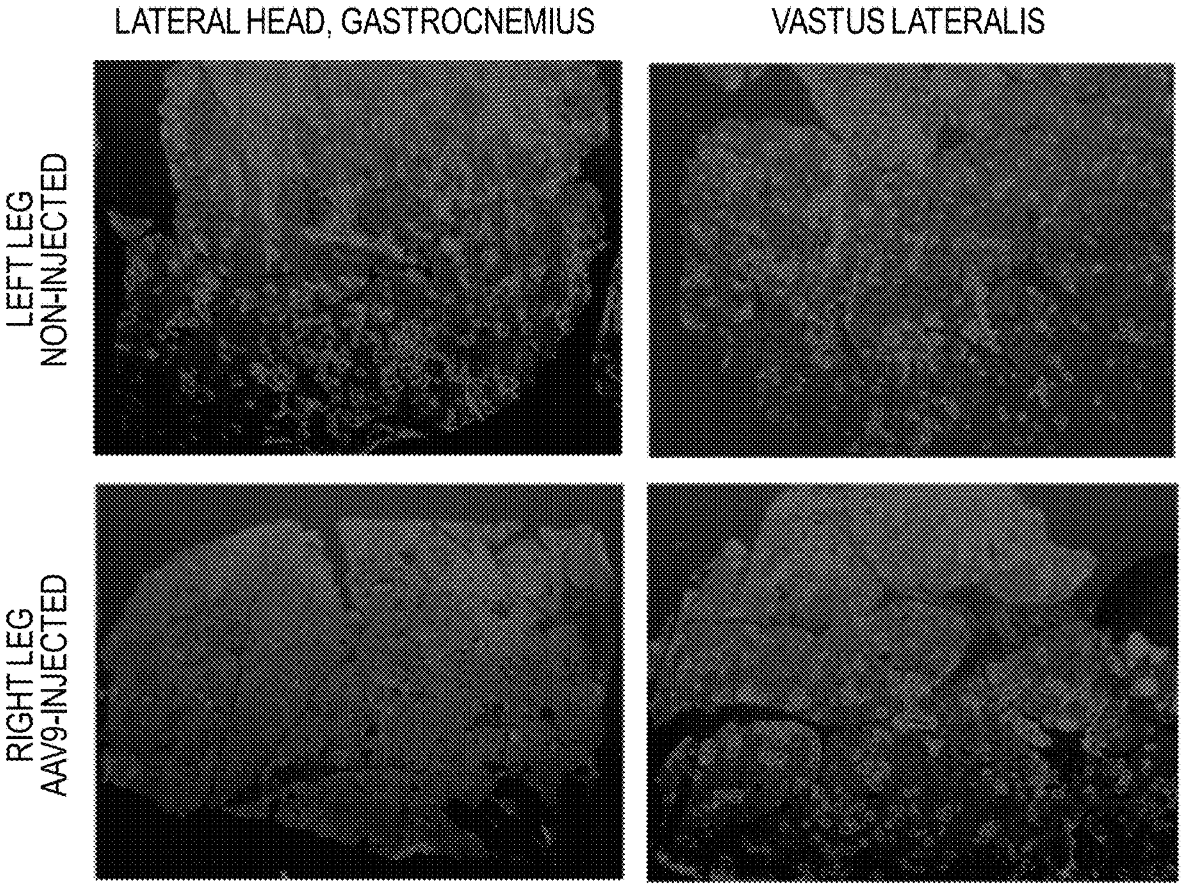
FIG. 15 shows IF staining of human mini-dystrophin Dys3978 expression at 2 years post vector injection in GRMD dog "Jelly." Biopsy samples of 2 different muscle groups in both right and left hind legs were examined. Note the non-injected left leg appeared to have more detectable Dys3978 than the injected leg.
Figure 16:
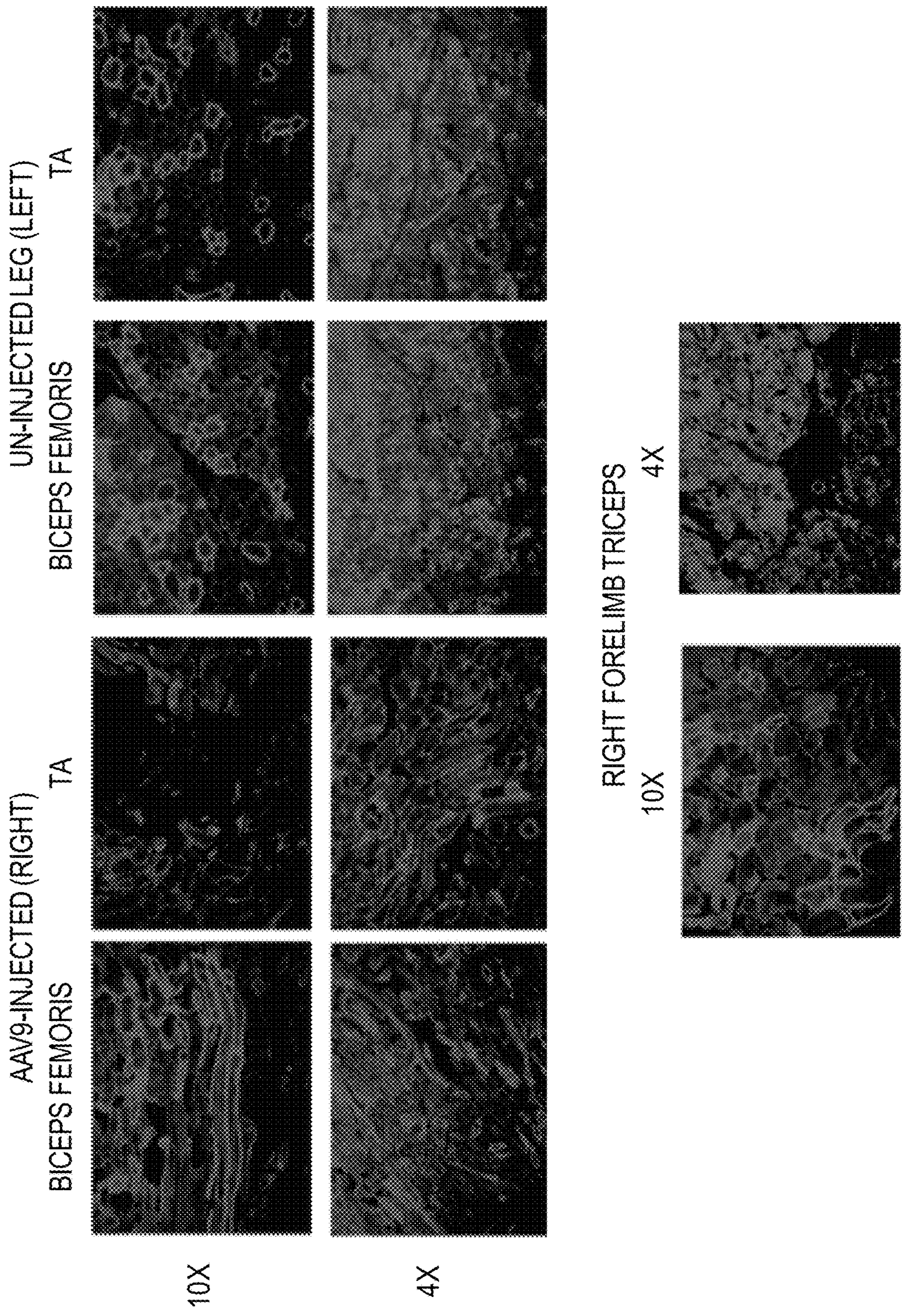
FIG. 16 shows IF staining of human mini-dystrophin Dys3978. Biopsy samples of two additional (compared with FIG. 15) muscle groups in both right and left hind legs and one sample in the forelimb were examined from GRMD dog "Jelly." Samples were also collected at 2 years post vector injection.
Figure 17:
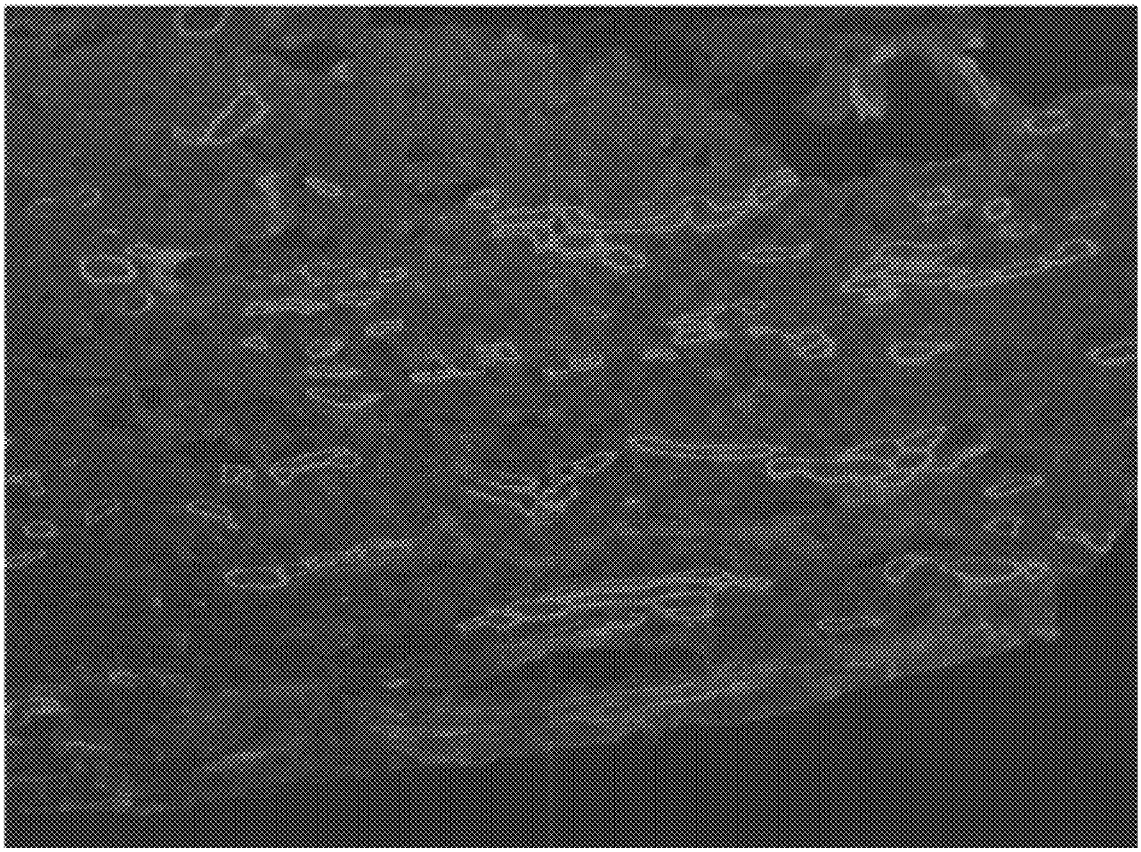
FIG. 17 shows IF staining of human mini-dystrophin Dys3978 at 4 years post vector injection in the non-injected left hind leg from GRMD dog "Jelly."
Figure 18:
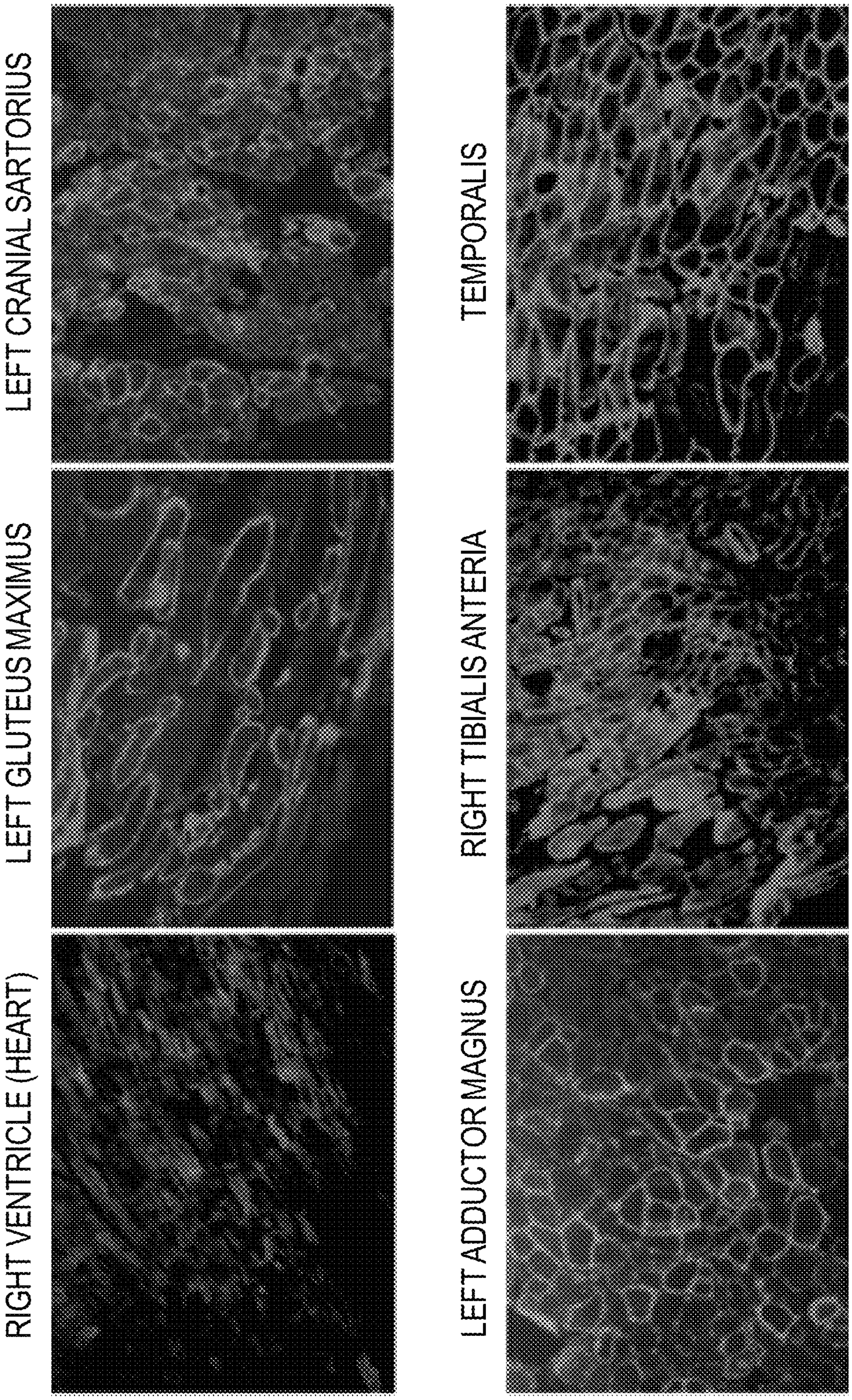
FIG. 18 shows IF staining of human mini-dystrophin Dys3978 at greater than 8 years post vector injection in GRMD dog "Jelly." Necropsy muscle samples of 5 different muscle groups and heart were examined.
Figure 19:
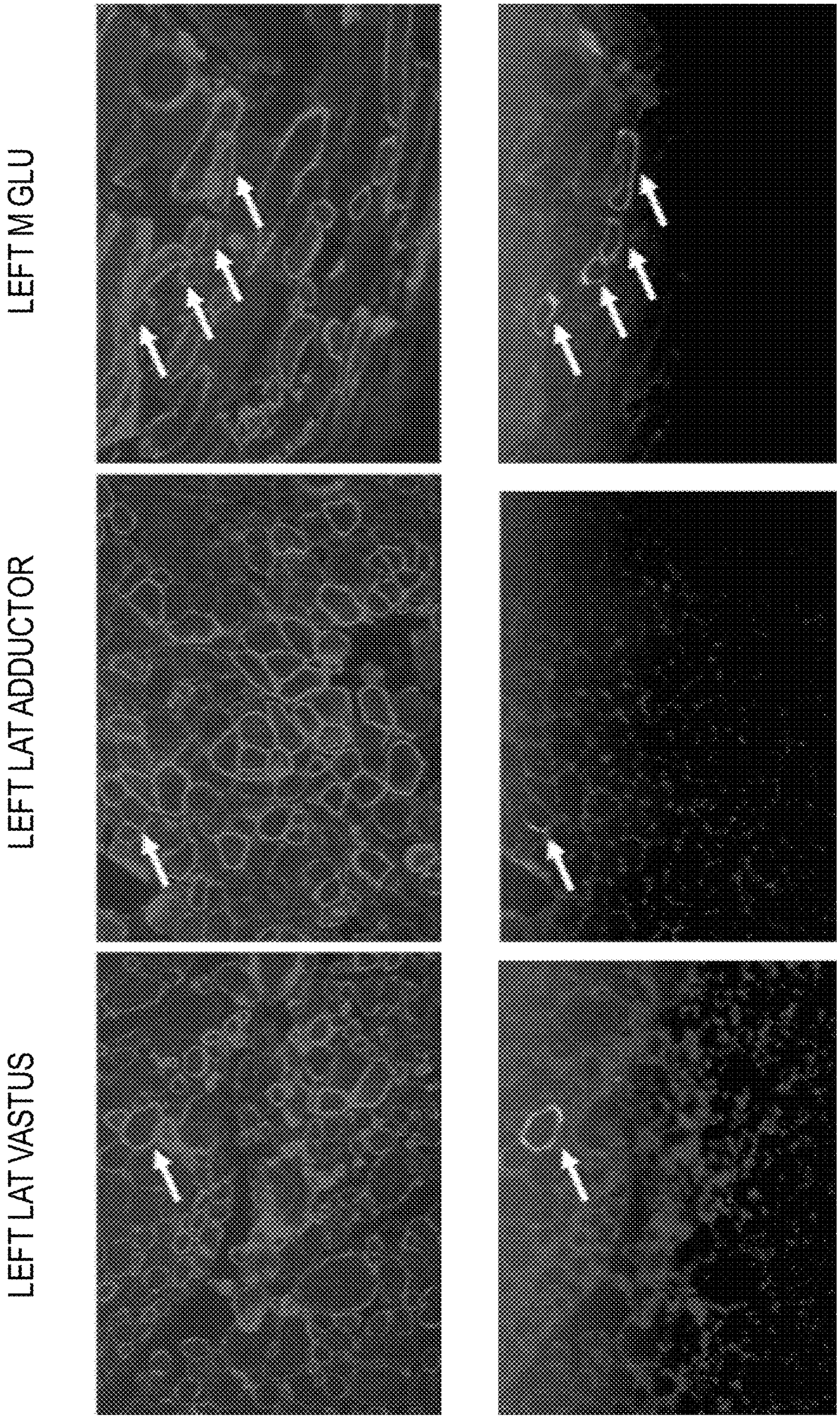
FIG. 19 shows IF staining of human mini-dystrophin Dys3978 and endogenous revertant dystrophin at greater than 8 years post vector injection in GRMD dog "Jelly." Necropsy muscle samples of three different muscle groups were stained with an antibody that recognized both human and dog dystrophin (upper panel) or an antibody that only recognized dog revertant dystrophin (lower panel). The revertant dystrophin positive myofibers were highlighted by arrows. Revertant fibers are rare muscle fibers that stain positively for dystrophin protein that occur in human DMD patients, as well as the mdx mouse and GRMD dogs. The precise mechanism by which revertant fibers occur is not completely understood, but may involve exon skipping in rare muscle cells that produces a shortened dystrophin with the epitopes recognized by antibody probes. See, for example, Lu, Q L, et al., J Cell Biol 148:985-96 (2000).
Figure 20:
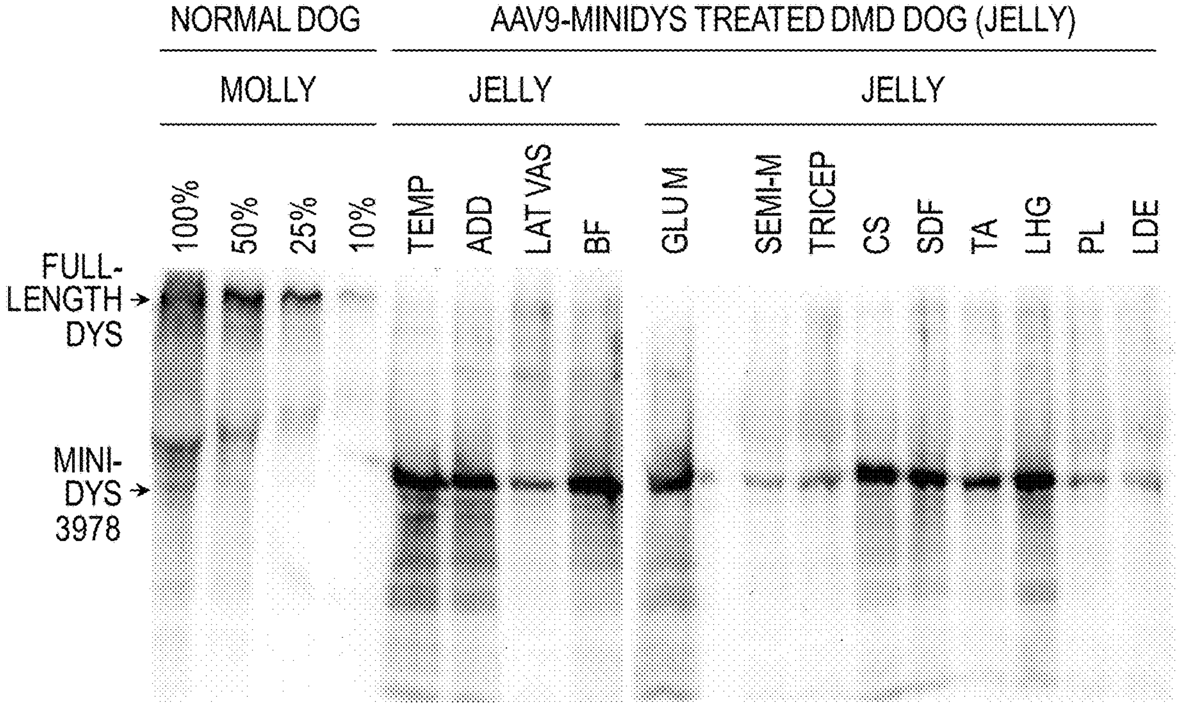
FIG. 20 shows Western blot analyses of human mini-dystrophin Dys3978 present in muscle samples of GRMD dog "Jelly" at necropsy more than 8 years after AAV9 vector injection. Western blot showed human mini-dystrophin Dys3978 was present in all skeletal muscles examined. Muscle from an age and sex matched normal dog named "Molly" was used as a positive control with serial 2-fold dilutions to indicate the quantitation of dystrophin protein. The molecular weight of wildtype full length dystrophin is about 400 kDa while the mini-dystrophin Dys3978 protein is about 150 kDa.

Results: Immunofluorescent (IF) staining showed long-term mini-dystrophin expression in a majority of muscle samples examined up to final necropsy. Interestingly, the injected limb initially (at 2 months post-injection biopsy) had lower expression than the non-injected limb, suggesting procedure-related inflammation and partial inactivation of the CMV promoter (FIG. 12). Nonetheless, the human mini-dystrophin expression persisted for 8 years in "Jelly" despite initial inflammation in the injected limb. Muscle biopsies and immunofluorescent staining and Western blot of the human mini-dystrophin at subsequent time points (7 months, 1 year, 2 years, and 4 years post vector injection) showed persistent gene expression (FIGS. 13-17). While the percentages of mini-dystrophin-positive myofibers varied among different muscles, certain muscles had greater than 90% of myofibers positive upon necropsy (FIG. 18). Co-staining of mini-dystrophin and revertant myofibers (anti-C-terminus antibody) showed co-existence of both (FIG. 19). Mini-dystrophin was also observed in approximately 20% of the cardiomyocytes (FIG. 18). Overall gene expression was largely stable. For example, positive myofibers in the cranial sartorius muscle remained comparable throughout the 6 time points, from 2 and 7 months to 1, 4 and 8 years (compare FIGS. 12, 13, 14, 17 and 18). Western blot confirmed the IF staining results (FIG. 20).

Figure 21:
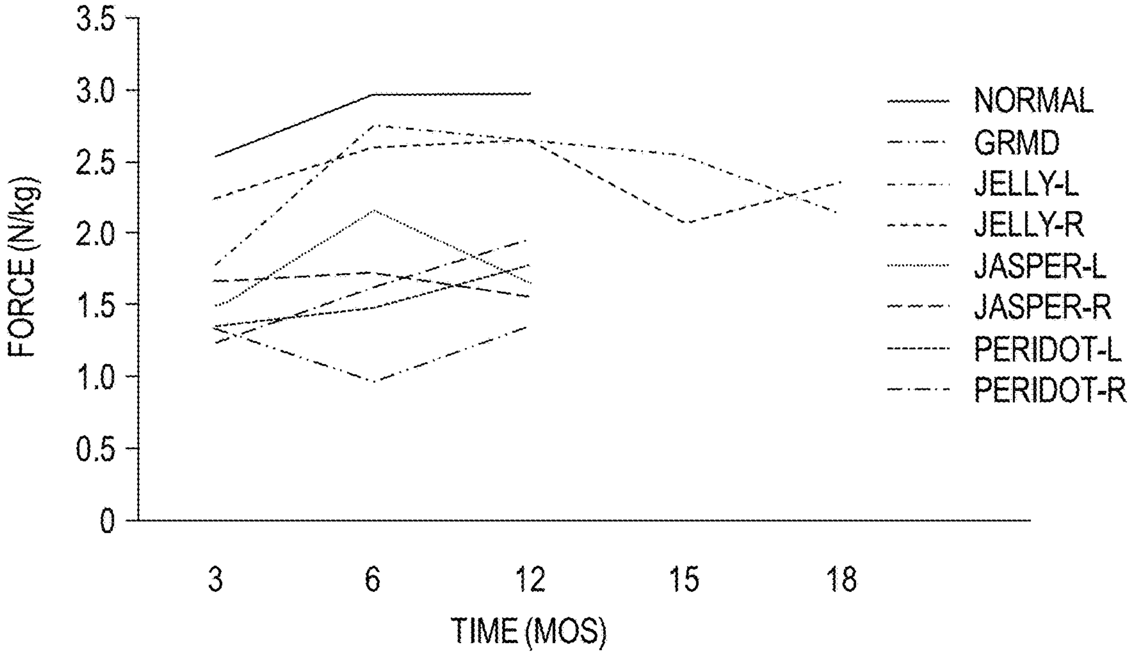
FIG. 21 shows muscle contractile force improvement in GRMD dog "Jelly" after injection of the AAV9-CMV-Hopti-Dys3978 vector and body wide gene expression. The top curve represents the muscle force of a normal dog, while the bottom curve represents the muscle force of the untreated GRMD dog. The two curves extended into more time points represents the muscle force of dog "Jelly." Two more GRMD dogs treated with AAV9-CMV-canine-mini-dystrophin Dys3849 vector (Wang, et al., PNAS 97(25):13714-9 (2000)) were also examined for muscle force, and showed improvement ("Jasper" and "Peridot").

Contractile force measurement showed partial improvement when compared to the untreated dogs (FIG. 21).

"Jelly" remained ambulant throughout the greater than 8 year post treatment period of observation and was euthanized due to cardiomyopathy in the final year. No tumors were found in any of the tissues upon necropsy and examination by a pathologist. DNA sequencing showed that "Jelly" did not carry the disease-modifying Jagged 1 mutation found in two phenotypically mild GRMD dogs as recently reported (Vieira et al., *Cell* 163:1204 (2015)).

EXAMPLE 5 hCK-Copti-Dys3978 in GRMD Dog

In this study, AAV9-hCK-Copti-Dys3978 vector (a modified creatine kinase promoter driving a canine codon-optimized human mini-dystrophin 3978) was used in a GRMD dog named "Dunkin." The gene encodes the same human mini-dystrophin Dys3978 protein used in other studies, but was canine codon-optimized. The DNA sequence is 94% identical to the human codon-optimized gene. Transfection experiments in human HEK 293 cells comparing CK-Copti-Dys3978 (canine codon-optimized) and CK-Hopti-Dys3978 (human codon-optimized) revealed essentially the same level of expression. Multiple experiments comparing both constructs in mdx mice also showed essentially the same expression levels.

Experimental procedure: GRMD dog "Dunkin" (female, 2.5 m old, 6.5 kg) was intravenously injected with AAV9-hCK-Copti-Dys3978 vector at the dose of $4\times10^{13}$ vg/kg via the great saphenous vein. The dog was not sedated during injection. There was no noticeable adverse reaction or behavior change. A muscle biopsy was done 4 months post vector injection and necropsy was done at 14 months post injection.

Figure 22:
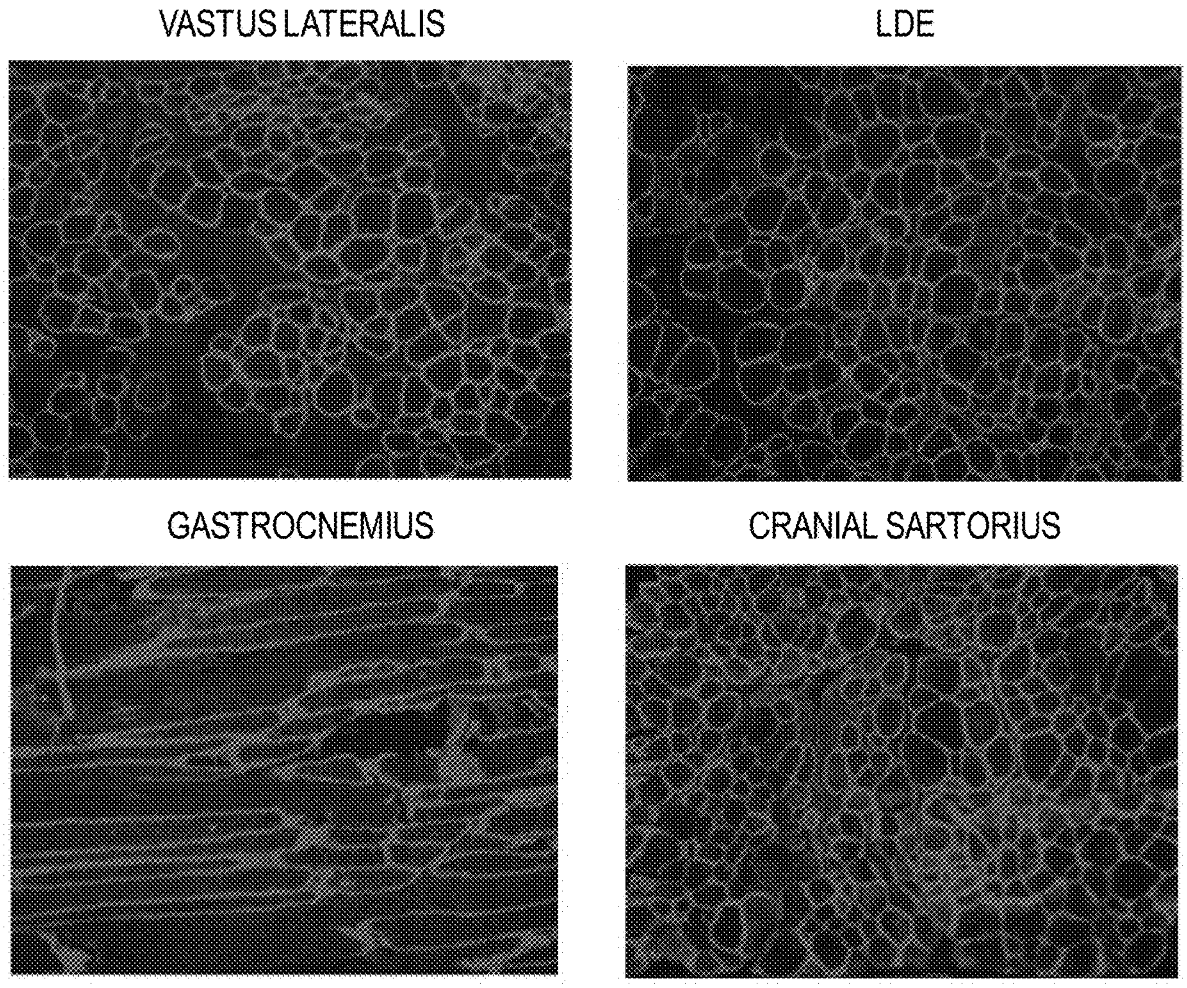
FIG. 22 shows muscle biopsy IF staining of human mini-dystrophin expression at 4 months post AAV9-hCK-Copti-Dys3978 vector injection in GRMD dog "Dunkin." The vector was delivered by intravenous injection to achieve body wide gene expression. Biopsy samples of 4 different muscle groups in the hind limbs were examined. Note nearly uniform mini-dystrophin Dys3978 detected in all muscle groups.
Figure 23:
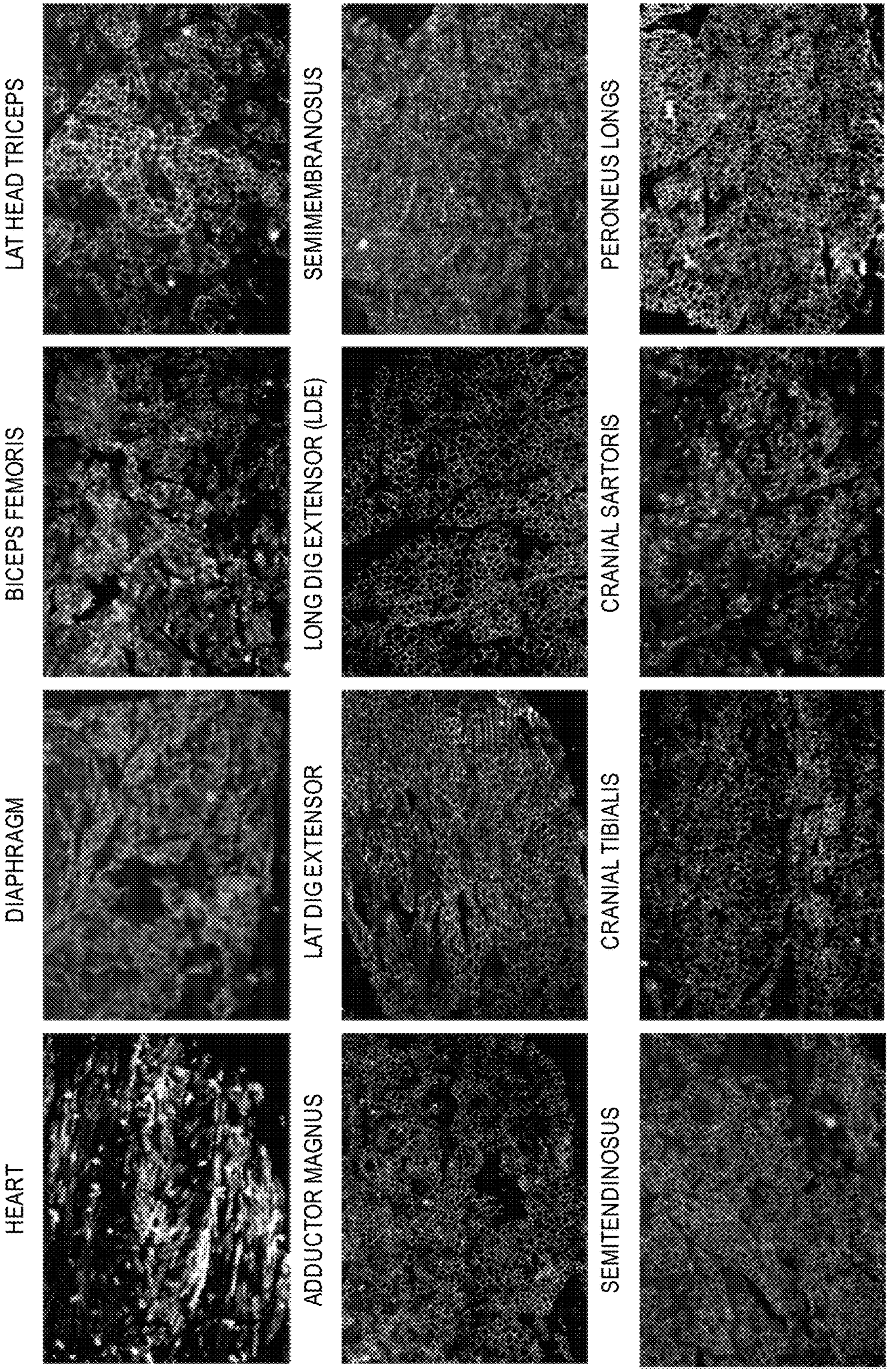
FIG. 23 shows IF staining of human mini-dystrophin expression at 14 months post AAV9-hCK-Copti-Dys3978 vector injection in GRMD dog "Dunkin." Necropsy samples were taken and examined. Note widespread and robust levels of mini-dystrophin Dys3978 detected in heart and all muscle groups. Magnification 4×.
Figure 24:
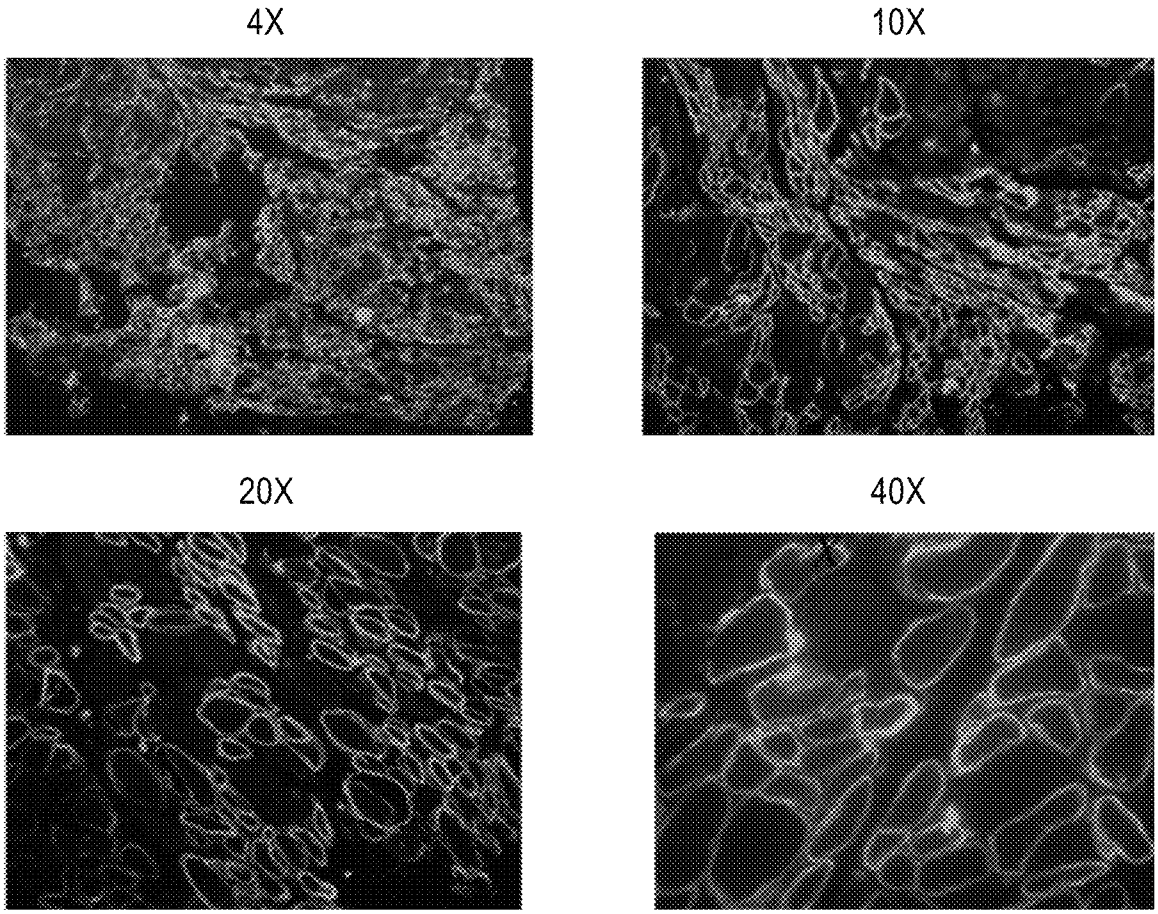
FIG. 24 shows IF staining of diaphragm muscle with robust levels of human mini-dystrophin detected at 14 months post AAV9-hCK-Copti-Dys3978 vector injection in GRMD dog "Dunkin."
Figure 25:
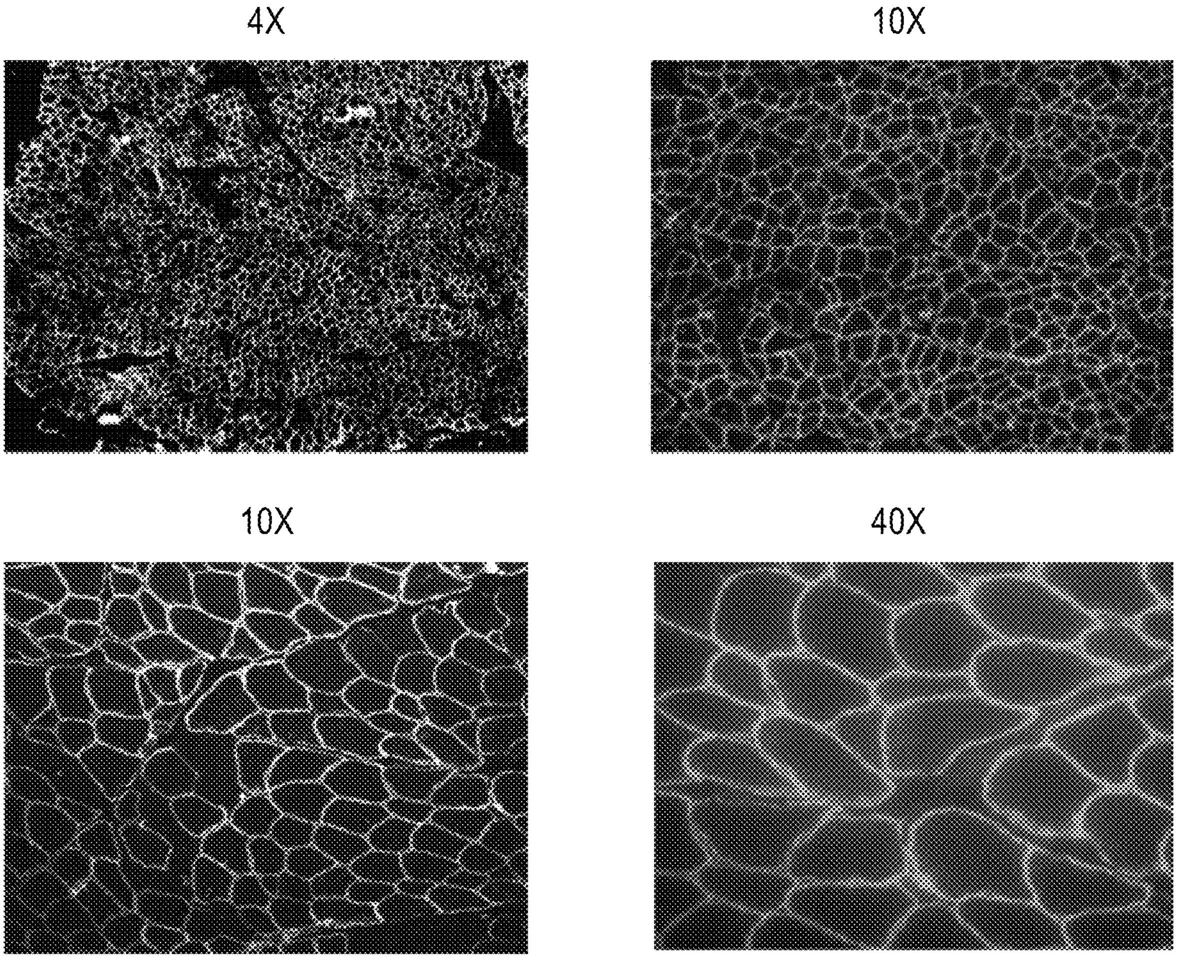
FIG. 25 shows IF staining of peroneus longus muscle with robust levels of human mini-dystrophin detected at 14 months post AAV9-hCK-Copti-Dys3978 vector injection in GRMD dog "Dunkin."
Figure 26:
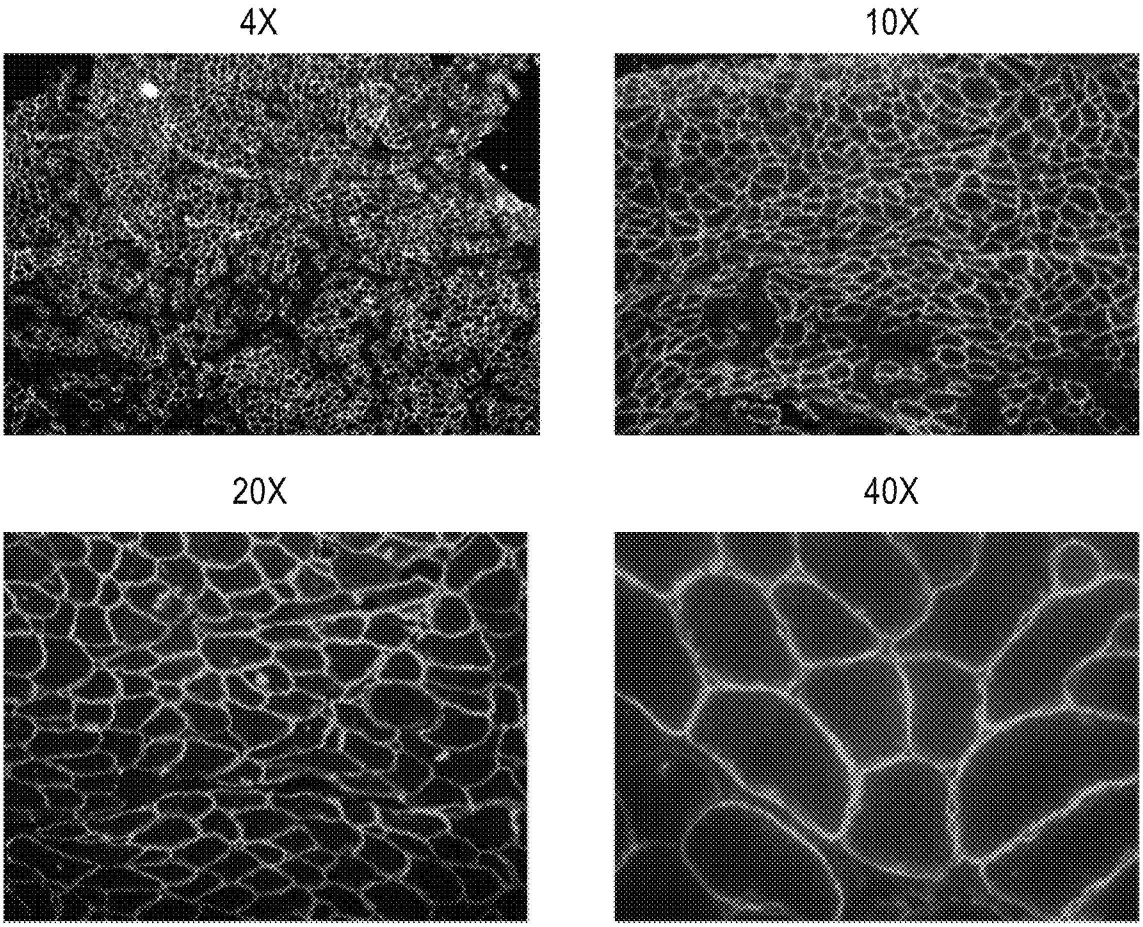
FIG. 26 shows IF staining of semi-membranosus muscle with robust levels of human mini-dystrophin detected at 14 months post AAV9-hCK-Copti-Dys3978 vector injection in GRMD dog "Dunkin."

Results: Very high level and nearly uniform mini-dystrophin expression was observed by immunofluorescent staining of mini-dystrophin 3978 on skeletal muscle samples from 4-month post injection biopsy (FIG. 22) to 14-month post injection necropsy (FIGS. 23-26 for necropsy).

Figure 27:
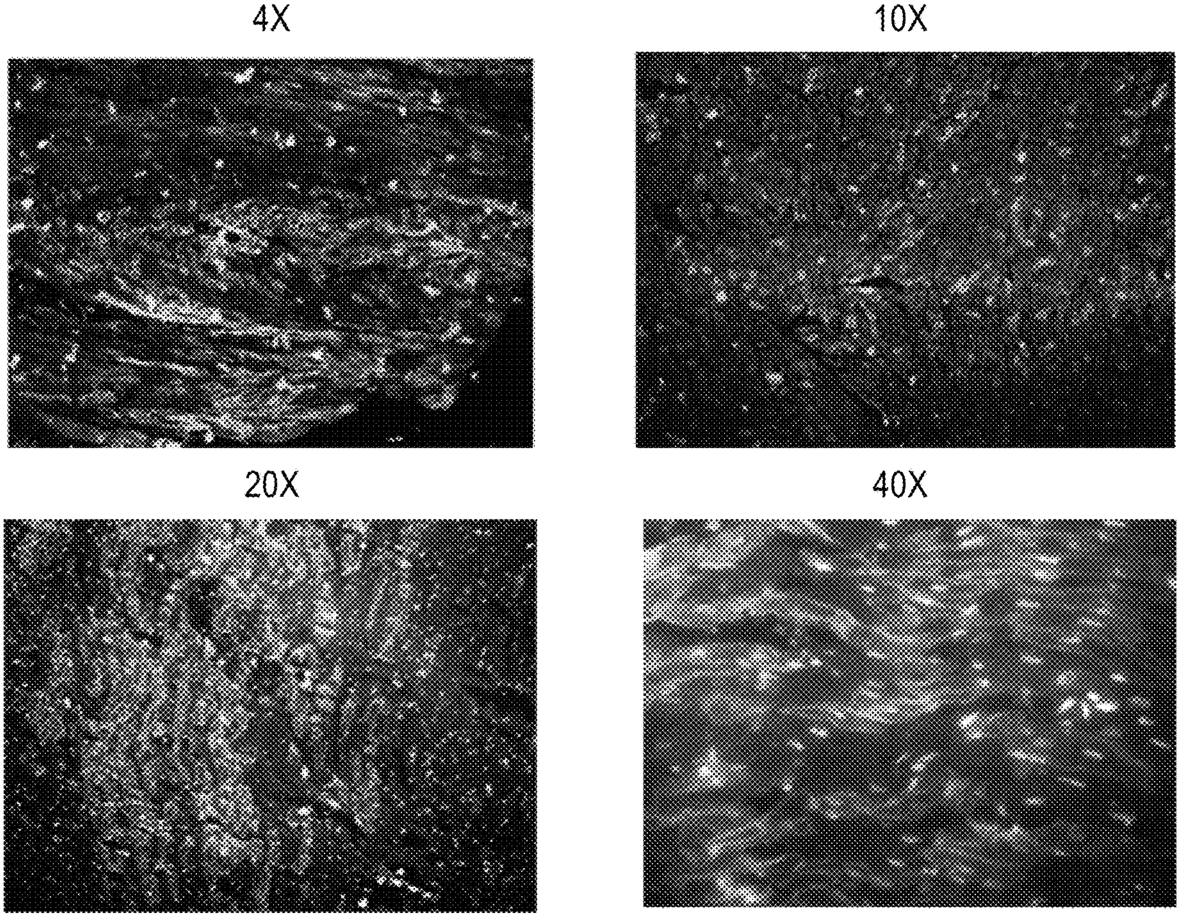
FIG. 27 shows IF staining of heart left ventricle (LV) muscle with robust levels of human mini-dystrophin detected at 14 months post AAV9-hCK-Copti-Dys3978 vector injection in GRMD dog "Dunkin."

Significantly high levels of mini-dystrophin in cardiac muscles was also observed by IF staining (FIG. 27). The expression from the CK promoter appeared stronger and more uniform than from the CMV promoter.

Figure 28:
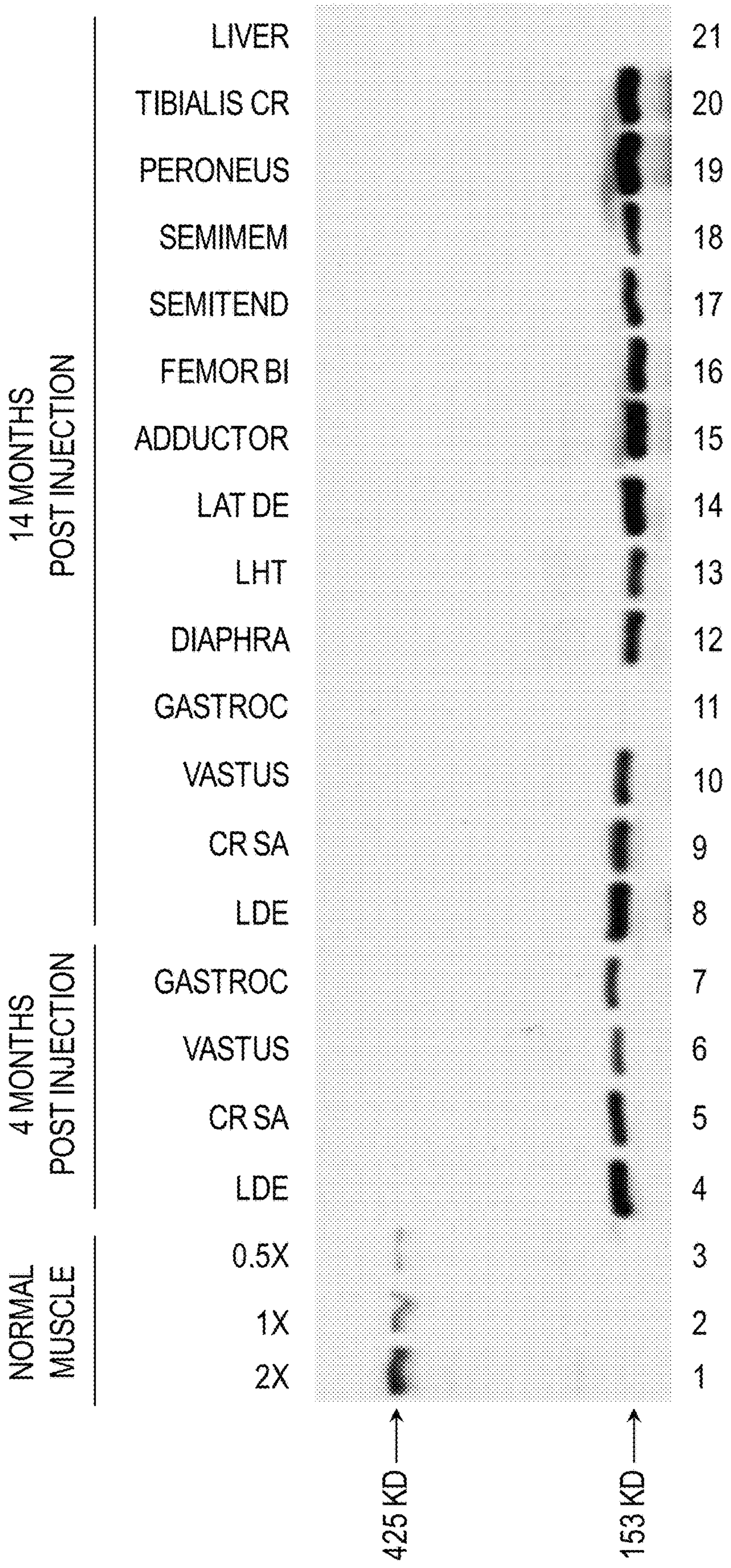
FIG. 28 shows detection by Western blot of human mini-dystrophin Dys3978 in muscle samples of GRMD dog "Dunkin" at 4 months and 14 months post vector injection. Muscle from an age matched normal dog was used as a positive control with serial 2-fold dilutions to indicate the quantitation of dystrophin protein. The molecular weight of wildtype full length dystrophin is about 400 kDa while the mini-dystrophin Dys3978 is about 150 kDa. Note that no mini-dystrophin Dys3978 was detected in the liver.
Figure 29:
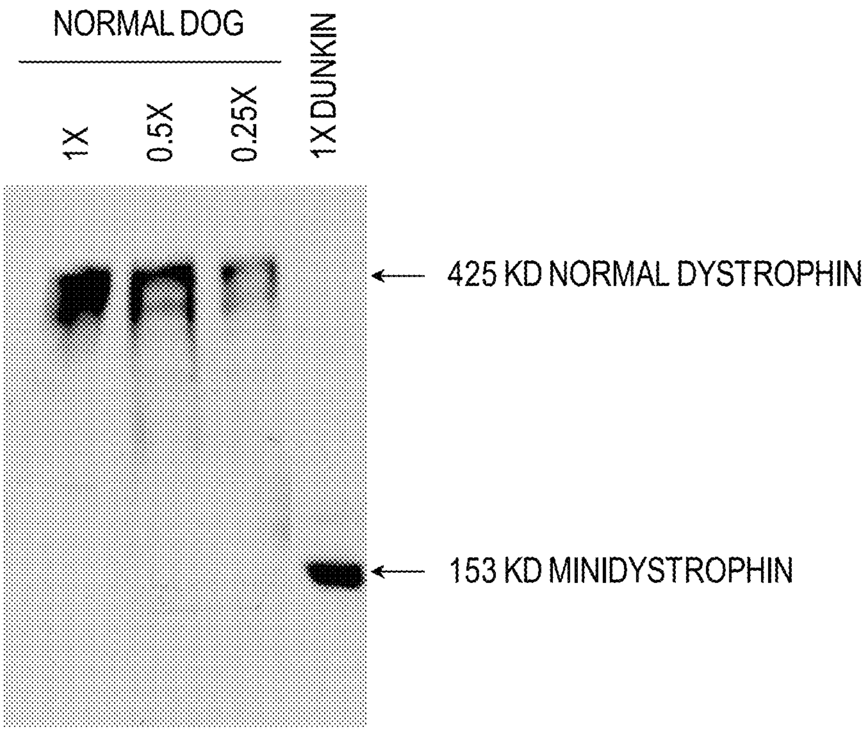
FIG. 29 shows detection by Western blot of human mini-dystrophin Dys3978 expression in heart (LV) sample of GRMD dog "Dunkin" at 14 months post vector injection. Heart sample from an age-matched normal dog was used as a positive control with serial 2-fold dilutions to indicate the quantitation of dystrophin protein.

Western blot analysis confirmed the IF staining results. In the skeletal muscles, the mini-dystrophin levels were mostly higher than the normal level of wildtype dystrophin from the normal dog control (FIG. 28). The level of Dys3978 in the heart was roughly half that of the wildtype dystrophin level (FIG. 29).

Figure 30:
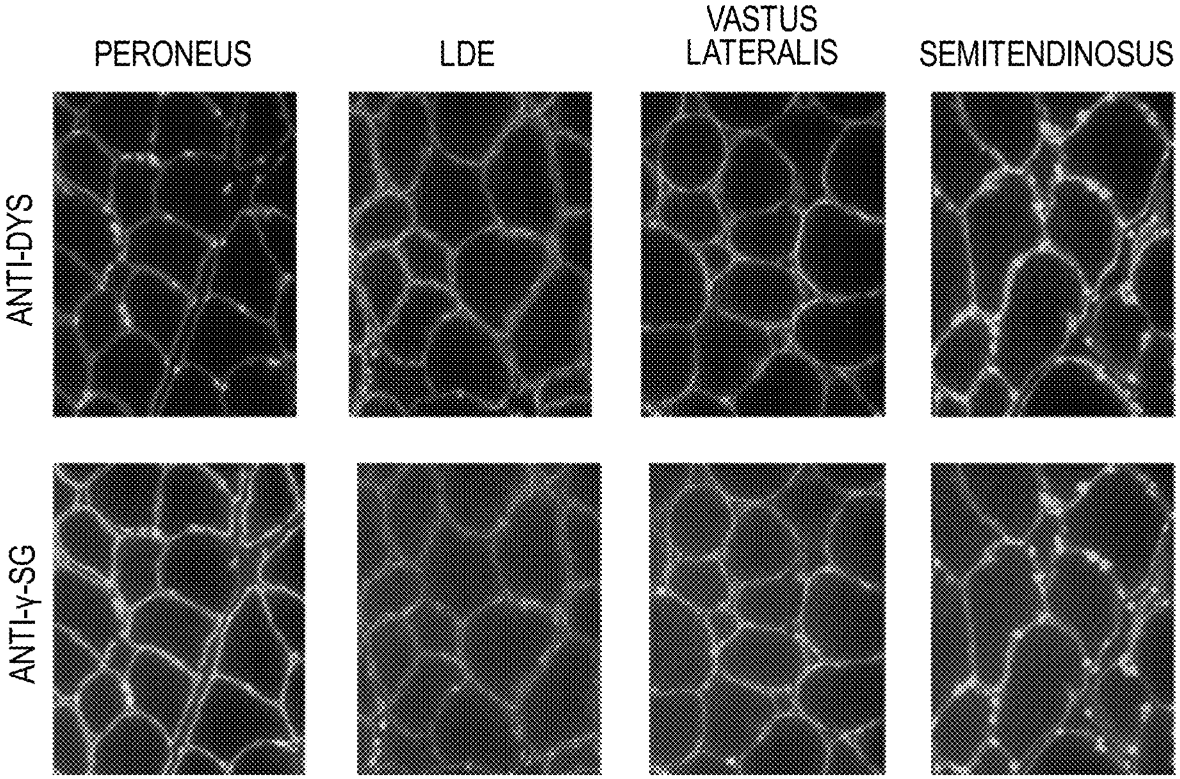
FIG. 30 shows restoration of dystrophin associated protein complex as shown by IF staining of human mini-dystrophin Dys 3978 as well as gamma-sarcoglycan (r-SG) of various muscle groups.

Expression of Dys3978 from the canine codon-optimized gene Copti-Dys3978 effectively restored dystrophin associated protein complex including gamma-sarcoglycan (FIG. 30).

Figure 31:
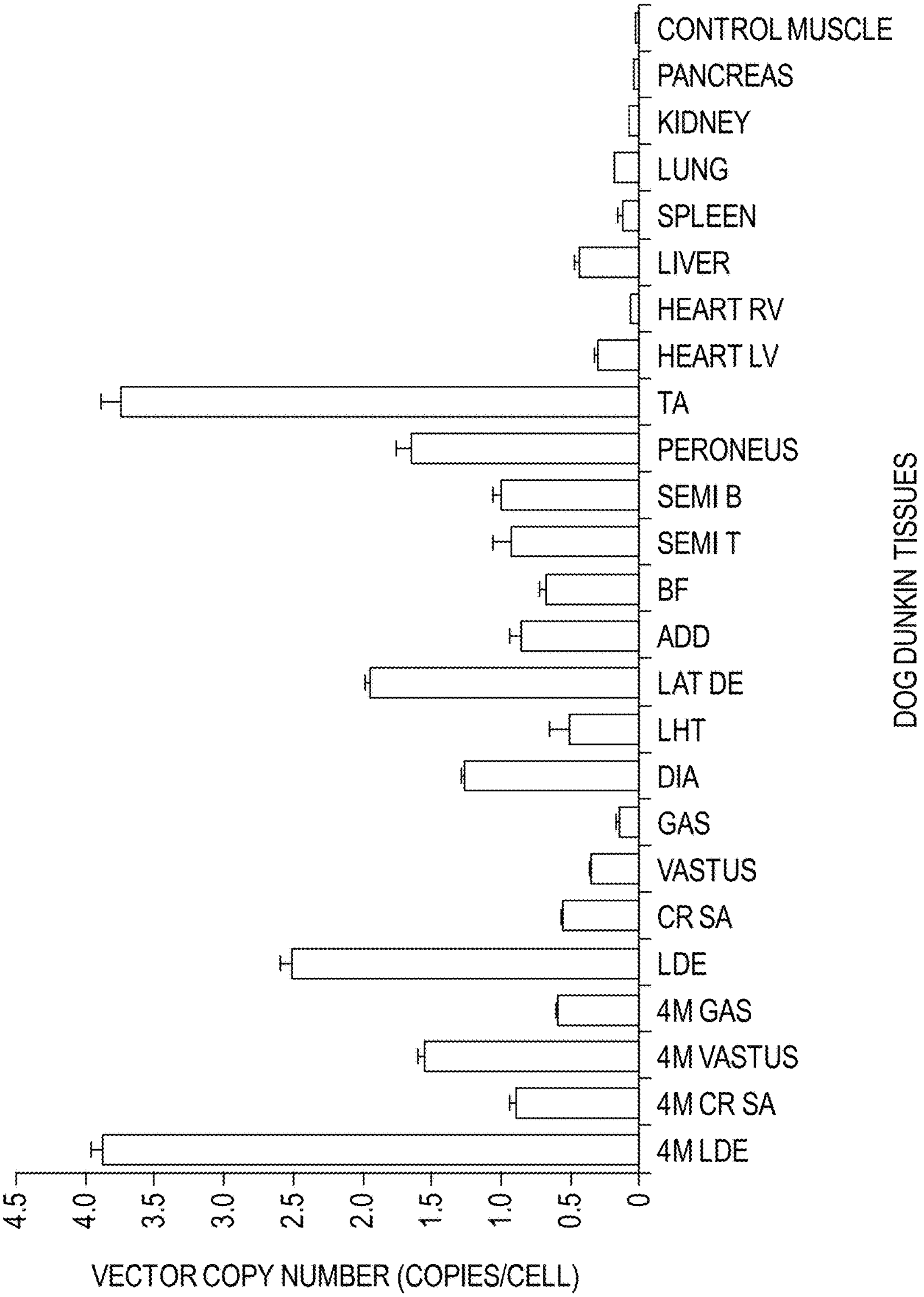
FIG. 31 shows analysis of AAV9-CMV-Copti-Dys3978 vector DNA copy in various muscle and tissues. Quantitative PCR (qPCR) was performed to determine the AAV vector DNA genome copy numbers, which were normalized on a per diploid cell basis.

Quantitative PCR of vector DNA copy numbers showed a consistent trend to the mini-dystrophin protein expression levels (FIG. 31).

There was no innate or cellular immune responses found in all the samples examined. This is very different from the results of AAV9-CMV-opH-dys3978, suggesting the muscle-specific hCK promoter was not only strong but also safer than the CMV promoter.

Figure 32:
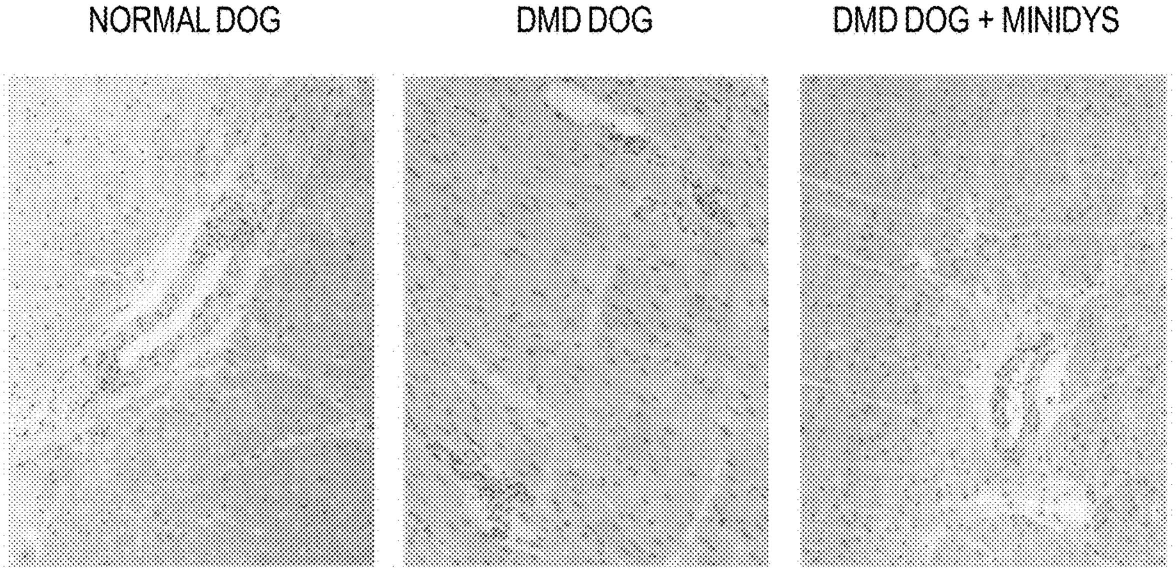
FIG. 32 shows improvement of dystrophic histopathology in the heart of AAV9-CMV-Copti-Dys3978 vector GRMD dog "Dunkin" compared to age-matched normal and untreated GRMD dog. HE staining.
Figure 33:
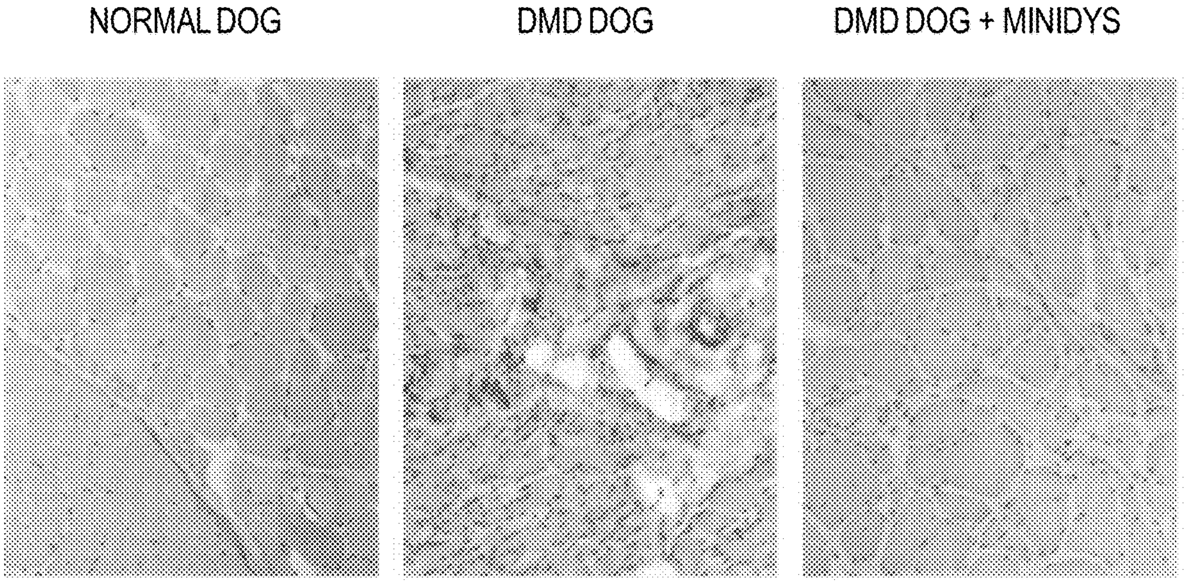
FIG. 33 shows improvement of dystrophic histopathology in the diaphragm muscle of AAV9-CMV-Copti-Dys3978 vector GRMD dog "Dunkin." Compared to age-matched normal and untreated GRMD dog. HE staining.
Figure 34:
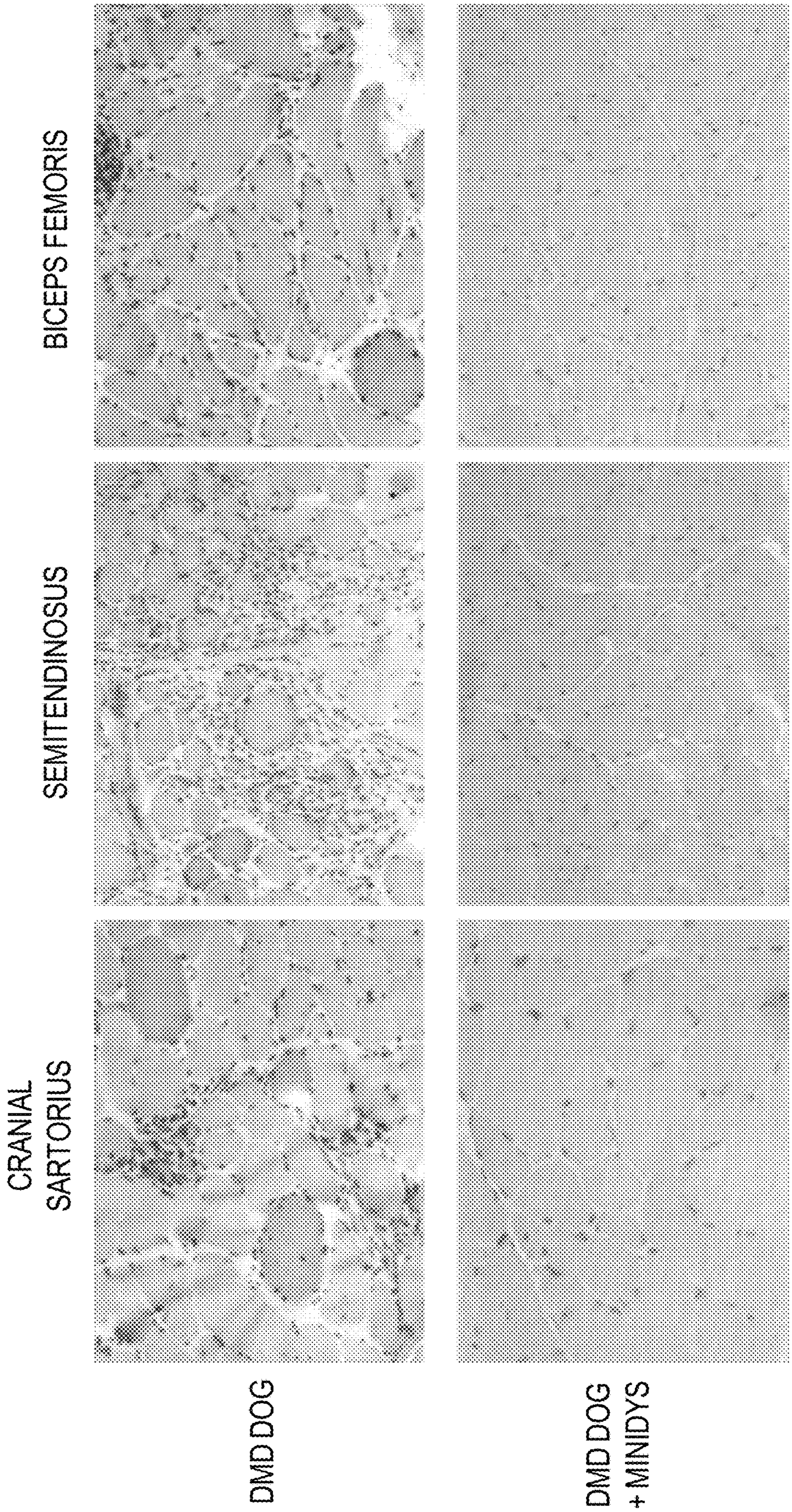
FIG. 34 shows improvement of dystrophic histopathology in the limb muscles of AAV9-CMV-Copti-Dys3978 vector GRMD dog "Dunkin" compared to age-matched untreated GRMD dog. HE staining.
Figure 35:
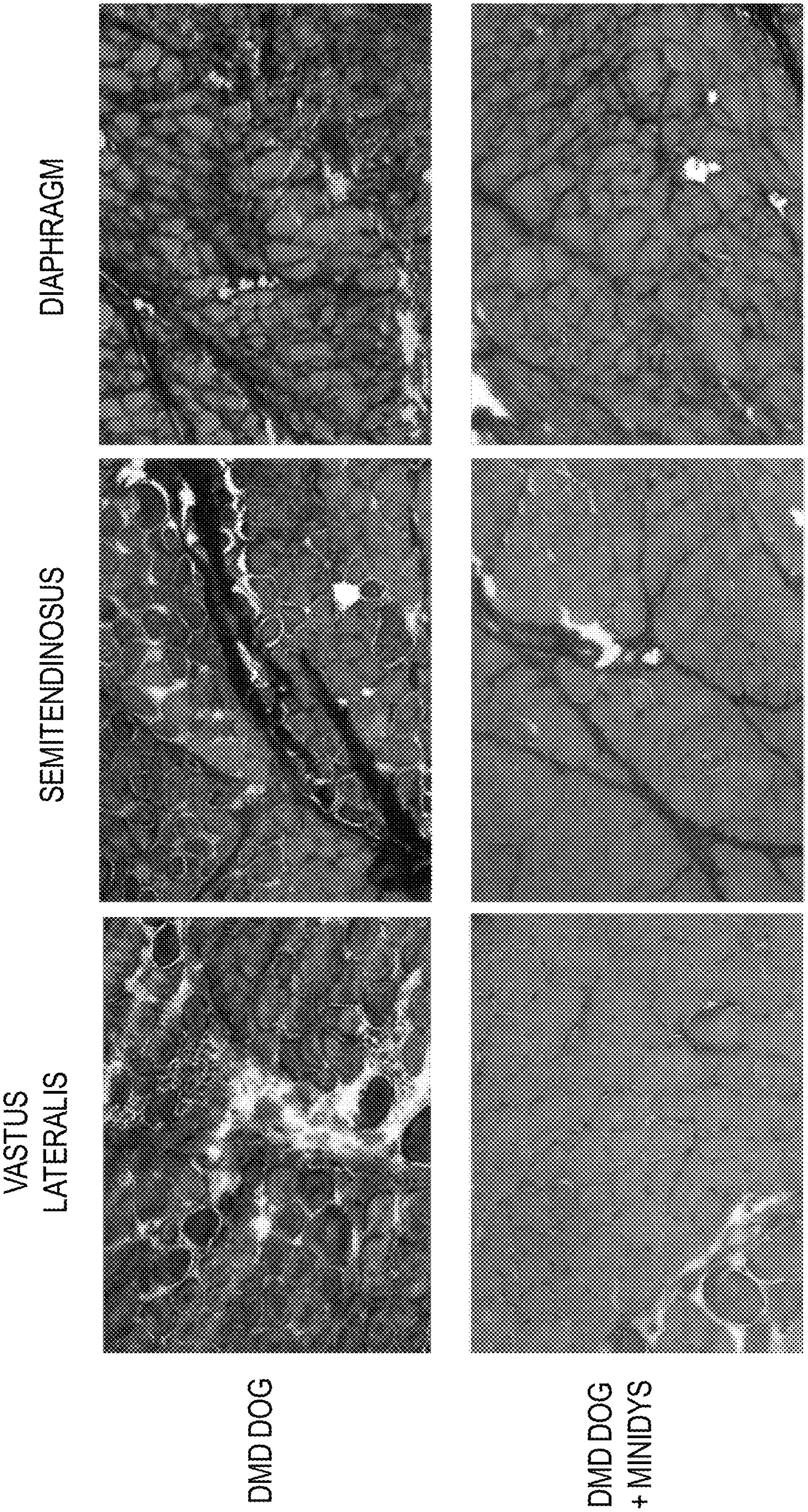
FIG. 35 shows inhibition of fibrosis in limb muscle and diaphragm of GRMD dog "Dunkin" compared to age-matched untreated GRMD dog. Mason Trichrome blue staining.
Figure 36A:
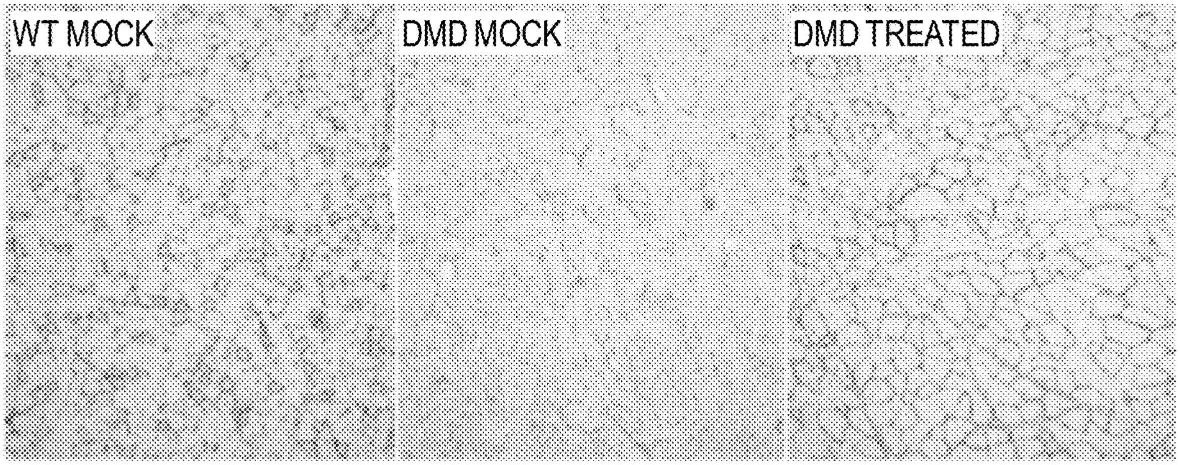
FIG. 36A provides photomicrographs showing immunolabeling with anti-dystrophin DYSB antibody of biceps femoris muscle obtained from a WT rat mock treated with PBS (left panel), a mock treated DMD rat (central panel), and a $Dmd^{mdx}$ rat treated with AAV9.hCK.Hopti-Dys3978.spA vector (right panel). The dark outline around the fibers shows the subsarcolemmal localization of the dystrophin in WT rat and mini-dystrophin in vector treated $Dmd^{mdx}$ rat.
Figure 36B:
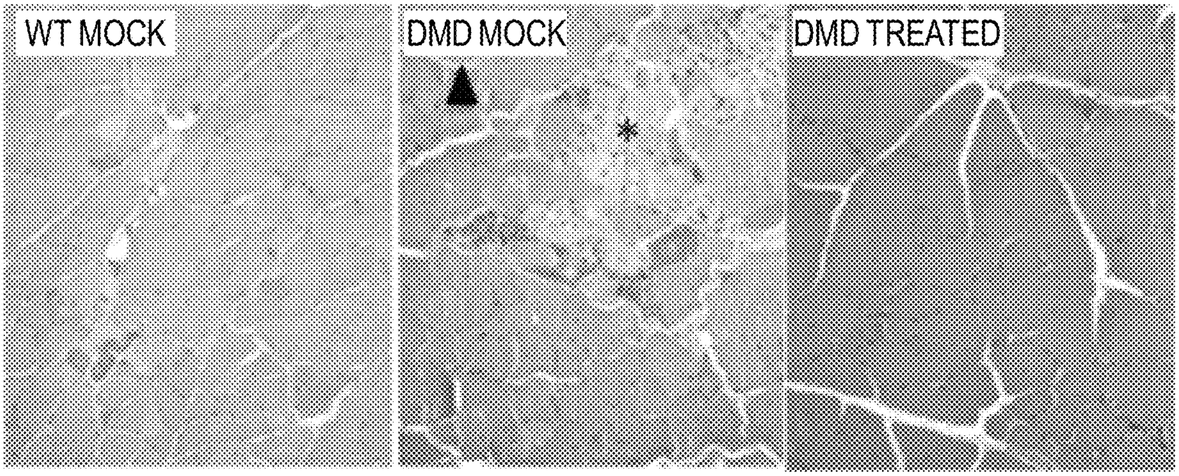
FIG. 36B provides photomicrographs showing haematoxylin and eosin (HES) stained biceps femoris muscle obtained from a mock treated WT rat (left panel), a mock treated $Dmd^{mdx}$ rat (central panel) and a DMD rat treated with AAV9.hCK.Hopti-Dys3978.spA vector (right panel). Cluster of necrotic fibers (*) and endomysial mild fibrosis (black arrowhead) are shown.
Figure 36C:
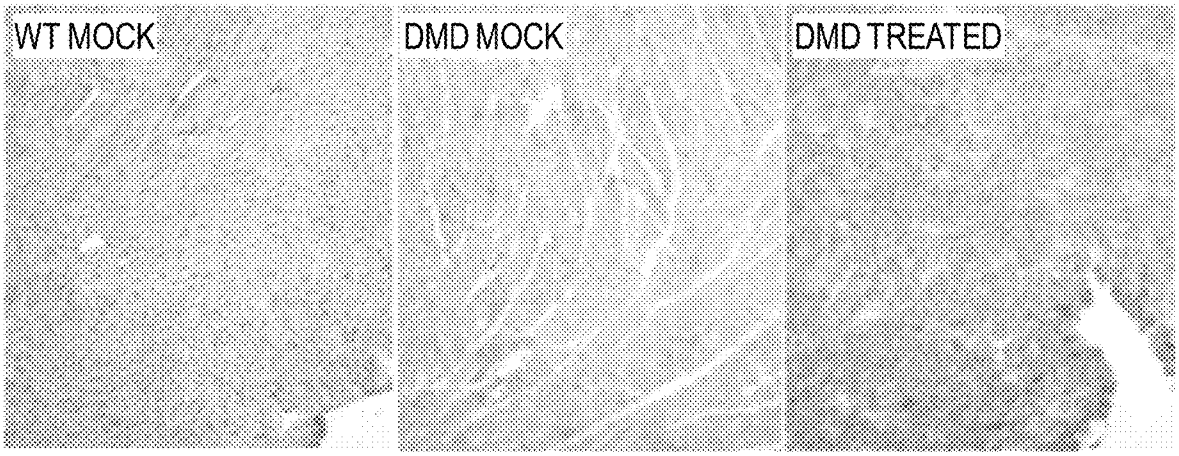
FIG. 36C provides photomicrographs showing immunolabeling with anti-dystrophin DYSB antibody of cardiac muscle obtained from a mock treated WT rat (left panel), a mock treated $Dmd^{mdx}$ rat (central panel) and a $Dmd^{mdx}$ rat treated with AAV9.hCK.Hopti-Dys3978.spA vector (right panel). The dark outline around the fibers shows the subsarcolemmal localization of the dystrophin in WT rat and mini-dystrophin in vector treated $Dmd^{mdx}$ rat.
Figure 36D:
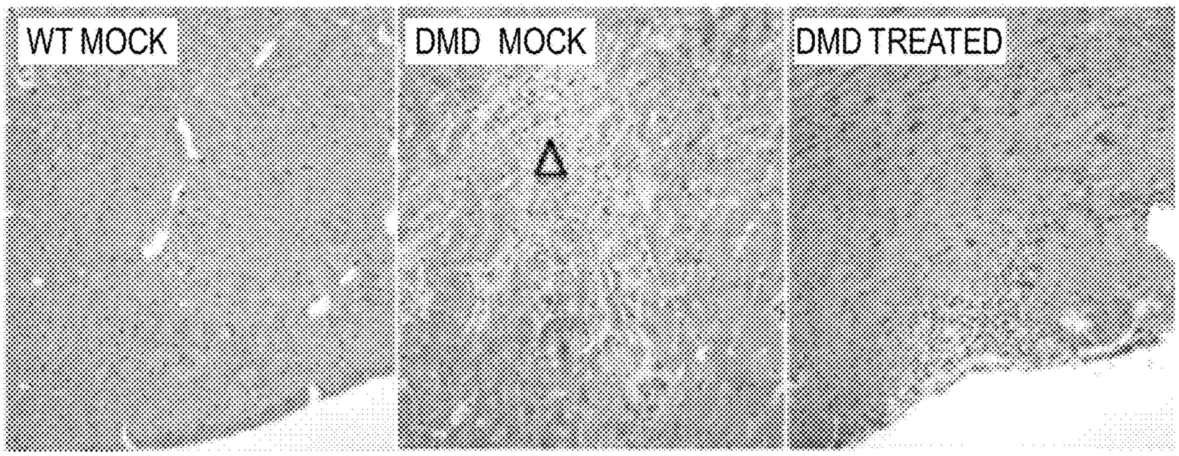
FIG. 36D provides photomicrographs showing HES stained cardiac muscle obtained from a mock treated WT rat (left panel), a mock treated $Dmd^{mdx}$ rat (central panel) and a $Dmd^{mdx}$ rat treated with AAV9.hCK.Hopti-Dys3978.spA vector (right panel). A focus of fibrosis (open arrowhead) is shown in the center panel, and a focus of mononuclear cell infiltration is illustrated in the right panel.

Dystrophic pathology was largely ameliorated as shown by H&E staining for histology of the heart (FIG. 32), diaphragm (FIG. 33) and limb muscles (FIG. 34). Trichrome Mason blue staining also showed significant reduction of fibrosis in limb muscle and diaphragm (FIG. 35).

EXAMPLE 6

Preparation of AAV9.hCK.Hopti-Dys3978.spA Vector for In Vivo Experiments

The AAV9.hCK.Hopti-Dys3978.spA vector used in $Dmd^{mdx}$ rat studies described further in Examples 7, 8 and 9 includes an AAV9 capsid and an expression cassette designed to express a miniaturized version of human dystrophin protein including the N-terminus region, hinge 1 (H1), rod 1 (R1), rod 2 (R2), hinge 3 (H3), rod 22 (R22), rod 23 (R23), rod 24 (R24), hinge 4 (H4), cysteine-rich (CR) domain, and portion of the carboxy-terminal (CT) domain from full length human Dp427m dystrophin protein (SEQ ID NO:25), which are domains minimally required for function. The protein sequence of the mini-dystrophin protein is provided as the amino acid sequence of SEQ ID NO:7, which is encoded by the human codon-optimized DNA sequence provided as the nucleic acid sequence of SEQ ID NO:1. The vector genome of the AAV9.hCK.Hopti-Dys3978.spA vector is provided as the nucleic acid sequence of SEQ ID NO:18, or its reverse complement when the single-stranded genome is packaged in its minus polarity.

The vector genome comprises 5' and 3' flanking AAV2 inverted terminal repeats (ITRs) (having the DNA sequence of SEQ ID NO:14 or SEQ ID NO:15, respectively), a synthetic hybrid enhancer and promoter derived from the creatine kinase (CK) gene to serve as a muscle specific transcription regulatory element (hCK; having the DNA sequence of SEQ ID NO:16), a 3978 base pair long human codon-optimized gene encoding the human mini-dystrophin protein described above (i.e., the Hopti-Dys3978 gene), and a small synthetic transcription termination sequence including a polyadenylation (polyA) signal (spA; having the DNA sequence of SEQ ID NO:17).

Vector was manufactured using the triple transfection technique and a serum free non-adherent cell line derived from HEK 293 cells. The plasmids used included a helper plasmid to express adenovirus helper proteins required for efficient replication and packaging of the vector, a packaging plasmid expressing the AAV2 rep gene and the AAV9 capsid proteins, and a third plasmid containing the sequence of the expression cassette described above.

Cells were grown and expanded from a working cell bank sample, and once sufficient volume and cell density had been reached, the cells were transfected using a transfection reagent. After incubation to permit vector production from the transfected cells, the cells were lysed to release vector, the lysate clarified, and vector purified using a nuclease treatment step to remove contaminating nucleic acids, followed by iodixanol step gradient centrifugation, anion exchange chromatography, dialysis against the formulation buffer, sterile filtration, and then storage at 2-8° C.

EXAMPLE 7

Effects of Single Dose of AAV9.hCK.Hopti-Dys3978.spA in a Rat Model of DMD

This example describes testing AAV9.hCK.Hopti-Dys3978.spA in a recently developed $Dmd^{mdx}$ rat model, which has certain advantages compared to the classic mdx mouse and GRMD dog models. Larcher, T., et al., Characterization of dystrophin deficient rats: a new model for Duchenne muscular dystrophy. PLoS One. 2014; 9(10): e110371. In particular, in the $Dmd^{mdx}$ rat model, the skeletal and cardiac disease are both present at an early stage and develop in a sequential manner similar to the disease progression seen in humans.

In these studies, male $Dmd^{mdx}$ rats 5-6 weeks of age were systemically administered by IV injection into tail veins a single dose ($1\times10^{14}$ vector genomes per kilogram body weight, or vg/kg) of Dys3978 vector suspended in PBS. As a control, wild-type ("WT") rats from the same genetic background (Sprague Dawley) were also treated in this way. All procedures were conducted blinded to the rat genotype or treatment cohort to avoid bias. Three $Dmd^{mdx}$ rats and 4

WT rats were treated with vector, whereas 3 $Dmd^{mdx}$ rats and 2 WT rats were administered PBS only as a negative control (mock treatment). Three months post-injection, animals were euthanized and underwent necropsy for tissue analysis by histology and immunocytochemistry for dystrophin protein expression.

For histopathological evaluation, tissue samples were fixed in 10% neutral buffered formalin, embedded in paraffin wax, and 5-μm-thick sectioned before staining with hematoxylin eosin saffron (HES). For dystrophin immunolabelling, additional samples (liver, heart, biceps femoris, pectoralis and diaphragm muscles) were frozen and 8-μm-thick sectioned. Mouse monoclonal antibody NCL-DYSB for dystrophin (Novocastra Laboratories, Newcastle on Tyne, UK) was used for both dystrophin and mini-dystrophin protein detection (1:50), since this antibody does not distinguish between full length wild type dystrophin and the engineered mini-dystrophin. All necropsies and histological observations were performed in blinded fashion.

By histological examination, no lesions were observed in skeletal or cardiac muscle of PBS and vector treated WT rats. In all $Dmd^{mdx}$ rats, skeletal muscle fiber lesions showing individual necrosis, clusters of regenerative small fibers, scattered giant hyaline fibers, anisocytosis, centronucleation, endomysial fibrosis and sporadic adiposis were present and characteristic of DMD skeletal muscle. The incidence and intensity of these lesions was globally decreased in $Dmd^{mdx}$ rats treated with vector compared to those treated only PBS. In the heart, lesions of multifocal necrosis, mononuclear cell focal infiltration and mild focal extensive fibrosis were present in one of the $Dmd^{mdx}$ rats (rat 49) treated with PBS, which is characteristic of DMID cardiac muscle. In all the $Dmd^{mdx}$ rats treated with vector, cardiac muscle presentation was similar and showed mild mononuclear cell focal infiltration as seen in the $Dmd^{mdx}$ rat receiving PBS, but in contrast, no fibrotic foci were observed in the hearts of the vector treated $Dmd^{mdx}$ rats.

Using immunocytochemistry, WT rats displayed subsarcolemmal dystrophin detected in skeletal, diaphragm and cardiac muscle fibers, and localization of dystrophin detected did not differ between rats treated with vector compared to only PBS. However, mini-dystrophin detection in the vector treated WT rats could not be confirmed using this assay because the anti-dystrophin antibody used could not distinguish between wild type dystrophin and the mini-dystrophin protein. By contrast, one of the $Dmd^{mdx}$ rats (rat 49) displayed rare skeletal muscle fibers (from about 5% to 10%) with subsarcolemmal dystrophin detectable, which is in accordance with the previous description of the presence of scattered revertant fibers in this model with a frequency of about 5% (Larcher et al., PlosOne, 2014). However no dystrophin was detected in diaphragm or cardiac muscle fibers from this rat. In all Dys3978 vector treated $Dmd^{mdx}$ rats, subsarcolemmal dystrophin was also detected in about 80% to 95% of skeletal muscle fibers, about 30% to 50% in diaphragm muscle fibers, and about 70% to 80% in heart muscle fibers, although no systematic counting performed. In these rats, very rare skeletal muscle fibers (1 or 2 per muscle section) displayed some cytoplasmic interfibrillar dystrophin. In both vector treated WT and $Dmd^{mdx}$ rats, there was no evidence of inflammatory cell infiltrates or increased necrosis that might indicate that a cellular immune response had been stimulated by vector transduction, or production of the mini-dystrophin.

In sum, 3 months after systemic administration of $1\times10^{14}$ vg/kg of AAV9.hCK.opti-Dys3978.spA vector, no histological alteration of the muscle tissues was observed in WT rats treated with vector compared to PBS, suggesting that expression of the mini-dystrophin protein was well tolerated in healthy animals. Furthermore, vector treatment of the $Dmd^{mdx}$ rats resulted in a significant and generalized detection of mini-dystrophin in fibers of all muscles studied (biceps femoris, pectoralis, diaphragm and heart) with a pattern of subsarcolemmal localization similar to that in WT rat muscles. The expression of mini-dystrophin Dys3978 from the vector was associated with reduction in fibrosis and necrosis (FIGS. 36A-36D).

EXAMPLE 8

Effects of Increasing Doses of AAV9.hCK.Hopti-Dys3978.spA in $Dmd^{mdx}$, Rats Determined at 3 Months and 6 Months Post-Injection This example describes the results of treating $Dmd^{mdx}$ rats, an animal model for Duchenne muscular dystrophy, with increasing doses of AAV9.hCK.Hopti-Dys3978.spA, and measuring the effects at 3 months and 6 months after administration.

Rats were dosed at 7-8 weeks of age by IV injection into the dorsal penile vein, which resulted in systemic administration of the test articles. Four different vector doses were tested in 10-12 $Dmd^{mdx}$ rats: $1\times10^{13}$ vg/kg (5 rats at the 3 month time point and 6 rats at the 6 month time point), $3\times10^{13}$ vg/kg (6 rats at the 3 month time point and 5 rats at the 6 month time point), $1\times10^{14}$ vg/kg (7 rats at the 3 month time point and 6 rats at the 6 month time point), and $3\times10^{14}$ vg/kg (5 rats at the 3 month time point and 5 rats at the 6 month time point). In addition, $Dmd^{mdx}$ rats and WT rats each received vehicle only (1×PBS, 215 mM NaCl, 1.25% human serum albumin, 5% (w/v) sorbitol) as a negative control (6 $Dmd^{mdx}$ rats at the 3 month time point, 4 $Dmd^{mdx}$ rats at the 6 month time point, 5 WT rats at the 3 month time point, and 7 WT rats at the 6 month time point). Five untreated (that is, no vector and no vehicle either) $Dmd^{mdx}$ rats were also included as further negative controls. At 3 months and 6 months post-injection, rats from each test arm were euthanized and necropsied to take tissue samples for further analysis. Prior to sacrifice, cardiac function and grip strength tests were carried out in the test animals to assess the effect of vector treatment on DMD disease progression.

Note that vector doses may be represented in two different numerically equivalent ways in the text and figures. Thus, "$1\times10^{13}$" is equivalent to "1E13," "$3\times10^{13}$" is equivalent to "3E13," "$1\times10^{14}$" is equivalent to "1E14," and "$3\times10^{14}$" is equivalent to "3E14."

Body Weight

Figure 37:
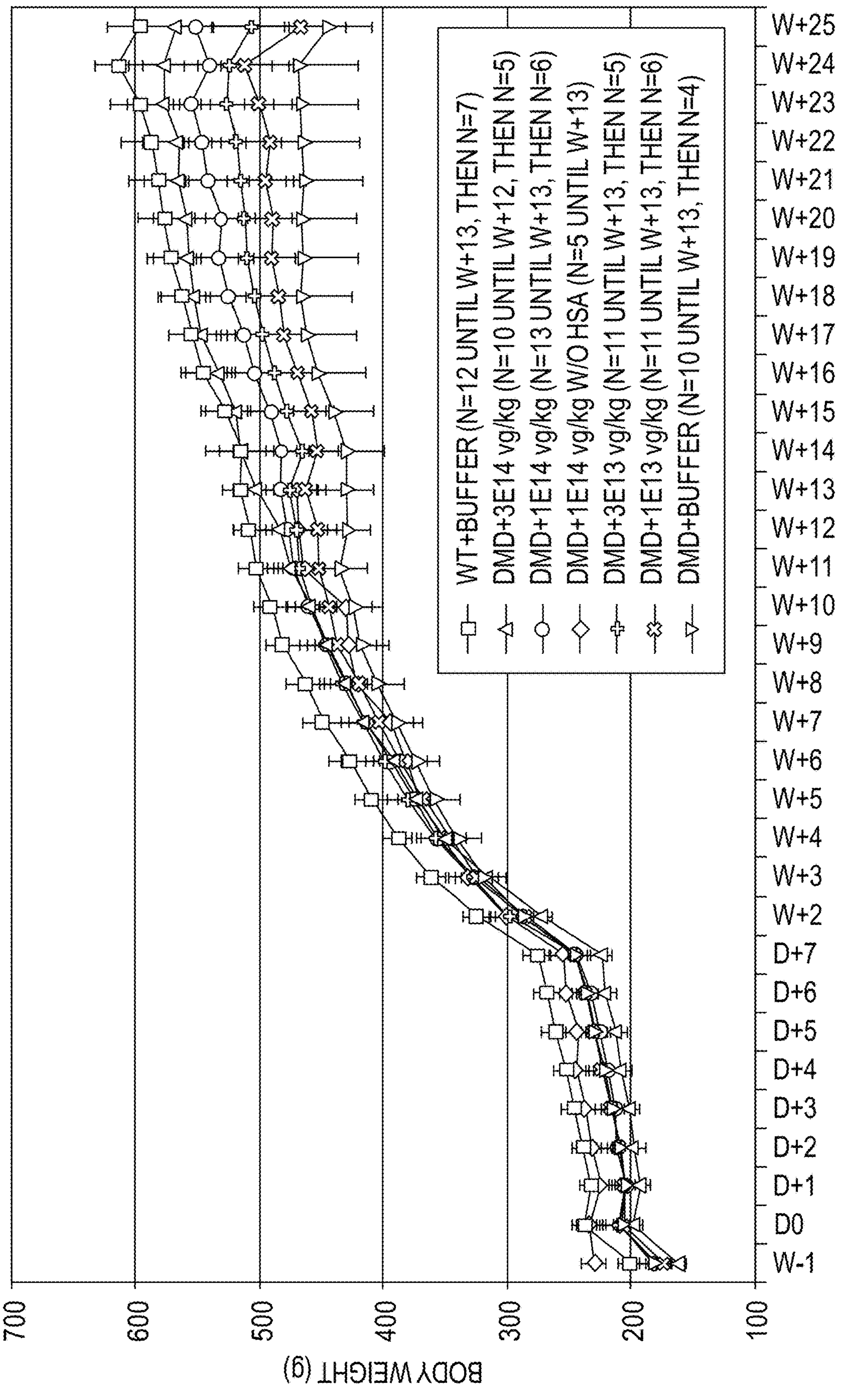
FIG. 37 shows average body weight in grams of WT rats treated with vehicle (buffer) and $Dmd^{mdx}$ rats treated with vehicle and increasing doses of AAV9.hCK.Hopti-Dys3978.spA vector over time to 25 weeks after dosing. "WT" refers to wild type rats; "DMD" refers to $Dmd^{mdx}$ rats.

After treatment and prior to sacrifice, rats in each treatment arm were weighed daily for the first week, and weekly thereafter until sacrifice. The average weight of all rats in each treatment arm is listed in Table 2 (pre-injection until 9 weeks post-injection) and Table 3 (weeks 10-25 post-injection) and are graphed against time in FIG. 37. In the graph, error bars represent the standard error of the mean (SEM), which are also reported in the table. At all times, the average weight of WT rats exceeded that of $Dmd^{mdx}$ rats, including those that were treated with vector. Due to age differences and natural variability in body mass among the $Dmd^{mdx}$ rats there was no consistent correlation between dose and body weight until by 4 weeks post-injection when weights of all vector treated $Dmd^{mdx}$ rats except in the highest dose arm were higher than untreated $Dmd^{mdx}$ rats, but lower than WT rats. By 12 weeks post-injection, a dose effect in all treatment arms was evident, with body weight being proportional to vector dose at all doses tested through the end of the study.

TABLE 2

| MEAN WEIGHTS (g) | W − 1 | D 0 | D + 1 | D + 2 | D + 3 | D + 4 | D + 5 | D + 6 | D + 7 | W + 2 | W + 3 | W + 4 | W + 5 | W + 6 | W + 7 | W + 8 | W + 9 |
|---|---|---|---|---|---|---|---|---|---|---|---|---|---|---|---|---|---|
| WT + Buffer (n = 12 until W + 13, then n = 7) | 200.0 | 237.9 | 231.7 | 237.9 | 247.1 | 253.1 | 262.1 | 268.7 | 276.6 | 325.0 | 361.8 | 388.8 | 410.2 | 428.8 | 449.6 | 463.4 | 482.1 |
| SEM | 10.9 | 10.5 | 10.1 | 10.5 | 10.1 | 9.8 | 10.0 | 10.4 | 10.7 | 10.8 | 11.7 | 11.9 | 13.6 | 14.8 | 15.4 | 15.5 | 14.1 |
| DMD + Buffer (n = 10 until W + 13, then n = 4) | 180.4 | 207.4 | 203.4 | 208.8 | 214.5 | 221.5 | 229.8 | 235.4 | 244.3 | 286.3 | 318.4 | 340.5 | 358.7 | 374.4 | 389.1 | 403.6 | 418.6 |
| SEM | 11.9 | 12.3 | 11.9 | 12.6 | 12.4 | 13.0 | 12.4 | 13.1 | 12.6 | 15.1 | 17.7 | 18.7 | 19.4 | 20.3 | 21.3 | 21.0 | 22.3 |
| DMD + 1E13 vg/kg (n = 11 until W + 13, then n = 6) | 173.4 | 206.4 | 205.8 | 208.4 | 216.7 | 223.8 | 229.8 | 236.8 | 243.1 | 286.3 | 325.6 | 346.5 | 368.6 | 388.1 | 403.8 | 419.5 | 439.1 |
| SEM | 10.3 | 8.3 | 7.9 | 7.5 | 7.9 | 7.2 | 7.6 | 7.8 | 8.7 | 9.5 | 12.6 | 13.2 | 14.2 | 15.6 | 16.1 | 16.7 | 16.2 |
| DMD + 3E13 vg/kg (n = 11 until W + 13, then n = 5) | 180.2 | 210.8 | 206.3 | 209.1 | 217.6 | 224.9 | 230.9 | 237.2 | 245.2 | 297.7 | 329.5 | 357.3 | 380.8 | 398.4 | 416.7 | 432.9 | 448.2 |
| SEM | 11.9 | 10.9 | 10.3 | 10.9 | 11.3 | 10.5 | 10.6 | 10.7 | 11.0 | 13.4 | 13.5 | 15.3 | 16.5 | 17.1 | 18.0 | 19.4 | 19.3 |
| DMD + 1E14 vg/kg (n = 13 until W + 13, then n = 6) | 178.2 | 209.4 | 204.3 | 210.5 | 213.0 | 220.1 | 225.3 | 232.5 | 244.5 | 288.2 | 329.6 | 356.6 | 375.9 | 395.7 | 413.4 | 431.5 | 448.6 |
| SEM | 9.6 | 7.9 | 7.5 | 7.7 | 7.5 | 7.4 | 7.0 | 7.5 | 9.9 | 9.6 | 11.7 | 12.3 | 12.2 | 12.4 | 12.7 | 13.8 | 13.3 |
| DMD + 1E14 vg/kg w/o HSA (n = 5 until W + 13) | 230.1 | 234.9 | 224.5 | 233.7 | 238.7 | 245.3 | 243.0 | 252.7 | 254.9 | 300.6 | 331.7 | 352.7 | 370.3 | 382.2 | 392.3 | 421.3 | 428.5 |
| SEM | 10.2 | 9.9 | 9.3 | 9.3 | 9.5 | 9.5 | 9.3 | 9.8 | 10.4 | 13.0 | 15.4 | 15.8 | 17.1 | 18.1 | 16.3 | 17.2 | 22.7 |
| DMD + 3E14 vg/kg (n = 10 until W + 12, then n = 5) | 161.8 | 198.4 | 193.2 | 197.1 | 202.3 | 208.6 | 212.3 | 220.6 | 223.7 | 272.6 | 316.2 | 350.7 | 373.0 | 393.3 | 414.9 | 429.2 | 445.8 |
| SEM | 6.1 | 7.5 | 8.8 | 9.9 | 9.3 | 8.9 | 8.7 | 8.7 | 8.5 | 8.2 | 8.7 | 10.5 | 11.4 | 13.9 | 13.6 | 14.4 | 14.7 |

TABLE 3

| MEAN WEIGHTS (g) | W + 10 | W + 11 | W + 12 | W + 13 | W + 14 | W + 15 | W + 16 | W + 17 |
|---|---|---|---|---|---|---|---|---|
| WT + Buffer (n = 12 until W + 13, then n = 7) | 490.7 | 505.2 | 509.1 | 516.8 | 514.0 | 527.8 | 545.0 | 553.8 |
| SEM | 14.0 | 12.4 | 13.2 | 13.3 | 18.8 | 19.6 | 19.2 | 18.5 |
| DMD + Buffer (n = 10 until W + 13, then n = 4) | 423.0 | 435.2 | 428.2 | 430.3 | 430.2 | 440.6 | 452.7 | 461.8 |
| SEM | 22.8 | 21.8 | 17.4 | 21.6 | 30.5 | 32.3 | 37.7 | 39.4 |
| DMD + 1E13 vg/kg (n = 11 until W + 13, then n = 6) | 444.8 | 452.5 | 453.5 | 464.5 | 453.2 | 457.7 | 469.9 | 481.3 |
| SEM | 16.6 | 17.3 | 15.4 | 17.7 | 17.4 | 17.2 | 18.7 | 17.6 |
| DMD + 3E13 vg/kg (n = 11 until W + 13, then n = 5) | 458.2 | 467.4 | 469.7 | 476.1 | 465.8 | 478.5 | 489.1 | 496.9 |
| SEM | 20.2 | 19.4 | 20.7 | 23.1 | 28.9 | 31.4 | 34.2 | 34.2 |
| DMD + 1E14 vg/kg (n = 13 until W + 13, then n = 6) | 459.3 | 472.7 | 478.0 | 483.2 | 482.1 | 492.5 | 504.5 | 513.6 |
| SEM | 12.7 | 12.3 | 11.8 | 12.2 | 13.7 | 14.1 | 14.3 | 13.0 |
| DMD + 1E14 vg/kg w/o HSA (n = 5 until W + 13) | 430.2 | 464.5 | 469.1 | 470.3 | N/A | N/A | N/A | N/A |
| SEM | 20.4 | 18.0 | 18.7 | 18.1 | N/A | N/A | N/A | N/A |
| DMD + 3E14 vg/kg (n = 10 until W + 12, then n = 5) | 457.4 | 475.3 | 483.9 | 502.1 | 515.9 | 519.1 | 532.8 | 547.1 |
| SEM | 14.8 | 15.0 | 15.6 | 27.5 | 26.7 | 24.9 | 27.2 | 26.5 |

| MEAN WEIGHTS (g) | W + 18 | W + 19 | W + 20 | W + 21 | W + 22 | W + 23 | W + 24 | W + 25 |
|---|---|---|---|---|---|---|---|---|
| WT + Buffer (n = 12 until W + 13, then n = 7) | 562.2 | 572.0 | 577.2 | 581.9 | 586.9 | 597.3 | 613.8 | 596.4 |
| SEM | 19.4 | 18.8 | 21.6 | 22.9 | 24.1 | 23.1 | 19.5 | 26.6 |
| DMD + Buffer (n = 10 until W + 13, then n = 4) | 464.8 | 463.5 | 464.9 | 463.0 | 465.8 | 467.1 | 467.4 | 444.8 |
| SEM | 39.2 | 42.7 | 43.6 | 46.5 | 46.6 | 46.6 | 46.6 | 34.9 |
| DMD + 1E13 vg/kg (n = 11 until W + 13, then n = 6) | 484.8 | 491.7 | 490.1 | 496.3 | 491.6 | 513.3 | 513.3 | 467.2 |
| SEM | 18.3 | 21.2 | 23.7 | 24.2 | 27.0 | 35.8 | 35.8 | 36.4 |
| DMD + 3E13 vg/kg (n = 11 until W + 13, then n = 5) | 505.2 | 510.7 | 512.6 | 517.4 | 519.7 | 525.7 | 525.7 | 507.0 |
| SEM | 35.3 | 39.4 | 38.9 | 38.3 | 37.7 | 35.6 | 35.6 | 30.4 |
| DMD + 1E14 vg/kg (n = 13 until W + 13, then n = 6) | 525.0 | 532.7 | 530.6 | 541.9 | 545.9 | 539.7 | 539.7 | 551.3 |
| SEM | 14.8 | 15.4 | 13.8 | 14.8 | 15.4 | 9.2 | 9.2 | 15.1 |
| DMD + 1E14 vg/kg w/o HSA (n = 5 until W + 13) | N/A | N/A | N/A | N/A | N/A | N/A | N/A | N/A |

TABLE 3-continued

| | | | | | | | | |
|---|---|---|---|---|---|---|---|---|
| SEM | N/A | N/A | N/A | N/A | N/A | N/A | N/A | N/A |
| DMD + 3E14 vg/kg (n = 10 until W + 12, then n = 5) | 552.6 | 558.0 | 558.1 | 565.9 | 566.4 | 577.6 | 577.6 | 566.9 |
| SEM | 27.4 | 27.2 | 27.3 | 27.3 | 28.8 | 29.2 | 29.2 | 28.5 |

Quantification of Vector Transduction and RNA and Protein Expression in Dmd$^{mdx}$ Rats Treated with AAV9.hCK.Hopti-Dys3978.spA Vector Materials and Methods Standard molecular biology techniques were used to quantitate the transgene copy number by quantitative PCR (qPCR), relative expression levels of the mini-dystrophin mRNA transcripts by reverse transcriptase qPCR (RT-qPCR), and the amount of mini-dystrophin protein expression qualitatively by Western blot analysis.

For qPCR, genomic DNA (gDNA) was purified from tissues using the Gentra Puregene kit from Qiagen. Samples were then analyzed using a StepOne Plus' Real Time PCR System (Applied Biosystems®, Thermo Fisher Scientific) using 50 ng gDNA in duplicate. All reactions were performed in duplex in a final volume of 20 μL containing template DNA, Premix Ex taq (Ozyme), 0.3 μL of ROX reference Dye (Ozyme), 0.2 μmol/L of each primer and 0.1 μmol/L of Tagman® probe.

Vector copy numbers were determined using primers and probe designed to amplify a region of the mini-dystrophin transgene:

```
                                        SEQ ID NO: 19
Forward: 5'-CCAACAAAGTGCCCTACTACATC-3'

                                        SEQ ID NO: 20
Reverse: 5'- GGTTGTGCTGGTCCAGGGCGT-3'

                                        SEQ ID NO: 21
Probe: 5'-FAM-CCGAGCTGTATCAGAGCCTGGCC-TAMRA-3'
```

Endogenous gDNA copy numbers were determined using primers and probe designed to amplify the rat HPRT1 gene:

```
Forward:
                                        SEQ ID NO: 22
5'- GCGAAAGTGGAAAAGCCAAGT -3'

Reverse:
                                        SEQ ID NO: 23
5'-GCCACATCAACAGGACTCTTGTAG-3'

Probe:
                                        SEQ ID NO: 24
5'- JOE- CAAAGCCTAAAAGACAGCGGCAAGTTGAAT-TAMRA-3'
```

For each sample, threshold cycle (Ct) values were compared with those obtained with different dilutions of linearized standard plasmids (containing either the mini-dystrophin expression cassette or the rat HPRT1 gene). The absence of qPCR inhibition in the presence of gDNA was checked by analyzing 50 ng of gDNA extracted from tissues samples from a control animal, spiked with different dilutions of standard plasmid. Duplex qPCR (amplification of the 2 sequences in the same reaction) was used and results were expressed in vector genome per diploid genome (vg/dg). The sensitivity of the test was 0.003 vg/dg.

For RT-qPCR, total RNA was extracted from tissue samples with TRIzol@reagent (Thermo Fisher Scientific), and then treated with RNAse-free DNAse I from the TURBO DNA-free kit (Thermo Fischer Scientific). Total RNA (500 ng) was reverse transcribed using random primers (Thermo Fischer Scientific) and M-MLV reverse transcriptase (Thermo Fischer Scientific) in a final volume of 25 μL. Duplex qPCR analysis was then performed 1/15-diluted cDNA using the same mini-dystrophin and rat HPRT1 specific primers and probes as for the quantification of transgene copy numbers by qPCR. The absence of qPCR inhibition in the presence of cDNA was checked by analyzing cDNA obtained from tissues samples from a control animal spiked with different dilutions of standard plasmid. For each RNA sample, Ct values were compared with those obtained with different dilutions of standard plasmids (containing either the mini-dystrophin expression cassette or the rat HPRT1 gene). Results were expressed in relative quantities (RQ):

$$RQ=2^{-\Delta Ct}=2^{-(Ct\ target-Ct\ endogenous\ control)}$$

For each RNA sample, the absence of DNA contamination was also confirmed by analysis of "cDNA-like samples" obtained without addition of reverse transcriptase in the reaction mix.

For Western blot analysis of expressed protein levels, total proteins were extracted from tissue samples using RIPA buffer containing a protease inhibitor cocktail (Sigma-Aldrich). Protein extracts, 50 μg for biceps femoris, heart and diaphragm, or 100 μg for liver, were loaded on a NuPAGE® Novex 3-8% Tris Acetate gel and analyzed using the NuPAGE® large protein blotting kit (Thermo Fischer Scientific). A final concentration of 200 mM DTT was used to reduce proteins before loading. Membranes were then blocked in 5% skim milk, 1% NP40 (Sigma-Aldrich) in TBST (tris-buffered saline, 0.1% Tween 20) and hybridized with an anti-dystrophin antibody specific for exons 10 and 11 of the dystrophin protein (1:100, MANEX 1011C monoclonal antibody) and with a secondary anti-mouse IgG HRP-conjugated antibody (1:2000, Dako). For protein loading control, the same membrane was also hybridized with an anti-rat alpha-tubulin antibody (1:10000, Sigma) and with a secondary anti-mouse IgG HRP-conjugated antibody (1:2000, Dako). Immunoblots were visualized by ECL Chemiluminescent analysis system (Thermo Fisher Scientific).

Human Mini-Dystrophin Transgene Copy Numbers at 3 and 6 Months Post-Injection

Results of testing for transgene copy numbers (as vector genomes per diploid genome (vg/dg)) in whole blood, spleen, heart, biceps femoris, pectoralis, diaphragm, and liver in Dmd$^{mdx}$ rats treated with vector and vehicle, and in WT rats administered vehicle only are described in the tables below. Data at 3 months post-injection is provided in Table 4, and at 6 months post-injection is provided in Table 5. Data are the mean of results from individual test animals.

TABLE 4

| 3 Months Post-Injection | | | | | | |
|---|---|---|---|---|---|---|
| | DMD + vehicle | WT + vehicle | DMD + 1 × $10^{13}$ vg/kg | DMD + 3 × $10^{13}$ vg/kg | DMD + 1 × $10^{14}$ vg/kg | DMD + 3 × $10^{14}$ vg/kg |
| Whole blood | <0.002 | <0.002 | <0.002 | <0.002 | <0.002 | <0.002 |
| Spleen | <0.002 | <0.002 | <0.002 | 0.010 | 0.005 | 0.013 |
| Heart (basal part) | <0.002 | <0.002 | 0.090 | 0.270 | 0.670 | 4.350 |
| Biceps femoris | <0.002 | <0.002 | <0.002 | 0.070 | 0.260 | 1.700 |
| Pectoralis | <0.002 | <0.002 | 0.010 | 0.030 | 0.400 | 0.760 |
| Diaphragm | <0.002 | <0.002 | 0.003 | 0.030 | 2.410 | 2.810 |
| Liver (central lobe) | <0.002 | <0.002 | 0.830 | 5.460 | 30.780 | 112.880 |

TABLE 5

| 6 Months Post-Injection | | | | | | |
|---|---|---|---|---|---|---|
| | DMD + vehicle | WT + vehicle | DMD + 1 × $10^{13}$ vg/kg | DMD + 3 × $10^{13}$ vg/kg | DMD + 1 × $10^{14}$ vg/kg | DMD + 3 × $10^{14}$ vg/kg |
| Whole blood | <0.002 | <0.002 | <0.002 | <0.002 | <0.002 | <0.002 |
| Spleen | <0.002 | <0.002 | <0.002 | <0.002 | <0.002 | 0.010 |
| Heart (basal part) | <0.002 | <0.002 | 0.160 | 0.140 | 1.460 | 5.380 |
| Biceps femoris | <0.002 | <0.002 | 0.009 | 0.020 | 0.390 | 1.400 |
| Pectoralis | <0.002 | <0.002 | 0.006 | 0.020 | 0.530 | 0.800 |
| Diaphragm | <0.002 | <0.002 | 0.010 | 0.010 | 4.850 | 1.270 |
| Liver (central lobe) | <0.002 | <0.002 | 1.080 | 8.130 | 30.490 | 82.230 |

No qPCR signal was detected in the Dmd$^{mdx}$ or WT rats injected with vehicle only, confirming that these animals had not received any vector, and no qPCR signal was detected in whole blood at 3 and 6 months post-injection.

Mini-dystrophin DNA was detected in Dmd$^{mdx}$ rats that had been injected with vector at both 3 and 6 months post-injection. Transgene copy numbers in the tissues under study followed a pattern of prevalence of liver>heart>biceps femoris≈diaphragm≈pectoralis>spleen. Of the tissues analyzed, liver was by far the most efficiently transduced, with vector copy numbers reaching up to an average of 80-110 vg/dg in rats administered with 3×$10^{14}$ vg/kg vector. Vector copy numbers in liver were 7-45 fold higher than in heart and 40-300 fold higher than in biceps femoris, diaphragm, or pectoralis muscles. In heart, vector copy numbers averaged about 1.0 vg/dg in rats dosed with 1×$10^{14}$ vg/kg vector and about 5.0 vg/dg in rats dosed with 3×$10^{14}$ vg/kg vector. At a dose of 1×$10^{14}$ vg/kg, transgene copy numbers in biceps femoris and pectoralis were similar and never exceeded about 0.5 vg/dg. When the vector dose increased to 3×$10^{14}$ vg/kg, the average transgene copy number increased to about 1.2 vg/dg. The data was particularly variable for diaphragm due to certain unusually high results among 4 animals that had received the two highest dose levels of vector, in which the transgene copy numbers ranged from about 9-15 vg/dg. If these outlying data points are excluded, then the transduction efficiency of diaphragm is relatively low at both the 3 and 6 month time points, with transgene copy numbers averaging about 0.2-0.4 vg/dg at the 1×$10^{14}$ vg/kg dose and about 1.05-1.3 vg/dg at the 3×$10^{14}$ vg/kg dose.

Human Mini-Dystrophin mRNA Expression at 3 and 6 Months Post-Injection

Two to four animals per treatment arm were randomly chosen for analysis by RT-qPCR to quantify levels of human mini-dystrophin mRNA transcripts in samples of biceps femoris, diaphragm, heart, spleen, and liver obtained at sacrifice. The results obtained from test animals sacrificed at 3 months and 6 months post-injection are provided in Table 6 and Table 7, respectively. Data is expressed in relative quantities (RQ) of mini-dystrophin mRNA relative to mRNA from the rat HPRT1 gene.

No transcripts were detected in any tissue from animals in the negative control arms (WT rats and Dmd$^{mdx}$ rats treated with vehicle), or in spleen of animals treated with vector, regardless of dose. In all other tissues examined, vector-derived transcripts were detected, the levels of which tended to increase in a dose-responsive manner, although with some variability in the data. Transcript levels in the tissues followed the pattern biceps femoris>heart≈diaphragm>liver. As discussed above, liver was the most transduced tissue among those sampled, with vector copy numbers varying about 60-130 fold higher than in biceps femoris muscle. Despite this, the level of mini-dystrophin mRNA in liver was about 5-15 fold lower than in biceps femoris, evidence of the highly muscle-specific activity of the promoter used in the vectors.

TABLE 6

| 3 Months Post-Injection | | | | | | | | | | | | | | |
|---|---|---|---|---|---|---|---|---|---|---|---|---|---|---|
| | Rat 1 RQ DMD + vehicle | Rat 2 RQ DMD + vehicle | Rat 3 RQ WT + vehicle | Rat 4 RQ WT + vehicle | Rat 5 RQ DMD + 1 × $10^{13}$ vg/kg | Rat 6 RQ DMD + 1 × $10^{13}$ vg/kg | Rat 7 RQ DMD + 3 × $10^{13}$ vg/kg | Rat 8 RQ DMD + 3 × $10^{13}$ vg/kg | Rat 9 RQ DMD + 1 × $10^{14}$ vg/kg | Rat 10 RQ DMD + 1 × $10^{14}$ vg/kg | Rat 11 RQ DMD + 1 × $10^{14}$ vg/kg | Rat 12 RQ DMD + 1 × $10^{14}$ vg/kg | Rat 13 RQ DMD + 3 × $10^{14}$ vg/kg | Rat 14 RQ DMD + 3 × $10^{14}$ vg/kg |
| Spleen | <0.03 | <0.03 | <0.03 | <0.03 | <0.03 | <0.03 | <0.03 | <0.03 | <0.03 | <0.03 | <0.03 | <0.03 | <0.03 | <0.03 |
| Biceps femoris | <0.03 | <0.03 | <0.03 | <0.03 | 2.6 | 0.9 | 7.8 | 7.2 | 23.8 | 18.4 | 40.9 | 79.6 | 33.1 | 33.3 |
| Heart (basal part) | <0.03 | <0.03 | <0.03 | <0.03 | 1.7 | 1.8 | 3.3 | 1.4 | 4.5 | 4.5 | 3.2 | 6.5 | 9.6 | 12.4 |
| Diaphragm | <0.03 | <0.03 | <0.03 | <0.03 | 0.2 | 0.3 | 1.6 | 2.7 | 13.6 | 5.1 | 4.2 | 23.2 | 9.7 | 18.8 |
| Liver (central lobe) | <0.03 | <0.03 | <0.03 | <0.03 | 0.1 | 0.2 | 0.7 | 0.8 | 2.2 | 4.7 | 3.8 | 0.8 | 7.4 | 3.3 |

TABLE 7

| 6 Months Post-Injection | | | | | | | | | | | | |
|---|---|---|---|---|---|---|---|---|---|---|---|---|
| | Rat 15 RQ DMD + vehicle | Rat 16 RQ DMD + vehicle | Rat 17 RQ WT + vehicle | Rat 18 RQ WT + vehicle | Rat 19 RQ DMD + 1 × $10^{13}$ vg/kg | Rat 20 RQ DMD + 1 × $10^{13}$ vg/kg | Rat 21 RQ DMD + 3 × $10^{13}$ vg/kg | Rat 22 RQ DMD + 3 × $10^{13}$ vg/kg | Rat 23 RQ DMD + 1 × $10^{14}$ vg/kg | Rat 24 RQ DMD + 1 × $10^{14}$ vg/kg | Rat 25 RQ DMD + 3 × $10^{14}$ vg/kg | Rat 26 RQ DMD + 3 × $10^{14}$ vg/kg |
| Spleen | <0.03 | <0.03 | <0.03 | <0.03 | <0.03 | <0.03 | <0.03 | <0.03 | <0.03 | <0.03 | <0.03 | <0.03 |
| Biceps femoris | <0.03 | <0.03 | <0.03 | <0.03 | 0.6 | 0.3 | 3.0 | 8.9 | 15.8 | 24.2 | 64.0 | 19.7 |
| Heart (basal part) | <0.03 | <0.03 | <0.03 | <0.03 | 1.2 | 1.6 | 1.3 | 1.4 | 3.7 | 4.3 | 9.2 | 6.1 |
| Diaphragm | <0.03 | <0.03 | <0.03 | <0.03 | 0.5 | 0.1 | 1.4 | 1.1 | 4.5 | 8.0 | 19.7 | 17.1 |
| Liver (central lobe) | <0.03 | <0.03 | <0.03 | <0.03 | 0.1 | 0.1 | 0.2 | 0.5 | 0.7 | 0.6 | 4.6 | 2.1 |

Human Mini-Dystrophin Protein Expression at 3 and 6 Months Post-Injection

The same animals randomly selected for analysis to determine human mini-dystrophin mRNA levels were also analyzed to determine mini-dystrophin protein levels using Western blot. No mini-dystrophin protein was detected in any tissue from animals in the negative control arms (WT rats and $Dmd^{mdx}$ rats treated with vehicle). At both the 3 and 6 month time points, mini-dystrophin protein was detected in biceps femoris, heart and diaphragm of $Dmd^{mdx}$ rats dosed with vector. At the lowest dose tested (1×$10^{13}$ vg/kg), mini-dystrophin protein was detected less frequently in the tissue samples compared to rats dosed with vector at higher levels. These results are summarized qualitatively in Table 8.

TABLE 8

| Rat | Time | Dose | Biceps femoris | Heart (basal part) | Diaphragm |
|---|---|---|---|---|---|
| 5 | 3 mo | 1 × $10^{13}$ vg/kg | + | + | + |
| 6 | 3 mo | 1 × $10^{13}$ vg/kg | − | + | − |
| 7 | 3 mo | 3 × $10^{13}$ vg/kg | + | + | + |
| 8 | 3 mo | 3 × $10^{13}$ vg/kg | + | + | + |
| 9 | 3 mo | 1 × $10^{14}$ vg/kg | + | + | + |
| 10 | 3 mo | 1 × $10^{14}$ vg/kg | + | + | + |
| 11 | 3 mo | 1 × $10^{14}$ vg/kg | + | + | + |
| 12 | 3 mo | 1 × $10^{14}$ vg/kg | + | − | + |
| 13 | 3 mo | 3 × $10^{14}$ vg/kg | + | + | + |
| 14 | 3 mo | 3 × $10^{14}$ vg/kg | + | + | + |
| 19 | 6 mo | 1 × $10^{13}$ vg/kg | + | + | − |

TABLE 8-continued

| Rat | Time | Dose | Biceps femoris | Heart (basal part) | Diaphragm |
|---|---|---|---|---|---|
| 20 | 6 mo | 1 × $10^{13}$ vg/kg | − | + | − |
| 21 | 6 mo | 3 × $10^{13}$ vg/kg | + | + | + |
| 22 | 6 mo | 3 × $10^{13}$ vg/kg | + | + | − |
| 23 | 6 mo | 1 × $10^{14}$ vg/kg | + | + | + |
| 24 | 6 mo | 1 × $10^{14}$ vg/kg | + | + | + |
| 25 | 6 mo | 3 × $10^{14}$ vg/kg | + | + | + |
| 26 | 6 mo | 3 × $10^{14}$ vg/kg | + | + | + |

There was a positive correlation between the amount of protein detected by Western blot and the vector dose, as well as the amount of mini-dystrophin mRNA in the same tissue samples. A mini-dystrophin mRNA RQ of approximately 1.5 was required to permit detection of the protein. Consistent with the low levels of mini-dystrophin transcript measured in liver, no mini-dystrophin protein was detected in this tissue, even at the highest vector dose used.

Histopathological Assessment

Immediately after sacrifice of WT and $Dmd^{mdx}$ rats, tissue samples were obtained for histopathological and immunocytochemical analysis.

Materials and Methods

Tissue samples vehicle treated WT rats, vehicle and vector treated $Dmd^{mdx}$ rats were obtained during whole necropsy evaluation at 3 and 6 months post-injection. Samples were also obtained from untreated $Dmd^{mdx}$ rats sacrificed at 7-9 weeks of age to serve as a baseline comparison. Tissues were immediately fixed in formalin for histopathology or snap frozen for immunohistochemistry (immunolabeling) and stored until processing. For histopathology, tissue samples were fixed in 10% neutral buffered formalin, embedded in paraffin wax, and sectioned (5 m) before staining with hematoxylin eosin saffron (HES) stain. An additional section of paraffin embedded heart tissue was stained to visualize collagen with picrosirius red F3B (Sigma-Aldrich Chimie SARL, Lyon, FR). To identify dystrophin and connective tissue by immunolabeling, samples were frozen and sectioned (8 m). A mouse monoclonal antibody, NCL-DYSB (1:50, Novocastra Laboratories, Newcastle on Tyne, UK), that specifically binds to rat dystrophin as well as human mini-dystrophin opti-Dys3978 was used in immunolabeling studies to visualize dystrophin protein. Alexa Fluor 555 wheat germ agglutinin (WGA) conjugate (1:500, Molecular Probes, Eugene, OR) was used to visualize connective tissue. Nuclei were stained with DRAQ5 (1:1000, BioStatus Ltd, Shepshed, UK). Necropsies and histological examination were performed blinded.

Quantification of the picrosirius positive areas in heart sections was performed using Nikon Imaging Software (Nikon, Champigny sur Marne, France). Quantification of DYSB positive fibers and WGA positive areas was performed using ImageJ open source image processing software (v 2.0.0-rc-49/1.51a).

Results

Histopathological Analysis of DMD Lesions in Muscle at 3 and 6 Months Post-Injection Tissue samples stained for histology were examined microscopically and lesions related to the DMD phenotype systematically recorded. Lesions in skeletal and cardiac muscle were scored semi-quantitatively as illustrated in FIG. 38A. In skeletal muscle (biceps femoris, pectoralis and diaphragm), a score of 0 corresponded to absence of significant lesion; a score of 1 corresponded to the presence of some regeneration activity as evidenced by centro-nucleated fibers and regeneration foci; a score of 2 corresponded to degenerative fibers, isolated or in small clusters; and a score of 3 corresponded to tissue remodeling and fiber replacement by fibrotic or adipose tissue. In the heart, scoring was based on the intensity of fibrosis (score of 1 for lower, and score of 2 for higher) and the presence of degenerative fibers (score of 3). A total lesion score for each rat was calculated as the mean of the animal's scores for biceps femoris, pectoralis, diaphragm and cardiac muscles. Lesion scores for individual rats within each treatment arm were also averaged.

Total lesion scores of individual rats and averages grouped by treatment arm at 3 months post-injection are shown in FIG. 38B, in which WT mock refers to WT rats treated with vehicle, for which lesion scores were 0. KO mock refers to $Dmd^{mdx}$ rats treated with vehicle, whereas KO 1E13, 3E13, and 1E14, refer to $Dmd^{mdx}$ rats treated with the indicated doses (i.e., $1\times10^{13}$, $3\times10^{13}$, and $1\times10^{14}$, respectively) of vector in vg/kg. As can be seen, the prevalence of muscular lesions associated with the dystrophic phenotype in $Dmd^{mdx}$ rats was reduced by vector treatment in a dose-responsive manner.

Statistical analysis of lesion scores (by multiple paired comparisons using Dunn's test) revealed the following differences among treatment arms. In samples of biceps femoris muscles at 3 months post-injection, there were no significant differences in lesion scores between WT rats treated with vehicle and $Dmd^{mdx}$ rats treated with vector at the two highest doses ($1\times10^{14}$ and $3\times10^{14}$ vg/kg) and at 6 months post-injection, there were no significant differences between WT treated with vehicle and $Dmd^{mdx}$ rats treated with vector at any of the four doses tested. In samples of pectoralis muscle and diaphragm at 3 months post-injection there were no significant differences in lesion scores between vehicle treated WT rats and $Dmd^{mdx}$ rats treated with the three highest vector doses tested ($3\times10^{13}$, $1\times10^{14}$ and $3\times10^{14}$ vg/kg) and at 6 months post-injection, there were no significant differences in scores between WT rats treated with vehicle and $Dmd^{mdx}$ rats treated with all four vector doses. Finally, in heart muscle, at both time points, there were no significant differences in lesion scores between vehicle treated WT rats and $Dmd^{mdx}$ rats treated with all four doses of vector.

Histomorphometry at 3 and 6 Months Post-Injection

After labeling tissue samples with the DYSB antibody, which specifically binds to both rat dystrophin and the human mini-dystrophin expressed from the vector, the percentage of positively stained muscle fibers in three randomly selected microscopic fields from each rat was calculated for biceps femoris, diaphragm, and cardiac muscles. In addition, the area in three randomly selected microscopic fields staining positively with WGA conjugate was calculated to determine the extent of connective tissue fibrosis in frozen tissue samples from biceps femoris and diaphragm. In a related analysis, the amount of connective tissue (collagen) in transverse sections of heart was determined by quantifying the area staining positive with picrosirius red in histological preparations. Results from these studies are provided in FIGS. 39A-39C, FIGS. 40A-40C, and FIGS. 41A-41C.

FIG. 39A shows representative photomicrographs of stained tissue sections from biceps femoris muscle samples from WT rats treated with vehicle (WT+buffer), $Dmd^{mdx}$ rats treated with vehicle (DMD+buffer), and $Dmd^{mdx}$ rats treated with vector at increasing doses of $1\times10^{13}$, $3\times10^{13}$, $1\times10^{14}$ and $3\times10^{14}$ vg/kg (DMD+1E13, 3E13, 1E14, and 3E14, respectively). The top panel of photos are from samples taken at 3 months post-injection and the bottom panel are from samples taken at 6 months post-injection. FIG. 39B is a graph showing the percentage of dystrophin positive fibers in biceps femoris muscle samples from WT rats and $Dmd^{mdx}$ rats, each treated with vehicle, and $Dmd^{mdx}$ rats treated with increasing doses of vector, at 3 and 6 month time points. Also included are results from untreated $Dmd^{mdx}$ rats 7-9 weeks of age ("DMD pathol status"). FIG. 39C is a graph showing the percentage area occupied by connective tissue (as a measure of fibrosis) in biceps femoris muscle samples from similarly treated WT and $Dmd^{mdx}$ rats at 3 and 6 month time points, and untreated $Dmd^{mdx}$ rats 7-9 weeks of age. In the graphs, the same letter over error bars indicates no statistically significant difference between the data, whereas no common letter indicates there is a significant difference (for example, two bars both having an "a" above them would not be significantly different from each other).

FIG. 40A shows representative photomicrographs of stained tissue sections from diaphragm samples from WT rats treated with vehicle (WT+buffer), $Dmd^{mdx}$ rats treated with vehicle (DMD+buffer), and $Dmd^{mdx}$ rats treated with vector at increasing doses of $1\times10^{13}$, $3\times10^{13}$, $1\times10^{14}$ and $3\times10^{14}$ vg/kg (DMD+1E13, 3E13, 1E14, and 3E14, respectively), all taken at 3 months post-injection. FIG. 40B is a graph showing the percentage of dystrophin positive fibers in diaphragm samples from WT rats and $Dmd^{mdx}$ rats, each treated with vehicle, and $Dmd^{mdx}$ rats treated with increasing doses of vector, at 3 and 6 month time points. Also included are results from untreated $Dmd^{mdx}$ rats 7-9 weeks of age ("DMD pathol status"). FIG. 40C is a graph showing the percentage area occupied by connective tissue (as a measure of fibrosis) in diaphragm samples from similarly treated WT and $Dmd^{mdx}$ rats at 3 and 6 month time points, and untreated $Dmd^{mdx}$ rats 7-9 weeks of age. In the graphs, the same letter over error bars indicates no statistically significant difference between the data, whereas no common letter indicates there is a significant difference (for example, two bars both having an "a" above them would not be significantly different from each other).

FIG. 41A shows representative photomicrographs of stained tissue sections from heart muscle samples from WT rats treated with vehicle (WT+buffer), $Dmd^{mdx}$ rats treated with vehicle (DMD+buffer), and $Dmd^{mdx}$ rats treated with vector at increasing doses of $1\times10^{13}$, $3\times10^{13}$, $1\times10^{14}$ and $3\times10^{14}$ vg/kg (DMD+1E13, 3E13, 1E14, and 3E14, respectively). The top and bottom panels show transverse sections of hearts from the third of the apex prepared histologically and stained with picrosirius red taken from test animals sacrificed at 3 and 6 months post-injection, respectively. The black bars indicate length of 2 mm. The middle panel shows immunolabeling with anti-dystrophin antibody and WGA conjugate in heart muscle samples taken at the 3 month time point. FIG. 41B is a graph showing the percentage of dystrophin positive fibers in heart muscle samples from WT rats and $Dmd^{mdx}$ rats, each treated with vehicle, and $Dmd^{mdx}$ rats treated with increasing doses of vector, at 3 and 6 month time points. Also included are results from untreated $Dmd^{mdx}$ rats 7-9 weeks of age ("DMD pathol status"). FIG. 41C is a graph showing the percentage area occupied by connective tissue (as a measure of fibrosis) in heart muscle samples from similarly treated WT and $Dmd^{mdx}$ rats at 3 and 6 month time points, and untreated $Dmd^{mdx}$ rats 7-9 weeks of age. In the graphs, the same letter over error bars indicates no statistically significant difference between the data, whereas no common letter indicates there is a significant difference (for example, two bars both having an "a" above them would not be significantly different from each other).

Statistical analysis (ANOVA analysis and Fisher's post-hoc bilateral test) of the data demonstrated that at both 3 and 6 months post-injection, there was a significant difference in dystrophin labeling in biceps femoris and heart between $Dmd^{mdx}$ rats treated with vehicle and $Dmd^{mdx}$ rats treated at all vector doses. In diaphragm, differences at 3 months post-injection were significant at the two highest doses tested, whereas at 6 months post-injection, the differences were significant at the three highest doses tested. Comparison between WT rats treated with vehicle and $Dmd^{mdx}$ rats treated with $3\times10^{14}$ vg/kg revealed no significant difference in biceps femoris muscle at 3 months post-injection or in cardiac muscle at 6 months post-injection.

In muscles from WT rats treated with vehicle, all muscle fibers displayed intense homogeneous subsarcolemmal labeling with the DYSB antibody. In muscles from $Dmd^{mdx}$ rats treated with vehicle, a small percentage of scattered revertant fibers displayed similar labeling (at 3 and 6 months post-injection, respectively: biceps femoris, 3.7±2.4% and 7.3±2.3%; diaphragm, 0.7±1.5% and 5.8±1.3%; cardiac muscle, 0.0±0.0% and 0.1±0.1%). In $Dmd^{mdx}$ rats administered vector, the percentage of fibers staining positive for dystrophin was increased in all observed muscles with fibers displaying weak to intense subsarcolemmal labeling. Labeling of two thirds of the fiber was required to be considered positive. At both 3 and 6 month time points, the percentage of dystrophin-positive fibers was similar between biceps femoris and cardiac muscle, which was higher than in diaphragm. In $Dmd^{mdx}$ rats treated with vector, the number and size of the fibrotic foci measured by the area occupied by connective tissue was reduced in skeletal muscle, and the intensity of fibrosis decreased in heart muscle.

In untreated $Dmd^{mdx}$ rats sacrificed at 7-9 weeks of age, no fibrosis was evident in biceps femoris or heart muscle, but there was already significant connective tissue expansion in diaphragm. Compared to WT rats, vehicle treated $Dmd^{mdx}$ rats displayed focal or generalized thickening of the endomysial and perimysial space in skeletal muscle, which is indicative of fibrosis. In the heart, these rats displayed scattered and extensive fibrotic foci in ventricular and septal subepicardial regions. In severe cases, transmural fibrosis was observed that altered the shape of the heart. Compared with $Dmd^{mdx}$ rats treated with vehicle, there was a significant reduction in the number and size of fibrotic foci at 3 months post-injection in the biceps femoris of $Dmd^{mdx}$ rats treated with $3\times10^{13}$ vg/kg vector and higher doses, and at 6 months post-injection in the diaphragm of $Dmd^{mdx}$ rats treated with $3\times10^{14}$ vg/kg vector. In heart, significant differences in fibrosis were found between $Dmd^{mdx}$ rats treated with vehicle and $Dmd^{mdx}$ rats treated at all vector doses at both time points. At 3 months post-injection, no significant difference in fibrosis was observed between WT rats treated with vehicle and $Dmd^{mdx}$ rats treated with vector at a dose of $3\times10^{13}$ vg/kg and higher. The amount of fibrosis observed and vector dose were negatively correlated ($p=0.019$ for biceps femoris; $p=0.004$ for diaphragm; and $p=0.003$ for cardiac muscle, all by linear regression).

In $Dmd^{mdx}$ rats treatment with vector induced mini-dystrophin expression in all muscles analyzed (biceps femoris, diaphragm, and heart), and the percentage of fibers expressing mini-dystrophin was positively correlated with vector dose ($p<0.001$ by linear regression). The number of mini-dystrophin-positive fibers in vector treated $Dmd^{mdx}$ rats was higher in biceps femoris and heart than in diaphragm, suggesting some heterogeneity in biodistribution or expression efficacy. Mini-dystrophin expression was similar in terms of its subsarcolemmal localization, regardless dose, and no abnormal localization was detected even at the highest dose analyzed, $3\times10^{14}$ vg/kg. In some fibers, discontinuous dystrophin staining was detected along the sarcolemma, although the frequency of this observation decreased with increasing vector dose.

Comparison of the number of mini-dystrophin positive muscle fibers between 3 and 6 months post-injection revealed no significant differences among treatment arms for biceps femoris. In diaphragm, there was a significant increase between 3 and 6 months post-injection at the $1\times10^{14}$ vg/kg dose, whereas in heart muscle, there was a significant increase between the two time points at the doses $1\times10^{13}$, $3\times10^{13}$, and $1\times10^{14}$ vg/kg.

The incidence and degree of certain classic DMD related muscle lesions varied among the treatment groups. For example, there were fewer necrotic or degenerative fibers vector treated $Dmd^{mdx}$ rats compared to those that received only vehicle, and newly regenerated fibers were observed in all $Dmd^{mdx}$ rats, but their number tended to decrease as vector dose was increased.

Grip Force and Muscle Fatigue Measurements

Forelimb grip force of $Dmd^{mdx}$ rats injected with vehicle or increasing doses of vector were tested 3 and 6 months post-injection. WT rats injected with vehicle were included as negative controls. Rats were injected when they were 7-9 weeks old so that grip force testing was conducted when they were about 4.5 and 7.5 months old. Maximum grip force and grip force after repeated trials as an indication of fatigue were both measured.

Materials and Methods

A grip meter (Bio-GT3, BIOSEB, France) attached to a force transducer was used to measure the peak force generated when rats were placed with their forepaws on the T-bar and gently pulled backward until they released their grip. Five tests were performed in sequence with a short latency (20-40 seconds) between each test, and the reduction in strength between the first and the last determination taken as an index of fatigue. Results are expressed in grams (g) and are normalized to the body weight (g/g BW). Grip test measurements were performed by an experimenter blind to genotype and treatment arm. Data are presented as the mean±SEM, and evaluated statistically using the non-parametric Kruskal-Wallis test to analyze differences between groups. Where significant overall effects were detected, differences between groups were assessed using Dunn's post-hoc test. Evolution of grip force was analyzed using the Friedman test, followed by Dunn's post-hoc test. All data analyses were performed using GraphPad Prism 5 (GraphPad Software Inc., La Jolla, CA). In figures, significant differences at confidence levels of 95%, 99%, and 99.9% are represented by one, two and three symbols, respectively.

Results

Results of grip force tests for rats sacrificed at 3 months post-injection are provided in Table 9 and Table 10. As shown in Table 9, vehicle treated $Dmd^{mdx}$ rats exhibited a reduction in absolute grip strength (i.e., not corrected for body mass differences) compared to vehicle treated WT rats (decrease of 24±2%). By contrast, $Dmd^{mdx}$ rats that were treated with vector exhibited a dose-dependent increase in absolute grip strength compared to vehicle treated $Dmd^{mdx}$ rat controls. At the two lowest doses, $1\times10^{13}$ and $3\times10^{13}$ vg/kg, grip force increased by 13±7% and 24±8%, respectively, but did not reach statistical significance, while at the two highest doses, $1\times10^{14}$ and $3\times10^{14}$ vg/kg, grip force increased by 40±9% and 55±6%, respectively, which did reach statistical significance ($p<0.01$ and $p<0.001$, respectively). Also as shown in Table 9, when forelimb grip force was corrected for differences in body mass, there was no statistically significant difference between grip force of WT and $Dmd^{mdx}$ rats when both were treated with vehicle. However, there was a dose responsive increase in relative grip force of vector treated $Dmd^{mdx}$ rats compared with $Dmd^{mdx}$ rats treated with vehicle, which reached statistical significance at the two highest doses tested, $1\times10^{14}$ and $3\times10^{14}$ vg/kg (27±8% increase, $p<0.05$, and 39±6% increase, $p<0.001$, respectively).

Forelimb grip force was also measured during five closely spaced repeated trials to determine the extent to which vector treatment might affect the muscle fatigue known to occur in the $Dmd^{mdx}$ rat model. As shown in FIG. 42A, vehicle treated $Dmd^{mdx}$ rats exhibited a marked decrease of forelimb strength between the first and fifth trials (reduction of 63±5%), whereas WT rats treated with vehicle were just as strong after the fifth trial as after the first, an effect seen before in this model (Larcher, et al., 2014).

In contrast, a dose-dependent improvement was observed in vector treated $Dmd^{mdx}$ rats compared to similar rats treated only with vehicle. As indicated in Table 10, at the two lowest doses tested ($1\times10^{13}$ and $3\times10^{13}$ vg/kg) there was delay before a decrease in grip strength manifested, suggesting a reduction in fatigue, at least early in the trials. However, at the lower doses, by the fifth trial, there was still not a statistically significant difference between grip strength of the vector treated $Dmd^{mdx}$ rats and $Dmd^{mdx}$ rats treated only with vehicle. Nevertheless, a strong trend toward waning reduction in grip strength was apparent even at these lower doses. At the two highest doses, $1\times10^{14}$ and $3\times10^{14}$ vg/kg, the $Dmd^{mdx}$ rats showed no statistically significant difference in the extent of fatigue compared to WT rats treated with vehicle. In other words, after five trials, these vector treated $Dmd^{mdx}$ rats were indistinguishable from wild type. In fact, in all trials, the mean grip force of $Dmd^{mdx}$ rats treated with the highest vector dose was higher than that of WT controls, although the difference was not statistically significant.

Results of grip force tests for rats sacrificed at 6 months post-injection are provided in Table 11 and Table 12. As shown in Table 11, vehicle treated $Dmd^{mdx}$ rats exhibited a reduction in grip strength (i.e., not corrected for body mass differences) compared to vehicle treated WT rats (decrease of 38±3% in absolute grip force). This difference was statistically significant when measured in absolute terms, but not when measured in relative terms. By contrast, $Dmd^{mdx}$ rats that were treated with vector exhibited a dose-dependent increase in absolute grip strength compared to vehicle treated $Dmd^{mdx}$ rat controls. At the two lowest doses, $1\times10^{13}$ and $3\times10^{13}$ vg/kg, grip force increased by 20±5% and 21±6%, respectively, but did not reach statistical significance, while at the two highest doses, $1\times10^{14}$ and $3\times10^{14}$ vg/kg, grip force increased by 39±9% and 41±5%, respectively, which did reach statistical significance ($p<0.05$ and $p<0.01$, respectively).

Similar to the $Dmd^{mdx}$ rats sacrificed 3 months after injection, vehicle treated $Dmd^{mdx}$ rats sacrificed at 6 months post-injection also exhibited a substantial decrease of forelimb strength between the first and fifth trials (reduction of 57±3%) (FIG. 42B), although this difference was not statistically significant compared to the slight reduction in grip force over five trials seen with WT rats treated with vehicle, most likely due to the small sample sizes involved in these studies.

In contrast, a dose-dependent improvement was observed in vector treated $Dmd^{mdx}$ rats compared to similar rats treated only with vehicle. As indicated in Table 12, while the two lowest doses ($1\times10^{13}$ and $3\times10^{13}$ vg/kg) did not significantly impact the decline in grip strength over multiple trials, at the two highest doses ($1\times10^{14}$ and $3\times10^{14}$ vg/kg), the $Dmd^{mdx}$ rats showed no statistically significant difference in the extent of fatigue compared to WT rats treated with vehicle. Further, at the highest dose, the grip force of vector treated $Dmd^{mdx}$ rats was statistically significantly higher than $Dmd^{mdx}$ rats treated with vehicle at every trial. In other words, after five trials, these vector treated $Dmd^{mdx}$ rats were indistinguishable from wild type. In fact, in all trials, the mean grip force of $Dmd^{mdx}$ rats treated with the highest vector dose was higher than that of WT controls, although the difference was not statistically significant.

Based on these studies, it is evident that at both 3 and 6 months post-injection, a vector dose of $1\times10^{14}$ vg/kg was sufficient to reverse the reduction in grip force exhibited by $Dmd^{mdx}$ rats and the muscle fatigue caused by multiple closely spaced grip force tests. Furthermore, a vector dose of $3\times10^{14}$ vg/kg actually improved grip force and fatigue resistance in the $Dmd^{mdx}$ rats to a level that exceeded WT rats of the same genetic background.

TABLE 9

| Grip Force at 4.5 Months of Age (3 Months Post-Injection) | | | | | | |
|---|---|---|---|---|---|---|
| Genotype | WT | DMD$^{mdx}$ | DMD$^{mdx}$ | DMD$^{mdx}$ | DMD$^{mdx}$ | DMD$^{mdx}$ |
| Treatment | — | — | AAV9-optidys3978 | AAV9-optidys3978 | AAV9-optidys3978 | AAV9-optidys3978 |
| Dose (vg/kg) | — | — | 1E+13 | 3E+13 | 1E+14 | 3E+14 |
| Body weight (g) | 510.0 ± 12.2 | 438.1 ± 22.0* | 462.7 ± 16.2 | 469.1 ± 21.0 | 477.2 ± 11.3 | 482.9 ± 15.8 |
| Maximum forelimb grip force | | | | | | |
| g | 1743.1 ± 77.2 | 1318.8 ± 41.8* | 1493.6 ± 87.3 | 1640.1 ± 102.7 | 1848.5 ± 124.8□□ | 2044.2 ± 83.1□□ |
| g/g BW | 3.43 ± 0.15 | 3.06 ± 0.14 | 3.25 ± 0.19 | 3.50 ± 0.19 | 3.87 ± 0.24□ | 4.24 ± 0.13*□ |
| n | 12 | 10 | 11 | 11 | 11 | 10 |

Animal body weight (g); maximum absolute forelimb grip force (g); and relative forelimb grip force (g/g of body weight)
Values are mean ± SEM
n: number of animals tested
*$p < 0.05$ vs WT
□$p < 0.05$,
□□$p < 0.01$ vs Dmd$^{mdx}$ treated with vehicle

TABLE 10

| Grip Force Fatigue at 4.5 Months of Age (3 Months Post-Injection) | | | | | | |
|---|---|---|---|---|---|---|
| Genotype | WT | DMD$^{mdx}$ | DMD$^{mdx}$ | DMD$^{mdx}$ | DMD$^{mdx}$ | DMD$^{mdx}$ |
| Treatment | — | — | AAV9-optidys3978 | AAV9-optidys3978 | AAV9-optidys3978 | AAV9-optidys3978 |
| Dose (vg/kg) | — | — | 1E+13 | 3E+13 | 1E+14 | 3E+14 |
| Relative forelimb grip force g/g BW | | | | | | |
| Trial 1 | 2.98 ± 0.23 | 2.97 ± 0.14 | 3.14 ± 0.16 | 3.16 ± 0.18 | 3.35 ± 0.31 | 3.65 ± 0.13□ |
| Trial 2 | 2.92 ± 0.21 | 2.44 ± 0.31§ | 2.868 ± 0.23 | 2.9 ± 0.25 | 3.35 ± 0.29 | 3.70 ± 0.13□□ |
| Trial 3 | 2.89 ± 0.20 | 1.79 ± 0.26§§§ | 2.52 ± 0.31§ | 3.02 ± 0.28□ | 3.07 ± 0.28□ | 3.66 ± 0.26□□□ |
| Trial 4 | 3.09 ± 0.16 | 1.45 ± 0.24**§§§ | 1.81 ± 0.27*§§§ | 2.32 ± 0.23§§§ | 3.14 ± 0.31□□ | 3.84 ± 0.24□□□ |
| Trial 5 | 3.08 ± 0.20 | 1.10 ± 0.17***§§§ | 1.66 ± 0.18**§§§ | 2.12 ± 0.25§§§ | 2.82 ± 0.26□□□ | 3.59 ± 0.22□□□ |
| Total decrease Trial 5 vs Trial 1 (% Trial 1) | 6.13 ± 5.21 | −63.53 ± 5.49*** | −46.65 ± 5.88*** | −33.23 ± 7.04* | −7.35 ± 11.83□□ | −1.70 ± 4.95□□□ |
| n | 11 | 10 | 11 | 11 | 11 | 10 |

Relative forelimb grip force (g/g of body weight) and decrease in grip force between 1st and 5th trials expressed as percent decrease from 1st trial
Values are mean ± SEM
n: number of animals tested
*$p < 0.05$,
**$p < 0.01$,
***$p < 0.001$ vs WT
□$p < 0.05$,
□□$p < 0.01$,
□□□$p < 0.001$ vs Dmd$^{mdx}$ treated with vehicle
§$p < 0.05$,
§§§$p < 0.001$ vs 1st trial

TABLE 11

| Grip Force at 7.5 Months of Age (6 Months Post-Injection) | | | | | | |
|---|---|---|---|---|---|---|
| Genotype | WT | DMD$^{mdx}$ | DMD$^{mdx}$ | DMD$^{mdx}$ | DMD$^{mdx}$ | DMD$^{mdx}$ |
| Treatment | — | — | AAV9-optidys3978 | AAV9-optidys3978 | AAV9-optidys3978 | AAV9-optidys3978 |
| Dose (vg/kg) | — | — | $1^E$+13 | $3^E$+13 | $1^E$+14 | $3^E$+14 |
| Body weight (g) | 601. ± 24.3 | 464.7 ± 48.8* | 502.6 ± 29.1 | 527.6 ± 38.0 | 556.1 ± 14.4 | 577.6 ± 29.2 |

TABLE 11-continued

| Grip Force at 7.5 Months of Age (6 Months Post-Injection) | | | | | | |
|---|---|---|---|---|---|---|
| Genotype | WT | $DMD^{mdx}$ | $DMD^{mdx}$ | $DMD^{mdx}$ | $DMD^{mdx}$ | $DMD^{mdx}$ |
| Maximum forelimb grip force | | | | | | |
| g | 2142.7 ± 98.0 | 1324.0 ± 73.6* | 1760.0 ± 150.7 | 1825.4 ± 72.8 | 2223.8 ± 122.9□□ | 2350.0 ± 134.1□ |
| g/g BW | 3.59 ± 0.21 | 2.90 ± 0.17 | 3.48 ± 0.16 | 3.50 ± 0.16 | 4.02 ± 0.26□ | 4.07 ± 0.15□□ |
| n | 7 | 4 | 6 | 6 | 6 | 5 |

Animal body weight (g); maximum absolute forelimb grip force (g); and relative forelimb grip force (g/g of body weight)
Values are mean ± SEM
n: number of animals tested
*$p < 0.05$ vs WT
□□$p < 0.01$;
□□□$p < 0.001$ vs $Dmd^{mdx}$ treated with vehicle

TABLE 12

| Grip Force Fatigue at 7.5 Months of Age (6 Months Post-Injection) | | | | | | |
|---|---|---|---|---|---|---|
| Genotype | WT | $DMD^{mdx}$ | $DMD^{mdx}$ | $DMD^{mdx}$ | $DMD^{mdx}$ | $DMD^{mdx}$ |
| Treatment | — | — | AAV9-optidys3978 | AAV9-optidys3978 | AAV9-optidys3978 | AAV9-optidys3978 |
| Dose (vg/kg) | — | — | 1E+13 | 3E+13 | 1E+14 | 3E+14 |
| Relative forelimb grip force g/g BW | | | | | | |
| Trial 1 | 3.48 ± 0.23 | 2.86 ± 0.18 | 3.27 ± 0.23 | 3.44 ± 0.20 | 3.60 ± 0.32 | 4.00 ± 0.14□□ |
| Trial 2 | 3.22 ± 0.30 | 2.58 ± 0.27 | 3.07 ± 0.20 | 3.21 ± 0.12 | 3.31 ± 0.34 | 3.78 ± 0.12□ |
| Trial 3 | 3.45 ± 0.19 | 2.07 ± 0.26*§§ | 2.46 ± 0.32§ | 2.40 ± 0.35§§ | 3.72 ± 0.33□ | 3.66 ± 0.14□ |
| Trial 4 | 3.01 ± 0.16 | 1.52 ± 0.17*§§§ | 2.19 ± 0.27§§ | 1.83 ± 0.14§§§ | 3.00 ± 0.38 | 3.76 ± 0.20□□□ |
| Trial 5 | 3.01 ± 0.16 | 1.24 ± 0.14*§§§ | 1.87 ± 0.33§§§§ | 1.63 ± 0.16§§§ | 2.91 ± 0.51□ | 3.54 ± 0.21§□□ |
| Total decrease trial 5 vs Trial 1 (% Trial 1) | −12.27 ± 5.56 | −56.61 ± 3.52 | −39.55 ± 13.94 | −50.81 ± 8.11 | −19.48 ± 11.88 | −11.11 ± 5.69 |
| n | 7 | 4 | 6 | 5 | 6 | 5 |

Relative forelimb grip force (g/g of body weight) and decrease in grip force between 1st and 5th trials expressed as percent decrease from 1st trial
Values are mean ± SEM
n: number of animals tested
*$p < 0.05$ vs WT
□$p < 0.05$,
□□$p < 0.01$,
□□□$p < 0.001$ vs $Dmd^{mdx}$ treated with vehicle
§$p < 0.05$,
§§$p < 0.01$,
§§§$p < 0.001$ vs 1st trial Cardiac Function Cardiac function of $Dmd^{mdx}$ rats and WT controls were tested 3 and 6 months post-injection (about 5 and 8 months of age, respectively) to determine if vector treatment could improve the structural or functional effects on heart of the muscular dystrophy disease process in the rat DMD model. Using two-dimensional echocardiography, free wall diastolic thickness, LV end-diastolic diameter, LV ejection fraction, and E/A ratio were measured 3 and 6 months post-injection.

Materials and Methods

Echocardiographic measurements were conducted by an experimenter blind as to genotype and treatment arm. Two-dimensional (2D) echocardiography was performed on test animals using a Vivid 7 Dimension ultrasound (GE Healthcare) with a 14-MHz transducer. To observe possible structural remodeling, left ventricular end-diastolic diameter and free wall end-diastolic thickness were measured during diastole from long and short-axis images obtained with M-mode echocardiography. Systolic function was assessed by the ejection fraction, and diastolic function was determined by taking trans-mitral flow measurements of ventricular filling velocity using pulsed Doppler in an apical four-chamber orientation to determine the E/A ratio, isovolumetric relaxation time, and the E wave deceleration time, indicators of diastolic dysfunction explained further below.

The E/A ratio is the ratio of the peak velocity of blood movement from the left atrium to the left ventricle during two stages of atrial emptying and ventricular filling. Blood is transferred from the left atrium to the left ventricle in two steps. In the first, the blood in the left atrium moves passively into the ventricle below when the mitral valve opens due to negative pressure created by the relaxing ventricle. The speed at which the blood moves during this initial action is called the "E," for early, ventricular filling velocity. Later in time, the left atrium contracts to eject any remaining blood in the atrium, and the speed at which the blood moves at this stage is called the "A," for atrium, ventricular filling velocity. The E/A ratio is the ratio of the early (E) to late (A) ventricular filling velocities. In healthy heart, the E/A ratio is greater than 1. In Duchenne myopathy, however, the left ventricular wall becomes stiff, reducing ventricular relaxation and pull on atrial blood, thereby slowing the early (E) filling velocity and lowering the E/A ratio. The isovolumetric relaxation time (IVRT) is the interval between the closure of the aortic valve to onset of ventricular filling by opening of the mitral valve, or the time until ventricular filling starts after relaxation begins. Longer than normal IVRT indicates poor ventricular relaxation, which has been described in both human DMD patients (RC Bahler et al., J Am Soc Echocardiogr 18(6), 666-73 (2005); L W Markham et al., J Am Soc Echocardiogr 19(7), 865-71 (2006)) and the DMD dog model (V Chetboul et al., Eur Heart J 25(21), 1934-39 (2004); V Chetboul et al., Am J Vet Res 65(10), 1335-41 (2004)), and precede the dilated cardiomyopathy associated with DMD. Lastly, the E wave deceleration time (DT) corresponds to the time in milliseconds between peak E velocity and its return to baseline, an increase in which is indicative of a diastolic dysfunction.

Results

At both 3 and 6 months post-injection, no significant differences in free wall diastolic thickness between WT rats and $Dmd^{mdx}$ rats, both treated with vehicle, indicating that this measurement was not informative regarding disease course in this model at the ages examined. At 6 months, but not 3 months, post-injection, however, there was a trend toward increasing left ventricular end-diastolic diameter in $Dmd^{mdx}$ rats treated with vehicle compared to WT controls, which was reversed when the $Dmd^{mdx}$ rats were treated with vector, although statistical significance was not reached (FIG. 43).

To assess systolic function, left ventricular (LV) ejection fraction was measured. No difference was found in $Dmd^{mdx}$ rats 3 months post-injection, but at 6 months post-injection, $Dmd^{mdx}$ rats administered vehicle only exhibited reduced LV ejection fraction that was prevented by treatment with vector, although the difference was statistically significant only at one of the lower doses, $3\times10^{13}$ vg/kg (FIG. 44).

To assess diastolic dysfunction, Doppler echocardiography was used to measure early (E) and late diastolic (A) velocities, the E/A ratio, isovolumetric relaxation time (IVRT), and deceleration time (DT). At 3 months post-injection there was a statistically significant reduction in the E/A ratio for $Dmd^{mdx}$ rats treated with vehicle compared to WT controls, and a trend suggesting return to a normal E/A ratio in $Dmd^{mdx}$ rats treated with the highest vector dose, $3\times10^{14}$ vg/kg, although the difference did not reach statistical significance (FIG. 45A). At 6 months post-injection, the E/A ratio of $Dmd^{mdx}$ rats treated with vehicle were also significantly reduced compared to WT controls, and as with the earlier time point, there was a trend suggesting some treatment effect of the vector, although the data was quite variable and did not reach statistical significance (FIG. 45B).

At 3 months post-injection, IVRT was elevated in $Dmd^{mdx}$ rats treated with vehicle compared to WT controls, and there was a slight trend suggesting a dose responsive reduction in IVRT in $Dmd^{mdx}$ rats treated with vector, although none of the differences in the data reached statistical significance (FIG. 46A). At 6 months post-injection, $Dmd^{mdx}$ rats treated with vehicle had an IVRT that was significantly higher compared to WT controls, whereas vector treatment resulted in a strong trend suggesting return of IVRT to normal levels, which reached statistical significance at the lowest vector dose, $1\times10^{13}$ vg/kg (FIG. 46B).

Finally, DT could only be measured in older rats due to technical difficulties with an anesthesia protocol. When examined at 6 months post-injection, however, DT was significantly elevated in $Dmd^{mdx}$ rats treated with vehicle compared to WT controls, and there was a strong trend toward restoration to normal values after vector treatment at all doses tested (FIG. 47).

Despite variability in the data, the results of these studies strongly suggest the existence of diastolic dysfunction in the hearts of 5 and 8 month old $Dmd^{mdx}$ rats, which could be at least partially reversed by treatment with AAV9.hCK.Hopti-Dys3978.spA vector.

Blood Chemistry

Prior to treatment and at the time of sacrifice, blood samples from the rats were taken and stored for eventual analysis. Tests were carried out to determine serum concentrations of urea, creatinine, alkaline phosphatase (ALK), alanine aminotransferase (ALT), aspartate aminotransferase (AST), lactate dehydrogenase (LDH), creatine kinase (CK), troponin I, and antibodies against the mini-dystrophin protein and AAV9 capsid. ALT, AST, CK, and LDH are all enzymes released into the blood from damaged muscle cells, and are known to be elevated in human DMD patients.

At 3 months and 6 months post-injection, the levels of urea, creatinine, ALK, total serum proteins, total bilirubin and troponin I were not significantly different between the different experimental groups. By contrast, AST, ALT, LDH and total CK levels were all elevated in vehicle treated $Dmd^{mdx}$ rats compared to WT rats and responded with varying degrees to vector treatment.

At both 3 and 6 months post-injection, AST levels were elevated in $Dmd^{mdx}$ rats treated with vehicle compared to WT rats, although due to variability in the data, significance existed only at the 6 month time point. When $Dmd^{mdx}$ rats were treated with vector, a trend towards lower AST levels (albeit with wide inter-individual variability) was observed in the $1\times10^{14}$ and $3\times10^{14}$ vg/kg dose groups at 3 months post-injection and in the $3\times10^{14}$ vg/kg dose group at 6 months post-injection. Again, due to variability in the data, these differences did not reach statistical significance. These results are shown in FIG. 48A and FIG. 48B, which reports data for the 3 month and 6 month post-injection time points, respectively.

The pattern of ALT, LDH, and total CK levels all responded to age and vector treatment in similar ways. At 3 months post-injection, ALT, LDH and total CK levels were all significantly elevated in $Dmd^{mdx}$ rats treated with vehicle compared to WT rats. Treating the $Dmd^{mdx}$ rats with the mini-dystrophin vector resulted in a trend suggesting a dose responsive reduction in ALT, LDH and total CK levels relative to vehicle treated $Dmd^{mdx}$ rats, which in some cases achieved statistical significance. These results are shown in FIG. 49A, FIG. 50A, and FIG. 51A, respectively. At 6 months post-injection, there was a trend in the data suggesting elevated levels of ALT and LDH in $Dmd^{mdx}$ rats treated with vehicle compared to WT rats, which was reversed at highest vector dose tested, but none of the differences were statistically significant. These results are shown in FIG. 49B and FIG. 50B, respectively. In contrast, similar to the pattern seen at 3 months post-injection, total CK was significantly elevated in $Dmd^{mdx}$ rats treated with vehicle at 6 months post-injection compared to WT rats, and vector treatment resulted in a trend toward reduced levels that achieved statistical significance at the highest vector dose tested (FIG. 51B).

Total CK levels within treatment arms were also compared on the day of injection and 3 and 6 months after. As shown in FIG. 52A and FIG. 52B, blood total CK levels were consistently low in WT rats administered vehicle, while CK levels declined in all Dmd$^{mdx}$ rats, including those treated only with vehicle and the lowest vector dose. In contrast, the reduction of CK levels after 3 and 6 months was much greater for Dmd$^{mdx}$ rats treated with the three highest doses of vector. These observations are consistent with the natural course of DMID in humans, where CK levels, while elevated compared to controls, decline as the disease progresses due to replacement of muscle with adipose and fibrotic tissue, but also with a dose-responsive therapeutic effect at the higher vector doses tested.

Differences in CK isoenzymes were also observed. Before dosing, the CK-MM isoform predominated in Dmd$^{mdx}$ rats (mean >90%), whereas the CK-MM and CK-BB isoforms were comparable in WT rats (mean 40-60%), and CK-MB levels were higher in WT than in Dmd$^{mdx}$ rats (4-6% versus ≈1%). At 3 and 6 months post-injection, Dmd$^{mdx}$ rats treated with vector doses above $1\times10^{13}$ vg/kg showed a slight increase in the proportion of the CK-BB isoform and a slight decrease in the proportion of the CK-MM isoform, with a trend towards a dose-related effect. No clear alteration in the proportion of the CK-MB isoform was observed in vector treated Dmd$^{mdx}$ rats.

Immunology

The humoral and cellular immune response in Dmd$^{mdx}$ rats treated with AAV9.hCK.Hopti-Dys3978.spA vector were measured before treatment and at 3 and 6 months post-injection and compared to negative and positive controls. Serum samples were obtained before injection of vehicle or vector, and at euthanasia 3 months post-injection. Splenocytes for analysis of T cell response were harvested at euthanasia at 3 and 6 months post-injection.

Humoral response to expression of the mini-dystrophin protein was assessed qualitatively by Western blot analysis of sera obtained from the test animals and diluted 1:500. Sera from all rats, whether WT or Dmd$^{mdx}$, were negative for antibodies against mini-dystrophin protein when administered vehicle, or prior to receiving vector. By contrast most Dmd$^{mdx}$ rats treated with vector, even at the lowest dose of $1\times10^{13}$ vg/kg, produced IgG antibodies that bound mini-dystrophin in Western blots. Between 80%-100% of Dmd$^{mdx}$ rats sacrificed at 3 months post-injection, and between 60%-100% of Dmd$^{mdx}$ rats sacrificed at 6 months post-injection produced IgG specific for the mini-dystrophin protein depending on dose.

Presence of antibodies to the AAV9 vector capsid was tested by ELISA. Serum from WT and Dmd$^{mdx}$ rats treated with vehicle had no detectable IgG that reacted with AAV9. By contrast, all rats treated with vector, regardless of dose or whether sacrificed 3 or 6 months post-injection, produced anti-AAV9 IgG with a titer higher than 1:10240, the highest dilution tested. Neutralizing antibodies against AAV9 were also tested with a cell transduction inhibition assay using a recombinant AAV9 vector that expresses LacZ reporter gene detected using a luminometer. The titer was defined as the lowest dilution that inhibited transduction >50%. Neutralizing antibodies against AAV9 were detected in the serum from all Dmd$^{mdx}$ rats that had received vector, regardless of dose or whether sacrificed 3 or 6 months post-injection, but not in the same animals prior to injection or WT and Dmd$^{mdx}$ rats that had received vehicle only. Titers ranged from 1:5000 to ≥1:500000 with no clear dose effect.

Presence of a cellular immune response to vector was evaluated using an IFNγ ELISpot assay on splenocytes isolated from vehicle treated WT and Dmd$^{mdx}$ rats, and Dmd$^{mdx}$ rats that had received vector. T cell response to the human mini-dystrophin protein expressed by the vector genome was tested using an overlapping peptide bank covering the whole sequence of opti-dys3978 protein (length of 15 amino acids, overlap of 10 amino acids, total of 263 peptides) and a rat specific IFNγ-ELISpot$^{BASIC}$ kit (Mabtech). Negative control consisted of unstimulated splenocytes and positive control consisted of cells stimulated with the mitogen concanavalin A. IFNγ secretion was quantified as the number of spot-forming cells (SFC) per $10^6$ cells, and a positive response was defined as >50 SFC/$10^6$ cells or at least 3-fold the value obtained for the negative control. No specific T cell response against any peptide sequences derived from the mini-dystrophin protein was found in splenocytes obtained from any of the test animals, at either 3 months or 6 months post-injection, including from Dmd$^{mdx}$ rats treated at the highest vector dose of $3\times10^{14}$ vg/kg.

T cell response against the AAV9 capsid was also tested using the IFNγ ELISpot assay screened against peptide sequences derived from AAV9 (15-mers overlapping by 10 amino acids divided into 3 pools). There was a positive IFNγ response in between 16%-60% of vector treated Dmd$^{mdx}$ rats sacrificed at 3 months post-injection, and between 16%-66% of vector treated Dmd$^{mdx}$ rats sacrificed at 6 months post-injection, that was positively correlated with vector dose. By contrast, all WT and Dmd$^{mdx}$ rats treated with vehicle were negative for T cell response against AAV9 capsid.

EXAMPLE 9

Grip Strength in Older Dmd$^{mdx}$ Rats Treated with AAV9.hCK.Hopti-Dys3978.spA

The studies described in Example 8, above, were initiated in young rats 7-9 weeks of age. This example describes muscle function analysis of older Dmd$^{mdx}$ rats first treated with the AAV9.hCK.Hopti-Dys3978.spA vector when they were 4 months of age and 6 months of age, respectively. The average life span of Sprague Dawley rats is 24-36 months. The goal of these experiments was to determine if treatment with vector later in a Dmd$^{mdx}$ rat's life might be effective. Positive results would suggest that treating older human DMD patients, such as older children, adolescents, or even young adults, with vector might also improve their muscle function.

The experiments described in this example were conducted using similar materials and methods as those described in Example 8. More specifically, Dmd$^{mdx}$ rats at 4 and 6 months of age (n=6 for each age group) were separately treated with $1\times10^{14}$ vg/kg of AAV9.hCK.Hopti-Dys3978.spA vector. As negative controls, WT rats and Dmd$^{mdx}$ rats (n=6 for each age group) 4 months and 6 months of age were separately treated with vehicle only. At 3 months post-injection, rats were tested for grip strength as described previously. As with the younger rats, maximum forelimb grip strength and grip strength over multiple repeated trials with short latency periods between each trial were tested. The latter test was intended to measure muscle fatigue.

As shown in FIG. 53A, at 3 months post-injection, maximum forelimb grip strength of Dmd$^{mdx}$ rats treated with vehicle at 4 months of age was on average slightly lower compared to 4 month old WT rats treated with vehicle, although the difference did not reach statistical significance. By contrast, Dmd$^{mdx}$ rats injected with $1\times10^{14}$ vg/kg vector at 4 months of age had greater average maximum forelimb grip strength than Dmd$^{mdx}$ rats treated only with vehicle at the same age, a difference that did reach statistical significance. The strength of the vector treated rats was even greater than WT rats, although that difference was not statistically significant. The results were similar when the data was normalized for body weight, as shown in FIG. 53B. In FIG. 53A and FIG. 53B, the symbol "¤" indicates a statistically significant difference between vector versus vehicle treated Dmd$^{mdx}$ rats ($p<0.01$).

With respect to muscle fatigue, as shown in FIG. 53C, Dmd$^{mdx}$ rats treated with vehicle at 4 months exhibited fatigue after the 2nd grip test, whereas WT rats exhibited no fatigue even after 4 tests. By contrast, 4 month old Dmd$^{mdx}$ rats treated with vector exhibited minimal, if any, muscle fatigue between the 1st and 5th grip tests. The vector treated Dmd$^{mdx}$ rats also appeared stronger overall compared to WT rats treated with vehicle. In FIG. 53C, the symbol "*" indicates a statistically significant difference between vector treated Dmd$^{mdx}$ rats and WT rats treated with vehicle ($p<0.05$); "¤¤" indicates a statistically significant difference between vector versus vehicle treated Dmd$^{mdx}$ rats ($p<0.01$); and "§§" and "§§§" indicate a statistically significant difference between vehicle treated Dmd$^{mdx}$ rats at the 4th and 5th grip tests, respectively, compared to the 1st grip test (at $p<0.01$ and $p<0.001$, respectively).

As shown in FIG. 54A, at 3 months post-injection, maximum forelimb grip strength of Dmd$^{mdx}$ rats treated with vehicle at 6 months of age was significantly lower compared to 6 month old WT rats treated with vehicle. This effect was maintained even when the results were normalized for body weight, as shown in FIG. 54B. Treating Dmd$^{mdx}$ rats with $1\times10^{14}$ vg/kg vector at 6 months of age increased the average maximum forelimb grip strength compared with Dmd$^{mdx}$ rats treated only with vehicle, a difference that reached statistical significance when normalized for body weight (FIG. 54B). In FIG. 54A and FIG. 54B, the symbols "*" and "**" indicate a statistically significant difference between vehicle treated Dmd$^{mdx}$ and WT rats (at $p<0.05$ and $p<0.01$, respectively); and "¤" indicates a statistically significant difference between vector versus vehicle treated Dmd$^{mdx}$ rats ($p<0.05$).

With respect to muscle fatigue, as shown in FIG. 54C, Dmd$^{mdx}$ rats treated with vehicle at 6 months exhibited fatigue after the 2nd grip test, whereas WT rats exhibited no fatigue even after 4 tests. In contrast with rats treated at 4 months, 6 month old Dmd$^{mdx}$ rats treated with vector exhibited some reduced strength over the multiple grip tests, although not to the same extent as that seen with vehicle treated control Dmd$^{mdx}$ rats. Also in contrast to the tests conducted with rats treated at 4 months of age, the strength of the WT rats appeared to be greater than that of Dmd$^{mdx}$ rats treated with vector at 6 months over the course of the experiment. In FIG. 54C, the symbols "" and "*" indicate a statistically significant difference between vector treated Dmd$^{mdx}$ rats and WT rats treated with vehicle (at $p<0.01$ and $p<0.001$, respectively); "¤" indicates a statistically significant difference between vector versus vehicle treated Dmd$^{mdx}$ rats ($p<0.05$); and "§§" indicates a statistically significant difference between vehicle treated Dmd$^{mdx}$ rats at the 5th grip test compared to the 1st grip test ($p<0.01$).

TABLE 13

TABLE OF SEQUENCES

| SEQ ID NO | DESCRIPTION AND SEQUENCE | |
|---|---|---|
| SEQ ID | DNA sequence of human codon-optimized gene encoding human mini-dystrophin 3978 (Hopti-Dys3978) | |
| NO: 1 | atgctttggt gggaggaagt ggaggactgc tacgagagag aggacgtgca gaagaaaacc | 60 |
| | ttcaccaagt gggtgaacgc ccagttcagc aagttcggca agcagcacat cgagaacctg | 120 |
| | ttcagcgacc tgcaggatgg caggagactg ctggacctgc tggagggcct gaccggccag | 180 |
| | aagctgccca aggagaaggg cagcaccaga gtgcacgccc tgaacaacgt gaacaaggcc | 240 |
| | ctgagagtgc tgcagaacaa caacgtggac ctggtgaaca tcggcagcac cgacatcgtg | 300 |
| | gacggcaacc acaagctgac cctgggcctg atctggaaca tcatcctgca ctggcaggtg | 360 |
| | aagaacgtga tgaagaacat catggccggc ctgcagcaga ccaacagcga gaagatcctg | 420 |
| | ctgagctggg tgaggcagag caccagaaac tacccccagg tgaacgtgat caacttcacc | 480 |
| | acctcctgga gcgacggcct ggccctgaac gccctgatcc acagccacag acccgacctg | 540 |
| | ttcgactgga acagcgtggt gtgtcagcag agcgccaccc agagactgga gcacgccttc | 600 |
| | aacatcgcca gataccagct gggcatcgag aagctgctgg accccgagga cgtggacacc | 660 |
| | acctaccccg acaagaaaag catcctcatg tacattacca gcctgttcca ggtgctgccc | 720 |
| | cagcaggtgt ccatcgaggc catccaggaa gtggaaatgc tgcccaggcc ccccaaagtg | 780 |
| | accaaggagg agcacttcca gctgcaccac cagatgcact acagccagca gatcacagtg | 840 |
| | agcctggccc agggctatga gagaaccagc agccccaagc ccagattcaa gagctacgcc | 900 |
| | tacacccagg ccgcctacgt gaccacctcc gaccccacca gaagcccctt ccccagccag | 960 |
| | cacctggagg cccccgagga caagagcttc ggcagcagcc tgatggagag cgaagtgaac | 1020 |
| | ctggacagat accagaccgc cctggaggaa gtgctgtcct ggctgctgag cgccgaggac | 1080 |
| | accctgcagg cccagggcga gatcagcaac gacgtggaag tggtgaagga ccagttccac | 1140 |
| | acccacgagg gctacatgat ggatctgacc gcccaccagg gcagagtggg caatatcctg | 1200 |
| | cagctgggca gcaagctgat cggcaccggc aagctgagcg aggacgagga gaccgaagtg | 1260 |
| | caggagcaga tgaacctgct gaacagcaga tgggagtgcc tgagagtggc cagcatggag | 1320 |
| | aagcagagca acctgcacag agtgctgatg gacctgcaga accagaagct gaaggagctg | 1380 |
| | aacgactggc tgaccaagac cgaggagcgg accagaaaga tggaggagga gcccctgggc | 1440 |
| | cccgacctgg aggacctgaa gagacaggtg cagcagcaca aagtgctgca ggaggacctg | 1500 |
| | gagcaggagc aggtgcgcgt gaacagcctg acccacatgg tggtggtcgt ggacgagagc | 1560 |
| | agcggcgacc acgccacagc cgccctggaa gagcagctga aagtgctggg cgacagatgg | 1620 |
| | gccaatattt gtaggtggac cgaggacaga tgggtgctgc tgcaggacca gcccgacctg | 1680 |
| | gcccctggcc tgaccaccat cggcgccagc cccacccaga ccgtgaccct ggtgacccag | 1740 |
| | cccgtggtga caaaggagac cgccatcagc aagctggaga tgcccagctc cctgatgctg | 1800 |
| | gaagtgccca cccaccgcct gctccagcag ttcccccctgg acctggagaa gttcctggcc | 1860 |
| | tggctgaccg aggccgaaac caccgccaat gtgctccagg acgccactag aaaggagagg | 1920 |
| | ctgctggagg acagcaaggg cgtgaaagag ctgatgaagc agtggcagga tctgcagggc | 1980 |
| | gaaatcgagg cccacaccga cgtgtaccac aacctggacg agaacagcca gaagattctg | 2040 |
| | aggagcctgg agggcagcga cgacgccgtc ctgctccaga ggaggctgga caacatgaac | 2100 |
| | ttcaagtgga gcgagctgcg gaagaagagc ctgaacatcc ggagccacct ggaagccagc | 2160 |
| | agcgaccagt ggaagagact gcacctgagc ctgcaggagc tgctggtgtg gctgcagctg | 2220 |

TABLE 13-continued

TABLE OF SEQUENCES

| SEQ ID NO | DESCRIPTION AND SEQUENCE | |
|---|---|---|
| | aaggacgacg agctgagcag acaggccccc atcggcggcg acttccccgc cgtgcagaag | 2280 |
| | cagaacgacg tgcaccgggc cttcaagagg gagctgaaaa ccaaggaacc cgtgatcatg | 2340 |
| | agcaccctgg agacagtgcg gatcttcctg accgagcagc ccctggaggg actggagaag | 2400 |
| | ctgtaccagg agcccagaga gctgcccccc gaggagagag cccagaacgt gaccaggctg | 2460 |
| | ctgagaaagc aggccgagga agtgaatacc gagtgggaga agctgaatct gcacagcgcc | 2520 |
| | gactggcaga gaaagatcga cgagaccctg gagagactcc aggaactgca ggaagccacc | 2580 |
| | gacgagctgg acctgaagct gagacaggcc gaagtgatca agggcagctg gcagcctgtg | 2640 |
| | ggcgatctgc tgatcgactc cctgcaggat cacctggaga aagtgaaggc cctgcggggc | 2700 |
| | gagatcgccc ccctgaagga gaatgtgagc cacgtgaacg acctggccag acagctgacc | 2760 |
| | accctgggca tccagctgag cccctacaac ctgagcacac tggaggatct gaacacccgg | 2820 |
| | tggaaactgc tgcaggtggc cgtggaggat agagtgaggc agctgcacga agcccacaga | 2880 |
| | gacttcggcc ctgcctccca gcacttcctg agcaccagcg tgcagggccc ctgggagaga | 2940 |
| | gccatctccc ccaacaaagt gccctactac atcaaccacg agacccagac cacctgctgg | 3000 |
| | gaccacccta agatgaccga gctgtatcag agcctggccg acctgaacaa tgtgcggttc | 3060 |
| | agcgcctaca gaaccgccat gaagctgcgg agactgcaga aggccctgtg cctggatctg | 3120 |
| | ctgagcctga gcgccgcctg cgacgccctg gaccagcaca acctgaagca gaatgaccag | 3180 |
| | cccatggaca tcctgcagat catcaactgc ctgaccacaa tctacgaccg gctggaacag | 3240 |
| | gagcacaaca acctggtgaa tgtgcccctg tgcgtggaca tgtgcctgaa ttggctgctg | 3300 |
| | aacgtgtacg acaccggcag gaccggcaga atccgcgtgc tgagcttcaa gaccggcatc | 3360 |
| | atcagcctgt gcaaggccca cctggaggat aagtaccgct acctgttcaa gcaggtggcc | 3420 |
| | agcagcaccg gcttctgcga tcagaggaga ctgggcctgc tgctgcacga tagcatccag | 3480 |
| | atccctaggc agctgggcga agtggccagc tttggcggca gcaacatcga gccctctgtg | 3540 |
| | aggagctgct tccagttcgc caacaacaag cccgagatcg aggccgccct gttcctggac | 3600 |
| | tggatgaggc tggagcctca gagcatggtg tggctgcctg tgctgcacag agtggccgcc | 3660 |
| | gccgagaccg ccaagcacca ggccaagtgc aatatctgca aggagtgccc catcatcggc | 3720 |
| | ttccggtaca ggagcctgaa gcacttcaac tacgacatct gccagagctg ctttttcagc | 3780 |
| | ggcagagtgg ccaagggcca caaaatgcac taccccatgg tggagtactg cacccccacc | 3840 |
| | acctccggcg aggatgtgag agacttcgcc aaagtgctga agaataagtt ccggaccaag | 3900 |
| | cggtactttg ccaagcaccc caggatgggc tacctgcccg tgcagaccgt gctggaaggc | 3960 |
| | gacaacatgg agacctga | 3978 |
| SEQ ID NO: 2 | DNA sequence of human codon-optimized gene encoding human mini-dystrophin 3837 (Hopti-Dys3837) | |
| | atgctttggt gggaggaagt ggaggactgc tacgagagag aggacgtgca gaagaaaacc | 60 |
| | ttcaccaagt gggtgaacgc ccagttcagc aagttcggca agcagcacat cgagaacctg | 120 |
| | ttcagcgacc tgcaggatgg caggagactg ctggacctgc tggagggcct gaccggccag | 180 |
| | aagctgccca aggagaaggg cagcaccaga gtgcacgccc tgaacaacgt gaacaaggcc | 240 |
| | ctgagagtgc tgcagaacaa caacgtggac ctggtgaaca tcggcagcac cgacatcgtg | 300 |
| | gacggcaacc acaagctgac cctgggcctg atctggaaca tcatcctgca ctggcaggtg | 360 |
| | aagaacgtga tgaagaacat catggccggc ctgcagcaga ccaacagcga gaagatcctg | 420 |
| | ctgagctggg tgaggcagag caccagaaac tacccccagg tgaacgtgat caacttcacc | 480 |
| | acctcctgga gcgacggcct ggccctgaac gccctgatcc acagccacag acccgacctg | 540 |
| | ttcgactgga acagcgtggt gtgtcagcag agcgccaccc agagactgga gcacgccttc | 600 |
| | aacatcgcca gataccagct gggcatcgag aagctgctgg accccgagga cgtggacacc | 660 |
| | acctaccccg acaagaaaag catcctcatg tacattacca gcctgttcca ggtgctgccc | 720 |
| | cagcaggtgt ccatcgaggc catccaggaa gtggaaatgc tgcccaggcc ccccaaagtg | 780 |
| | accaaggagg agcacttcca gctgcaccac cagatgcact acagccagca gatcacagtg | 840 |
| | agcctggccc agggctatga gagaaccagc agccccaagc ccagattcaa gagctacgcc | 900 |
| | tacacccagg ccgcctacgt gaccacctcc gaccccacca gaagcccctt ccccagccag | 960 |
| | cacctggagg cccccgagga caagagcttc ggcagcagcc tgatggagag cgaagtgaac | 1020 |
| | ctggacagat accagaccgc cctggaggaa gtgctgtcct ggctgctgag cgccgaggac | 1080 |
| | accctgcagg cccagggcga gatcagcaac gacgtggaag tggtgaagga ccagttccac | 1140 |
| | acccacgagg gctacatgat ggatctgacc gcccaccagg gcagagtggg caatatcctg | 1200 |
| | cagctgggca gcaagctgat cggcaccggc aagctgagcg aggacgagga gaccgaagtg | 1260 |
| | caggagcaga tgaacctgct gaacagcaga tgggagtgcc tgagagtggc cagcatggag | 1320 |
| | aagcagagca acctgcacag agtgctgatg gacctgcaga accagaagct gaaggagctg | 1380 |
| | aacgactggc tgaccaagac cgaggagcgg accagaaaga tggaggagga gcccctgggc | 1440 |
| | cccgacctgg aggacctgaa gagacaggtg cagcagcaca aagtgctgca ggaggacctg | 1500 |
| | gagcaggagc aggtgcgcgt gaacagcctg acccacatgg tggtggtcgt ggacgagagc | 1560 |
| | agcggcgacc acgccacagc cgccctggaa gagcagctga aagtgctggg cgacagatgg | 1620 |
| | gccaatattt gtaggtggac cgaggacaga tgggtgctgc tgcaggacac ccaccgcctg | 1680 |
| | ctccagcagt tcccccctgga cctggagaag ttcctggcct ggctgaccga ggccgaaacc | 1740 |
| | accgccaatg tgctccagga cgccactaga aaggagaggc tgctggagga cagcaagggc | 1800 |
| | gtgaaagagc tgatgaagca gtggcaggat ctgcagggcg aaatcgaggc ccacaccgac | 1860 |
| | gtgtaccaca acctggacga gaacagccag aagattctga ggagcctgga gggcagcgac | 1920 |
| | gacgccgtcc tgctccagag gaggctggac aacatgaact tcaagtggag cgagctgcgg | 1980 |
| | aagaagagcc tgaacatccg gagccacctg gaagccagca gcgaccagtg gaagagactg | 2040 |
| | cacctgagcc tgcaggagct gctggtgtgg ctgcagctga aggacgacga gctgagcaga | 2100 |
| | caggccccca tcggcggcga cttccccgcc gtgcagaagc agaacgacgt gcaccgggcc | 2160 |
| | ttcaagaggg agctgaaaac caaggaaccc gtgatcatga gcaccctgga gacagtgcgg | 2220 |
| | atcttcctga ccgagcagcc cctggaggga ctggagaagc tgtaccagga gcccagagag | 2280 |
| | ctgccccccg aggagagagc ccagaacgtg accaggctgc tgagaaagca ggccgaggaa | 2340 |
| | gtgaataccg agtgggagaa gctgaatctg cacagcgccg actggcagag aaagatcgac | 2400 |
| | gagaccctgg agagactcca ggaactgcag gaagccaccg acgagctgga cctgaagctg | 2460 |
| | agacaggccg aagtgatcaa gggcagctgg cagcctgtgg gcgatctgct gatcgactcc | 2520 |
| | ctgcaggatc acctggagaa agtgaaggcc ctgcggggcg agatcgcccc cctgaaggag | 2580 |

TABLE 13-continued

| SEQ ID NO | TABLE OF SEQUENCES DESCRIPTION AND SEQUENCE | |
|---|---|---|
| | aatgtgagcc acgtgaacga cctggccaga cagctgacca ccctgggcat ccagctgagc | 2640 |
| | ccctacaacc tgagcacact ggaggatctg aacacccggt ggaaactgct gcaggtggcc | 2700 |
| | gtggaggata gagtgaggca gctgcacgaa gcccacagag acttcggccc tgcctcccag | 2760 |
| | cacttcctga gcaccagcgt gcagggcccc tgggagagag ccatctcccc caacaaagtg | 2820 |
| | ccctactaca tcaaccacga gacccagacc acctgctggg accaccctaa gatgaccgag | 2880 |
| | ctgtatcaga gcctggccga cctgaacaat gtgcggttca gcgcctacag aaccgccatg | 2940 |
| | aagctgcgga gactgcagaa ggccctgtgc ctggatctgc tgagcctgag cgccgcctgc | 3000 |
| | gacgccctgg accagcacaa cctgaagcag aatgaccagc ccatggacat cctgcagatc | 3060 |
| | atcaactgcc tgaccacaat ctacgaccgg ctggaacagg agcacaacaa cctggtgaat | 3120 |
| | gtgcccctgt gcgtggacat gtgcctgaat tggctgctga acgtgtacga caccggcagg | 3180 |
| | accggcagaa tccgcgtgct gagcttcaag accggcatca tcagcctgtg caaggcccac | 3240 |
| | ctggaggata agtaccgcta cctgttcaag caggtggcca gcagcaccgg cttctgcgat | 3300 |
| | cagaggagac tgggcctgct gctgcacgat agcatccaga tccctaggca gctgggcgaa | 3360 |
| | gtggccagct ttggcggcag caacatcgag ccctctgtga ggagctgctt ccagttcgcc | 3420 |
| | aacaacaagc ccgagatcga ggccgccctg ttcctggact ggatgaggct ggagcctcag | 3480 |
| | agcatggtgt ggctgcctgt gctgcacaga gtggccgccg ccgagaccgc caagcaccag | 3540 |
| | gccaagtgca atatctgcaa ggagtgcccc atcatcggct tccggtacag gagcctgaag | 3600 |
| | cacttcaact acgacatctg ccagagctgc tttttcagcg gcagagtggc caagggccac | 3660 |
| | aaaatgcact accccatggt ggagtactgc accccccacca cctccggcga ggatgtgaga | 3720 |
| | gacttcgcca aagtgctgaa gaataagttc cggaccaagc ggtactttgc caagcacccc | 3780 |
| | aggatgggct acctgcccgt gcagaccgtg ctggaaggcg acaacatgga gacctga | 3837 |
| SEQ ID NO: 3 | DNA sequence of canine codon-optimized gene encoding human mini-dystrophin 3978 (Copti-Dys3978) | |
| | atgctttggt gggaggaagt ggaggactgc tacgagcggg aggacgtgca gaagaaaacc | 60 |
| | ttcaccaagt gggtgaacgc ccagttcagc aagttcggca agcagcacat cgagaacctg | 120 |
| | ttcagcgacc tgcaggacgg caggcggctg ctggacctcc tggaaggcct gaccggccag | 180 |
| | aagctgccca aagagaaggg cagcaccagg gtgcacgccc tgaacaacgt gaacaaggcc | 240 |
| | ctgagggtgc tgcagaacaa caacgtggac ctggtgaaca tcggcagcac cgacatcgtg | 300 |
| | gacggcaacc acaagctgac cctgggcctg atctggaaca tcatcctgca ctggcaggtc | 360 |
| | aagaacgtga tgaagaacat catggccggc ctgcagcaga ccaacagcga gaagatcctg | 420 |
| | ctgtcctggg tgcggcagag caccaggaac taccccccagg tcaacgtgat caacttcacc | 480 |
| | acctcttgga gcgacggcct ggccctgaac gccctgatcc acagccacag gcccgacctg | 540 |
| | ttcgactgga acagcgtggt gtgccagcag agcgccaccc agaggctgga acacgccttc | 600 |
| | aacatcgcca gataccagct gggcatcgag aagctgctgg atcccgagga cgtggacacc | 660 |
| | acctaccccg acaagaaaag catcctcatg tacatcacca gcctgttcca ggtgctgccc | 720 |
| | cagcaggtgt ccatcgaggc catccaggaa gtggagatgc tgcccaggcc ccccaaggtc | 780 |
| | accaaagagg aacacttcca gctgcaccac cagatgcact acagccagca gatcaccgtg | 840 |
| | agcctggccc agggctacga gaggaccagc agccccaagc ccaggttcaa gagctacgcc | 900 |
| | tacacccagg ccgcctacgt gaccacctcc gaccccacca ggtccccctt ccccagccag | 960 |
| | catctcgaag cccccgagga caagagcttc ggcagcagcc tgatggaaag cgaggtgaac | 1020 |
| | ctggacagat accagaccgc cctggaagaa gtgctgtctt ggctgctgtc cgccgaggac | 1080 |
| | accctgcagg cccagggcga gatcagcaac gacgtggagg tcgtgaagga ccagttccac | 1140 |
| | acccacgagg gctacatgat ggacctgacc gcccaccagg gcagagtggg caacatcctg | 1200 |
| | cagctgggca gcaagctgat cggcaccggc aagctgtccg aggacgagga aaccgaggtg | 1260 |
| | caggaacaga tgaacctgct gaacagcaga tgggagtgcc tgagggtggc cagcatggaa | 1320 |
| | aagcagagca acctgcacag ggtgctgatg gatctgcaga accagaagct caaagagctg | 1380 |
| | aacgactggc tgaccaagac cgaggaaagg acccggaaga tggaagagga acccctgggc | |
| | cccgatctcg aagatctgaa gaggcaggtg cagcagcaca aggtgctgca ggaagatctc | 1500 |
| | gaacaggaac aggtccgggt caacagcctg acccacatgg tcgtggtggt ggacgagagc | 1560 |
| | agcggcgacc acgccaccgc tgccctggaa gagcagctga aggtgctggg cgacagatgg | 1620 |
| | gccaacatct gccggtggac cgaggacaga tgggtcctcc tgcaggacca gcccgacctg | 1680 |
| | gcccctggcc tgacaaccat cggcgccagc cccacccaga ccgtgaccct ggtgacccag | 1740 |
| | cccgtggtga ccaaagagac cgccatcagc aagctggaaa tgcccagctc cctgatgctg | 1800 |
| | gaagtgccca cccacaggct cctccagcag ttccccctgg acctggaaaa gttcctggcc | 1860 |
| | tggctgaccg aggccgagac caccgccaac gtgctgcagg acgccaccag gaaagagagg | 1920 |
| | ctgctggaag atagcaaggg cgtgaaagag ctgatgaagc agtggcagga cctgcagggg | 1980 |
| | gagattgagg cccacaccga cgtgtaccac aacctggacg agaacagcca gaaaatcctg | 2040 |
| | agaagcctgg aaggcagcga cgacgccgtg ctgctgcaga ggcggctgga caacatgaac | 2100 |
| | ttcaagtgga gcgagctgag gaagaagagc ctgaacatca ggtcccatct ggaagccagc | 2160 |
| | agcgaccagt ggaagaggct gcacctgagc ctgcaggaac tgctcgtctg gctgcagctg | 2220 |
| | aaagacgacg agctgtccag gcaggccccc atcggcggcg acttccccgc cgtgcagaaa | 2280 |
| | cagaacgacg tgcacagggc cttcaagcgg gagctgaaaa ccaaagagcc cgtgatcatg | 2340 |
| | agcaccctgg aaaccgtgag gatcttcctg accgagcagc ccctggaagg actggaaaag | 2400 |
| | ctgtaccagg aacccagaga gctgccccccc gaggaacggg cccagaacgt gaccaggctg | 2460 |
| | ctgagaaagc aggccgagga agtgaacacc gagtgggaga agctgaacct gcactccgcc | 2520 |
| | gactggcaga ggaagatcga cgagaccctg gaaaggctcc aggaactgca ggaagccacc | 2580 |
| | gacgagctgg acctgaagct gagacaggcc gaggtgatca agggcagctg gcagcccgtg | 2640 |
| | ggcgacctgc tgatcgactc cctgcaggat cacctggaaa aagtgaaggc cctgcggggc | 2700 |
| | gagatcgccc ccctgaaaga gaacgtcagc cacgtcaacg acctggccag gcagctgacc | 2760 |
| | accctgggca tccagctgtc cccctacaac ctgtccaccc tggaagatct gaacacaagg | 2820 |
| | tggaagctgc tgcaggtggc cgtggaggac agagtgaggc agctgcacga ggcccacagg | 2880 |
| | gacttcggcc ctgcctccca gcacttcctg agcaccagcg tgcagggccc ctgggagagg | 2940 |
| | gccatctccc ccaacaaggt gccctactac atcaaccacg agacccagac cacctgctgg | 3000 |
| | gaccacccta agatgaccga gctgtaccag tccctggccg acctgaacaa tgtgcggttc | 3060 |
| | agcgcctacc ggaccgccat gaagctgagg cggctgcaga aagccctgtg cctggatctg | 3120 |

TABLE 13-continued

| TABLE OF SEQUENCES | | |
|---|---|---|
| SEQ ID NO | DESCRIPTION AND SEQUENCE | |
| | ctgtccctga gcgccgcctg cgacgccctg gaccagcaca acctgaagca gaacgaccag | 3180 |
| | cccatggata tcctgcagat catcaactgt ctgaccacca tctacgacag gctggaacag | 3240 |
| | gaacacaaca acctggtcaa cgtgcccctg tgcgtggaca tgtgcctgaa ctggctgctg | 3300 |
| | aacgtgtacg acaccggcag gaccggccgg atcagggtgc tgtccttcaa gaccggcatc | 3360 |
| | atcagcctgt gcaaggccca cctggaagat aagtaccgct acctgttcaa gcaggtggcc | 3420 |
| | agctctaccg gcttctgcga ccagcggagg ctgggcctgc tgctgcacga cagcatccag | 3480 |
| | atcccccggc agctgggcga ggtggcctcc ttcggcggca gcaacatcga gcccagcgtg | 3540 |
| | cggagctgct tccagttcgc caacaacaag cccgagatcg aggccgccct gttcctggac | 3600 |
| | tggatgcggc tggaacccca gagcatggtc tggctgcccg tgctgcacag agtggctgcc | 3660 |
| | gccgagaccg ccaagcacca ggccaagtgc aacatctgca aagagtgccc catcatcggc | 3720 |
| | ttcaggtaca gaagcctgaa gcacttcaac tacgacatct gccagagctg tttcttcagc | 3780 |
| | ggcagggtgg ccaagggcca caaaatgcac taccccatgg tggagtactg cacccccacc | 3840 |
| | acctccggcg aggacgtgag ggacttcgcc aaggtgctga agaataagtt ccggaccaag | 3900 |
| | cggtacttcg ccaaacaccc caggatgggc tacctgcccg tgcagaccgt gctggaaggc | 3960 |
| | gacaacatgg aaacctga | 3978 |
| SEQ ID NO: 4 | DNA sequence of synthetic hybrid muscle-specific promoter hCK | |
| | gaattcggta ccccactacg ggtttaggct gcccatgtaa ggaggcaagg cctggggaca | 60 |
| | cccgagatgc ctggttataa ttaacccaga catgtggctg cccccccccc ccccaacacc | 120 |
| | tgctgcctct aaaaataacc ctgtccctgg tggatcccct gcatgcgaag atcttcgaac | 180 |
| | aaggctgtgg gggactgagg gcaggctgta acaggcttgg gggccagggc ttatacgtgc | 240 |
| | ctgggactcc caaagtatta ctgttccatg ttcccggcga agggccagct gtcccccgcc | 300 |
| | agctagactc agcacttagt ttaggaacca gtgagcaagt cagcccttgg ggcagcccat | 360 |
| | acaaggccat ggggctgggc aagctgcacg cctgggtccg ggtgggcac ggtgcccggg | 420 |
| | caacgagctg aaagctcatc tgctctcagg ggcccctccc tggggacagc ccctcctggc | 480 |
| | tagtcacacc ctgtaggctc ctctatataa cccaggggca caggggctgc cctcattcta | 540 |
| | ccaccacctc cacagcacag acagacactc aggagccagc cagcgtcgag cggccgatcc | 600 |
| | gccacc | 606 |
| SEQ ID NO: 5 | DNA sequence of synthetic hybrid muscle-specific promoter hCKplus | |
| | gaattcggta ccccactacg ggtctaggct gcccatgtaa ggaggcaagg cctggggaca | 60 |
| | cccgagatgc ctggttataa ttaaccccaa cacctgctgc cccccccccc ccaacacctg | 120 |
| | ctgcctctaa aaataaccct gtccctggtg gatcccctgc atgccccact acgggtttag | 180 |
| | gctgcccatg taaggaggca aggcctgggg acacccgaga tgcctggtta taattaaccc | 240 |
| | agacatgtgg ctgccccccc cccccccaac acctgctgcc tctaaaaata accctgtccc | 300 |
| | tggtggatcc cctgcatgcg aagatcttcg aacaaggctg tgggggactg agggcaggct | 360 |
| | gtaacaggct tgggggccag ggcttatacg tgcctgggac tcccaaagta ttactgttcc | 420 |
| | atgttcccgg cgaagggcca gctgtccccc gccagctaga ctcagcactt agtttaggaa | 480 |
| | ccagtgagca agtcagccct tggggcagcc catacaaggc catggggctg ggcaagctgc | 540 |
| | acgcctgggt ccggggtggg cacggtgccc gggcaacgag ctgaaagctc atctgctctc | 600 |
| | aggggcccct ccctggggac agcccctcct ggctagtcac accctgtagg ctcctctata | 660 |
| | taacccaggg gcacaggggc tgccctcatt ctaccaccac ctccacagca cagacagaca | 720 |
| | ctcaggagcc agccagcgtc gagcggccga tccgccacc | 759 |
| SEQ ID NO: 6 | DNA sequence of small synthetic polyadenylation element | |
| | tgaggagctc gagaggccta ataaagagct cagatgcatc gatcagagtg tgttggtttt | 60 |
| | ttgtgtg | 67 |
| SEQ ID NO: 7 | Amino acid sequence encoded by Hopti-Dys3978 gene (Dys3978 protein) | |
| | MLWWEEVEDC YEREDVQKKT FTKWVNAQFS KFGKQHIENL FSDLQDGRRL LDLLEGLTGQ | 60 |
| | KLPKEKGSTR VHALNNVNKA LRVLQNNNVD LVNIGSTDIV DGNHKLTLGL IWNIILHWQV | 120 |
| | KNVMKNIMAG LQQTNSEKIL LSWVRQSTRN YPQVNVINFT TSWSDGLALN ALIHSHRPDL | 180 |
| | FDWNSVVCQQ SATQRLEHAF NIARYQLGIE KLLDPEDVDT TYPDKKSILM YITSLFQVLP | 240 |
| | QQVSIEAIQE VEMLPRPPKV TKEEHFQLHH QMHYSQQITV SLAQGYERTS SPKPRFKSYA | 300 |
| | YTQAAYVTTS DPTRSPFPSQ HLEAPEDKSF GSSLMESEVN LDRYQTALEE VLSWLLSAED | 360 |
| | TLQAQGEISN DVEVVKDQFH THEGYMMDLT AHQGRVGNIL QLGSKLIGTG KLSEDEETEV | 420 |
| | QEQMNLLNSR WECLRVASME KQSNLHRVLM DLQNQKLKEL NDWLTKTEER TRKMEEEPLG | 480 |
| | PDLEDLKRQV QQHKVLQEDL EQEQVRVNSL THMVVVVDES SGDHATAALE EQLKVLGDRW | 540 |
| | ANICRWTEDR WVLLQDQPDL APGLTTIGAS PTQTVTLVTQ PVVTKETAIS KLEMPSSLML | 600 |
| | EVPTHRLLQQ FPLDLEKFLA WLTEAETTAN VLQDATRKER LLEDSKGVKE LMKQWQDLQG | 660 |
| | EIEAHTDVYH NLDENSQKIL RSLEGSDDAV LLQRRLDNMN FKWSELRKKS LNIRSHLEAS | 720 |
| | SDQWKRLHLS LQELLVWLQL KDDELSRQAP IGGDFPAVQK QNDVHRAFKR ELKTKEPVIM | 780 |
| | STLETVRIFL TEQPLEGLEK LYQEPRELPP EERAQNVTRL LRKQAEEVNT EWEKLNLHSA | 840 |
| | DWQRKIDETL ERLQELQEAT DELDLKLRQA EVIKGSWQPV GDLLIDSLQD HLEKVKALRG | 900 |
| | EIAPLKENVS HVNDLARQLT TLGIQLSPYN LSTLEDLNTR WKLLQVAVED RVRQLHEAHR | 960 |
| | DFGPASQHFL STSVQGPWER AISPNKVPYY INHETQTTCW DHPKMTELYQ SLADLNNVRF | 1020 |
| | SAYRTAMKLR RLQKALCLDL LSLSAACDAL DQHNLKQNDQ PMDILQIINC LTTIYDRLEQ | 1080 |
| | EHNNLVNVPL CVDMCLNWLL NVYDTGRTGR IRVLSFKTGI ISLCKAHLED KYRYLFKQVA | 1140 |
| | SSTGFCDQRR LGLLLHDSIQ IPRQLGEVAS FGGSNIEPSV RSCFQFANNK PEIEAALFLD | 1200 |
| | WMRLEPQSMV WLPVLHRVAA AETAKHQAKC NICKECPIIG FRYRSLKHFN YDICQSCFFS | 1260 |
| | GRVAKGHKMH YPMVEYCTPT TSGEDVRDFA KVLKNKFRTK RYFAKHPRMG YLPVQTVLEG | 1320 |
| | DNMET | 1325 |

TABLE 13-continued

TABLE OF SEQUENCES

| SEQ ID NO | DESCRIPTION AND SEQUENCE | |
|---|---|---|
| SEQ ID | Amino acid sequence encoded by Hopti-Dys3837 gene (Dys3837 protein) | |
| NO: 8 | MLWWEEVEDC YEREDVQKKT FTKWVNAQFS KFGKQHIENL FSDLQDGRRL LDLLEGLTGQ | 60 |
| | KLPKEKGSTR VHALNNVNKA LRVLQNNNVD LVNIGSTDIV DGNHKLTLGL IWNIILHWQV | 120 |
| | KNVMKNIMAG LQQTNSEKIL LSWVRQSTRN YPQVNVINFT TSWSDGLALN ALIHSHRPDL | 180 |
| | FDWNSVVCQQ SATQRLEHAF NIARYQLGIE KLLDPEDVDT TYPDKKSILM YITSLFQVLP | 240 |
| | QQVSIEAIQE VEMLPRPPKV TKEEHFQLHH QMHYSQQITV SLAQGYERTS SPKPRFKSYA | 300 |
| | YTQAAYVTTS DPTRSPFPSQ HLEAPEDKSF GSSLMESEVN LDRYQTALEE VLSWLLSAED | 360 |
| | TLQAQGEISN DVEVVKDQFH THEGYMMDLT AHQGRVGNIL QLGSKLIGTG KLSEDEETEV | 420 |
| | QEQMNLLNSR WECLRVASME KQSNLHRVLM DLQNQKLKEL NDWLTKTEER TRKMEEEPLG | 480 |
| | PDLEDLKRQV QQHKVLQEDL EQEQVRVNSL THMVVVVDES SGDHATAALE EQLKVLGDRW | 540 |
| | ANICRWTEDR WVLLQDTHRL LQQFPLDLEK FLAWLTEAET TANVLQDATR KERLLEDSKG | 600 |
| | VKELMKQWQD LQGEIEAHTD VYHNLDENSQ KILRSLEGSD DAVLLQRRLD NMNFKWSELR | 660 |
| | KKSLNIRSHL EASSDQWKRL HLSLQELLVW LQLKDDELSR QAPIGGDFPA VQKQNDVHRA | 720 |
| | FKRELKTKEP VIMSTLETVR IFLTEQPLEG LEKLYQEPRE LPPEERAQNV TRLLRKQAEE | 780 |
| | VNTEWEKLNL HSADWQRKID ETLERLQELQ EATDELDLKL RQAEVIKGSW QPVGDLLIDS | 840 |
| | LQDHLEKVKA LRGEIAPLKE NVSHVNDLAR QLTTLGIQLS PYNLSTLEDL NTRWKLLQVA | 900 |
| | VEDRVRQLHE AHRDFGPASQ HELSTSVQGP WERAISPNKV PYYINHETQT TCWDHPKMTE | 960 |
| | LYQSLADLNN VRFSAYRTAM KLRRLQKALC LDLLSLSAAC DALDQHNLKQ NDQPMDILQI | 1020 |
| | INCLTTIYDR LEQEHNNLVN VPLCVDMCLN WLLNVYDTGR TGRIRVLSFK TGIISLCKAH | 1080 |
| | LEDKYRYLFK QVASSTGFCD QRRLGLLLHD SIQIPRQLGE VASFGGSNIE PSVRSCFQFA | 1140 |
| | NNKPEIEAAL FLDWMRLEPQ SMVWLPVLHR VAAAETAKHQ AKCNICKECP IIGFRYRSLK | 1200 |
| | HFNYDICQSC FFSGRVAKGH KMHYPMVEYC TPTTSGEDVR DFAKVLKNKF RTKRYFAKHP | 1260 |
| | RMGYLPVQTV LEGDNMET | 1278 |
| SEQ ID | DNA sequence of a human-codon optimized human mini-dystrophin 3978 (Hopti-Dys3978) gene | |
| NO: 9 | expression cassette | |
| | ttggccactc cctctctgcg cgctcgctcg ctcactgagg ccgggcgacc aaaggtcgcc | 60 |
| | cgacgcccgg gctttgcccg ggcggcctca gtgagcgagc gagcgcgcag agagggagtg | 120 |
| | gccaactcca tcactagggg ttcctagatc tgaattcggt accccactac gggtttaggc | 180 |
| | tgcccatgta aggaggcaag gcctggggac acccgagatg cctggttata attaacccag | 240 |
| | acatgtggct gccccccccc cccccaacac ctgctgcctc taaaaataac cctgtccctg | 300 |
| | gtggatcccc tgcatgcgaa gatcttcgaa caaggctgtg gggactgag ggcaggctgt | 360 |
| | aacaggcttg gggccagggg cttatacgtg cctgggactc ccaaagtatt actgttccat | 420 |
| | gttcccggcg aagggccagc tgtcccccgc cagctagact cagcacttag tttaggaacc | 480 |
| | agtgagcaag tcagcccttg gggcagccca tacaaggcca tggggctggg caagctgcac | 540 |
| | gcctgggtcc ggggtgggca cggtgcccgg gcaacgagct gaaagctcat ctgctctcag | 600 |
| | gggcccctcc ctggggacag cccctcctgg ctagtcacac cctgtaggct cctctatata | 660 |
| | acccaggggc acaggggctg ccctcattct accaccacct ccacagcaca gacagacact | 720 |
| | caggagccag ccagcgtcga gcggccgatc cgccaccatg ctttggtggg aggaagtgga | 780 |
| | ggactgctac gagagagagg acgtgcagaa gaaaaccttc accaagtggg tgaacgccca | 840 |
| | gttcagcaag ttcggcaagc agcacatcga gaacctgttc agcgacctgc aggatggcag | 900 |
| | gagactgctg gacctgctgg agggcctgac cggccagaag ctgcccaagg agaagggcag | 960 |
| | caccagagtg cacgccctga acaacgtgaa caaggccctg agagtgctgc agaacaacaa | 1020 |
| | cgtggacctg gtgaacatcg gcagcaccga catcgtggac ggcaaccaca agctgaccct | 1080 |
| | gggcctgatc tggaacatca tcctgcactg gcaggtgaag aacgtgatga agaacatcat | 1140 |
| | ggccggcctg cagcagacca acagcgagaa gatcctgctg agctgggtga ggcagagcac | 1200 |
| | cagaaactac ccccaggtga acgtgatcaa cttcaccacc tcctggagcg acggcctggc | 1260 |
| | cctgaacgcc ctgatccaca gccacagacc cgacctgttc gactggaaca gcgtggtgtg | 1320 |
| | tcagcagagc gccacccaga gactggagca cgccttcaac atcgccagat accagctggg | 1380 |
| | catcgagaag ctgctggacc ccgaggacgt ggacaccacc taccccgaca agaaaagcat | 1440 |
| | cctcatgtac attaccagcc tgttccaggt gctgccccag caggtgtcca tcgaggccat | 1500 |
| | ccaggaagtg gaaatgctgc ccaggccccc caaagtgacc aaggaggage acttccagct | 1560 |
| | gcaccaccag atgcactaca gccagcagat cacagtgagc ctggcccagg gctatgagag | 1620 |
| | aaccagcagc cccaagccca gattcaagag ctacgcctac acccaggccg cctacgtgac | 1680 |
| | cacctccgac cccaccagaa gccccttccc cagccagcac ctggaggccc ccgaggacaa | 1740 |
| | gagcttcggc agcagcctga tggagagcga agtgaacctg gacagatacc agaccgccct | 1800 |
| | ggaggaagtg ctgtcctggc tgctgagcgc cgaggacacc ctgcaggccc agggcgagat | 1860 |
| | cagcaacgac gtggaagtgg tgaaggacca gttccacacc cacgagggct acatgatgga | 1920 |
| | tctgaccgcc caccagggca gagtgggcaa tatcctgcag ctgggcagca agctgatcgg | 1980 |
| | caccggcaag ctgagcgagg acgaggagac cgaagtgcag gagcagatga acctgctgaa | 2040 |
| | cagcagatgg gagtgcctga gagtggccag catggagaag cagagcaacc tgcacagagt | 2100 |
| | gctgatggac ctgcagaacc agaagctgaa ggagctgaac gactggctga ccaagaccga | 2160 |
| | ggagcggacc agaaagatgg aggaggagcc cctgggcccc gacctggagg acctgaagag | 2220 |
| | acaggtgcag cagcacaaag tgctgcagga ggacctggag caggagcagg tgcgcgtgaa | 2280 |
| | cagcctgacc cacatggtgg tggtcgtgga cgagagcage ggcgaccacg ccacagccgc | 2340 |
| | cctggaagag cagctgaaag tgctgggcga cagatgggcc aatatttgta ggtggaccga | 2400 |
| | ggacagatgg gtgctgctgc aggaccagcc cgacctggcc cctggcctga ccaccatcgg | 2460 |
| | cgccagcccc acccagaccg tgaccctggt gacccagccc gtggtgacaa aggagaccgc | 2520 |
| | catcagcaag ctggagatgc ccagctccct gatgctggaa gtgcccaccc accgcctgct | 2580 |
| | ccagcagttc cccctggacc tggagaagtt cctggcctgg ctgaccgagg ccgaaaccac | 2640 |
| | cgccaatgtg ctccaggacg ccactagaaa ggagaggctg ctggaggaca gcaagggcgt | 2700 |
| | gaaagagctg atgaagcagt ggcaggatct gcagggcgaa atcgaggccc acaccgacgt | 2760 |
| | gtaccacaac ctggacgaga acagccagaa gattctgagg agcctggagg gcagcgacga | 2820 |
| | cgccgtcctg ctccagagga ggctggacaa catgaacttc aagtggagcg agctgcggaa | 2880 |
| | gaagagcctg aacatccgga gccacctgga agccagcagc gaccagtgga agagactgca | 2940 |

TABLE 13-continued

| TABLE OF SEQUENCES | | |
|---|---|---|
| SEQ ID NO | DESCRIPTION AND SEQUENCE | |
| | cctgagcctg caggagctgc tggtgtggct gcagctgaag gacgacgagc tgagcagaca | 3000 |
| | ggcccccatc ggcggcgact tccccgccgt gcagaagcag aacgacgtgc accgggcctt | 3060 |
| | caagagggag ctgaaaacca aggaacccgt gatcatgagc accctggaga cagtgcggat | 3120 |
| | cttcctgacc gagcagcccc tggagggact ggagaagctg taccaggagc ccagagagct | 3180 |
| | gccccccgag gagagagccc agaacgtgac caggctgctg agaaagcagg ccgaggaagt | 3240 |
| | gaataccgag tgggagaagc tgaatctgca cagcgccgac tggcagagaa agatcgacga | 3300 |
| | gaccctggag agactccagg aactgcagga agccaccgac gagctggacc tgaagctgag | 3360 |
| | acaggccgaa gtgatcaagg gcagctggca gcctgtgggc gatctgctga tcgactccct | 3420 |
| | gcaggatcac ctggagaaag tgaaggccct gcggggcgag atcgcccccc tgaaggagaa | 3480 |
| | tgtgagccac gtgaacgacc tggccagaca gctgaccacc ctgggcatcc agctgagccc | 3540 |
| | ctacaacctg agcacactgg aggatctgaa caccccggtgg aaactgctgc aggtggccgt | 3600 |
| | ggaggataga gtgaggcagc tgcacgaagc ccacagagac ttcggccctg cctcccagca | 3660 |
| | cttcctgagc accagcgtgc agggcccctg ggagagagcc atctccccca acaaagtgcc | 3720 |
| | ctactacatc aaccacgaga cccagaccac ctgctgggac caccctaaga tgaccgagct | 3780 |
| | gtatcagagc ctggccgacc tgaacaatgt gcggttcagc gcctacagaa ccgccatgaa | 3840 |
| | gctgcggaga ctgcagaagg ccctgtgcct ggatctgctg agcctgagcg ccgcctgcga | 3900 |
| | cgccctggac cagcacaacc tgaagcagaa tgaccagccc atggacatcc tgcagatcat | 3960 |
| | caactgcctg accacaatct acgaccggct ggaacaggag cacaacaacc tggtgaatgt | 4020 |
| | gcccctgtgc gtggacatgt gcctgaattg gctgctgaac gtgtacgaca ccggcaggac | 4080 |
| | cggcagaatc cgcgtgctga gcttcaagac cggcatcatc agcctgtgca aggcccacct | 4140 |
| | ggaggataag taccgctacc tgttcaagca ggtggccagc agcaccggct tctgcgatca | 4200 |
| | gaggagactg ggcctgctgc tgcacgatag catccagatc cctaggcagc tgggcgaagt | 4260 |
| | ggccagcttt ggcggcagca acatcgagcc ctctgtgagg agctgcttcc agttcgccaa | 4320 |
| | caacaagccc gagatcgagg ccgccctgtt cctggactgg atgaggctgg agcctcagag | 4380 |
| | catggtgtgg ctgcctgtgc tgcacagagt ggccgccgcc gagaccgcca agcaccaggc | 4440 |
| | caagtgcaat atctgcaagg agtgccccat catcggcttc cggtacagga gcctgaagca | 4500 |
| | cttcaactac gacatctgcc agagctgctt tttcagcggc agagtggcca agggccacaa | 4560 |
| | aatgcactac cccatggtgg agtactgcac ccccaccacc tccggcgagg atgtgagaga | 4620 |
| | cttcgccaaa gtgctgaaga ataagttccg gaccaagcgg tactttgcca agcaccccag | 4680 |
| | gatgggctac ctgcccgtgc agaccgtgct ggaaggcgac aacatggaga cctgatgagg | 4740 |
| | agctcgagag gcctaataaa gagctcagat gcatcgatca gagtgtgttg gtttttttgtg | 4800 |
| | tgagatctag gaacccctag tgatggagtt ggccactccc tctctgcgcg ctcgctcgct | 4860 |
| | cactgaggcc gcccgggcaa agcccgggcg tcgggcgacc tttggtcgcc cggcctcagt | 4920 |
| | gagcgagcga gcgcgcagag agggagtggc caa | 4953 |
| SEQ ID | DNA sequence of AAV-hCK-Hopti-Dys3837 gene expression cassette | |
| NO: 10 | ttggccactc cctctctgcg cgctcgctcg ctcactgagg ccgggcgacc aaaggtcgcc | 60 |
| | cgacgcccgg gctttgcccg ggcggcctca gtgagcgagc gagcgcgcag agagggagtg | 120 |
| | gccaactcca tcactagggg ttcctagatc tgaattcggt accccactac gggtttaggc | 180 |
| | tgcccatgta aggaggcaag gcctggggac acccgagatg cctggttata attaacccag | 240 |
| | acatgtggct gccccccccc cccccaacac ctgctgcctc taaaaataac cctgtccctg | 300 |
| | gtggatcccc tgcatgcgaa gatcttcgaa caaggctgtg gggggactgag ggcaggctgt | 360 |
| | aacaggcttg gggccaggg cttatacgtg cctgggactc ccaaagtatt actgttccat | 420 |
| | gttcccggcg aagggccagc tgtcccccgc cagctagact cagcacttag tttaggaacc | 480 |
| | agtgagcaag tcagcccttg gggcagccca tacaaggcca tggggctggg caagctgcac | 540 |
| | gcctgggtcc ggggtgggca cggtgcccgg gcaacgagct gaaagctcat ctgctctcag | 600 |
| | gggcccctcc ctggggacag cccctcctgg ctagtcacac cctgtaggct cctctatata | 660 |
| | acccaggggc acaggggctg ccctcattct accaccacct ccacagcaca gacagacact | 720 |
| | caggagccag ccagcgtcga gcggccgatc cgccaccatg ctttggtggg aggaagtgga | 780 |
| | ggactgctac gagagagagg acgtgcagaa gaaaaccttc accaagtggg tgaacgccca | 840 |
| | gttcagcaag ttcggcaagc agcacatcga gaacctgttc agcgacctgc aggatggcag | 900 |
| | gagactgctg gacctgctgg agggcctgac cggccagaag ctgcccaagg agaagggcag | 960 |
| | caccagagtg cacgccctga acaacgtgaa caaggccctg agagtgctgc agaacaacaa | 1020 |
| | cgtggacctg gtgaacatcg gcagcaccga catcgtggac ggcaaccaca agctgaccct | 1080 |
| | gggcctgatc tggaacatca tcctgcactg gcaggtgaag aacgtgatga agaacatcat | 1140 |
| | ggccggcctg cagcagacca acagcgagaa gatcctgctg agctgggtga ggcagagcac | 1200 |
| | cagaaactac ccccaggtga acgtgatcaa cttcaccacc tcctggagcg acggcctggc | 1260 |
| | cctgaacgcc ctgatccaca gccacagacc cgacctgttc gactggaaca gcgtggtgtg | 1320 |
| | tcagcagagc gccacccaga gactggagca cgccttcaac atcgccagat accagctggg | 1380 |
| | catcgagaag ctgctggacc ccgaggacgt ggacaccacc taccccgaca agaaaagcat | 1440 |
| | cctcatgtac attaccagcc tgttccaggt gctgccccag caggtgtcca tcgaggccat | 1500 |
| | ccaggaagtg gaaatgctgc ccaggccccc caaagtgacc aaggaggagc acttccagct | 1560 |
| | gcaccaccag atgcactaca gccagcagat cacagtgagc ctggcccagg gctatgagag | 1620 |
| | aaccagcagc cccaagccca gattcaagag ctacgcctac acccaggccg cctacgtgac | 1680 |
| | cacctccgac cccaccagaa gccccttccc cagccagcac ctggaggccc ccgaggacaa | 1740 |
| | gagcttcggc agcagcctga tggagagcga agtgaacctg gacagatacc agaccgccct | 1800 |
| | ggaggaagtg ctgtcctggc tgctgagcgc cgaggacacc ctgcaggccc agggcgagat | 1860 |
| | cagcaacgac gtggaagtgg tgaaggacca gttccacacc cacgagggct acatgatgga | 1920 |
| | tctgaccgcc caccagggca gagtgggcaa tatcctgcag ctgggcagca agctgatcgg | 1980 |
| | caccggcaag ctgagcgagg acgaggagac cgaagtgcag gagcagatga acctgctgaa | 2040 |
| | cagcagatgg gagtgcctga gagtggccag catggagaag cagagcaacc tgcacagagt | 2100 |
| | gctgatggac ctgcagaacc agaagctgaa ggagctgaac gactggctga ccaagaccga | 2160 |
| | ggagcggacc agaaagatgg aggaggagcc cctgggcccc gacctggagg acctgaagag | 2220 |
| | acaggtgcag cagcacaaag tgctgcagga ggacctggag caggagcagg tgcgcgtgaa | 2280 |
| | cagcctgacc cacatggtgg tggtcgtgga cgagagcagc ggcgaccacg ccacagccgc | 2340 |

TABLE 13-continued

TABLE OF SEQUENCES

| SEQ ID NO | DESCRIPTION AND SEQUENCE | |
|---|---|---|
| | cctggaagag cagctgaaag tgctgggcga cagatgggcc aatatttgta ggtggaccga | 2400 |
| | ggacagatgg gtgctgctgc aggacaccca ccgcctgctc cagcagttcc ccctggacct | 2460 |
| | ggagaagttc ctggcctggc tgaccgaggc cgaaaccacc gccaatgtgc tccaggacgc | 2520 |
| | cactagaaag gagaggctgc tggaggacag caagggcgtg aaagagctga tgaagcagtg | 2580 |
| | gcaggatctg cagggcgaaa tcgaggccca caccgacgtg taccacaacc tggacgagaa | 2640 |
| | cagccagaag attctgagga gcctggaggg cagcgacgac gccgtcctgc tccagaggag | 2700 |
| | gctggacaac atgaacttca agtggagcga gctgcggaag aagagcctga acatccggag | 2760 |
| | ccacctggaa gccagcagcg accagtggaa gagactgcac ctgagcctgc aggagctgct | 2820 |
| | ggtgtggctg cagctgaagg acgacgagct gagcagacag gcccccatcg gcggcgactt | 2880 |
| | ccccgccgtg cagaagcaga acgacgtgca ccgggccttc aagagggagc tgaaaaccaa | 2940 |
| | ggaacccgtg atcatgagca ccctggagac agtgcggatc ttcctgaccg agcagcccct | 3000 |
| | ggagggactg gagaagctgt accaggagcc cagagagctg ccccccgagg agagagccca | 3060 |
| | gaacgtgacc aggctgctga gaaagcaggc cgaggaagtg aataccgagt gggagaagct | 3120 |
| | gaatctgcac agcgccgact ggcagagaaa gatcgacgag accctggaga gactccagga | 3180 |
| | actgcaggaa gccaccgacg agctggacct gaagctgaga caggccgaag tgatcaaggg | 3240 |
| | cagctggcag cctgtgggcg atctgctgat cgactccctg caggatcacc tggagaaagt | 3300 |
| | gaaggccctg cggggcgaga tcgcccccct gaaggagaat gtgagccacg tgaacgacct | 3360 |
| | ggccagacag ctgaccaccc tgggcatcca gctgagcccc tacaacctga gcacactgga | 3420 |
| | ggatctgaac acccggtgga aactgctgca ggtggccgtg gaggatagag tgaggcagct | 3480 |
| | gcacgaagcc cacagagact tcggccctgc ctcccagcac ttcctgagca ccagcgtgca | 3540 |
| | gggcccctgg gagagagcca tctcccccaa caaagtgccc tactacatca accacgagac | 3600 |
| | ccagaccacc tgctgggacc accctaagat gaccgagctg tatcagagcc tggccgacct | 3660 |
| | gaacaatgtg cggttcagcg cctacagaac cgccatgaag ctgcggagac tgcagaaggc | 3720 |
| | cctgtgcctg gatctgctga gcctgagcgc cgcctgcgac gccctggacc agcacaacct | 3780 |
| | gaagcagaat gaccagccca tggacatcct gcagatcatc aactgcctga ccacaatcta | 3840 |
| | cgaccggctg gaacaggagc acaacaacct ggtgaatgtg cccctgtgcg tggacatgtg | 3900 |
| | cctgaattgg ctgctgaacg tgtacgacac cggcaggacc ggcagaatcc gcgtgctgag | 3960 |
| | cttcaagacc ggcatcatca gcctgtgcaa ggcccacctg gaggataagt accgctacct | 4020 |
| | gttcaagcag gtggccagca gcaccggctt ctgcgatcag aggagactgg gcctgctgct | 4080 |
| | gcacgatagc atccagatcc ctaggcagct gggcgaagtg gccagctttg gcggcagcaa | 4140 |
| | catcgagccc tctgtgagga gctgcttcca gttcgccaac aacaagcccg agatcgaggc | 4200 |
| | cgccctgttc ctggactgga tgaggctgga gcctcagagc atggtgtggc tgcctgtgct | 4260 |
| | gcacagagtg gccgccgccg agaccgccaa gcaccaggcc aagtgcaata tctgcaagga | 4320 |
| | gtgccccatc atcggcttcc ggtacaggag cctgaagcac ttcaactacg acatctgcca | 4380 |
| | gagctgcttt ttcagcggca gagtggccaa gggccacaaa atgcactacc ccatggtgga | 4440 |
| | gtactgcacc cccaccacct ccggcgagga tgtgagagac ttcgccaaag tgctgaagaa | 4500 |
| | taagttccgg accaagcggt actttgccaa gcaccccagg atgggctacc tgcccgtgca | 4560 |
| | gaccgtgctg gaaggcgaca acatggagac ctgatgagga gctcgagagg cctaataaag | 4620 |
| | agctcagatg catcgatcag agtgtgttgg tttttttgtgt gagatctagg aacccctagt | 4680 |
| | gatggagttg gccactccct ctctgcgcgc tcgctcgctc actgaggccg cccgggcaaa | 4740 |
| | gcccgggcgt cgggcgacct ttggtcgccc ggcctcagtg agcgagcgag cgcgcagaga | 4800 |
| | gggagtggcc aa | 4812 |
| SEQ ID NO: 11 | DNA sequence of AAV-hCKplus-Hopti-Dys3837 gene expression cassette | |
| | ttggccactc cctctctgcg cgctcgctcg ctcactgagg ccgggcgacc aaaggtcgcc | 60 |
| | cgacgcccgg gctttgcccg ggcggcctca gtgagcgagc gagcgcgcag agagggagtg | 120 |
| | gccaactcca tcactagggg ttcctagatc tgaattcggt accccactac gggtctaggc | 180 |
| | tgcccatgta aggaggcaag gcctggggac acccgagatg cctggttata attaacccca | 240 |
| | acacctgctg cccccccccc cccaacacct gctgcctcta aaaataaccc tgtccctggt | 300 |
| | ggatcccctg catgccccac tacgggttta ggctgcccat gtaaggaggc aaggcctggg | 360 |
| | gacacccgag atgcctggtt ataattaacc cagacatgtg gctgcccccc cccccccaa | 420 |
| | cacctgctgc ctctaaaaat aaccctgtcc ctggtggatc ccctgcatgc gaagatcttc | 480 |
| | gaacaaggct gtgggggact gagggcaggc tgtaacaggc ttgggggcca gggcttatac | 540 |
| | gtgcctggga ctcccaaagt attactgttc catgttcccg gcgaagggcc agctgtcccc | 600 |
| | cgccagctag actcagcact tagtttagga accagtgagc aagtcagccc ttggggcagc | 660 |
| | ccatacaagg ccatggggct gggcaagctg cacgcctggg tccggggtgg gcacggtgcc | 720 |
| | cgggcaacga gctgaaagct catctgctct caggggcccc tccctgggga cagcccctcc | 780 |
| | tggctagtca caccctgtag gctcctctat ataacccagg ggcacagggg ctgccctcat | 840 |
| | tctaccacca cctccacagc acagacagac actcaggagc cagccagcgt cgagcggccg | 900 |
| | atccgccacc atgctttggt gggaggaagt ggaggactgc tacgagagag aggacgtgca | 960 |
| | gaagaaaacc ttcaccaagt gggtgaacgc ccagttcagc aagttcggca agcagcacat | 1020 |
| | cgagaacctg ttcagcgacc tgcaggatgg caggagactg ctggacctgc tggagggcct | 1080 |
| | gaccggccag aagctgccca aggagaaggg cagcaccaga gtgcacgccc tgaacaacgt | 1140 |
| | gaacaaggcc ctgagagtgc tgcagaacaa caacgtggac ctggtgaaca tcggcagcac | 1200 |
| | cgacatcgtg gacggcaacc acaagctgac cctgggcctg atctggaaca tcatcctgca | 1260 |
| | ctggcaggtg aagaacgtga tgaagaacat catggccggc ctgcagcaga ccaacagcga | 1320 |
| | gaagatcctg ctgagctggg tgaggcagag caccagaaac tacccccagg tgaacgtgat | 1380 |
| | caacttcacc acctcctgga gcgacggcct ggccctgaac gccctgatcc acagccacag | 1440 |
| | acccgacctg ttcgactgga acagcgtggt gtgtcagcag agcgccaccc agagactgga | 1500 |
| | gcacgccttc aacatcgcca gataccagct gggcatcgag aagctgctgg accccgagga | 1560 |
| | cgtggacacc acctaccccg acaagaaaag catcctcatg tacattacca gcctgttcca | 1620 |
| | ggtgctgccc cagcaggtgt ccatcgaggc catccaggaa gtggaaatgc tgcccaggcc | 1680 |
| | ccccaaagtg accaaggagg agcacttcca gctgcaccac cagatgcact acagccagca | 1740 |
| | gatcacagtg agcctggccc agggctatga gagaaccagc agccccaagc ccagattcaa | 1800 |
| | gagctacgcc tacacccagg ccgcctacgt gaccacctcc gaccccacca gaagcccctt | 1860 |

TABLE 13-continued

TABLE OF SEQUENCES

| SEQ ID NO | DESCRIPTION AND SEQUENCE |
|---|---|
| | ccccagccag cacctggagg cccccgagga caagagcttc ggcagcagcc tgatggagag 1920 |
| | cgaagtgaac ctggacagat accagaccgc cctggaggaa gtgctgtcct ggctgctgag 1980 |
| | cgccgaggac accctgcagg cccagggcga gatcagcaac gacgtggaag tggtgaagga 2040 |
| | ccagttccac acccacgagg gctacatgat ggatctgacc gcccaccagg gcagagtggg 2100 |
| | caatatcctg cagctgggca gcaagctgat cggcaccggc aagctgagcg aggacgagga 2160 |
| | gaccgaagtg caggagcaga tgaacctgct gaacagcaga tgggagtgcc tgagagtggc 2220 |
| | cagcatggag aagcagagca acctgcacag agtgctgatg gacctgcaga accagaagct 2280 |
| | gaaggagctg aacgactggc tgaccaagac cgaggagcgg accagaaaga tggaggagga 2340 |
| | gcccctgggc cccgacctgg aggacctgaa gagacaggtg cagcagcaca aagtgctgca 2400 |
| | ggaggacctg gagcaggagc aggtgcgcgt gaacagcctg acccacatgg tggtggtcgt 2460 |
| | ggacgagagc agcggcgacc acgccacagc cgccctggaa gagcagctga aagtgctggg 2520 |
| | cgacagatgg gccaatattt gtaggtggac cgaggacaga tgggtgctgc tgcaggacac 2580 |
| | ccaccgcctg ctccagcagt tcccccctgga cctggagaag ttcctggcct ggctgaccga 2640 |
| | ggccgaaacc accgccaatg tgctccagga cgccactaga aaggagaggc tgctggagga 2700 |
| | cagcaagggc gtgaaagagc tgatgaagca gtggcaggat ctgcagggcg aaatcgaggc 2760 |
| | ccacaccgac gtgtaccaca acctggacga gaacagccag aagattctga ggagcctgga 2820 |
| | gggcagcgac gacgccgtcc tgctccagag gaggctggac aacatgaact tcaagtggag 2880 |
| | cgagctgcgg aagaagagcc tgaacatccg gagccacctg gaagccagca gcgaccagtg 2940 |
| | gaagagactg cacctgagcc tgcaggagct gctggtgtgg ctgcagctga aggacgacga 3000 |
| | gctgagcaga caggccccca tcggcggcga cttccccgcc gtgcagaagc agaacgacgt 3060 |
| | gcaccgggcc ttcaagaggg agctgaaaac caaggaaccc gtgatcatga gcaccctgga 3120 |
| | gacagtgcgg atcttcctga ccgagcagcc cctggaggga ctggagaagc tgtaccagga 3180 |
| | gcccagagag ctgccccccg aggagagagc ccagaacgtg accaggctgc tgagaaagca 3240 |
| | ggccgaggaa gtgaataccg agtgggagaa gctgaatctg cacagcgccg actggcagag 3300 |
| | aaagatcgac gagaccctgg agagactcca ggaactgcag gaagccaccg acgagctgga 3360 |
| | cctgaagctg agacaggccg aagtgatcaa gggcagctgg cagcctgtgg gcgatctgct 3420 |
| | gatcgactcc ctgcaggatc acctggagaa agtgaaggcc ctgcggggcg agatcgcccc 3480 |
| | cctgaaggag aatgtgagcc acgtgaacga cctggccaga cagctgacca ccctgggcat 3540 |
| | ccagctgagc ccctacaacc tgagcacact ggaggatctg aacacccggt ggaaactgct 3600 |
| | gcaggtggcc gtggaggata gagtgaggca gctgcacgaa gcccacagag acttcggccc 3660 |
| | tgcctcccag cacttcctga gcaccagcgt gcagggcccc tgggagagag ccatctcccc 3720 |
| | caacaaagtg ccctactaca tcaaccacga gacccagacc acctgctggg accaccctaa 3780 |
| | gatgaccgag ctgtatcaga gcctggccga cctgaacaat gtgcggttca gcgcctacag 3840 |
| | aaccgccatg aagctgcgga gactgcagaa ggccctgtgc ctggatctgc tgagcctgag 3900 |
| | cgccgcctgc gacgccctgg accagcacaa cctgaagcag aatgaccagc ccatggacat 3960 |
| | cctgcagatc atcaactgcc tgaccacaat ctacgaccgg ctggaacagg agcacaacaa 4020 |
| | cctggtgaat gtgcccctgt gcgtggacat gtgcctgaat tggctgctga acgtgtacga 4080 |
| | caccggcagg accggcagaa tccgcgtgct gagcttcaag accggcatca tcagcctgtg 4140 |
| | caaggcccac ctggaggata agtaccgcta cctgttcaag caggtggcca gcagcaccgg 4200 |
| | cttctgcgat cagaggagac tgggcctgct gctgcacgat agcatccaga tccctaggca 4260 |
| | gctgggcgaa gtggccagct ttggcggcag caacatcgag ccctctgtga ggagctgctt 4320 |
| | ccagttcgcc aacaacaagc ccgagatcga ggccgccctg ttcctggact ggatgaggct 4380 |
| | ggagcctcag agcatggtgt ggctgcctgt gctgcacaga gtggccgccg ccgagaccgc 4440 |
| | caagcaccag gccaagtgca atatctgcaa ggagtgcccc atcatcggct tccggtacag 4500 |
| | gagcctgaag cacttcaact acgacatctg ccagagctgc tttttcagcg gcagagtggc 4560 |
| | caagggccac aaaatgcact accccatggt ggagtactgc acccccacca cctccggcga 4620 |
| | ggatgtgaga gacttcgcca aagtgctgaa gaataagttc cggaccaagc ggtactttgc 4680 |
| | caagcacccc aggatgggct acctgcccgt gcagaccgtg ctggaaggcg acaacatgga 4740 |
| | gacctgatga ggagctcgag aggcctaata aagagctcag atgcatcgat cagagtgtgt 4800 |
| | tggtttttttg tgtgagatct aggaacccct agtgatggag ttggccactc cctctctgcg 4860 |
| | cgctcgctcg ctcactgagg ccgcccgggc aaagcccggg cgtcgggcga cctttggtcg 4920 |
| | cccggcctca gtgagcgagc gagcgcgcag agagggagtg gccaa 4965 |
| SEQ ID NO: 12 | DNA sequence of AAV-hCK-Copti-Dys3978 gene expression cassette |
| | ttggccactc cctctctgcg cgctcgctcg ctcactgagg ccgggcgacc aaaggtcgcc 60 |
| | cgacgcccgg gctttgcccg ggcggcctca gtgagcgagc gagcgcgcag agagggagtg 120 |
| | gccaactcca tcactagggg ttcctcagat ctgaattcgg taccccacta cgggtttagg 180 |
| | ctgcccatgt aaggaggcaa ggcctgggga cacccgagat gcctggttat aattaaccca 240 |
| | gacatgtggc tgcccccccc ccccccaaca cctgctgcct ctaaaaataa ccctgtccct 300 |
| | ggtggatccc ctgcatgcga agatcttcga acaaggctgt gggggactga gggcaggctg 360 |
| | taacaggctt gggggccagg gcttatacgt gcctgggact cccaaagtat tactgttcca 420 |
| | tgttcccggc gaagggccag ctgtcccccg ccagctagac tcagcactta gtttaggaac 480 |
| | cagtgagcaa gtcagccctt ggggcagccc atacaaggcc atggggctgg gcaagctgca 540 |
| | cgcctgggtc cggggtgggc acggtgcccg ggcaacgagc tgaaagctca tctgctctca 600 |
| | ggggcccctc cctggggaca gcccctcctg gctagtcaca ccctgtaggc tcctctatat 660 |
| | aacccagggg cacaggggct gccctcattc taccaccacc tccacagcac agacagacac 720 |
| | tcaggagcca gccagcgtcg agcggccgcc accatgcttt ggtgggagga agtggaggac 780 |
| | tgctacgagc gggaggacgt gcagaagaaa accttcacca agtgggtgaa cgcccagttc 840 |
| | agcaagttcg gcaagcagca catcgagaac ctgttcagcg acctgcagga cggcaggcgg 900 |
| | ctgctggacc tcctggaagg cctgaccggc cagaagctgc ccaaagagaa gggcagcacc 960 |
| | agggtgcacg ccctgaacaa cgtgaacaag gccctgaggg tgctgcagaa caacaacgtg 1020 |
| | gacctggtga acatcggcag caccgacatc gtggacggca accacaagct gaccctgggc 1080 |
| | ctgatctgga acatcatcct gcactggcag gtcaagaacg tgatgaagaa catcatggcc 1140 |
| | ggcctgcagc agaccaacag cgagaagatc ctgctgtcct gggtgcggca gagcaccagg 1200 |
| | aactaccccc aggtcaacgt gatcaacttc accacctctt ggagcgacgg cctggccctg 1260 |

TABLE 13-continued

TABLE OF SEQUENCES

| SEQ ID NO | DESCRIPTION AND SEQUENCE | |
|---|---|---|
| | aacgccctga tccacagcca caggcccgac ctgttcgact ggaacagcgt ggtgtgccag | 1320 |
| | cagagcgcca cccagaggct ggaacacgcc ttcaacatcg ccagatacca gctgggcatc | 1380 |
| | gagaagctgc tggatcccga ggacgtggac accacctacc ccgacaagaa aagcatcctc | 1440 |
| | atgtacatca ccagcctgtt ccaggtgctg ccccagcagg tgtccatcga ggccatccag | 1500 |
| | gaagtggaga tgctgcccag gccccccaag gtcaccaaag aggaacactt ccagctgcac | 1560 |
| | caccagatgc actacagcca gcagatcacc gtgagcctgg cccagggcta cgagaggacc | 1620 |
| | agcagcccca agcccaggtt caagagctac gcctacaccc aggccgccta cgtgaccacc | 1680 |
| | tccgacccca ccaggtcccc cttccccagc cagcatctcg aagcccccga ggacaagagc | 1740 |
| | ttcggcagca gcctgatgga aagcgaggtg aacctggaca gataccagac cgccctggaa | 1800 |
| | gaagtgctgt cttggctgct gtccgccgag gacaccctgc aggcccaggg cgagatcagc | 1860 |
| | aacgacgtgg aggtcgtgaa ggaccagttc cacacccacg agggctacat gatggacctg | 1920 |
| | accgcccacc agggcagagt gggcaacatc ctgcagctgg gcagcaagct gatcggcacc | 1980 |
| | ggcaagctgt ccgaggacga ggaaaccgag gtgcaggaac agatgaacct gctgaacagc | 2040 |
| | agatgggagt gcctgagggt ggccagcatg gaaaagcaga gcaacctgca cagggtgctg | 2100 |
| | atggatctgc agaaccagaa gctcaaagag ctgaacgact ggctgaccaa gaccgaggaa | 2160 |
| | aggacccgga agatggaaga ggaacccctg ggccccgatc tggaagatct gaagaggcag | 2220 |
| | gtgcagcagc acaaggtgct gcaggaagat ctcgaacagg aacaggtccg ggtcaacagc | 2280 |
| | ctgacccaca tggtcgtggt ggtggacgag agcagcggcg accacgccac cgctgccctg | 2340 |
| | gaagagcagc tgaaggtgct gggcgacaga tgggccaaca tctgccggtg gaccgaggac | 2400 |
| | agatgggtcc tcctgcagga ccagcccgac ctggcccctg gcctgacaac catcggcgcc | 2460 |
| | agccccaccc agaccgtgac cctggtgacc cagcccgtgg tgaccaaaga gaccgccatc | 2520 |
| | agcaagctgg aaatgcccag ctccctgatg ctggaagtgc ccacccacag gctcctccag | 2580 |
| | cagttccccc tggacctgga aaagttcctg gcctggctga ccgaggccga gaccaccgcc | 2640 |
| | aacgtgctgc aggacgccac caggaaagag aggctgctgg aagatagcaa gggcgtgaaa | 2700 |
| | gagctgatga agcagtggca ggacctgcag ggggagattg aggcccacac cgacgtgtac | 2760 |
| | cacaacctgg acgagaacag ccagaaaatc ctgagaagcc tggaaggcag cgacgacgcc | 2820 |
| | gtgctgctgc agaggcggct ggacaacatg aacttcaagt ggagcgagct gaggaagaag | 2880 |
| | agcctgaaca tcaggtccca tctggaagcc agcagcgacc agtggaagag gctgcacctg | 2940 |
| | agcctgcagg aactgctcgt ctggctgcag ctgaaagacg acgagctgtc caggcaggcc | 3000 |
| | cccatcggcg gcgacttccc cgccgtgcag aaacagaacg acgtgcacag ggccttcaag | 3060 |
| | cgggagctga aaaccaaaga gcccgtgatc atgagcaccc tggaaaccgt gaggatcttc | 3120 |
| | ctgaccgagc agcccctgga aggactggaa aagctgtacc aggaacccag agagctgccc | 3180 |
| | cccgaggaac gggcccagaa cgtgaccagg ctgctgagaa agcaggccga ggaagtgaac | 3240 |
| | accgagtggg agaagctgaa cctgcactcc gccgactggc agaggaagat cgacgagacc | 3300 |
| | ctggaaaggc tccaggaact gcaggaagcc accgacgagc tggacctgaa gctgagacag | 3360 |
| | gccgaggtga tcaagggcag ctggcagccc gtgggcgacc tgctgatcga ctccctgcag | 3420 |
| | gatcacctgg aaaaagtgaa ggccctgcgg ggcgagatcg ccccccctgaa agagaacgtc | 3480 |
| | agccacgtca acgacctggc caggcagctg accaccctgg gcatccagct gtccccctac | 3540 |
| | aacctgtcca ccctggaaga tctgaacaca aggtggaagc tgctgcaggt ggccgtggag | 3600 |
| | gacagagtga ggcagctgca cgaggcccac agggacttcg gccctgcctc ccagcacttc | 3660 |
| | ctgagcacca gcgtgcaggg cccctgggag agggccatct cccccaacaa ggtgccctac | 3720 |
| | tacatcaacc acgagaccca gaccacctgc tgggaccacc ctaagatgac cgagctgtac | 3780 |
| | cagtccctgg ccgacctgaa caatgtgcgg ttcagcgcct accggaccgc catgaagctg | 3840 |
| | aggcggctgc agaaagccct gtgcctggat ctgctgtccc tgagcgccgc ctgcgacgcc | 3900 |
| | ctggaccagc acaacctgaa gcagaacgac cagcccatgg atatcctgca gatcatcaac | 3960 |
| | tgtctgacca ccatctacga caggctggaa caggaacaca acaacctggt caacgtgccc | 4020 |
| | ctgtgcgtgg acatgtgcct gaactggctg ctgaacgtgt acgacaccgg caggaccggc | 4080 |
| | cggatcaggg tgctgtcctt caagaccggc atcatcagcc tgtgcaaggc ccacctggaa | 4140 |
| | gataagtacc gctacctgtt caagcaggtg gccagctcta ccggcttctg cgaccagcgg | 4200 |
| | aggctgggcc tgctgctgca cgacagcatc cagatccccc ggcagctggg cgaggtggcc | 4260 |
| | tccttcggcg gcagcaacat cgagcccagc gtgcggagct gcttccagtt cgccaacaac | 4320 |
| | aagcccgaga tcgaggccgc cctgttcctg gactggatgc ggctggaacc ccagagcatg | 4380 |
| | gtctggctgc ccgtgctgca cagagtggct gccgccgaga ccgccaagca ccaggccaag | 4440 |
| | tgcaacatct gcaaagagtg ccccatcatc ggcttcaggt acagaagcct gaagcacttc | 4500 |
| | aactacgaca tctgccagag ctgtttcttc agcggcaggg tggccaaggg ccacaaaatg | 4560 |
| | cactacccca tggtggagta ctgcaccccc accacctccg gcgaggacgt gagggacttc | 4620 |
| | gccaaggtgc tgaagaataa gttccggacc aagcggtact tcgccaaaca ccccaggatg | 4680 |
| | ggctacctgc ccgtgcagac cgtgctggaa ggcgacaaca tggaaacctg ataacacgcg | 4740 |
| | tcgactcgag aggcctaata aagagctcag atgcatcgat cagagtgtgt tggttttttg | 4800 |
| | tgtgagatct aggaacccct agtgatggag ttggccactc cctctctgcg cgctcgctcg | 4860 |
| | ctcactgagg ccgcccgggc aaagcccggg cgtcgggcga cctttggtcg cccggcctca | 4920 |
| | gtgagcgagc gagcgcgcag agagggagtg gccaa | 4955 |
| SEQ ID NO: 13 | Amino acid sequence of AAV9 capsid VP1 protein | |
| | MAADGYLPDW LEDNLSEGIR EWWALKPGAP QPKANQQHQD NARGLVLPGY KYLGPGNGLD | 60 |
| | KGEPVNAADA AALEHDKAYD QQLKAGDNPY LKYNHADAEF QERLKEDTSF GGNLGRAVFQ | 120 |
| | AKKRLLEPLG LVEEAAKTAP GKKRPVEQSP QEPDSSAGIG KSGAQPAKKR LNFGQTGDTE | 180 |
| | SVPDPQPIGE PPAAPSGVGS LTMASGGGAP VADNNEGADG VGSSSGNWHC DSQWLGDRVI | 240 |
| | TTSTRTWALP TYNNHLYKQI SNSTSGGSSN DNAYFGYSTP WGYFDFNRFH CHFSPRDWQR | 300 |
| | LINNNWGFRP KRLNFKLFNI QVKEVTDNNG VKTIANNLTS TVQVFTDSDY QLPYVLGSAH | 360 |
| | EGCLPPFPAD VFMIPQYGYL TLNDGSQAVG RSSFYCLEYF PSQMLRTGNN FQFSYEFENV | 420 |
| | PFHSSYAHSQ SLDRLMNPLI DQYLYYLSKT INGSGQNQQT LKFSVAGPSN MAVQGRNYIP | 480 |
| | GPSYRQQRVS TTVTQNNNSE FAWPGASSWA LNGRNSLMNP GPAMASHKEG EDRFFPLSGS | 540 |
| | LIFGKQGTGR DNVDADKVMI TNEEEIKTTN PVATESYGQV ATNHQSAQAQ AQTGWVQNQG | 600 |
| | ILPGMVWQDR DVYLQGPIWA KIPHTDGNFH PSPLMGGFGM KHPPPQILIK NTPVPADPPT | 660 |

TABLE 13-continued

TABLE OF SEQUENCES

| SEQ ID NO | DESCRIPTION AND SEQUENCE | |
|---|---|---|
| | AFNKDKLNSF ITQYSTGQVS VEIEWELQKE NSKRWNPEIQ YTSNYYKSNN VEFAVNTEGV | 720 |
| | YSEPRPIGTR YLTRNL | 736 |
| SEQ ID | Left AAV2 ITR | |
| NO: 14 | ttggccactc cctctctgcg cgctcgctcg ctcactgagg ccgggcgacc aaaggtcgcc | 60 |
| | cgacgcccgg gctttgcccg ggcggcctca gtgagcgagc gagcgcgcag agagggagtg | 120 |
| | gccaactcca tcactagggg ttcct | 145 |
| SEQ ID | Right AAV2 ITR | |
| NO: 15 | aggaacccct agtgatggag ttggccactc cctctctgcg cgctcgctcg ctcactgagg | 60 |
| | ccgcccgggc aaagcccggg cgtcgggcga cctttggtcg cccggcctca gtgagcgagc | 120 |
| | gagcgcgcag agagggagtg gccaa | 145 |
| SEQ ID | DNA sequence of synthetic muscle-specific enhancer and promoter | |
| NO: 16 | ccactacggg tctaggctgc ccatgtaagg aggcaaggcc tggggacacc cgagatgcct | 60 |
| | ggttataatt aacccagaca tgtggctgcc cccccccccc ccaacacctg ctgcctctaa | 120 |
| | aaataaccct gtccctggtg gatcccctgc atgcgaagat cttcgaacaa ggctgtgggg | 180 |
| | gactgagggc aggctgtaac aggcttgggg gccagggctt atacgtgcct gggactccca | 240 |
| | aagtattact gttccatgtt cccggcgaag ggccagctgt cccccgccag ctagactcag | 300 |
| | cacttagttt aggaaccagt gagcaagtca gcccttgggg cagcccatac aaggccatgg | 360 |
| | ggctgggcaa gctgcacgcc tgggtccggg gtgggcacgg tgcccgggca acgagctgaa | 420 |
| | agctcatctg ctctcagggg cccctccctg gggacagccc ctcctggcta gtcacaccct | 480 |
| | gtaggctcct ctatataacc caggggcaca ggggctgccc tcattctacc accacctcca | 540 |
| | cagcacagac agacactcag gagccagcca gcgtcga | 577 |
| SEQ ID | DNA sequence of transcription terminator | |
| NO: 17 | aggcctaata aagagctcag atgcatcgat cagagtgtgt tggttttttg tgtg | 54 |
| SEQ ID | DNA sequence of AAV9.hCK.Hopti-Dys3978.spA vector genome | |
| NO: 18 | ttggccactc cctctctgcg cgctcgctcg ctcactgagg ccgggcgacc aaaggtcgcc | 60 |
| | cgacgcccgg gctttgcccg ggcggcctca gtgagcgagc gagcgcgcag agagggagtg | 120 |
| | gccaactcca tcactagggg ttcctcagat ctgaattcgg taccccacta cgggtctagg | 180 |
| | ctgcccatgt aaggaggcaa ggcctgggga cacccgagat gcctggttat aattaaccca | 240 |
| | gacatgtggc tgcccccccc cccccaaca cctgctgcct ctaaaaataa ccctgtccct | 300 |
| | ggtggatccc ctgcatgcga agatcttcga acaaggctgt gggggactga gggcaggctg | 360 |
| | taacaggctt gggggccagg gcttatacgt gcctgggact cccaaagtat tactgttcca | 420 |
| | tgttcccggc gaagggccag ctgtcccccg ccagctagac tcagcactta gtttaggaac | 480 |
| | cagtgagcaa gtcagccctt ggggcagccc atacaaggcc atggggctgg gcaagctgca | 540 |
| | cgcctgggtc cggggtgggc acggtgcccg ggcaacgagc tgaaagctca tctgctctca | 600 |
| | ggggcccctc cctggggaca gcccctcctg gctagtcaca ccctgtaggc tcctctatat | 660 |
| | aacccagggg cacaggggct gccctcattc taccaccacc tccacagcac agacagacac | 720 |
| | tcaggagcca gccagcgtcg agcggccgat ccgccaccat gctttggtgg gaggaagtgg | 780 |
| | aggactgcta cgagagagag gacgtgcaga agaaaacctt caccaagtgg gtgaacgccc | 840 |
| | agttcagcaa gttcggcaag cagcacatcg agaacctgtt cagcgacctg caggatggca | 900 |
| | ggagactgct ggacctgctg gagggcctga ccggccagaa gctgcccaag gagaagggca | 960 |
| | gcaccagagt gcacgccctg aacaacgtga acaaggccct gagagtgctg cagaacaaca | 1020 |
| | acgtggacct ggtgaacatc ggcagcaccg acatcgtgga cggcaaccac aagctgaccc | 1080 |
| | tgggcctgat ctggaacatc atcctgcact ggcaggtgaa gaacgtgatg aagaacatca | 1140 |
| | tggccggcct gcagcagacc aacagcgaga agatcctgct gagctgggtg aggcagagca | 1200 |
| | ccagaaacta cccccaggtg aacgtgatca acttcaccac ctcctggagc gacggcctgg | 1260 |
| | ccctgaacgc cctgatccac agccacagac ccgacctgtt cgactggaac agcgtggtgt | 1320 |
| | gtcagcagag cgccacccag agactggagc acgccttcaa catcgccaga taccagctgg | 1380 |
| | gcatcgagaa gctgctggac cccgaggacg tggacaccac ctaccccgac aagaaaagca | 1440 |
| | tcctcatgta cattaccagc ctgttccagg tgctgcccca gcaggtgtcc atcgaggcca | 1500 |
| | tccaggaagt ggaaatgctg cccaggcccc ccaaagtgac caaggaggag cacttccagc | 1560 |
| | tgcaccacca gatgcactac agccagcaga tcacagtgag cctggcccag ggctatgaga | 1620 |
| | gaaccagcag ccccaagccc agattcaaga gctacgccta cacccaggcc gcctacgtga | 1680 |
| | ccacctccga ccccaccaga agccccttcc ccagccagca cctggaggcc cccgaggaca | 1740 |
| | agagcttcgg cagcagcctg atggagagcg aagtgaacct ggacagatac cagaccgccc | 1800 |
| | tggaggaagt gctgtcctgg ctgctgagcg ccgaggacac cctgcaggcc cagggcgaga | 1860 |
| | tcagcaacga cgtggaagtg gtgaaggacc agttccacac ccacgagggc tacatgatgg | 1920 |
| | atctgaccgc ccaccagggc agagtgggca atatcctgca gctgggcagc aagctgatcg | 1980 |
| | gcaccggcaa gctgagcgag gacgaggaga ccgaagtgca ggagcagatg aacctgctga | 2040 |
| | acagcagatg ggagtgcctg agagtggcca gcatggagaa gcagagcaac ctgcacagag | 2100 |
| | tgctgatgga cctgcagaac cagaagctga aggagctgaa cgactggctg accaagaccg | 2160 |
| | aggagcggac cagaaagatg gaggaggagc ccctgggccc cgacctggag gacctgaaga | 2220 |
| | gacaggtgca gcagcacaaa gtgctgcagg aggacctgga gcaggagcag gtgcgcgtga | 2280 |
| | acagcctgac ccacatggtg gtggtcgtgg acgagagcag cggcgaccac gccacagccg | 2340 |
| | ccctggaaga gcagctgaaa gtgctgggcg acagatgggc caatatttgt aggtggaccg | 2400 |
| | aggacagatg ggtgctgctg caggaccagc ccgacctggc ccctggcctg accaccatcg | 2460 |
| | gcgccagccc cacccagacc gtgaccctgg tgacccagcc cgtggtgaca aaggagaccg | 2520 |
| | ccatcagcaa gctggagatg cccagctccc tgatgctgga agtgcccacc caccgcctgc | 2580 |
| | tccagcagtt cccccctggac ctggagaagt tcctggcctg gctgaccgag gccgaaacca | 2640 |
| | ccgccaatgt gctccaggac gccactagaa aggagaggct gctggaggac agcaagggcg | 2700 |
| | tgaaagagct gatgaagcag tggcaggatc tgcagggcga aatcgaggcc cacaccgacg | 2760 |

TABLE 13-continued

TABLE OF SEQUENCES

| SEQ ID NO | DESCRIPTION AND SEQUENCE | |
|---|---|---|
| | tgtaccacaa cctggacgag aacagccaga agattctgag gagcctggag ggcagcgacg | 2820 |
| | acgccgtcct gctccagagg aggctggaca acatgaactt caagtggagc gagctgcgga | 2880 |
| | agaagagcct gaacatccgg agccacctgg aagccagcag cgaccagtgg aagagactgc | 2940 |
| | acctgagcct gcaggagctg ctggtgtggc tgcagctgaa ggacgacgag ctgagcagac | 3000 |
| | aggcccccat cggcggcgac ttccccgccg tgcagaagca gaacgacgtg caccgggcct | 3060 |
| | tcaagaggga gctgaaaacc aaggaacccg tgatcatgag caccctggag acagtgcgga | 3120 |
| | tcttcctgac cgagcagccc ctggagggac tggagaagct gtaccaggag cccagagagc | 3180 |
| | tgcccccccga ggagagagcc cagaacgtga ccaggctgct gagaaagcag gccgaggaag | 3240 |
| | tgaataccga gtgggagaag ctgaatctgc acagcgccga ctggcagaga aagatcgacg | 3300 |
| | agaccctgga gagactccag gaactgcagg aagccaccga cgagctggac ctgaagctga | 3360 |
| | gacaggccga agtgatcaag ggcagctggc agcctgtggg cgatctgctg atcgactccc | 3420 |
| | tgcaggatca cctggagaaa gtgaaggccc tgcggggcga gatcgccccc ctgaaggaga | 3480 |
| | atgtgagcca cgtgaacgac ctggccagac agctgaccac cctgggcatc cagctgagcc | 3540 |
| | cctacaacct gagcacactg gaggatctga acacccggtg gaaactgctg caggtggccg | 3600 |
| | tggaggatag agtgaggcag ctgcacgaag cccacagaga cttcggccct gcctcccagc | 3660 |
| | acttcctgag caccagcgtg cagggcccct gggagagagc catctccccc aacaaagtgc | 3720 |
| | cctactacat caaccacgag acccagacca cctgctggga ccaccctaag atgaccgagc | 3780 |
| | tgtatcagag cctggccgac ctgaacaatg tgcggttcag cgcctacaga accgccatga | 3840 |
| | agctgcggag actgcagaag gccctgtgcc tggatctgct gagcctgagc gccgcctgcg | 3900 |
| | acgccctgga ccagcacaac ctgaagcaga atgaccagcc catggacatc ctgcagatca | 3960 |
| | tcaactgcct gaccacaatc tacgaccggc tggaacagga gcacaacaac ctggtgaatg | 4020 |
| | tgcccctgtg cgtggacatg tgcctgaatt ggctgctgaa cgtgtacgac accggcagga | 4080 |
| | ccggcagaat ccgcgtgctg agcttcaaga ccggcatcat cagcctgtgc aaggcccacc | 4140 |
| | tggaggataa gtaccgctac ctgttcaagc aggtggccag cagcaccggc ttctgcgatc | 4200 |
| | agaggagact gggcctgctg ctgcacgata gcatccagat ccctaggcag ctgggcgaag | 4260 |
| | tggccagctt tggcggcagc aacatcgagc cctctgtgag gagctgcttc cagttcgcca | 4320 |
| | acaacaagcc cgagatcgag gccgccctgt tcctggactg gatgaggctg gagcctcaga | 4380 |
| | gcatggtgtg gctgcctgtg ctgcacagag tggccgccgc cgagaccgcc aagcaccagg | 4440 |
| | ccaagtgcaa tatctgcaag gagtgcccca tcatcggctt ccggtacagg agcctgaagc | 4500 |
| | acttcaacta cgacatctgc cagagctgct ttttcagcgg cagagtggcc aagggccaca | 4560 |
| | aaatgcacta ccccatggtg gagtactgca cccccaccac ctccggcgag gatgtgagag | 4620 |
| | acttcgccaa agtgctgaag aataagttcc ggaccaagcg gtactttgcc aagcacccca | 4680 |
| | ggatgggcta cctgcccgtg cagaccgtgc tggaaggcga caacatggag acctgatgag | 4740 |
| | gagctcgaga ggcctaataa agagctcaga tgcatcgatc agagtgtgtt ggttttttgt | 4800 |
| | gtgagatctg aggaacccct agtgatggag ttggccactc cctctctgcg cgctcgctcg | 4860 |
| | ctcactgagg ccgcccgggc aaagcccggg cgtcgggcga cctttggtcg cccggcctca | 4920 |
| | gtgagcgagc gagcgcgcag agagggagtg gccaa | 4955 |
| SEQ ID NO: 19 | DNA sequence of PCR forward primer for mini-dystrophin gene<br>ccaacaaagt gccctactac atc | 23 |
| SEQ ID NO: 20 | DNA sequence of PCR reverse primer for mini-dystrophin gene<br>ggttgtgctg gtccagggcg t | 21 |
| SEQ ID NO: 21 | DNA sequence of probe for mini-dystrophin gene<br>ccgagctgta tcagagcctg gcc | 23 |
| SEQ ID NO: 22 | DNA sequence of PCR forward primer for rat HPRT1 gene<br>gcgaaagtgg aaaagccaag t | 21 |
| SEQ ID NO: 23 | DNA sequence of PCR reverse primer for rat HPRT1 gene<br>gccacatcaa caggactctt gtag | 24 |
| SEQ ID NO: 24 | DNA sequence of probe for rat HPRT1 gene<br>caaagcctaa aagacagcgg caagttgaat | 30 |
| SEQ ID NO: 25 | Amino acid sequence of human muscle dystrophin (Dp427m isoform)<br>MLWWEEVEDC YEREDVQKKT FTKWVNAQFS KFGKQHIENL FSDLQDGRRL LDLLEGLTGQ | 60 |
| | KLPKEKGSTR VHALNNVNKA LRVLQNNNVD LVNIGSTDIV DGNHKLTLGL IWNIILHWQV | 120 |
| | KNVMKNIMAG LQQTNSEKIL LSWVRQSTRN YPQVNVINFT TSWSDGLALN ALIHSHRPDL | 180 |
| | FDWNSVVCQQ SATQRLEHAF NIARYQLGIE KLLDPEDVDT TYPDKKSILM YITSLFQVLP | 240 |
| | QQVSIEAIQE VEMLPRPPKV TKEEHFQLHH QMHYSQQITV SLAQGYERTS SPKPRFKSYA | 300 |
| | YTQAAYVTTS DPTRSPFPSQ HLEAPEDKSF GSSLMESEVN LDRYQTALEE VLSWLLSAED | 360 |
| | TLQAQGEISN DVEVVKDQFH THEGYMMDLT AHQGRVGNIL QLGSKLIGTG KLSEDEETEV | 420 |
| | QEQMNLLNSR WECLRVASME KQSNLHRVLM DLQNQKLKEL NDWLTKTEER TRKMEEEPLG | 480 |
| | PDLEDLKRQV QQHKVLQEDL EQEQVRVNSL THMVVVVDES SGDHATAALE EQLKVLGDRW | 540 |
| | ANICRWTEDR WVLLQDILLK WQRLTEEQCL FSAWLSEKED AVNKIHTTGF KDQNEMLSSL | 600 |
| | QKLAVLKADL EKKKQSMGKL YSLKQDLLST LKNKSVTQKT EAWLDNFARC WDNLVQKLEK | 660 |
| | STAQISQAVT TTQPSLTQTT VMETVTTVTT REQILVKHAQ EELPPPPPQK KRQITVDSEI | 720 |
| | RKRLDVDITE LHSWITRSEA VLQSPEFAIF RKEGNFSDLK EKVNAIEREK AEKFRKLQDA | 780 |
| | SRSAQALVEQ MVNEGVNADS IKQASEQLNS RWIEFCQLLS ERLNWLEYQN NIIAFYNQLQ | 840 |
| | QLEQMTTTAE NWLKIQPTTP SEPTAIKSQL KICKDEVNRL SGLQPQIERL KIQSIALKEK | 900 |
| | GQGPMFLDAD FVAFTNHFKQ VESDVQAREK ELQTIFDTLP PMRYQETMSA IRTWVQQSET | 960 |
| | KLSIPQLSVT DYEIMEQRLG ELQALQSSLQ EQQSGLYYLS TTVKEMSKKA PSEISRKYQS | 1020 |
| | EFEEIEGRWK KLSSQLVEHC QKLEEQMNKL RKIQNHIQTL KKWMAEVDVF LKEEWPALGD | 1080 |

TABLE 13-continued

TABLE OF SEQUENCES

| SEQ ID NO | DESCRIPTION AND SEQUENCE | |
|---|---|---|
| | SEILKKQLKQ CRLLVSDIQT IQPSLNSVNE GGQKIKNEAE PEFASRLETE LKELNTQWDH | 1140 |
| | MCQQVYARKE ALKGGLEKTV SLQKDLSEMH EWMTQAEEEY LERDFEYKTP DELQKAVEEM | 1200 |
| | KRAKEEAQQK EAKVKLLTES VNSVIAQAPP VAQEALKKEL ETLTTNYQWL CTRLNGKCKT | 1260 |
| | LEEVWACWHE LLSYLEKANK WLNEVEFKLK TTENIPGGAE EISEVLDSLE NLMRHSEDNP | 1320 |
| | NQIRILAQTL TDGGVMDELI NEELETFNSR WRELHEEAVR RQKLLEQSIQ SAQETEKSLH | 1380 |
| | LIQESLTFID KQLAAYIADK VDAAQMPQEA QKIQSDLTSH EISLEEMKKH NQGKEAAQRV | 1440 |
| | LSQIDVAQKK LQDVSMKFRL FQKPANFEQR LQESKMILDE VKMHLPALET KSVEQEVVQS | 1500 |
| | QLNHCVNLYK SLSEVKSEVE MVIKTGRQIV QKKQTENPKE LDERVTALKL HYNELGAKVT | 1560 |
| | ERKQQLEKCL KLSRKMRKEM NVLTEWLAAT DMELTKRSAV EGMPSNLDSE VAWGKATQKE | 1620 |
| | IEKQKVHLKS ITEVGEALKT VLGKKETLVE DKLSLLNSNW IAVTSRAEEW LNLLLEYQKH | 1680 |
| | METFDQNVDH ITKWIIQADT LLDESEKKKP QQKEDVLKRL KAELNDIRPK VDSTRDQAAN | 1740 |
| | LMANRGDHCR KLVEPQISEL NHRFAAISHR IKTGKASIPL KELEQFNSDI QKLLEPLEAE | 1800 |
| | IQQGVNLKEE DFNKDMNEDN EGTVKELLQR GDNLQQRITD ERKREEIKIK QQLLQTKHNA | 1860 |
| | LKDLRSQRRK KALEISHQWY QYKRQADDLL KCLDDIEKKL ASLPEPRDER KIKEIDRELQ | 1920 |
| | KKKEELNAVR RQAEGLSEDG AAMAVEPTQI QLSKRWREIE SKFAQFRRLN FAQIHTVREE | 1980 |
| | TMMVMTEDMP LEISYVPSTY LTEITHVSQA LLEVEQLLNA PDLCAKDFED LFKQEESLKN | 2040 |
| | IKDSLQQSSG RIDIIHSKKT AALQSATPVE RVKLQEALSQ LDFQWEKVNK MYKDRQGRFD | 2100 |
| | RSVEKWRRFH YDIKIFNQWL TEAEQFLRKT QIPENWEHAK YKWYLKELQD GIGQRQTVVR | 2160 |
| | TLNATGEEII QQSSKTDASI LQEKLGSLNL RWQEVCKQLS DRKKRLEEQK NILSEFQRDL | 2220 |
| | NEFVLWLEEA DNIASIPLEP GKEQQLKEKL EQVKLLVEEL PLRQGILKQL NETGGPVLVS | 2280 |
| | APISPEEQDK LENKLKQTNL QWIKVSRALP EKQGEIEAQI KDLGQLEKKL EDLEEQLNHL | 2340 |
| | LLWLSPIRNQ LEIYNQPNQE GPFDVQETEI AVQAKQPDVE EILSKGQHLY KEKPATQPVK | 2400 |
| | RKLEDLSSEW KAVNRLLQEL RAKQPDLAPG LTTIGASPTQ TVTLVTQPVV TKETAISKLE | 2460 |
| | MPSSLMLEVP ALADFNRAWT ELTDWLSLLD QVIKSQRVMV GDLEDINEMI IKQKATMQDL | 2520 |
| | EQRRPQLEEL ITAAQNLKNK TSNQEARTII TDRIERIQNQ WDEVQEHLQN RRQQLNEMLK | 2580 |
| | DSTQWLEAKE EAEQVLGQAR AKLESWKEGP YTVDAIQKKI TETKQLAKDL RQWQTNVDVA | 2640 |
| | NDLALKLLRD YSADDTRKVH MITENINASW RSIHKRVSER EAALEETHRL LQQFPLDLEK | 2700 |
| | FLAWLTEAET TANVLQDATR KERLLEDSKG VKELMKQWQD LQGEIEAHTD VYHNLDENSQ | 2760 |
| | KILRSLEGSD DAVLLQRRLD NMNFKWSELR KKSLNIRSHL EASSDQWKRL HLSLQELLVW | 2820 |
| | LQLKDDELSR QAPIGGDFPA VQKQNDVHRA FKRELKTKEP VIMSTLETVR IFLTEQPLEG | 2880 |
| | LEKLYQEPRE LPPEERAQNV TRLLRKQAEE VNTEWEKLNL HSADWQRKID ETLERLQELQ | 2940 |
| | EATDELDLKL RQAEVIKGSW QPVGDLLIDS LQDHLEKVKA LRGEIAPLKE NVSHVNDLAR | 3000 |
| | QLTTLGIQLS PYNLSTLEDL NTRWKLLQVA VEDRVRQLHE AHRDFGPASQ HFLSTSVQGP | 3060 |
| | WERAISPNKV PYYINHETQT TCWDHPKMTE LYQSLADLNN VRFSAYRTAM KLRRLQKALC | 3120 |
| | LDLLSLSAAC DALDQHNLKQ NDQPMDILQI INCLTTIYDR LEQEHNNLVN VPLCVDMCLN | 3180 |
| | WLLNVYDTGR TGRIRVLSFK TGIISLCKAH LEDKYRYLFK QVASSTGFCD QRRLGLLLHD | 3240 |
| | SIQIPRQLGE VASFGGSNIE PSVRSCFQFA NNKPEIEAAL FLDWMRLEPQ SMVWLPVLHR | 3300 |
| | VAAAETAKHQ AKCNICKECP IIGFRYRSLK HFNYDICQSC FFSGRVAKGH KMHYPMVEYC | 3360 |
| | TPTTSGEDVR DFAKVLKNKF RTKRYFAKHP RMGYLPVQTV LEGDNMETPV TLINFWPVDS | 3420 |
| | APASSPQLSH DDTHSRIEHY ASRLAEMENS NGSYLNDSIS PNESIDDEHL LIQHYCQSLN | 3480 |
| | QDSPLSQPRS PAQILISLES EERGELERIL ADLEEENRNL QAEYDRLKQQ HEHKGLSPLP | 3540 |
| | SPPEMMPTSP QSPRDAELIA EAKLLRQHKG RLEARMQILE DHNKQLESQL HRLRQLLEQP | 3600 |
| | QAEAKVNGTT VSSPSTSLQR SDSSQPMLLR VVGSQTSDSM GEEDLLSPPQ DTSTGLEEVM | 3660 |
| | EQLNNSFPSS RGRNTPGKPM REDTM | 3685 |
| SEQ ID NO: 26 | DNA sequence of non-codon-optimized gene encoding human mini-dystrophin Dys3987 | |
| | atgctttggt gggaagaagt agaggactgt tatgaaagag aagatgttca aaagaaaaca | 60 |
| | ttcacaaaat gggtaaatgc acaattttct aagtttggga agcagcatat tgagaacctc | 120 |
| | ttcagtgacc tacaggatgg gaggcgcctc ctagacctcc tcgaaggcct gacagggcaa | 180 |
| | aaactgccaa aagaaaaagg atccacaaga gttcatgccc tgaacaatgt caacaaggca | 240 |
| | ctgcgggttt tgcagaacaa taatgttgat ttagtgaata ttggaagtac tgacatcgta | 300 |
| | gatggaaatc ataaactgac tcttggtttg atttggaata taatcctcca ctggcaggtc | 360 |
| | aaaaatgtaa tgaaaaatat catggctgga ttgcaacaaa ccaacagtga aaagattctc | 420 |
| | ctgagctggg tccgacaatc aactcgtaat tatccacagg ttaatgtaat caacttcacc | 480 |
| | accagctggt ctgatggcct ggctttgaat gctctcatcc atagtcatag gccagaccta | 540 |
| | tttgactgga atagtgtggt ttgccagcag tcagccacac aacgactgga acatgcattc | 600 |
| | aacatcgcca gatatcaatt aggcatagag aaactactcg atcctgaaga tgttgatacc | 660 |
| | acctatccag ataagaagtc catcttaatg tacatcacat cactcttcca agttttgcct | 720 |
| | caacaagtga gcattgaagc catccaggaa gtggaaatgt tgccaaggcc acctaaagtg | 780 |
| | actaaagaag aacattttca gttacatcat caaatgcact attctcaaca gatcacggtc | 840 |
| | agtctagcac agggatatga gagaacttct tcccctaagc ctcgattcaa gagctatgcc | 900 |
| | tacacacagg ctgcttatgt caccacctct gaccctacac ggagcccatt tccttcacag | 960 |
| | catttggaag ctcctgaaga caagtcattt ggcagttcat tgatggagag tgaagtaaac | 1020 |
| | ctggaccgtt atcaaacagc tttagaagaa gtattatcgt ggcttctttc tgctgaggac | 1080 |
| | acattgcaag cacaaggaga gatttctaat gatgtggaag tggtgaaaga ccagtttcat | 1140 |
| | actcatgagg ggtacatgat ggatttgaca gcccatcagg gccgggttgg taatattcta | 1200 |
| | caattgggaa gtaagctgat tggaacagga aaattatcag aagatgaaga aactgaagta | 1260 |
| | caagagcaga tgaatctcct aaattcaaga tgggaatgcc tcagggtagc tagcatggaa | 1320 |
| | aaacaaagca atttacatag agttttaatg gatctccaga atcagaaact gaaagagttg | 1380 |
| | aatgactggc taacaaaaac agaagaaaga acaaggaaaa tggaggaaga gcctcttgga | 1440 |
| | cctgatcttg aagacctaaa acgccaagta caacaacata aggtgcttca agaagatcta | 1500 |
| | gaacaagaac aagtcagggt caattctctc actcacatgg tggtggtagt tgatgaatct | 1560 |
| | agtggagatc acgcaactgc tgctttggaa gaacaactta aggtattggg agatcgatgg | 1620 |
| | gcaaacatct gtagatggac agaagaccgc tggtttcttt tacaagacca gcctgaccta | 1680 |
| | gctcctggac tgaccactat tggagcctct cctactcaga ctgttactct ggtgacacaa | 1740 |

TABLE 13-continued

TABLE OF SEQUENCES

| SEQ ID NO | DESCRIPTION AND SEQUENCE | |
|---|---|---|
| | cctgtggtta ctaaggaaac tgccatctcc aaactagaaa tgccatcttc cttgatgttg | 1800 |
| | gaggtaccta ctcatagatt actgcaacag ttccccctgg acctggaaaa gtttcttgcc | 1860 |
| | tggcttacag aagctgaaac aactgccaat gtcctacagg atgctacccg taaggaaagg | 1920 |
| | ctcctagaag actccaaggg agtaaaagag ctgatgaaac aatggcaaga cctccaaggt | 1980 |
| | gaaattgaag ctcacacaga tgtttatcac aacctggatg aaaacagcca aaaaatcctg | 2040 |
| | agatccctgg aaggttccga tgatgcagtc ctgttacaaa gacgtttgga taacatgaac | 2100 |
| | ttcaagtgga gtgaacttcg gaaaaagtct ctcaacatta ggtcccattt ggaagccagt | 2160 |
| | tctgaccagt ggaagcgtct gcaccttttct ctgcaggaac ttctggtgtg gctacagctg | 2220 |
| | aaagatgatg aattaagccg gcaggcacct attggaggcg actttccagc agttcagaag | 2280 |
| | cagaacgatg tacatagggc cttcaagagg gaattgaaaa ctaaagaacc tgtaatcatg | 2340 |
| | agtactcttg agactgtacg aatatttctg acagagcagc ctttggaagg actagagaaa | 2400 |
| | ctctaccagg agcccagaga gctgcctcct gaggagagag cccagaatgt cactcggctt | 2460 |
| | ctacgaaagc aggctgagga ggtcaatact gagtgggaaa aattgaacct gcactccgct | 2520 |
| | gactggcaga gaaaaataga tgagaccctt gaaagactcc aggaacttca agaggccacg | 2580 |
| | gatgagctgg acctcaagct gcgccaagct gaggtgatca agggatcctg gcagcccgtg | 2640 |
| | ggcgatctcc tcattgactc tctccaagat cacctcgaga aagtcaaggc acttcgagga | 2700 |
| | gaaattgcgc ctctgaaaga gaacgtgagc cacgtcaatg accttgctcg ccagcttacc | 2760 |
| | actttgggca ttcagctctc accgtataac ctcagcactc tggaagacct gaacaccaga | 2820 |
| | tggaagcttc tgcaggtggc cgtcgaggac cgagtcaggc agctgcatga agcccacagg | 2880 |
| | gactttggtc cagcatctca gcactttctt tccacgtctg tccagggtcc ctgggagaga | 2940 |
| | gccatctcgc caaacaaagt gccctactat atcaaccacg agactcaaac aacttgctgg | 3000 |
| | gaccatccca aaatgacaga gctctaccag tctttagctg acctgaataa tgtcagattc | 3060 |
| | tcagcttata ggactgccat gaaactccga agactgcaga aggccctttg cttggatctc | 3120 |
| | ttgagcctgt cagctgcatg tgatgccttg gaccagcaca acctcaagca aaatgaccag | 3180 |
| | cccatggata tcctgcagat tattaattgt ttgaccacta tttatgaccg cctggagcaa | 3240 |
| | gagcacaaca atttggtcaa cgtccctctc tgcgtggata tgtgtctgaa ctggctgctg | 3300 |
| | aatgtttatg atacgggacg aacagggagg atccgtgtcc tgtcttttaa aactggcatc | 3360 |
| | atttccctgt gtaaagcaca tttggaagac aagtacagat accttttcaa gcaagtggca | 3420 |
| | agttcaacag gattttgtga ccagcgcagg ctgggcctcc ttctgcatga ttctatccaa | 3480 |
| | attccaagac agttgggtga agttgcatcc tttgggggca gtaacattga gccaagtgtc | 3540 |
| | cggagctgct tccaatttgc taataataag ccagagatcg aagcggccct cttcctagac | 3600 |
| | tggatgagac tggaacccca gtccatggtg tggctgcccg tcctgcacag agtggctgct | 3660 |
| | gcagaaactg ccaagcatca ggccaaatgt aacatctgca aagagtgtcc aatcattgga | 3720 |
| | ttcaggtaca ggagtctaaa gcactttaat tatgacatct gccaaagctg ctttttttct | 3780 |
| | ggtcgagttg caaaaggcca taaaatgcac tatcccatgg tggaatattg cactccgact | 3840 |
| | acatcaggag aagatgttcg agactttgcc aaggtactaa aaaacaaatt tcgaaccaaa | 3900 |
| | aggtattttg cgaagcatcc ccgaatgggc tacctgccag tgcagactgt cttagagggg | 3960 |
| | gacaacatgg aaacttag | 3978 |
| SEQ ID NO: 27 | Amino acid sequence of human mini-dystrophin protein 43990 | |
| | MVWWEEVEDC YEREDVQKKT FTKWVNAQFS KFGKQHIENL FSDLQDGRRL LDLLEGLTGQ | 60 |
| | KLPKEKGSTR VHALNNVNKA LRVLQNNNVD LVNIGSTDIV DGNHKLTLGL IWNIILHWQV | 120 |
| | KNVMKNIMAG LQQTNSEKIL LSWVRQSTRN YPQVNVINFT TSWSDGLALN ALIHSHRPDL | 180 |
| | FDWNSVVCQQ SATQRLEHAF NIARYQLGIE KLLDPEDVDT TYPDKKSILM YITSLFQVLP | 240 |
| | QQVSIEAIQE VEMLPRPPKV TKEEHFQLHH QMHYSQQITV SLAQGYERTS SPKPRFKSYA | 300 |
| | YTQAAYVTTS DPTRSPFPSQ HLEAPEDKSF GSSLMESEVN LDRYQTALEE VLSWLLSAED | 360 |
| | TLQAQGEISN DVEVVKDQFH THEGYMMDLT AHQGRVGNIL QLGSKLIGTG KLSEDEETEV | 420 |
| | QEQMNLLNSR WECLRVASME KQSNLHRVLM DLQNQKLKEL NDWLTKTEER TRKMEEEPLG | 480 |
| | PDLEDLKRQV QQHKVLQEDL EQEQVRVNSL THMVVVVDES SGDHATAALE EQLKVLGDRW | 540 |
| | ANICRWTEDR WVLLQDQPDL APGLTTIGAS PTQTVTLVTQ PVVTKETAIS KLEMPSSLML | 600 |
| | EVPTHRLLQQ FPLDLEKFLA WLTEAETTAN VLQDATRKER LLEDSKGVKE LMKQWQDLQG | 660 |
| | EIEAHTDVYH NLDENSQKIL RSLEGSDDAV LLQRRLDNMN FKWSELRKKS LNIRSHLEAS | 720 |
| | SDQWKRLHLS LQELLVWLQL KDDELSRQAP IGGDFPAVQK QNDVHRAFKR ELKTKEPVIM | 780 |
| | STLETVRIFL TEQPLEGLEK LYQEPRELPP EERAQNVTRL LRKQAEEVNT EWEKLNLHSA | 840 |
| | DWQRKIDETL ERLQELQEAT DELDLKLRQA EVIKGSWQPV GDLLIDSLQD HLEKVKALRG | 900 |
| | EIAPLKENVS HVNDLARQLT TLGIQLSPYN LSTLEDLNTR WKLLQVAVED RVRQLHEAHR | 960 |
| | DFGPASQHFL STSVQGPWER AISPNKVPYY INHETQTTCW DHPKMTELYQ SLADLNNVRF | 1020 |
| | SAYRTAMKLR RLQKALCLDL LSLSAACDAL DQHNLKQNDQ PMDILQIINC LTTIYDRLEQ | 1080 |
| | EHNNLVNVPL CVDMCLNWLL NVYDTGRTGR IRVLSFKTGI ISLCKAHLED KYRYLFKQVA | 1140 |
| | SSTGFCDQRR LGLLLHDSIQ IPRQLGEVAS FGGSNIEPSV RSCFQFANNK PEIEAALFLD | 1200 |
| | WMRLEPQSMV WLPVLHRVAA AETAKHQAKC NICKECPIIG FRYRSLKHFN YDICQSCFFS | 1260 |
| | GRVAKGHKMH YPMVEYCTPT TSGEDVRDFA KVLKNKFRTK RYFAKHPRMG YLPVQTVLEG | 1320 |
| | DNMETPDTM | 1329 |
| SEQ ID NO: 28 | DNA sequence of human mini-dystrophin gene 43990 | |
| | atggtttggt gggaagaagt agaggactgt tatgaaagag aagatgttca aaagaaaaca | 60 |
| | ttcacaaaat gggtaaatgc acaattttct aagtttggga agcagcatat tgagaacctc | 120 |
| | ttcagtgacc tacaggatgg gaggcgcctc ctagacctcc tcgaaggcct gacagggcaa | 180 |
| | aaactgccaa aagaaaaagg atccacaaga gttcatgccc tgaacaatgt caacaaggca | 240 |
| | ctgcgggttt tgcagaacaa taatgttgat ttagtgaata ttggaagtac tgacatcgta | 300 |
| | gatggaaatc ataaactgac tcttggtttg atttggaata taatcctcca ctggcaggtc | 360 |
| | aaaaatgtaa tgaaaaatat catggctgga ttgcaacaaa ccaacagtga aaagattctc | 420 |
| | ctgagctggg tccgacaatc aactcgtaat tatccacagg ttaatgtaat caacttcacc | 480 |
| | accagctggt ctgatggcct ggctttgaat gctctcatcc atagtcatag gccagaccta | 540 |
| | tttgactgga atagtgtggt ttgccagcag tcagccacac aacgactgga acatgcattc | 600 |

TABLE 13-continued

TABLE OF SEQUENCES

| SEQ ID NO | DESCRIPTION AND SEQUENCE | |
|---|---|---|
| | aacatcgcca gatatcaatt aggcatagag aaactactcg atcctgaaga tgttgatacc | 660 |
| | acctatccag ataagaagtc catcttaatg tacatcacat cactcttcca agttttgcct | 720 |
| | caacaagtga gcattgaagc catccaggaa gtggaaatgt tgccaaggcc acctaaagtg | 780 |
| | actaaagaag aacattttca gttacatcat caaatgcact attctcaaca gatcacggtc | 840 |
| | agtctagcac agggatatga gagaacttct tcccctaagc ctcgattcaa gagctatgcc | 900 |
| | tacacacagg ctgcttatgt caccacctct gaccctacac ggagcccatt tccttcacag | 960 |
| | catttggaag ctcctgaaga caagtcattt ggcagttcat tgatggagag tgaagtaaac | 1020 |
| | ctggaccgtt atcaaacagc tttagaagaa gtattatcgt ggcttctttc tgctgaggac | 1080 |
| | acattgcaag cacaaggaga gatttctaat gatgtggaag tggtgaaaga ccagtttcat | 1140 |
| | actcatgagg ggtacatgat ggatttgaca gcccatcagg gccgggttgg taatattcta | 1200 |
| | caattgggaa gtaagctgat tggaacagga aaattatcag aagatgaaga aactgaagta | 1260 |
| | caagagcaga tgaatctcct aaattcaaga tgggaatgcc tcagggtagc tagcatggaa | 1320 |
| | aaacaaagca atttacatag agttttaatg gatctccaga atcagaaact gaaagagttg | 1380 |
| | aatgactggc taacaaaaac agaagaaaga acaaggaaaa tggaggaaga gcctcttgga | 1440 |
| | cctgatcttg aagacctaaa acgccaagta caacaacata aggtgcttca agaagatcta | 1500 |
| | gaacaagaac aagtcagggt caattctctc actcacatgg tggtggtagt tgatgaatct | 1560 |
| | agtggagatc acgcaactgc tgctttggaa gaacaactta aggtattggg agatcgatgg | 1620 |
| | gcaaacatct gtagatggac agaagaccgc tgggttcttt tacaagacca gcctgaccta | 1680 |
| | gctcctggac tgaccactat tggagcctct cctactcaga ctgttactct ggtgacacaa | 1740 |
| | cctgtggtta ctaaggaaac tgccatctcc aaactagaaa tgccatcttc cttgatgttg | 1800 |
| | gaggtaccta ctcatagatt actgcaacag ttccccctgg acctggaaaa gtttcttgcc | 1860 |
| | tggcttacag aagctgaaac aactgccaat gtcctacagg atgctacccg taaggaaagg | 1920 |
| | ctcctagaag actccaaggg agtaaaagag ctgatgaaac aatggcaaga cctccaaggt | 1980 |
| | gaaattgaag ctcacacaga tgtttatcac aacctggatg aaaacagcca aaaaatcctg | 2040 |
| | agatccctgg aaggttccga tgatgcagtc ctgttacaaa gacgtttgga taacatgaac | 2100 |
| | ttcaagtgga gtgaacttcg gaaaaagtct ctcaacatta ggtcccattt ggaagccagt | 2160 |
| | tctgaccagt ggaagcgtct gcacctttct ctgcaggaac ttctggtgtg gctacagctg | 2220 |
| | aaagatgatg aattaagccg gcaggcacct attggaggcg actttccagc agttcagaag | 2280 |
| | cagaacgatg tacatagggc cttcaagagg gaattgaaaa ctaaagaacc tgtaatcatg | 2340 |
| | agtactcttg agactgtacg aatatttctg acagagcagc ctttggaagg actagagaaa | 2400 |
| | ctctaccagg agcccagaga gctgcctcct gaggagagag cccagaatgt cactcggctt | 2460 |
| | ctacgaaagc aggctgagga ggtcaatact gagtgggaaa aattgaacct gcactccgct | 2520 |
| | gactggcaga gaaaaataga tgagaccctt gaaagactcc aggaacttca agaggccacg | 2580 |
| | gatgagctgg acctcaagct gcgccaagct gaggtgatca agggatcctg gcagcccgtg | 2640 |
| | ggcgatctcc tcattgactc tctccaagat cacctcgaga aagtcaaggc acttcgagga | 2700 |
| | gaaattgcgc ctctgaaaga gaacgtgagc cacgtcaatg accttgctcg ccagcttacc | 2760 |
| | actttgggca ttcagctctc accgtataac ctcagcactc tggaagacct gaacaccaga | 2820 |
| | tggaagcttc tgcaggtggc cgtcgaggac cgagtcaggc agctgcatga agcccacagg | 2880 |
| | gactttggtc cagcatctca gcactttctt tccacgtctg tccagggtcc ctgggagaga | 2940 |
| | gccatctcgc caaacaaagt gccctactat atcaaccacg agactcaaac aacttgctgg | 3000 |
| | gaccatccca aaatgacaga gctctaccag tctttagctg acctgaataa tgtcagattc | 3060 |
| | tcagcttata ggactgccat gaaactccga agactgcaga aggccctttg cttggatctc | 3120 |
| | ttgagcctgt cagctgcatg tgatgccttg gaccagcaca acctcaagca aaatgaccag | 3180 |
| | cccatggata tcctgcagat tattaattgt ttgaccacta tttatgaccg cctggagcaa | 3240 |
| | gagcacaaca atttggtcaa cgtccctctc tgcgtggata tgtgtctgaa ctggctgctg | 3300 |
| | aatgtttatg atacgggacg aacagggagg atccgtgtcc tgtcttttaa aactggcatc | 3360 |
| | atttccctgt gtaaagcaca tttggaagac aagtacagat accttttcaa gcaagtggca | 3420 |
| | agttcaacag gattttgtga ccagcgcagg ctgggcctcc ttctgcatga ttctatccaa | 3480 |
| | attccaagac agttgggtga agttgcatcc tttgggggca gtaacattga gccaagtgtc | 3540 |
| | cggagctgct tccaatttgc taataataag ccagagatcg aagcggccct cttcctagac | 3600 |
| | tggatgagac tggaacccca gtccatggtg tggctgcccg tcctgcacag agtggctgct | 3660 |
| | gcagaaactg ccaagcatca ggccaaatgt aacatctgca aagagtgtcc aatcattgga | 3720 |
| | ttcaggtaca ggagtctaaa gcactttaat tatgacatct gccaaagctg cttttttct | 3780 |
| | ggtcgagttg caaaaggcca taaaatgcac tatcccatgg tggaatattg cactccgact | 3840 |
| | acatcaggag aagatgttcg agactttgcc aaggtactaa aaaacaaatt tcgaaccaaa | 3900 |
| | aggtattttg cgaagcatcc ccgaatgggc tacctgccag tgcagactgt cttagagggg | 3960 |
| | gacaacatgg aaactcccga cacaatgtag | 3990 |

The foregoing is illustrative of the present invention, and is not to be construed as limiting thereof. The invention is defined by the following claims, with equivalents of the claims to be included therein.

That which is claimed is:

1. A recombinant AAV (rAAV) particle comprising an AAV9 capsid and a vector genome, said genome comprising a first AAV2 inverted terminal repeat (ITR), a muscle-specific transcriptional regulatory element operably linked to a nucleotide sequence encoding a human mini-dystrophin protein consisting of the amino acid sequence of SEQ ID NO: 7, a transcription termination sequence, and a second AAV2 ITR.

2. The rAAV particle of claim 1, wherein said vector genome is single-stranded DNA.

3. The rAAV particle of claim 1, wherein said nucleotide sequence encoding human mini-dystrophin protein is codon-optimized.

4. The rAAV particle of claim 3, wherein codon-optimization increases GC content relative to wild-type coding sequence.

5. The rAAV particle of claim 4, wherein the GC content of said nucleotide sequence is at least 60%.

6. The rAAV particle of claim 3, wherein said nucleotide sequence encoding human mini-dystrophin protein is human codon-optimized.

7. The rAAV particle of claim 1, wherein said muscle-specific transcriptional regulatory element confers muscle tissue-specific expression in skeletal and cardiac muscle.

8. The rAAV particle of claim 7, wherein said muscle-specific transcriptional regulatory element is a synthetic enhancer and promoter derived from a muscle creatinine kinase gene.

9. The rAAV particle of claim 3, wherein said nucleotide sequence encoding human mini-dystrophin protein is at least 90% identical to the nucleotide sequence of SEQ ID NO:1.

10. The rAAV particle of claim 9, wherein said muscle-specific transcriptional regulatory element comprises the nucleotide sequence of SEQ ID NO:16.

11. The rAAV particle of claim 10, wherein said transcription termination sequence comprises the nucleotide sequence of SEQ ID NO:17.

12. The rAAV particle of claim 11, wherein said vector genome comprises the nucleotide sequence of SEQ ID NO:18, or the reverse complement thereof.

13. A method of making the rAAV particle of claim 1, comprising:

introducing into a cell a polynucleotide comprising the nucleotide sequence of said vector genome, a polynucleotide comprising an AAV rep gene, a polynucleotide comprising an AAV9 cap gene and, optionally, a polynucleotide encoding one or more viral helper genes, incubating said cell; and purifying the rAAV particles produced thereby.

14. A rAAV particle produced by the method of claim 13.

* * * * *

UNITED STATES PATENT AND TRADEMARK OFFICE
CERTIFICATE OF CORRECTION

PATENT NO. : 12,257,321 B2
APPLICATION NO. : 18/150377
DATED : March 25, 2025
INVENTOR(S) : Xiao et al.

It is certified that error appears in the above-identified patent and that said Letters Patent is hereby corrected as shown below:

On the Title Page

Item (56) References Cited, OTHER PUBLICATIONS, Page 4, Column 1, Mendell, et al. cite, Line 8: Please correct “627:90-99” to read --527:90-99--

In the Specification

Column 19, Line 20: Please correct “(¤ ¤ <0.01; ¤ ¤ ¤ p<0.001)” to read --(¤¤p<0.01; ¤¤¤p<0.001)--

Column 19, Line 59: Please correct “mean SEM” to read --mean ± SEM--

Column 56, Line 35: Please correct “105” to read --$10^5$--

Column 63, Line 48: Please correct “$10^5$” to read --105--

Column 67, Line 30: Please correct “DMID” to read --DMD--

Column 71, Line 22: Please correct “Plus’” to read --Plus™--

Column 71, Line 29: Please correct “Tagman®” to read --Taqman®--

Column 77, Line 6: Please correct “(5 m)” to read --(5 µm)--

Column 77, Line 12: Please correct “(8 m)” to read --(8 µm)--

Columns 83-84, Table 10, Trial 2 Row, Dose (vg/kg) 1E+13 Column: Please correct “2.868 ± 0.23” to read --2.86 ± 0.23--

Columns 83-84, Table 10, Trial 2 Row, Dose (vg/kg) 3E+13 Column: Please correct “2.9 ± 0.25” to read --2.98 ± 0.25--

Signed and Sealed this
Nineteenth Day of August, 2025

Coke Morgan Stewart
*Acting Director of the United States Patent and Trademark Office*

Column 83, Table 11, Body weight (g) Row, WT Column: Please correct “601. ± 24.3” to read --601.3 ± 24.3--

Columns 85-86, Table 12, Trial 5 Row, 1E+13 Column: Please correct “1.87 ± 0.33§$^{§§§}$” to read --1.87 ± 0.33$^{§§§}$--

Column 89, Line 6: Please correct “DMID” to read --DMD--

Column 91, Line 4: Please correct ““‘¤’”” to read --“¤¤”--

SEQUENCE LISTING

```
Sequence total quantity: 28
SEQ ID NO: 1            moltype = DNA  length = 3978
FEATURE                 Location/Qualifiers
source                  1..3978
                        mol_type = other DNA
                        organism = synthetic construct
SEQUENCE: 1
```

-continued

```
atgctttggt gggaggaagt ggaggactgc tacgagagag aggacgtgca gaagaaaacc  60
ttcaccaagt gggtgaacgc ccagttcagc aagttcggca agcagcacat cgagaacctg  120
ttcagcgacc tgcaggatgg caggagactg ctggacctgc tggagggcct gaccggccag  180
aagctgccca aggagaaggg cagcaccaga gtgcacgccc tgaacaacgt gaacaaggcc  240
ctgagagtgc tgcagaacaa caacgtggac ctggtgaaca tcggcagcac cgacatcgtg  300
gacggcaacc acaagctgac cctgggcctg atctggaaca tcatcctgca ctggcaggtg  360
aagaacgtga tgaagaacat catggccggc ctgcagcaga ccaacagcga gaagatcctg  420
ctgagctggg tgaggcagag caccagaaac taccccaggg tgaacgtgat caacttcacc  480
acctcctgga gcgacggcct ggccctgaac gccctgatcc acagccacag acccgacctg  540
ttcgactgga acagcgtggt gtgtcagcag agcgccaccc agagactgga gcacgccttc  600
aacatcgcca gataccagct gggcatcgag aagctgctgg accccgagga cgtggacacc  660
acctaccccg acaagaaaag catcctcatg tacattacca gcctgttcca ggtgctgccc  720
cagcaggtgt ccatcgaggc catccaggaa gtggaaatgc tgcccaggcc ccccaaagtg  780
accaaggagg agcacttcca gctgcaccac cagatgcact acagccagca gatcacagtg  840
agcctggccc agggctatga gagaaccagc agccccaagc ccagattcaa gagctacgcc  900
tacacccagg ccgcctacgt gaccacctcc gaccccacca gaagcccctt ccccagccag  960
cacctggagg cccccgagga caagagcttc ggcagcagcc tgatggagag cgaagtgaac  1020
ctggacagat accagaccgc cctggaggaa gtgctgtcct ggctgctgag cgccgaggac  1080
accctgcagg cccagggcga gatcagcaac gacgtggaag tggtgaagga ccagttccac  1140
acccacgagg gctacatgat ggatctgacc gcccaccagg gcagagtggg caatatcctg  1200
cagctgggca gcaagctgat cggcaccggc aagctgagcg aggacgagga gaccgaagtg  1260
caggagcaga tgaacctgct gaacagcaga tgggagtgcc tgagagtggc cagcatggag  1320
aagcagagca acctgcacag agtgctgatg gacctgcaga accagaagct gaaggagctg  1380
aacgactggc tgaccaagac cgaggagcgg accagaaaga tggaggagga gcccctgggc  1440
cccgacctgg aggacctgaa gagacaggtg cagcagcaca aagtgctgca ggaggacctg  1500
gagcaggagc aggtgcgcgt gaacagcctg acccacatgg tggtggtcgt ggacgagagc  1560
agcggcgacc acgccacagc cgccctggaa gagcagctga aagtgctggg cgacagatgg  1620
gccaatattt gtaggtggac cgaggacaga tgggtgctgc tgcaggacca gcccgacctg  1680
gcccctggcc tgaccaccat cggcgccagc cccacccaga ccgtgaccct ggtgacccag  1740
cccgtggtga caaaggagac cgccatcagc aagctggaga tgcccagctc cctgatgctg  1800
gaagtgccca cccaccgcct gctccagcag ttcccccctgg acctggagaa gttcctggcc  1860
tggctgaccg aggccgaaac caccgccaat gtgctccagg acgccactag aaaggagagg  1920
ctgctggagg acagcaaggg cgtgaaagag ctgatgaagc agtggcagga tctgcagggc  1980
gaaatcgagg cccacaccga cgtgtaccac aacctggacg agaacagcca gaagattctg  2040
aggagcctgg agggcagcga cgacgccgtc ctgctccaga ggaggctgga caacatgaac  2100
ttcaagtgga gcgagctgcg gaagaagagc ctgaacatcc ggagccacct ggaagccagc  2160
agcgaccagt ggaagagact gcacctgagc ctgcaggagc tgctggtgtg gctgcagctg  2220
aaggacgacg agctgagcag acaggccccc atcggcggcg acttccccgc cgtgcagaag  2280
cagaacgacg tgcaccgggc cttcaagagg gagctgaaaa ccaaggaacc cgtgatcatg  2340
agcaccctgg agacagtgcg gatcttcctg accgagcagc ccctggaggg actggagaag  2400
ctgtaccagg agcccagaga gctgcccccc gaggagagag cccagaacgt gaccaggctg  2460
ctgagaaagc aggccgagga agtgaatacc gagtgggaga agctgaatct gcacagcgcc  2520
gactggcaga gaaagatcga cgagaccctg gagagactcc aggaactgca ggaagccacc  2580
gacgagctgg acctgaagct gagacaggcc gaagtgatca agggcagctg gcagcctgtg  2640
ggcgatctgc tgatcgactc cctgcaggat cacctggaga aagtgaaggc cctgcggggc  2700
gagatcgccc ccctgaagga gaatgtgagc cacgtgaacg acctggccag acagctgacc  2760
accctgggca tccagctgag cccctacaac ctgagcacac tggaggatct gaacacccgg  2820
tggaaactgc tgcaggtggc cgtggaggat agagtgaggc agctgcacga agcccacaga  2880
gacttcggcc ctgcctccca gcacttcctg agcaccagcg tgcagggccc ctgggagaga  2940
gccatctccc ccaacaaagt gccctactac atcaaccacg agacccagac cacctgctgg  3000
gaccacccta agatgaccga gctgtatcag agcctggccg acctgaacaa tgtgcggttc  3060
agcgcctaca gaaccgccat gaagctgcgg agactgcaga aggccctgtg cctggatctg  3120
ctgagcctga gcgccgcctg cgacgccctg gaccagcaca acctgaagca gaatgaccag  3180
cccatggaca tcctgcagat catcaactgc ctgaccacaa tctacgaccg gctggaacag  3240
gagcacaaca acctggtgaa tgtgccccctg tgcgtggaca tgtgcctgaa ttggctgctg  3300
aacgtgtacg acaccggcag gaccggcaga atccgcgtgc tgagcttcaa gaccggcatc  3360
atcagcctgt gcaaggccca cctggaggat aagtaccgct acctgttcaa gcaggtggcc  3420
agcagcaccg gcttctgcga tcagaggaga ctgggcctgc tgctgcacga tagcatccag  3480
atccctaggc agctgggcga agtggccagc tttggcggca gcaacatcga gccctctgtg  3540
aggagctgct tccagttcgc caacaacaag cccgagatcg aggccgccct gttcctggac  3600
tggatgaggc tggagcctca gagcatggtg tggctgcctg tgctgcacag agtggccgcc  3660
gccgagaccg ccaagcacca ggccaagtgc aatatctgca aggagtgccc catcatcggc  3720
ttccggtaca ggagcctgaa gcacttcaac tacgacatct gccagagctg ctttttcagc  3780
ggcagagtgg ccaagggcca caaaatgcac taccccatgg tggagtactg cacccccacc  3840
acctccggcg aggatgtgag agacttcgcc aaagtgctga agaataagtt ccggaccaag  3900
cggtactttg ccaagcaccc caggatgggc tacctgcccg tgcagaccgt gctggaaggc  3960
gacaacatgg agacctga                                                3978
```

```
SEQ ID NO: 2            moltype = DNA  length = 3837
FEATURE                 Location/Qualifiers
source                  1..3837
                        mol_type = other DNA
                        organism = synthetic construct
SEQUENCE: 2
atgctttggt gggaggaagt ggaggactgc tacgagagag aggacgtgca gaagaaaacc  60
ttcaccaagt gggtgaacgc ccagttcagc aagttcggca agcagcacat cgagaacctg  120
ttcagcgacc tgcaggatgg caggagactg ctggacctgc tggagggcct gaccggccag  180
aagctgccca aggagaaggg cagcaccaga gtgcacgccc tgaacaacgt gaacaaggcc  240
ctgagagtgc tgcagaacaa caacgtggac ctggtgaaca tcggcagcac cgacatcgtg  300
```

-continued

```
gacggcaacc acaagctgac cctgggcctg atctggaaca tcatcctgca ctggcaggtg  360
aagaacgtga tgaagaacat catggccggc ctgcagcaga ccaacagcga gaagatcctg  420
ctgagctggg tgaggcagag caccagaaac tacccccagg tgaacgtgat caacttcacc  480
acctcctgga gcgacggcct ggccctgaac gccctgatcc acagccacag acccgacctg  540
ttcgactgga acagcgtggt gtgtcagcag agcgccaccc agagactgga gcacgccttc  600
aacatcgcca gataccagct gggcatcgag aagctgctgg accccgagga cgtggacacc  660
acctaccccg acaagaaaag catcctcatg tacattacca gcctgttcca ggtgctgccc  720
cagcaggtgt ccatcgaggc catccaggaa gtggaaatgc tgcccaggcc ccccaaagtg  780
accaaggagg agcacttcca gctgcaccac cagatgcact acagccagca gatcacagtg  840
agcctggccc agggctatga gagaaccagc agccccaagc ccagattcaa gagctacgcc  900
tacacccagg ccgcctacgt gaccacctcc gaccccacca gaagcccctt ccccagccag  960
cacctggagg cccccgagga caagagcttc ggcagcagcc tgatggagag cgaagtgaac  1020
ctggacagat accagaccgc cctggaggaa gtgctgtcct ggctgctgag cgccgaggac  1080
accctgcagg cccagggcga gatcagcaac gacgtggaag tggtgaagga ccagttccac  1140
acccacgagg gctacatgat ggatctgacc gcccaccagg gcagagtggg caatatcctg  1200
cagctgggca gcaagctgat cggcaccggc aagctgagcg aggacgagga gaccgaagtg  1260
caggagcaga tgaacctgct gaacagcaga tgggagtgcc tgagagtggc cagcatggag  1320
aagcagagca acctgcacag agtgctgatg gacctgcaga accagaagct gaaggagctg  1380
aacgactggc tgaccaagac cgaggagcgg accagaaaga tggaggagga gcccctgggc  1440
cccgacctgg aggacctgaa gagacaggtg cagcagcaca aagtgctgca ggaggacctg  1500
gagcaggagc aggtgcgcgt gaacagcctg acccacatgg tggtggtcgt ggacgagagc  1560
agcggcgacc acgccacagc cgccctggaa gagcagctga aagtgctggg cgacagatgg  1620
gccaatattt gtaggtggac cgaggacaga tgggtgctgc tgcaggacac ccaccgcctg  1680
ctccagcagt tcccctgga cctggagaag ttcctggcct ggctgaccga ggccgaaacc  1740
accgccaatg tgctccagga cgccactaga aaggagaggc tgctggagga cagcaagggc  1800
gtgaaagagc tgatgaagca gtggcaggat ctgcagggcg aaatcgaggc ccacaccgac  1860
gtgtaccaca acctggacga gaacagccag aagattctga ggagcctgga gggcagcgac  1920
gacgccgtcc tgctccagag gaggctggac aacatgaact tcaagtggag cgagctgcgg  1980
aagaagagcc tgaacatccg gagccacctg gaagccagca gcgaccagtg gaagagactg  2040
cacctgagcc tgcaggagct gctggtgtgg ctgcagctga aggacgacga gctgagcaga  2100
caggccccca tcggcggcga cttccccgcc gtgcagaagc agaacgacgt gcaccgggcc  2160
ttcaagaggg agctgaaaac caaggaaccc gtgatcatga gcaccctgga gacagtgcgg  2220
atcttcctga ccgagcagcc cctggaggga ctggagaagc tgtaccagga gcccagagag  2280
ctgccccccg aggagagagc ccagaacgtg accaggctgc tgagaaagca ggccgaggaa  2340
gtgaataccg agtgggagaa gctgaatctg cacagcgccg actggcagag aaagatcgac  2400
gagaccctgg agagactcca ggaactgcag gaagccaccg acgagctgga cctgaagctg  2460
agacaggccg aagtgatcaa gggcagctgg cagcctgtgg gcgatctgct gatcgactcc  2520
ctgcaggatc acctggagaa agtgaaggcc ctgcggggcg agatcgcccc cctgaaggag  2580
aatgtgagcc acgtgaacga cctggccaga cagctgacca ccctgggcat ccagctgagc  2640
ccctacaacc tgagcacact ggaggatctg aacacccggt ggaaactgct gcaggtggcc  2700
gtggaggata gagtgaggca gctgcacgaa gcccacagag acttcggccc tgcctcccag  2760
cacttcctga gcaccagcgt gcagggcccc tgggagagag ccatctcccc caacaaagtg  2820
ccctactaca tcaaccacga gacccagacc acctgctggg accaccctaa gatgaccgag  2880
ctgtatcaga gcctggccga cctgaacaat gtgcggttca gcgcctacag aaccgccatg  2940
aagctgcgga gactgcagaa ggccctgtgc ctggatctgc tgagcctgag cgccgcctgc  3000
gacgccctgg accagcacaa cctgaagcag aatgaccagc ccatggacat cctgcagatc  3060
atcaactgcc tgaccacaat ctacgaccgg ctggaacagg agcacaacaa cctggtgaat  3120
gtgcccctgt gcgtggacat gtgcctgaat tggctgctga acgtgtacga caccggcagg  3180
accggcagaa tccgcgtgct gagcttcaag accggcatca tcagcctgtg caaggcccac  3240
ctggaggata agtaccgcta cctgttcaag caggtggcca gcagcaccgg cttctgcgat  3300
cagaggagac tgggcctgct gctgcacgat agcatccaga tccctaggca gctgggcgaa  3360
gtggccagct ttggcggcag caacatcgag ccctctgtga ggagctgctt ccagttcgcc  3420
aacaacaagc ccgagatcga ggccgccctg ttcctggact ggatgaggct ggagcctcag  3480
agcatggtgt ggctgcctgt gctgcacaga gtggccgccg ccgagaccgc caagcaccag  3540
gccaagtgca atatctgcaa ggagtgcccc atcatcggct tccggtacag gagcctgaag  3600
cacttcaact acgacatctg ccagagctgc tttttcagcg gcagagtggc caagggccac  3660
aaaatgcact accccatggt ggagtactgc acccccacca cctccggcga ggatgtgaga  3720
gacttcgcca aagtgctgaa gaataagttc cggaccaagc ggtactttgc caagcacccc  3780
aggatgggct acctgcccgt gcagaccgtg ctggaaggcg acaacatgga gacctga     3837

SEQ ID NO: 3           moltype = DNA  length = 3978
FEATURE                Location/Qualifiers
source                 1..3978
                       mol_type = other DNA
                       organism = synthetic construct
SEQUENCE: 3
atgctttggt gggaggaagt ggaggactgc tacgagcggg aggacgtgca gaagaaaacc  60
ttcaccaagt gggtgaacgc ccagttcagc aagttcggca agcagcacat cgagaacctg  120
ttcagcgacc tgcaggacgg caggcggctg ctggacctcc tggaaggcct gaccggccag  180
aagctgccca aagagaaggg cagcaccagg gtgcacgccc tgaacaacgt gaacaaggcc  240
ctgagggtgc tgcagaacaa caacgtggac ctggtgaaca tcggcagcac cgacatcgtg  300
gacggcaacc acaagctgac cctgggcctg atctggaaca tcatcctgca ctggcaggtc  360
aagaacgtga tgaagaacat catggccggc ctgcagcaga ccaacagcga gaagatcctg  420
ctgtcctggg tgcggcagag caccaggaac tacccccagg tcaacgtgat caacttcacc  480
acctcttgga gcgacggcct ggccctgaac gccctgatcc acagccacag gcccgacctg  540
ttcgactgga acagcgtggt gtgccagcag agcgccaccc agaggctgga acacgccttc  600
aacatcgcca gataccagct gggcatcgag aagctgctgg atcccgagga cgtggacacc  660
acctaccccg acaagaaaag catcctcatg tacatcacca gcctgttcca ggtgctgccc  720
cagcaggtgt ccatcgaggc catccaggaa gtggagatgc tgcccaggcc ccccaaggtc  780
```

-continued

```
accaaagagg aacacttcca gctgcaccac cagatgcact acagccagca gatcaccgtg  840
agcctggccc agggctacga gaggaccagc agccccaagc ccaggttcaa gagctacgcc  900
tacacccagg ccgcctacgt gaccacctcc gaccccacca ggtcccccct ccccagccag  960
catctcgaag cccccgagga caagagcttc ggcagcagcc tgatggaaag cgaggtgaac  1020
ctggacagat accagaccgc cctggaagaa gtgctgtctt ggctgctgtc cgccgaggac  1080
accctgcagg cccagggcga gatcagcaac gacgtggagg tcgtgaagga ccagttccac  1140
acccacgagg gctacatgat ggacctgacc gcccaccagg gcagagtggg caacatcctg  1200
cagctgggca gcaagctgat cggcaccggc aagctgtccg aggacgagga aaccgaggtg  1260
caggaacaga tgaacctgct gaacagcaga tgggagtgcc tgagggtggc cagcatggaa  1320
aagcagagca acctgcacag ggtgctgatg gatctgcaga accagaagct caaagagctg  1380
aacgactggc tgaccaagac cgaggaaagg acccggaaga tggaagagga acccctgggc  1440
cccgatctcg aagatctgaa gaggcaggtg cagcagcaca aggtgctgca ggaagatctc  1500
gaacaggaac aggtccgggt caacagcctg acccacatgg tcgtggtggt ggacgagagc  1560
agcggcgacc acgccaccgc tgccctggaa gagcagctga aggtgctggg cgacagatgg  1620
gccaacatct gccggtggac cgaggacaga tgggtcctcc tgcaggacca gcccgacctg  1680
gcccctggcc tgacaaccat cggcgccagc cccacccaga ccgtgaccct ggtgacccag  1740
cccgtggtga ccaaagagac cgccatcagc aagctggaaa tgcccagctc cctgatgctg  1800
gaagtgccca cccacaggct cctccagcag ttccccctgg acctggaaaa gttcctggcc  1860
tggctgaccg aggccgagac caccgccaac gtgctgcagg acgccaccag gaaagagagg  1920
ctgctggaag atagcaaggg cgtgaaagag ctgatgaagc agtggcagga cctgcagggg  1980
gagattgagg cccacaccga cgtgtaccac aacctggacg agaacagcca gaaaatcctg  2040
agaagcctgg aaggcagcga cgacgccgtg ctgctgcaga ggcggctgga caacatgaac  2100
ttcaagtgga gcgagctgag gaagaagagc ctgaacatca ggtcccatct ggaagccagc  2160
agcgaccagt ggaagaggct gcacctgagc ctgcaggaac tgctcgtctg gctgcagctg  2220
aaagacgacg agctgtccag gcaggccccc atcggcggcg acttccccgc cgtgcagaaa  2280
cagaacgacg tgcacagggc cttcaagcgg gagctgaaaa ccaaagagcc cgtgatcatg  2340
agcaccctgg aaaccgtgag gatcttcctg accgagcagc ccctggaagg actggaaaag  2400
ctgtaccagg aacccagaga gctgcccccc gaggaacggg cccagaacgt gaccaggctg  2460
ctgagaaagc aggccgagga agtgaacacc gagtgggaga agctgaacct gcactccgcc  2520
gactggcaga ggaagatcga cgagaccctg gaaaggctcc aggaactgca ggaagccacc  2580
gacgagctgg acctgaagct gagacaggcc gaggtgatca agggcagctg gcagcccgtg  2640
ggcgacctgc tgatcgactc cctgcaggat cacctggaaa aagtgaaggc cctgcggggc  2700
gagatcgccc ccctgaaaga gaacgtcagc cacgtcaacg acctggccag gcagctgacc  2760
accctgggca tccagctgtc cccctacaac ctgtccaccc tggaagatct gaacacaagg  2820
tggaagctgc tgcaggtggc cgtggaggac agagtgaggc agctgcacga ggcccacagg  2880
gacttcggcc ctgcctccca gcacttcctg agcaccagcg tgcagggccc ctgggagagg  2940
gccatctccc ccaacaaggt gccctactac atcaaccacg agacccagac cacctgctgg  3000
gaccacccta agatgaccga gctgtaccag tccctggccg acctgaacaa tgtgcggttc  3060
agcgcctacc ggaccgccat gaagctgagg cggctgcaga aagccctgtg cctggatctg  3120
ctgtccctga gcgccgcctg cgacgccctg gaccagcaca acctgaagca gaacgaccag  3180
cccatggata tcctgcagat catcaactgt ctgaccacca tctacgacag gctggaacag  3240
gaacacaaca acctggtcaa cgtgcccctg tgcgtggaca tgtgcctgaa ctggctgctg  3300
aacgtgtacg acaccggcag gaccggccgg atcagggtgc tgtccttcaa gaccggcatc  3360
atcagcctgt gcaaggccca cctggaagat aagtaccgct acctgttcaa gcaggtggcc  3420
agctctaccg gcttctgcga ccagcggagg ctgggcctgc tgctgcacga cagcatccag  3480
atcccccggc agctgggcga ggtggcctcc ttcggcggca gcaacatcga gcccagcgtg  3540
cggagctgct tccagttcgc caacaacaag cccgagatcg aggccgccct gttcctggac  3600
tggatgcggc tggaacccca gagcatggtc tggctgcccg tgctgcacag agtggctgcc  3660
gccgagaccg ccaagcacca ggccaagtgc aacatctgca aagagtgccc catcatcggc  3720
ttcaggtaca gaagcctgaa gcacttcaac tacgacatct gccagagctg tttcttcagc  3780
ggcagggtgg ccaagggcca caaaatgcac taccccatgg tggagtactg cacccccacc  3840
acctccggcg aggacgtgag ggacttcgcc aaggtgctga agaataagtt ccggaccaag  3900
cggtacttcg ccaaacaccc caggatgggc tacctgcccg tgcagaccgt gctggaaggc  3960
gacaacatgg aaacctga                                                3978
```

```
SEQ ID NO: 4            moltype = DNA  length = 606
FEATURE                 Location/Qualifiers
source                  1..606
                        mol_type = other DNA
                        organism = synthetic construct
SEQUENCE: 4
gaattcggta ccccactacg ggtttaggct gcccatgtaa ggaggcaagg cctggggaca  60
cccgagatgc ctggttataa ttaacccaga catgtggctg cccccccccc ccccaacacc  120
tgctgcctct aaaaataacc ctgtccctgg tggatcccct gcatgcgaag atcttcgaac  180
aaggctgtgg gggactgagg gcaggctgta acaggcttgg gggccagggc ttatacgtgc  240
ctgggactcc caaagtatta ctgttccatg ttcccggcga agggccagct gtcccccgcc  300
agctagactc agcacttagt ttaggaacca gtgagcaagt cagcccttgg ggcagcccat  360
acaaggccat ggggctgggc aagctgcacg cctgggtccg gggtgggcac ggtgcccggg  420
caacgagctg aaagctcatc tgctctcagg ggcccctccc tggggacagc ccctcctggc  480
tagtcacacc ctgtaggctc ctctatataa cccaggggca caggggctgc cctcattcta  540
ccaccacctc cacagcacag acagacactc aggagccagc cagcgtcgag cggccgatcc  600
gccacc                                                              606
```

```
SEQ ID NO: 5            moltype = DNA  length = 759
FEATURE                 Location/Qualifiers
source                  1..759
                        mol_type = other DNA
                        organism = synthetic construct
SEQUENCE: 5
```

-continued

```
gaattcggta ccccactacg ggtctaggct gcccatgtaa ggaggcaagg cctggggaca  60
cccgagatgc ctggttataa ttaaccccaa cacctgctgc cccccccccc ccaacacctg  120
ctgcctctaa aaataaccct gtccctggtg gatcccctgc atgccccact acgggtttag  180
gctgcccatg taaggaggca aggcctgggg acacccgaga tgcctggtta taattaaccc  240
agacatgtgg ctgccccccc cccccccaac acctgctgcc tctaaaaata accctgtccc  300
tggtggatcc cctgcatgcg aagatcttcg aacaaggctg tgggggactg agggcaggct  360
gtaacaggct tgggggccag ggcttatacg tgcctgggac tcccaaagta ttactgttcc  420
atgttcccgg cgaagggcca gctgtccccc gccagctaga ctcagcactt agtttaggaa  480
ccagtgagca agtcagccct tggggcagcc catacaaggc catggggctg ggcaagctgc  540
acgcctgggt ccggggtggg cacggtgccc gggcaacgag ctgaaagctc atctgctctc  600
aggggcccct ccctggggac agcccctcct ggctagtcac accctgtagg ctcctctata  660
taacccaggg gcacaggggc tgccctcatt ctaccaccac ctccacagca cagacagaca  720
ctcaggagcc agccagcgtc gagcggccga tccgccacc                          759

SEQ ID NO: 6            moltype = DNA  length = 67
FEATURE                 Location/Qualifiers
source                  1..67
                        mol_type = other DNA
                        organism = synthetic construct
SEQUENCE: 6
tgaggagctc gagaggccta ataaagagct cagatgcatc gatcagagtg tgttggtttt  60
ttgtgtg                                                             67

SEQ ID NO: 7            moltype = AA  length = 1325
FEATURE                 Location/Qualifiers
source                  1..1325
                        mol_type = protein
                        organism = synthetic construct
SEQUENCE: 7
MLWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDQPDL APGLTTIGAS PTQTVTLVTQ PVVTKETAIS KLEMPSSLML  600
EVPTHRLLQQ FPLDLEKFLA WLTEAETTAN VLQDATRKER LLEDSKGVKE LMKQWQDLQG  660
EIEAHTDVYH NLDENSQKIL RSLEGSDDAV LLQRRLDNMN FKWSELRKKS LNIRSHLEAS  720
SDQWKRLHLS LQELLVWLQL KDDELSRQAP IGGDFPAVQK QNDVHRAFKR ELKTKEPVIM  780
STLETVRIFL TEQPLEGLEK LYQEPRELPP EERAQNVTRL LRKQAEEVNT EWEKLNLHSA  840
DWQRKIDETL ERLQELQEAT DELDLKLRQA EVIKGSWQPV GDLLIDSLQD HLEKVKALRG  900
EIAPLKENVS HVNDLARQLT TLGIQLSPYN LSTLEDLNTR WKLLQVAVED RVRQLHEAHR  960
DFGPASQHFL STSVQGPWER AISPNKVPYY INHETQTTCW DHPKMTELYQ SLADLNNVRF  1020
SAYRTAMKLR RLQKALCLDL LSLSAACDAL DQHNLKQNDQ PMDILQIINC LTTIYDRLEQ  1080
EHNNLVNVPL CVDMCLNWLL NVYDTGRTGR IRVLSFKTGI ISLCKAHLED KYRYLFKQVA  1140
SSTGFCDQRR LGLLLHDSIQ IPRQLGEVAS FGGSNIEPSV RSCFQFANNK PEIEAALFLD  1200
WMRLEPQSMV WLPVLHRVAA AETAKHQAKC NICKECPIIG FRYRSLKHFN YDICQSCFFS  1260
GRVAKGHKMH YPMVEYCTPT TSGEDVRDFA KVLKNKFRTK RYFAKHPRMG YLPVQTVLEG  1320
DNMET                                                               1325

SEQ ID NO: 8            moltype = AA  length = 1278
FEATURE                 Location/Qualifiers
source                  1..1278
                        mol_type = protein
                        organism = synthetic construct
SEQUENCE: 8
MLWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDTHRL LQQFPLDLEK FLAWLTEAET TANVLQDATR KERLLEDSKG  600
VKELMKQWQD LQGEIEAHTD VYHNLDENSQ KILRSLEGSD DAVLLQRRLD NMNFKWSELR  660
KKSLNIRSHL EASSDQWKRL HLSLQELLVW LQLKDDELSR QAPIGGDFPA VQKQNDVHRA  720
FKRELKTKEP VIMSTLETVR IFLTEQPLEG LEKLYQEPRE LPPEERAQNV TRLLRKQAEE  780
VNTEWEKLNL HSADWQRKID ETLERLQELQ EATDELDLKL RQAEVIKGSW QPVGDLLIDS  840
LQDHLEKVKA LRGEIAPLKE NVSHVNDLAR QLTTLGIQLS PYNLSTLEDL NTRWKLLQVA  900
VEDRVRQLHE AHRDFGPASQ HFLSTSVQGP WERAISPNKV PYYINHETQT TCWDHPKMTE  960
LYQSLADLNN VRFSAYRTAM KLRRLQKALC LDLLSLSAAC DALDQHNLKQ NDQPMDILQI  1020
INCLTTIYDR LEQEHNNLVN VPLCVDMCLN WLLNVYDTGR TGRIRVLSFK TGIISLCKAH  1080
LEDKYRYLFK QVASSTGFCD QRRLGLLLHD SIQIPRQLGE VASFGGSNIE PSVRSCFQFA  1140
NNKPEIEAAL FLDWMRLEPQ SMVWLPVLHR VAAAETAKHQ AKCNICKECP IIGFRYRSLK  1200
```

-continued

HFNYDICQSC FFSGRVAKGH KMHYPMVEYC TPTTSGEDVR DFAKVLKNKF RTKRYFAKHP 1260
RMGYLPVQTV LEGDNMET 1278

SEQ ID NO: 9 moltype = DNA length = 4953
FEATURE Location/Qualifiers
source 1..4953
mol_type = other DNA
organism = synthetic construct
SEQUENCE: 9
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc tgaattcggt accccactac gggtttaggc 180
tgcccatgta aggaggcaag gcctggggac acccgagatg cctggttata attaacccag 240
acatgtggct gccccccccc cccccaacac ctgctgcctc taaaaataac cctgtccctg 300
gtggatcccc tgcatgcgaa gatcttcgaa caaggctgtg ggggactgag ggcaggctgt 360
aacaggcttg ggggccaggg cttatacgtg cctgggactc ccaaagtatt actgttccat 420
gttcccggcg aagggccagc tgtcccccgc cagctagact cagcacttag tttaggaacc 480
agtgagcaag tcagcccttg gggcagccca tacaaggcca tggggctggg caagctgcac 540
gcctgggtcc ggggtgggca cggtgcccgg gcaacgagct gaaagctcat ctgctctcag 600
gggcccctcc ctggggacag cccctcctgg ctagtcacac cctgtaggct cctctatata 660
acccaggggc acaggggctg ccctcattct accaccacct ccacagcaca gacagacact 720
caggagccag ccagcgtcga gcggccgatc cgccaccatg ctttggtggg aggaagtgga 780
ggactgctac gagagagagg acgtgcagaa gaaaaccttc accaagtggg tgaacgccca 840
gttcagcaag ttcggcaagc agcacatcga gaacctgttc agcgacctgc aggatggcag 900
gagactgctg gacctgctgg agggcctgac cggccagaag ctgcccaagg agaagggcag 960
caccagagtg cacgccctga acaacgtgaa caaggccctg agagtgctgc agaacaacaa 1020
cgtggacctg gtgaacatcg gcagcaccga catcgtggac ggcaaccaca agctgaccct 1080
gggcctgatc tggaacatca tcctgcactg gcaggtgaag aacgtgatga agaacatcat 1140
ggccggcctg cagcagacca acagcgagaa gatcctgctg agctgggtga ggcagagcac 1200
cagaaactac ccccaggtga acgtgatcaa cttcaccacc tcctggagcg acggcctggc 1260
cctgaacgcc ctgatccaca gccacagacc cgacctgttc gactggaaca gcgtggtgtg 1320
tcagcagagc gccacccaga gactggagca cgccttcaac atcgccagat accagctggg 1380
catcgagaag ctgctggacc ccgaggacgt ggacaccacc taccccgaca agaaaagcat 1440
cctcatgtac attaccagcc tgttccaggt gctgccccag caggtgtcca tcgaggccat 1500
ccaggaagtg gaaatgctgc ccaggccccc caaagtgacc aaggaggagc acttccagct 1560
gcaccaccag atgcactaca gccagcagat cacagtgagc ctggcccagg gctatgagag 1620
aaccagcagc cccaagccca gattcaagag ctacgcctac acccaggccg cctacgtgac 1680
cacctccgac cccaccagaa gccccttccc cagccagcac ctggaggccc ccgaggacaa 1740
gagcttcggc agcagcctga tggagagcga agtgaacctg gacagatacc agaccgccct 1800
ggaggaagtg ctgtcctggc tgctgagcgc cgaggacacc ctgcaggccc agggcgagat 1860
cagcaacgac gtggaagtgg tgaaggacca gttccacacc cacgagggct acatgatgga 1920
tctgaccgcc caccagggca gagtgggcaa tatcctgcag ctgggcagca agctgatcgg 1980
caccggcaag ctgagcgagg acgaggagac cgaagtgcag gagcagatga acctgctgaa 2040
cagcagatgg gagtgcctga gagtggccag catggagaag cagagcaacc tgcacagagt 2100
gctgatggac ctgcagaacc agaagctgaa ggagctgaac gactggctga ccaagaccga 2160
ggagcggacc agaaagatgg aggaggagcc cctgggcccc gacctggagg acctgaagag 2220
acaggtgcag cagcacaaag tgctgcagga ggacctggag caggagcagg tgcgcgtgaa 2280
cagcctgacc cacatggtgg tggtcgtgga cgagagcagc ggcgaccacg ccacagccgc 2340
cctggaagag cagctgaaag tgctgggcga cagatgggcc aatatttgta ggtggaccga 2400
ggacagatgg gtgctgctgc aggaccagcc cgacctggcc cctggcctga ccaccatcgg 2460
cgccagcccc acccagaccg tgaccctggt gacccagccc gtggtgacaa aggagaccgc 2520
catcagcaag ctggagatgc ccagctccct gatgctggaa gtgcccaccc accgcctgct 2580
ccagcagttc cccctggacc tggagaagtt cctggcctgg ctgaccgagg ccgaaaccac 2640
cgccaatgtg ctccaggacg ccactagaaa ggagaggctg ctggaggaca gcaagggcgt 2700
gaaagagctg atgaagcagt ggcaggatct gcagggcgaa atcgaggccc acaccgacgt 2760
gtaccacaac ctggacgaga acagccagaa gattctgagg agcctggagg gcagcgacga 2820
cgccgtcctg ctccagagga ggctggacaa catgaacttc aagtggagcg agctgcggaa 2880
gaagagcctg aacatccgga gccacctgga agccagcagc gaccagtgga agagactgca 2940
cctgagcctg caggagctgc tggtgtggct gcagctgaag gacgacgagc tgagcagaca 3000
ggcccccatc ggcggcgact tccccgccgt gcagaagcag aacgacgtgc accgggcctt 3060
caagagggag ctgaaaacca aggaacccgt gatcatgagc accctggaga cagtgcggat 3120
cttcctgacc gagcagcccc tggagggact ggagaagctg taccaggagc ccagagagct 3180
gccccccgag gagagagccc agaacgtgac caggctgctg agaaagcagg ccgaggaagt 3240
gaataccgag tgggagaagc tgaatctgca cagcgccgac tggcagagaa agatcgacga 3300
gaccctggag agactccagg aactgcagga agccaccgac gagctggacc tgaagctgag 3360
acaggccgaa gtgatcaagg gcagctggca gcctgtgggc gatctgctga tcgactccct 3420
gcaggatcac ctggagaaag tgaaggccct gcggggcgag atcgcccccc tgaaggagaa 3480
tgtgagccac gtgaacgacc tggccagaca gctgaccacc ctgggcatcc agctgagccc 3540
ctacaacctg agcacactgg aggatctgaa cacccggtgg aaactgctgc aggtggccgt 3600
ggaggataga gtgaggcagc tgcacgaagc ccacagagac ttcggccctg cctcccagca 3660
cttcctgagc accagcgtgc agggcccctg ggagagagcc atctccccca acaaagtgcc 3720
ctactacatc aaccacgaga cccagaccac ctgctgggac caccctaaga tgaccgagct 3780
gtatcagagc ctggccgacc tgaacaatgt gcggttcagc gcctacagaa ccgccatgaa 3840
gctgcggaga ctgcagaagg ccctgtgcct ggatctgctg agcctgagcg ccgcctgcga 3900
cgccctggac cagcacaacc tgaagcagaa tgaccagccc atggacatcc tgcagatcat 3960
caactgcctg accacaatct acgaccggct ggaacaggag cacaacaacc tggtgaatgt 4020
gcccctgtgc gtggacatgt gcctgaattg gctgctgaac gtgtacgaca ccggcaggac 4080
cggcagaatc cgcgtgctga gcttcaagac cggcatcatc agcctgtgca aggcccacct 4140
ggaggataag taccgctacc tgttcaagca ggtggccagc agcaccggct tctgcgatca 4200

-continued

```
gaggagactg ggcctgctgc tgcacgatag catccagatc cctaggcagc tgggcgaagt  4260
ggccagcttt ggcggcagca acatcgagcc ctctgtgagg agctgcttcc agttcgccaa  4320
caacaagccc gagatcgagg ccgccctgtt cctggactgg atgaggctgg agcctcagag  4380
catggtgtgg ctgcctgtgc tgcacagagt ggccgccgcc gagaccgcca agcaccaggc  4440
caagtgcaat atctgcaagg agtgccccat catcggcttc cggtacagga gcctgaagca  4500
cttcaactac gacatctgcc agagctgctt tttcagcggc agagtggcca agggccacaa  4560
aatgcactac cccatggtgg agtactgcac ccccaccacc tccggcgagg atgtgagaga  4620
cttcgccaaa gtgctgaaga ataagttccg gaccaagcgg tactttgcca agcaccccag  4680
gatgggctac ctgcccgtgc agaccgtgct ggaaggcgac aacatggaga cctgatgagg  4740
agctcgagag gcctaataaa gagctcagat gcatcgatca gagtgtgttg gttttttgtg  4800
tgagatctag gaacccctag tgatggagtt ggccactccc tctctgcgcg ctcgctcgct  4860
cactgaggcc gcccgggcaa agcccgggcg tcgggcgacc tttggtcgcc cggcctcagt  4920
gagcgagcga gcgcgcagag agggagtggc caa                              4953

SEQ ID NO: 10          moltype = DNA  length = 4812
FEATURE                Location/Qualifiers
source                 1..4812
                       mol_type = other DNA
                       organism = synthetic construct
SEQUENCE: 10
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctagatc tgaattcggt accccactac gggtttaggc  180
tgcccatgta aggaggcaag gcctggggac acccgagatg cctggttata attaacccag  240
acatgtggct gccccccccc cccccaacac ctgctgcctc taaaaataac cctgtccctg  300
gtggatcccc tgcatgcgaa gatcttcgaa caaggctgtg ggggactgag ggcaggctgt  360
aacaggcttg gggccaggg  cttatacgtg cctgggactc ccaaagtatt actgttccat  420
gttcccggcg aagggccagc tgtcccccgc cagctagact cagcacttag tttaggaacc  480
agtgagcaag tcagcccttg gggcagccca tacaaggcca tggggctggg caagctgcac  540
gcctgggtcc ggggtgggca cggtgcccgg gcaacgagct gaaagctcat ctgctctcag  600
gggcccctcc ctggggacag cccctcctgg ctagtcacac cctgtaggct cctctatata  660
acccaggggc acaggggctg ccctcattct accaccacct ccacagcaca gacagacact  720
caggagccag ccagcgtcga gcggccgatc cgccaccatg ctttggtggg aggaagtgga  780
ggactgctac gagagagagg acgtgcagaa gaaaaccttc accaagtggg tgaacgccca  840
gttcagcaag ttcggcaagc agcacatcga gaacctgttc agcgacctgc aggatggcag  900
gagactgctg gacctgctgg agggcctgac cggccagaag ctgcccaagg agaagggcag  960
caccagagtg cacgccctga acaacgtgaa caaggccctg agagtgctgc agaacaacaa  1020
cgtggacctg gtgaacatcg gcagcaccga catcgtggac ggcaaccaca agctgaccct  1080
gggcctgatc tggaacatca tcctgcactg gcaggtgaag aacgtgatga agaacatcat  1140
ggccggcctg cagcagacca acagcgagaa gatcctgctg agctgggtga ggcagagcac  1200
cagaaactac ccccaggtga acgtgatcaa cttcaccacc tcctggagcg acggcctggc  1260
cctgaacgcc ctgatccaca gccacagacc cgacctgttc gactggaaca gcgtggtgtg  1320
tcagcagagc gccacccaga gactggagca cgccttcaac atcgccagat accagctggg  1380
catcgagaag ctgctggacc ccgaggacgt ggacaccacc taccccgaca agaaaagcat  1440
cctcatgtac attaccagcc tgttccaggt gctgccccag caggtgtcca tcgaggccat  1500
ccaggaagtg gaaatgctgc ccaggccccc caaagtgacc aaggaggagc acttccagct  1560
gcaccaccag atgcactaca gccagcagat cacagtgagc ctggcccagg gctatgagag  1620
aaccagcagc cccaagccca gattcaagag ctacgcctac acccaggccg cctacgtgac  1680
cacctccgac cccaccagaa gccccttccc cagccagcac ctggaggccc ccgaggacaa  1740
gagcttcggc agcagcctga tggagagcga agtgaacctg gacagatacc agaccgccct  1800
ggaggaagtg ctgtcctggc tgctgagcgc cgaggacacc ctgcaggccc agggcgagat  1860
cagcaacgac gtggaagtgg tgaaggacca gttccacacc cacgagggct acatgatgga  1920
tctgaccgcc caccagggca gagtgggcaa tatcctgcag ctgggcagca agctgatcgg  1980
caccggcaag ctgagcgagg acgaggagac cgaagtgcag gagcagatga acctgctgaa  2040
cagcagatgg gagtgcctga gagtggccag catggagaag cagagcaacc tgcacagagt  2100
gctgatggac ctgcagaacc agaagctgaa ggagctgaac gactggctga ccaagaccga  2160
ggagcggacc agaaagatgg aggaggagcc cctgggcccc gacctggagg acctgaagag  2220
acaggtgcag cagcacaaag tgctgcagga ggacctggag caggagcagg tgcgcgtgaa  2280
cagcctgacc cacatggtgg tggtcgtgga cgagagcagc ggcgaccacg ccacagccgc  2340
cctggaagag cagctgaaag tgctgggcga cagatgggcc aatatttgta ggtggaccga  2400
ggacagatgg gtgctgctgc aggacaccca ccgcctgctc cagcagttcc ccctggacct  2460
ggagaagttc ctggcctggc tgaccgaggc cgaaaccacc gccaatgtgc tccaggacgc  2520
cactagaaag gagaggctgc tggaggacag caagggcgtg aaagagctga tgaagcagtg  2580
gcaggatctg cagggcgaaa tcgaggccca caccgacgtg taccacaacc tggacgagaa  2640
cagccagaag attctgagga gcctggaggg cagcgacgac gccgtcctgc tccagaggag  2700
gctggacaac atgaacttca agtggagcga gctgcggaag aagagcctga acatccggag  2760
ccacctggaa gccagcagcg accagtggaa gagactgcac ctgagcctgc aggagctgct  2820
ggtgtggctg cagctgaagg acgacgagct gagcagacag gcccccatcg gcggcgactt  2880
ccccgccgtg cagaagcaga acgacgtgca ccgggccttc aagagggagc tgaaaaccaa  2940
ggaacccgtg atcatgagca ccctggagac agtgcggatc ttcctgaccg agcagcccct  3000
ggagggactg gagaagctgt accaggagcc cagagagctg ccccccgagg agagagccca  3060
gaacgtgacc aggctgctga gaaagcaggc cgaggaagtg aataccgagt gggagaagct  3120
gaatctgcac agcgccgact ggcagagaaa gatcgacgag accctggaga gactccagga  3180
actgcaggaa gccaccgacg agctggacct gaagctgaga caggccgaag tgatcaaggg  3240
cagctggcag cctgtgggcg atctgctgat cgactccctg caggatcacc tggagaaagt  3300
gaaggccctg cggggcgaga tcgcccccct gaaggagaat gtgagccacg tgaacgacct  3360
ggccagacag ctgaccaccc tgggcatcca gctgagcccc tacaacctga gcacactgga  3420
ggatctgaac acccggtgga aactgctgca ggtggccgtg gaggatagag tgaggcagct  3480
gcacgaagcc cacagagact tcggccctgc ctcccagcac ttcctgagca ccagcgtgca  3540
```

-continued

```
gggcccctgg gagagagcca tctcccccaa caaagtgccc tactacatca accacgagac  3600
ccagaccacc tgctgggacc accctaagat gaccgagctg tatcagagcc tggccgacct  3660
gaacaatgtg cggttcagcg cctacagaac cgccatgaag ctgcggagac tgcagaaggc  3720
cctgtgcctg gatctgctga gcctgagcgc cgcctgcgac gccctggacc agcacaacct  3780
gaagcagaat gaccagccca tggacatcct gcagatcatc aactgcctga ccacaatcta  3840
cgaccggctg gaacaggagc acaacaacct ggtgaatgtg cccctgtgcg tggacatgtg  3900
cctgaattgg ctgctgaacg tgtacgacac cggcaggacc ggcagaatcc gcgtgctgag  3960
cttcaagacc ggcatcatca gcctgtgcaa ggcccacctg gaggataagt accgctacct  4020
gttcaagcag gtggccagca gcaccggctt ctgcgatcag aggagactgg gcctgctgct  4080
gcacgatagc atccagatcc ctaggcagct gggcgaagtg gccagctttg gcggcagcaa  4140
catcgagccc tctgtgagga gctgcttcca gttcgccaac aacaagcccg agatcgaggc  4200
cgccctgttc ctggactgga tgaggctgga gcctcagagc atggtgtggc tgcctgtgct  4260
gcacagagtg gccgccgccg agaccgccaa gcaccaggcc aagtgcaata tctgcaagga  4320
gtgccccatc atcggcttcc ggtacaggag cctgaagcac ttcaactacg acatctgcca  4380
gagctgcttt ttcagcggca gagtggccaa gggccacaaa atgcactacc ccatggtgga  4440
gtactgcacc cccaccacct ccggcgagga tgtgagagac ttcgccaaag tgctgaagaa  4500
taagttccgg accaagcggt actttgccaa gcaccccagg atgggctacc tgcccgtgca  4560
gaccgtgctg gaaggcgaca acatggagac ctgatgagga gctcgagagg cctaataaag  4620
agctcagatg catcgatcag agtgtgttgg tttttgtgt gagatctagg aacccctagt  4680
gatggagttg gccactccct ctctgcgcgc tcgctcgctc actgaggccg cccgggcaaa  4740
gcccgggcgt cgggcgacct ttggtcgccc ggcctcagtg agcgagcgag cgcgcagaga  4800
gggagtggcc aa                                                     4812
```

```
SEQ ID NO: 11          moltype = DNA  length = 4965
FEATURE                Location/Qualifiers
source                 1..4965
                       mol_type = other DNA
                       organism = synthetic construct
SEQUENCE: 11
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctagatc tgaattcggt accccactac gggtctaggc  180
tgcccatgta aggaggcaag gcctggggac acccgagatg cctggttata attaacccca  240
acacctgctg cccccccccc cccaacacct gctgcctcta aaaataaccc tgtccctggt  300
ggatcccctg catgccccac tacgggttta ggctgcccat gtaaggaggc aaggcctggg  360
gacacccgag atgcctggtt ataattaacc cagacatgtg gctgcccccc cccccccaa  420
cacctgctgc ctctaaaaat aaccctgtcc ctggtggatc ccctgcatgc gaagatcttc  480
gaacaaggct gtgggggact gagggcaggc tgtaacaggc ttgggggcca gggcttatac  540
gtgcctggga ctcccaaagt attactgttc catgttcccg gcgaagggcc agctgtcccc  600
cgccagctag actcagcact tagtttagga accagtgagc aagtcagccc ttggggcagc  660
ccatacaagg ccatggggct gggcaagctg cacgcctggg tccggggtgg gcacggtgcc  720
cgggcaacga gctgaaagct catctgctct caggggcccc tccctgggga cagcccctcc  780
tggctagtca caccctgtag gctcctctat ataacccagg ggcacagggg ctgccctcat  840
tctaccacca cctccacagc acagacagac actcaggagc cagccagcgt cgagcggccg  900
atccgccacc atgctttggt gggaggaagt ggaggactgc tacgagagag aggacgtgca  960
gaagaaaacc ttcaccaagt gggtgaacgc ccagttcagc aagttcggca agcagcacat  1020
cgagaacctg ttcagcgacc tgcaggatgg caggagactg ctggacctgc tggagggcct  1080
gaccggccag aagctgccca aggagaaggg cagcaccaga gtgcacgccc tgaacaacgt  1140
gaacaaggcc ctgagagtgc tgcagaacaa caacgtggac ctggtgaaca tcggcagcac  1200
cgacatcgtg gacggcaacc acaagctgac cctgggcctg atctggaaca tcatcctgca  1260
ctggcaggtg aagaacgtga tgaagaacat catggccggc ctgcagcaga ccaacagcga  1320
gaagatcctg ctgagctggg tgaggcagag caccagaaac taccccccagg tgaacgtgat  1380
caacttcacc acctcctgga gcgacggcct ggccctgaac gccctgatcc acagccacag  1440
acccgacctg ttcgactgga acagcgtggt gtgtcagcag agcgccaccc agagactgga  1500
gcacgccttc aacatcgcca gataccagct gggcatcgag aagctgctgg accccgagga  1560
cgtggacacc acctaccccg acaagaaaag catcctcatg tacattacca gcctgttcca  1620
ggtgctgccc cagcaggtgt ccatcgaggc catccaggaa gtggaaatgc tgcccaggcc  1680
ccccaaagtg accaaggagg agcacttcca gctgcaccac cagatgcact acagccagca  1740
gatcacagtg agcctggccc agggctatga gagaaccagc agccccaagc ccagattcaa  1800
gagctacgcc tacacccagg ccgcctacgt gaccacctcc gaccccacca gaagcccctt  1860
ccccagccag cacctggagg cccccgagga caagagcttc ggcagcagcc tgatggagag  1920
cgaagtgaac ctggacagat accagaccgc cctggaggaa gtgctgtcct ggctgctgag  1980
cgccgaggac accctgcagg cccagggcga gatcagcaac gacgtggaag tggtgaagga  2040
ccagttccac acccacgagg gctacatgat ggatctgacc gcccaccagg gcagagtggg  2100
caatatcctg cagctgggca gcaagctgat cggcaccggc aagctgagcg aggacgagga  2160
gaccgaagtg caggagcaga tgaacctgct gaacagcaga tgggagtgcc tgagagtggc  2220
cagcatggag aagcagagca acctgcacag agtgctgatg gacctgcaga accagaagct  2280
gaaggagctg aacgactggc tgaccaagac cgaggagcgg accagaaaga tggaggagga  2340
gcccctgggc cccgacctgg aggacctgaa gagacaggtg cagcagcaca aagtgctgca  2400
ggaggacctg gagcaggagc aggtgcgcgt gaacagcctg acccacatgg tggtggtcgt  2460
ggacgagagc agcggcgacc acgccacagc cgccctggaa gagcagctga aagtgctggg  2520
cgacagatgg gccaatattt gtaggtggac cgaggacaga tgggtgctgc tgcaggacac  2580
ccaccgcctg ctccagcagt tcccccctgga cctggagaag ttcctggcct ggctgaccga  2640
ggccgaaacc accgccaatg tgctccagga cgccactaga aaggagaggc tgctggagga  2700
cagcaagggc gtgaaagagc tgatgaagca gtggcaggat ctgcagggcg aaatcgaggc  2760
ccacaccgac gtgtaccaca acctggacga gaacagccag aagattctga ggagcctgga  2820
gggcagcgac gacgccgtcc tgctccagag gaggctggac aacatgaact tcaagtggag  2880
cgagctgcgg aagaagagcc tgaacatccg gagccacctg gaagccagca gcgaccagtg  2940
gaagagactg cacctgagcc tgcaggagct gctggtgtgg ctgcagctga aggacgacga  3000
```

-continued

```
gctgagcaga caggccccca tcggcggcga cttccccgcc gtgcagaagc agaacgacgt  3060
gcaccgggcc ttcaagaggg agctgaaaac caaggaaccc gtgatcatga gcaccctgga  3120
gacagtgcgg atcttcctga ccgagcagcc cctggaggga ctggagaagc tgtaccagga  3180
gcccagagag ctgcccccg aggagagagc ccagaacgtg accaggctgc tgagaaagca  3240
ggccgaggaa gtgaataccg agtgggagaa gctgaatctg cacagcgccg actggcagag  3300
aaagatcgac gagaccctgg agagactcca ggaactgcag gaagccaccg acgagctgga  3360
cctgaagctg agacaggccg aagtgatcaa gggcagctgg cagcctgtgg gcgatctgct  3420
gatcgactcc ctgcaggatc acctggagaa agtgaaggcc ctgcggggcg agatcgcccc  3480
cctgaaggag aatgtgagcc acgtgaacga cctggccaga cagctgacca ccctgggcat  3540
ccagctgagc ccctacaacc tgagcacact ggaggatctg aacacccggt ggaaactgct  3600
gcaggtggcc gtggaggata gagtgaggca gctgcacgaa gcccacagag acttcggccc  3660
tgcctcccag cacttcctga gcaccagcgt gcagggcccc tgggagagag ccatctcccc  3720
caacaaagtg ccctactaca tcaaccacga gacccagacc acctgctggg accaccctaa  3780
gatgaccgag ctgtatcaga gcctggccga cctgaacaat gtgcggttca gcgcctacag  3840
aaccgccatg aagctgcgga gactgcagaa ggccctgtgc ctggatctgc tgagcctgag  3900
cgccgcctgc gacgccctgg accagcacaa cctgaagcag aatgaccagc ccatggacat  3960
cctgcagatc atcaactgcc tgaccacaat ctacgaccgg ctggaacagg agcacaacaa  4020
cctggtgaat gtgcccctgt gcgtggacat gtgcctgaat tggctgctga acgtgtacga  4080
caccggcagg accggcagaa tccgcgtgct gagcttcaag accggcatca tcagcctgtg  4140
caaggcccac ctggaggata agtaccgcta cctgttcaag caggtggcca gcagcaccgg  4200
cttctgcgat cagaggagac tggcctgct gctgcacgat agcatccaga tccctaggca  4260
gctgggcgaa gtggccagct ttggcggcag caacatcgag ccctctgtga ggagctgctt  4320
ccagttcgcc aacaacaagc ccgagatcga ggccgccctg ttcctggact ggatgaggct  4380
ggagcctcag agcatggtgt ggctgcctgt gctgcacaga gtggccgccg ccgagaccgc  4440
caagcaccag gccaagtgca atatctgcaa ggagtgcccc atcatcggct tccggtacag  4500
gagcctgaag cacttcaact acgacatctg ccagagctgc tttttcagcg gcagagtggc  4560
caagggccac aaaatgcact accccatggt ggagtactgc acccccacca cctccggcga  4620
ggatgtgaga gacttcgcca aagtgctgaa gaataagttc cggaccaagc ggtactttgc  4680
caagcacccc aggatgggct acctgcccgt gcagaccgtg ctggaaggcg acaacatgga  4740
gacctgatga ggagctcgag aggcctaata aagagctcag atgcatcgat cagagtgtgt  4800
tggttttttg tgtgagatct aggaacccct agtgatggag ttggccactc cctctctgcg  4860
cgctcgctcg ctcactgagg ccgcccgggc aaagcccggg cgtcgggcga cctttggtcg  4920
cccggcctca gtgagcgagc gagcgcgcag agagggagtg gccaa                 4965

SEQ ID NO: 12           moltype = DNA  length = 4955
FEATURE                 Location/Qualifiers
source                  1..4955
                        mol_type = other DNA
                        organism = synthetic construct
SEQUENCE: 12
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctcagat ctgaattcgg taccccacta cgggtttagg  180
ctgcccatgt aaggaggcaa ggcctgggga cacccgagat gcctggttat aattaaccca  240
gacatgtggc tgcccccccc cccccaaca cctgctgcct ctaaaaataa ccctgtccct  300
ggtggatccc ctgcatgcga agatcttcga acaaggctgt gggggactga gggcaggctg  360
taacaggctt gggggccagg gcttatacgt gcctgggact cccaaagtat tactgttcca  420
tgttcccggc gaagggccag ctgtcccccg ccagctagac tcagcactta gtttaggaac  480
cagtgagcaa gtcagccctt ggggcagccc atacaaggcc atggggctgg gcaagctgca  540
cgcctgggtc cggggtgggc acggtgcccg ggcaacgagc tgaaagctca tctgctctca  600
ggggcccctc cctggggaca gcccctcctg gctagtcaca ccctgtaggc tcctctatat  660
aacccagggg cacaggggct gccctcattc taccaccacc tccacagcac agacagacac  720
tcaggagcca gccagcgtcg agcggccgcc accatgcttt ggtgggagga agtggaggac  780
tgctacgagc gggaggacgt gcagaagaaa accttcacca agtgggtgaa cgcccagttc  840
agcaagttcg gcaagcagca catcgagaac ctgttcagcg acctgcagga cggcaggcgg  900
ctgctggacc tcctggaagg cctgaccggc cagaagctgc ccaaagagaa gggcagcacc  960
agggtgcacg ccctgaacaa cgtgaacaag gccctgaggg tgctgcagaa caacaacgtg  1020
gacctggtga acatcggcag caccgacatc gtggacggca accacaagct gaccctgggc  1080
ctgatctgga acatcatcct gcactggcag gtcaagaacg tgatgaagaa catcatggcc  1140
ggcctgcagc agaccaacag cgagaagatc ctgctgtcct gggtgcggca gagcaccagg  1200
aactaccccc aggtcaacgt gatcaacttc accacctctt ggagcgacgg cctggccctg  1260
aacgccctga tccacagcca caggcccgac ctgttcgact ggaacagcgt ggtgtgccag  1320
cagagcgcca cccagaggct ggaacacgcc ttcaacatcg ccagatacca gctgggcatc  1380
gagaagctgc tggatcccga ggacgtggac accacctacc ccgacaagaa aagcatcctc  1440
atgtacatca ccagcctgtt ccaggtgctg ccccagcagg tgtccatcga ggccatccag  1500
gaagtggaga tgctgcccag gcccccccaag gtcaccaaag aggaacactt ccagctgcac  1560
caccagatgc actacagcca gcagatcacc gtgagcctgg cccagggcta cgagaggacc  1620
agcagcccca agcccaggtt caagagctac gcctacaccc aggccgccta cgtgaccacc  1680
tccgacccca ccaggtcccc cttccccagc cagcatctcg aagcccccga ggacaagagc  1740
ttcggcagca gcctgatgga aagcgaggtg aacctggaca gataccagac cgccctggaa  1800
gaagtgctgt cttggctgct gtccgccgag gacaccctgc aggcccaggg cgagatcagc  1860
aacgacgtgg aggtcgtgaa ggaccagttc cacacccacg agggctacat gatggacctg  1920
accgcccacc agggcagagt gggcaacatc ctgcagctgg gcagcaagct gatcggcacc  1980
ggcaagctgt ccgaggacga ggaaaccgag gtgcaggaac agatgaacct gctgaacagc  2040
agatgggagt gcctgagggt ggccagcatg gaaaagcaga gcaacctgca cagggtgctg  2100
atggatctgc agaaccagaa gctcaaagag ctgaacgact ggctgaccaa gaccgaggaa  2160
aggacccgga agatggaaga ggaacccctg ggccccgatc tcgaagatct gaagaggcag  2220
gtgcagcagc acaaggtgct gcaggaagat ctcgaacagg aacaggtccg ggtcaacagc  2280
ctgacccaca tggtcgtggt ggtggacgag agcagcggcg accacgccac cgctgccctg  2340
```

-continued gaagagcagc tgaaggtgct gggcgacaga tgggccaaca tctgccggtg gaccgaggac 2400
agatgggtcc tcctgcagga ccagcccgac ctggcccctg gcctgacaac catcggcgcc 2460
agccccaccc agaccgtgac cctggtgacc cagcccgtgg tgaccaaaga gaccgccatc 2520
agcaagctgg aaatgcccag ctccctgatg ctggaagtgc ccacccacag gctcctccag 2580
cagttccccc tggacctgga aaagttcctg gcctggctga ccgaggccga gaccaccgcc 2640
aacgtgctgc aggacgccac caggaaagag aggctgctgg aagatagcaa gggcgtgaaa 2700
gagctgatga agcagtggca ggacctgcag ggggagattg aggcccacac cgacgtgtac 2760
cacaacctgg acgagaacag ccagaaaatc ctgagaagcc tggaaggcag cgacgacgcc 2820
gtgctgctgc agaggcggct ggacaacatg aacttcaagt ggagcgagct gaggaagaag 2880
agcctgaaca tcaggtccca tctggaagcc agcagcgacc agtggaagag gctgcacctg 2940
agcctgcagg aactgctcgt ctggctgcag ctgaaagacg acgagctgtc caggcaggcc 3000
cccatcggcg gcgacttccc cgccgtgcag aaacagaacg acgtgcacag ggccttcaag 3060
cgggagctga aaaccaaaga gcccgtgatc atgagcaccc tggaaaccgt gaggatcttc 3120
ctgaccgagc agcccctgga aggactggaa aagctgtacc aggaacccag agagctgccc 3180
cccgaggaac gggcccagaa cgtgaccagg ctgctgagaa agcaggccga ggaagtgaac 3240
accgagtggg agaagctgaa cctgcactcc gccgactggc agaggaagat cgacgagacc 3300
ctggaaaggc tccaggaact gcaggaagcc accgacgagc tggacctgaa gctgagacag 3360
gccgaggtga tcaagggcag ctggcagccc gtgggcgacc tgctgatcga ctccctgcag 3420
gatcacctgg aaaaagtgaa ggccctgcgg ggcgagatcg ccccccctgaa agagaacgtc 3480
agccacgtca acgacctggc caggcagctg accaccctgg gcatccagct gtccccctac 3540
aacctgtcca ccctggaaga tctgaacaca aggtggaagc tgctgcaggt ggccgtggag 3600
gacagagtga ggcagctgca cgaggcccac agggacttcg gccctgcctc ccagcacttc 3660
ctgagcacca gcgtgcaggg cccctgggag agggccatct cccccaacaa ggtgccctac 3720
tacatcaacc acgagaccca gaccacctgc tgggaccacc ctaagatgac cgagctgtac 3780
cagtccctgg ccgacctgaa caatgtgcgg ttcagcgcct accggaccgc catgaagctg 3840
aggcggctgc agaaagccct gtgcctggat ctgctgtccc tgagcgccgc ctgcgacgcc 3900
ctggaccagc acaacctgaa gcagaacgac cagcccatgg atatcctgca gatcatcaac 3960
tgtctgacca ccatctacga caggctggaa caggaacaca acaacctggt caacgtgccc 4020
ctgtgcgtgg acatgtgcct gaactggctg ctgaacgtgt acgacaccgg caggaccggc 4080
cggatcaggg tgctgtcctt caagaccggc atcatcagcc tgtgcaaggc ccacctggaa 4140
gataagtacc gctacctgtt caagcaggtg gccagctcta ccggcttctg cgaccagcgg 4200
aggctgggcc tgctgctgca cgacagcatc cagatccccc ggcagctggg cgaggtggcc 4260
tccttcggcg gcagcaacat cgagcccagc gtgcggagct gcttccagtt cgccaacaac 4320
aagcccgaga tcgaggccgc cctgttcctg gactggatgc ggctggaacc ccagagcatg 4380
gtctggctgc ccgtgctgca cagagtggct gccgccgaga ccgccaagca ccaggccaag 4440
tgcaacatct gcaaagagtg ccccatcatc ggcttcaggt acagaagcct gaagcacttc 4500
aactacgaca tctgccagag ctgtttcttc agcggcaggg tggccaaggg ccacaaaatg 4560
cactacccca tggtggagta ctgcaccccc accacctccg gcgaggacgt gagggacttc 4620
gccaaggtgc tgaagaataa gttccggacc aagcggtact tcgccaaaca ccccaggatg 4680
ggctacctgc ccgtgcagac cgtgctggaa ggcgacaaca tggaaacctg ataacacgcg 4740
tcgactcgag aggcctaata aagagctcag atgcatcgat cagagtgtgt tggttttttg 4800
tgtgagatct aggaacccct agtgatggag ttggccactc cctctctgcg cgctcgctcg 4860
ctcactgagg ccgcccgggc aaagcccggg cgtcgggcga cctttggtcg cccggcctca 4920
gtgagcgagc gagcgcgcag agagggagtg gccaa 4955

SEQ ID NO: 13 moltype = AA length = 736
FEATURE Location/Qualifiers
source 1..736
mol_type = protein
organism = adeno-associated virus 9
SEQUENCE: 13
MAADGYLPDW LEDNLSEGIR EWWALKPGAP QPKANQQHQD NARGLVLPGY KYLGPGNGLD 60
KGEPVNAADA AALEHDKAYD QQLKAGDNPY LKYNHADAEF QERLKEDTSF GGNLGRAVFQ 120
AKKRLLEPLG LVEEAAKTAP GKKRPVEQSP QEPDSSAGIG KSGAQPAKKR LNFGQTGDTE 180
SVPDPQPIGE PPAAPSGVGS LTMASGGGAP VADNNEGADG VGSSSGNWHC DSQWLGDRVI 240
TTSTRTWALP TYNNHLYKQI SNSTSGGSSN DNAYFGYSTP WGYFDFNRFH CHFSPRDWQR 300
LINNNWGFRP KRLNFKLFNI QVKEVTDNNG VKTIANNLTS TVQVFTDSDY QLPYVLGSAH 360
EGCLPPFPAD VFMIPQYGYL TLNDGSQAVG RSSFYCLEYF PSQMLRTGNN FQFSYEFENV 420
PFHSSYAHSQ SLDRLMNPLI DQYLYYLSKT INGSGQNQQT LKFSVAGPSN MAVQGRNYIP 480
GPSYRQQRVS TTVTQNNNSE FAWPGASSWA LNGRNSLMNP GPAMASHKEG EDRFFPLSGS 540
LIFGKQGTGR DNVDADKVMI TNEEEIKTTN PVATESYGQV ATNHQSAQAQ AQTGWVQNQG 600
ILPGMVWQDR DVYLQGPIWA KIPHTDGNFH PSPLMGGFGM KHPPPQILIK NTPVPADPPT 660
AFNKDKLNSF ITQYSTGQVS VEIEWELQKE NSKRWNPEIQ YTSNYYKSNN VEFAVNTEGV 720
YSEPRPIGTR YLTRNL 736

SEQ ID NO: 14 moltype = DNA length = 145
FEATURE Location/Qualifiers
source 1..145
mol_type = other DNA
organism = adeno-associated virus 2
SEQUENCE: 14
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcct 145

SEQ ID NO: 15 moltype = DNA length = 145
FEATURE Location/Qualifiers
source 1..145
mol_type = other DNA

```
                         organism = adeno-associated virus 2
SEQUENCE: 15
aggaacccct agtgatggag ttggccactc cctctctgcg cgctcgctcg ctcactgagg  60
ccgcccgggc aaagcccggg cgtcgggcga cctttggtcg cccggcctca gtgagcgagc  120
gagcgcgcag agagggagtg gccaa                                        145

SEQ ID NO: 16            moltype = DNA  length = 577
FEATURE                  Location/Qualifiers
source                   1..577
                         mol_type = other DNA
                         organism = synthetic construct
SEQUENCE: 16
ccactacggg tctaggctgc ccatgtaagg aggcaaggcc tggggacacc cgagatgcct  60
ggttataatt aacccagaca tgtggctgcc cccccccccc ccaacacctg ctgcctctaa  120
aaataaccct gtccctggtg gatcccctgc atgcgaagat cttcgaacaa ggctgtgggg  180
gactgagggc aggctgtaac aggcttgggg gccagggctt atacgtgcct gggactccca  240
aagtattact gttccatgtt cccggcgaag ggccagctgt cccccgccag ctagactcag  300
cacttagttt aggaaccagt gagcaagtca gcccttgggg cagcccatac aaggccatgg  360
ggctgggcaa gctgcacgcc tggtccgggg gtgggcacgg tgcccgggca acgagctgaa  420
agctcatctg ctctcagggg cccctccctg ggacagcccc ctcctggcta gtcacaccct  480
gtaggctcct ctatataacc caggggcaca ggggctgccc tcattctacc accacctcca  540
cagcacagac agacactcag gagccagcca gcgtcga                            577

SEQ ID NO: 17            moltype = DNA  length = 54
FEATURE                  Location/Qualifiers
source                   1..54
                         mol_type = other DNA
                         organism = synthetic construct
SEQUENCE: 17
aggcctaata aagagctcag atgcatcgat cagagtgtgt tggttttttg tgtg        54

SEQ ID NO: 18            moltype = DNA  length = 4955
FEATURE                  Location/Qualifiers
source                   1..4955
                         mol_type = other DNA
                         organism = synthetic construct
SEQUENCE: 18
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctcagat ctgaattcgg taccccacta cgggtctagg  180
ctgcccatgt aaggaggcaa ggcctgggga cacccgagat gcctggttat aattaaccca  240
gacatgtggc tgcccccccc cccccaaca cctgctgcct ctaaaaataa ccctgtccct  300
ggtggatccc ctgcatgcga agatcttcga acaaggctgt gggggactga gggcaggctg  360
taacaggctt gggggccagg gcttatacgt gcctgggact cccaaagtat tactgttcca  420
tgttcccggc gaagggccag ctgtcccccg ccagctagac tcagcactta gtttaggaac  480
cagtgagcaa gtcagccctt ggggcagccc atacaaggcc atggggctgg gcaagctgca  540
cgcctgggtc cggggtgggc acggtgcccg ggcaacgagc tgaaagctca tctgctctca  600
ggggcccctc cctggggaca gccccctcctg gctagtcaca ccctgtaggc tcctctatat  660
aacccagggg cacaggggct gccctcattc taccaccacc tccacagcac agacagacac  720
tcaggagcca gccagcgtcg agcggccgat ccgccaccat gctttggtgg gaggaagtgg  780
aggactgcta cgagagagag gacgtgcaga agaaaacctt caccaagtgg gtgaacgccc  840
agttcagcaa gttcggcaag cagcacatcg agaacctgtt cagcgacctg caggatggca  900
ggagactgct ggacctgctg gagggcctga ccggccagaa gctgcccaag gagaagggca  960
gcaccagagt gcacgccctg aacaacgtga acaaggccct gagagtgctg cagaacaaca  1020
acgtggacct ggtgaacatc ggcagcaccg acatcgtgga cggcaaccac aagctgaccc  1080
tgggcctgat ctggaacatc atcctgcact ggcaggtgaa gaacgtgatg aagaacatca  1140
tggccggcct gcagcagacc aacagcgaga agatcctgct gagctgggtg aggcagagca  1200
ccagaaacta cccccaggtg aacgtgatca acttcaccac ctcctggagc gacggcctgg  1260
ccctgaacgc cctgatccac agccacagac ccgacctgtt cgactggaac agcgtggtgt  1320
gtcagcagag cgccacccag agactggagc acgccttcaa catcgccaga taccagctgg  1380
gcatcgagaa gctgctggac cccgaggacg tggacaccac ctaccccgac aagaaaagca  1440
tcctcatgta cattaccagc ctgttccagg tgctgcccca gcaggtgtcc atcgaggcca  1500
tccaggaagt ggaaatgctg cccaggcccc ccaaagtgac caaggaggag cacttccagc  1560
tgcaccacca gatgcactac agccagcaga tcacagtgag cctggcccag ggctatgaga  1620
gaaccagcag ccccaagccc agattcaaga gctacgccta cacccaggcc gcctacgtga  1680
ccacctccga ccccaccaga agccccttcc ccagccagca cctggaggcc cccgaggaca  1740
agagcttcgg cagcagcctg atggagagcg aagtgaacct ggacagatac cagaccgccc  1800
tggaggaagt gctgtcctgg ctgctgagcg ccgaggacac cctgcaggcc cagggcgaga  1860
tcagcaacga cgtggaagtg gtgaaggacc agttccacac ccacgagggc tacatgatgg  1920
atctgaccgc ccaccagggc agagtgggca atatcctgca gctgggcagc aagctgatcg  1980
gcaccggcaa gctgagcgag gacgaggaga ccgaagtgca ggagcagatg aacctgctga  2040
acagcagatg ggagtgcctg agagtggcca gcatggagaa gcagagcaac ctgcacagag  2100
tgctgatgga cctgcagaac cagaagctga aggagctgaa cgactggctg accaagaccg  2160
aggagcggac cagaaagatg gaggaggagc ccctgggccc cgacctggag gacctgaaga  2220
gacaggtgca gcagcacaaa gtgctgcagg aggacctgga gcaggagcag gtgcgcgtga  2280
acagcctgac ccacatggtg gtggtcgtgg acgagagcag cggcgaccac gccacagccg  2340
ccctggaaga gcagctgaaa gtgctgggcg acagatgggc caatatttgt aggtggaccg  2400
aggacagatg ggtgctgctg caggaccagc ccgacctggc ccctggcctg accaccatcg  2460
gcgccagccc cacccagacc gtgaccctgg tgacccagcc cgtggtgaca aaggagaccg  2520
```

-continued

```
ccatcagcaa gctggagatg cccagctccc tgatgctgga agtgcccacc caccgcctgc  2580
tccagcagtt ccccctggac ctggagaagt tcctggcctg gctgaccgag gccgaaacca  2640
ccgccaatgt gctccaggac gccactagaa aggagaggct gctggaggac agcaagggcg  2700
tgaaagagct gatgaagcag tggcaggatc tgcagggcga aatcgaggcc cacaccgacg  2760
tgtaccacaa cctggacgag aacagccaga agattctgag gagcctggag ggcagcgacg  2820
acgccgtcct gctccagagg aggctggaca acatgaactt caagtggagc gagctgcgga  2880
agaagagcct gaacatccgg agccacctgg aagccagcag cgaccagtgg aagagactgc  2940
acctgagcct gcaggagctg ctggtgtggc tgcagctgaa ggacgacgag ctgagcagac  3000
aggcccccat cggcggcgac ttccccgccg tgcagaagca gaacgacgtg caccgggcct  3060
tcaagaggga gctgaaaacc aaggaacccg tgatcatgag caccctggag acagtgcgga  3120
tcttcctgac cgagcagccc ctggagggac tggagaagct gtaccaggag cccagagagc  3180
tgcccccccga ggagagagcc cagaacgtga ccaggctgct gagaaagcag gccgaggaag  3240
tgaataccga gtgggagaag ctgaatctgc acagcgccga ctggcagaga aagatcgacg  3300
agaccctgga gagactccag gaactgcagg aagccaccga cgagctggac ctgaagctga  3360
gacaggccga agtgatcaag ggcagctggc agcctgtggg cgatctgctg atcgactccc  3420
tgcaggatca cctggagaaa gtgaaggccc tgcggggcga gatcgccccc ctgaaggaga  3480
atgtgagcca cgtgaacgac ctggccagac agctgaccac cctgggcatc cagctgagcc  3540
cctacaacct gagcacactg gaggatctga acacccggtg gaaactgctg caggtggccg  3600
tggaggatag agtgaggcag ctgcacgaag cccacagaga cttcggccct gcctcccagc  3660
acttcctgag caccagcgtg cagggcccct gggagagagc catctccccc aacaaagtgc  3720
cctactacat caaccacgag acccagacca cctgctggga ccaccctaag atgaccgagc  3780
tgtatcagag cctggccgac ctgaacaatg tgcggttcag cgcctacaga accgccatga  3840
agctgcggag actgcagaag gccctgtgcc tggatctgct gagcctgagc gccgcctgcg  3900
acgccctgga ccagcacaac ctgaagcaga atgaccagcc catggacatc ctgcagatca  3960
tcaactgcct gaccacaatc tacgaccggc tggaacagga gcacaacaac ctggtgaatg  4020
tgcccctgtg cgtggacatg tgcctgaatt ggctgctgaa cgtgtacgac accggcagga  4080
ccggcagaat ccgcgtgctg agcttcaaga ccggcatcat cagcctgtgc aaggcccacc  4140
tggaggataa gtaccgctac ctgttcaagc aggtggccag cagcaccggc ttctgcgatc  4200
agaggagact gggcctgctg ctgcacgata gcatccagat ccctaggcag ctgggcgaag  4260
tggccagctt tggcggcagc aacatcgagc cctctgtgag gagctgcttc cagttcgcca  4320
acaacaagcc cgagatcgag gccgccctgt tcctggactg gatgaggctg gagcctcaga  4380
gcatggtgtg gctgcctgtg ctgcacagag tggccgccgc cgagaccgcc aagcaccagg  4440
ccaagtgcaa tatctgcaag gagtgcccca tcatcggctt ccggtacagg agcctgaagc  4500
acttcaacta cgacatctgc cagagctgct ttttcagcgg cagagtggcc aagggccaca  4560
aaatgcacta ccccatggtg gagtactgca cccccaccac ctccggcgag gatgtgagag  4620
acttcgccaa agtgctgaag aataagttcc ggaccaagcg gtactttgcc aagcacccca  4680
ggatgggcta cctgcccgtg cagaccgtgc tggaaggcga caacatggag acctgatgag  4740
gagctcgaga ggcctaataa agagctcaga tgcatcgatc agagtgtgtt ggtttttttgt  4800
gtgagatctg aggaacccct agtgatggag ttggccactc cctctctgcg cgctcgctcg  4860
ctcactgagg ccgcccgggc aaagcccggg cgtcgggcga cctttggtcg cccggcctca  4920
gtgagcgagc gagcgcgcag agagggagtg gccaa                             4955

SEQ ID NO: 19          moltype = DNA  length = 23
FEATURE                Location/Qualifiers
source                 1..23
                       mol_type = other DNA
                       organism = synthetic construct
SEQUENCE: 19
ccaacaaagt gccctactac atc                                          23

SEQ ID NO: 20          moltype = DNA  length = 21
FEATURE                Location/Qualifiers
source                 1..21
                       mol_type = other DNA
                       organism = synthetic construct
SEQUENCE: 20
ggttgtgctg gtccagggcg t                                            21

SEQ ID NO: 21          moltype = DNA  length = 23
FEATURE                Location/Qualifiers
source                 1..23
                       mol_type = other DNA
                       organism = synthetic construct
SEQUENCE: 21
ccgagctgta tcagagcctg gcc                                          23

SEQ ID NO: 22          moltype = DNA  length = 21
FEATURE                Location/Qualifiers
source                 1..21
                       mol_type = other DNA
                       organism = synthetic construct
SEQUENCE: 22
gcgaaagtgg aaaagccaag t                                            21

SEQ ID NO: 23          moltype = DNA  length = 24
FEATURE                Location/Qualifiers
source                 1..24
                       mol_type = other DNA
                       organism = synthetic construct
```

```
SEQUENCE: 23
gccacatcaa caggactctt gtag                                         24

SEQ ID NO: 24          moltype = DNA  length = 30
FEATURE                Location/Qualifiers
source                 1..30
                       mol_type = other DNA
                       organism = synthetic construct
SEQUENCE: 24
caaagcctaa aagacagcgg caagttgaat                                   30

SEQ ID NO: 25          moltype = AA  length = 3685
FEATURE                Location/Qualifiers
source                 1..3685
                       mol_type = protein
                       organism = Homo sapiens
SEQUENCE: 25
MLWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDILLK WQRLTEEQCL FSAWLSEKED AVNKIHTTGF KDQNEMLSSL  600
QKLAVLKADL EKKKQSMGKL YSLKQDLLST LKNKSVTQKT EAWLDNFARC WDNLVQKLEK  660
STAQISQAVT TTQPSLTQTT VMETVTTVTT REQILVKHAQ EELPPPPPQK KRQITVDSEI  720
RKRLDVDITE LHSWITRSEA VLQSPEFAIF RKEGNFSDLK EKVNAIEREK AEKFRKLQDA  780
SRSAQALVEQ MVNEGVNADS IKQASEQLNS RWIEFCQLLS ERLNWLEYQN NIIAFYNQLQ  840
QLEQMTTTAE NWLKIQPTTP SEPTAIKSQL KICKDEVNRL SGLQPQIERL KIQSIALKEK  900
GQGPMFLDAD FVAFTNHFKQ VFSDVQAREK ELQTIFDTLP PMRYQETMSA IRTWVQQSET  960
KLSIPQLSVT DYEIMEQRLG ELQALQSSLQ EQQSGLYYLS TTVKEMSKKA PSEISRKYQS  1020
EFEEIEGRWK KLSSQLVEHC QKLEEQMNKL RKIQNHIQTL KKWMAEVDVF LKEEWPALGD  1080
SEILKKQLKQ CRLLVSDIQT IQPSLNSVNE GGQKIKNEAE PEFASRLETE LKELNTQWDH  1140
MCQQVYARKE ALKGGLEKTV SLQKDLSEMH EWMTQAEEEY LERDFEYKTP DELQKAVEEM  1200
KRAKEEAQQK EAKVKLLTES VNSVIAQAPP VAQEALKKEL ETLTTNYQWL CTRLNGKCKT  1260
LEEVWACWHE LLSYLEKANK WLNEVEFKLK TTENIPGGAE EISEVLDSLE NLMRHSEDNP  1320
NQIRILAQTL TDGGVMDELI NEELETFNSR WRELHEEAVR RQKLLEQSIQ SAQETEKSLH  1380
LIQESLTFID KQLAAYIADK VDAAQMPQEA QKIQSDLTSH EISLEEMKKH NQGKEAAQRV  1440
LSQIDVAQKK LQDVSMKFRL FQKPANFEQR LQESKMILDE VKMHLPALET KSVEQEVVQS  1500
QLNHCVNLYK SLSEVKSEVE MVIKTGRQIV QKKQTENPKE LDERVTALKL HYNELGAKVT  1560
ERKQQLEKCL KLSRKMRKEM NVLTEWLAAT DMELTKRSAV EGMPSNLDSE VAWGKATQKE  1620
IEKQKVHLKS ITEVGEALKT VLGKKETLVE DKLSLLNSNW IAVTSRAEEW LNLLLEYQKH  1680
METFDQNVDH ITKWIIQADT LLDESEKKKP QQKEDVLKRL KAELNDIRPK VDSTRDQAAN  1740
LMANRGDHCR KLVEPQISEL NHRFAAISHR IKTGKASIPL KELEQFNSDI QKLLEPLEAE  1800
IQQGVNLKEE DFNKDMNEDN EGTVKELLQR GDNLQQRITD ERKREEIKIK QQLLQTKHNA  1860
LKDLRSQRRK KALEISHQWY QYKRQADDLL KCLDDIEKKL ASLPEPRDER KIKEIDRELQ  1920
KKKEELNAVR RQAEGLSEDG AAMAVEPTQI QLSKRWREIE SKFAQFRRLN FAQIHTVREE  1980
TMMVMTEDMP LEISYVPSTY LTEITHVSQA LLEVEQLLNA PDLCAKDFED LFKQEESLKN  2040
IKDSLQQSSG RIDIIHSKKT AALQSATPVE RVKLQEALSQ LDFQWEKVNK MYKDRQGRFD  2100
RSVEKWRRFH YDIKIFNQWL TEAEQFLRKT QIPENWEHAK YKWYLKELQD GIGQRQTVVR  2160
TLNATGEEII QQSSKTDASI LQEKLGSLNL RWQEVCKQLS DRKKRLEEQK NILSEFQRDL  2220
NEFVLWLEEA DNIASIPLEP GKEQQLKEKL EQVKLLVEEL PLRQGILKQL NETGGPVLVS  2280
APISPEEQDK LENKLKQTNL QWIKVSRALP EKQGEIEAQI KDLGQLEKKL EDLEEQLNHL  2340
LLWLSPIRNQ LEIYNQPNQE GPFDVQETEI AVQAKQPDVE EILSKGQHLY KEKPATQPVK  2400
RKLEDLSSEW KAVNRLLQEL RAKQPDLAPG LTTIGASPTQ TVTLVTQPVV TKETAISKLE  2460
MPSSLMLEVP ALADFNRAWT ELTDWLSLLD QVIKSQRVMV GDLEDINEMI IKQKATMQDL  2520
EQRRPQLEEL ITAAQNLKNK TSNQEARTII TDRIERIQNQ WDEVQEHLQN RRQQLNEMLK  2580
DSTQWLEAKE EAEQVLGQAR AKLESWKEGP YTVDAIQKKI TETKQLAKDL RQWQTNVDVA  2640
NDLALKLLRD YSADDTRKVH MITENINASW RSIHKRVSER EAALEETHRL LQQFPLDLEK  2700
FLAWLTEAET TANVLQDATR KERLLEDSKG VKELMKQWQD LQGEIEAHTD VYHNLDENSQ  2760
KILRSLEGSD DAVLLQRRLD NMNFKWSELR KKSLNIRSHL EASSDQWKRL HLSLQELLVW  2820
LQLKDDELSR QAPIGGDFPA VQKQNDVHRA FKRELKTKEP VIMSTLETVR IFLTEQPLEG  2880
LEKLYQEPRE LPPEERAQNV TRLLRKQAEE VNTEWEKLNL HSADWQRKID ETLERLQELQ  2940
EATDELDLKL RQAEVIKGSW QPVGDLLIDS LQDHLEKVKA LRGEIAPLKE NVSHVNDLAR  3000
QLTTLGIQLS PYNLSTLEDL NTRWKLLQVA VEDRVRQLHE AHRDFGPASQ HFLSTSVQGP  3060
WERAISPNKV PYYINHETQT TCWDHPKMTE LYQSLADLNN VRFSAYRTAM KLRRLQKALC  3120
LDLLSLSAAC DALDQHNLKQ NDQPMDILQI INCLTTIYDR LEQEHNNLVN VPLCVDMCLN  3180
WLLNVYDTGR TGRIRVLSFK TGIISLCKAH LEDKYRYLFK QVASSTGFCD QRRLGLLLHD  3240
SIQIPRQLGE VASFGGSNIE PSVRSCFQFA NNKPEIEAAL FLDWMRLEPQ SMVWLPVLHR  3300
VAAAETAKHQ AKCNICKECP IIGFRYRSLK HFNYDICQSC FFSGRVAKGH KMHYPMVEYC  3360
TPTTSGEDVR DFAKVLKNKF RTKRYFAKHP RMGYLPVQTV LEGDNMETPV TLINFWPVDS  3420
APASSPQLSH DDTHSRIEHY ASRLAEMENS NGSYLNDSIS PNESIDDEHL LIQHYCQSLN  3480
QDSPLSQPRS PAQILISLES EERGELERIL ADLEEENRNL QAEYDRLKQQ HEHKGLSPLP  3540
SPPEMMPTSP QSPRDAELIA EAKLLRQHKG RLEARMQILE DHNKQLESQL HRLRQLLEQP  3600
QAEAKVNGTT VSSPSTSLQR SDSSQPMLLR VVGSQTSDSM GEEDLLSPPQ DTSTGLEEVM  3660
EQLNNSFPSS RGRNTPGKPM REDTM                                        3685
```

```
SEQ ID NO: 26          moltype = DNA  length = 3978
FEATURE                Location/Qualifiers
source                 1..3978
                       mol_type = other DNA
                       organism = synthetic construct
SEQUENCE: 26
atgctttggt gggaagaagt agaggactgt tatgaaagag aagatgttca aaagaaaaca  60
ttcacaaaat gggtaaatgc acaattttct aagtttggga agcagcatat tgagaacctc  120
ttcagtgacc tacaggatgg gaggcgcctc ctagacctcc tcgaaggcct gacagggcaa  180
aaactgccaa aagaaaaagg atccacaaga gttcatgccc tgaacaatgt caacaaggca  240
ctgcgggttt tgcagaacaa taatgttgat ttagtgaata ttggaagtac tgacatcgta  300
gatggaaatc ataaactgac tcttggtttg atttggaata taatcctcca ctggcaggtc  360
aaaaatgtaa tgaaaaatat catggctgga ttgcaacaaa ccaacagtga aaagattctc  420
ctgagctggg tccgacaatc aactcgtaat tatccacagg ttaatgtaat caacttcacc  480
accagctggt ctgatggcct ggctttgaat gctctcatcc atagtcatag gccagaccta  540
tttgactgga atagtgtggt ttgccagcag tcagccacac aacgactgga acatgcattc  600
aacatcgcca gatatcaatt aggcatagag aaactactcg atcctgaaga tgttgatacc  660
acctatccag ataagaagtc catcttaatg tacatcacat cactcttcca agttttgcct  720
caacaagtga gcattgaagc catccaggaa gtggaaatgt tgccaaggcc acctaaagtg  780
actaaagaag aacattttca gttacatcat caaatgcact attctcaaca gatcacggtc  840
agtctagcac agggatatga gagaacttct tcccctaagc ctcgattcaa gagctatgcc  900
tacacacagg ctgcttatgt caccacctct gaccctacac ggagcccatt tccttcacag  960
catttggaag ctcctgaaga caagtcattt ggcagttcat tgatggagag tgaagtaaac  1020
ctggaccgtt atcaaacagc tttagaagaa gtattatcgt ggcttctttc tgctgaggac  1080
acattgcaag cacaaggaga gatttctaat gatgtggaag tggtgaaaga ccagtttcat  1140
actcatgagg ggtacatgat ggatttgaca gcccatcagg gccgggttgg taatattcta  1200
caattgggaa gtaagctgat tggaacagga aaattatcag aagatgaaga aactgaagta  1260
caagagcaga tgaatctcct aaattcaaga tgggaatgcc tcagggtagc tagcatggaa  1320
aaacaaagca atttacatag agttttaatg gatctccaga atcagaaact gaaagagttg  1380
aatgactggc taacaaaaac agaagaaaga acaaggaaaa tggaggaaga gcctcttgga  1440
cctgatcttg aagacctaaa acgccaagta caacaacata aggtgcttca agaagatcta  1500
gaacaagaac aagtcagggt caattctctc actcacatgg tggtggtagt tgatgaatct  1560
agtggagatc acgcaactgc tgctttggaa gaacaactta aggtattggg agatcgatgg  1620
gcaaacatct gtagatggac agaagaccgc tgggttcttt tacaagacca gcctgaccta  1680
gctcctggac tgaccactat tggagcctct cctactcaga ctgttactct ggtgacacaa  1740
cctgtggtta ctaaggaaac tgccatctcc aaactagaaa tgccatcttc cttgatgttg  1800
gaggtaccta ctcatagatt actgcaacag ttccccctgg acctggaaaa gtttcttgcc  1860
tggcttacag aagctgaaac aactgccaat gtcctacagg atgctacccg taaggaaagg  1920
ctcctagaag actccaaggg agtaaaagag ctgatgaaac aatggcaaga cctccaaggt  1980
gaaattgaag ctcacacaga tgtttatcac aacctggatg aaaacagcca aaaaatcctg  2040
agatccctgg aaggttccga tgatgcagtc ctgttacaaa gacgtttgga taacatgaac  2100
ttcaagtgga gtgaacttcg gaaaaagtct ctcaacatta ggtcccattt ggaagccagt  2160
tctgaccagt ggaagcgtct gcacctttct ctgcaggaac ttctggtgtg gctacagctg  2220
aaagatgatg aattaagccg gcaggcacct attggaggcg actttccagc agttcagaag  2280
cagaacgatg tacatagggc cttcaagagg gaattgaaaa ctaaagaacc tgtaatcatg  2340
agtactcttg agactgtacg aatatttctg acagagcagc ctttggaagg actagagaaa  2400
ctctaccagg agcccagaga gctgcctcct gaggagagag cccagaatgt cactcggctt  2460
ctacgaaagc aggctgagga ggtcaatact gagtgggaaa aattgaacct gcactccgct  2520
gactggcaga gaaaaataga tgagaccctt gaaagactcc aggaacttca agaggccacg  2580
gatgagctgg acctcaagct gcgccaagct gaggtgatca agggatcctg gcagcccgtg  2640
ggcgatctcc tcattgactc tctccaagat cacctcgaga aagtcaaggc acttcgagga  2700
gaaattgcgc ctctgaaaga gaacgtgagc cacgtcaatg accttgctcg ccagcttacc  2760
actttgggca ttcagctctc accgtataac ctcagcactc tggaagacct gaacaccaga  2820
tggaagcttc tgcaggtggc cgtcgaggac cgagtcaggc agctgcatga agcccacagg  2880
gactttggtc cagcatctca gcactttctt tccacgtctg tccagggtcc ctgggagaga  2940
gccatctcgc caaacaaagt gccctactat atcaaccacg agactcaaac aacttgctgg  3000
gaccatccca aaatgacaga gctctaccag tctttagctg acctgaataa tgtcagattc  3060
tcagcttata ggactgccat gaaactccga agactgcaga aggccctttg cttggatctc  3120
ttgagcctgt cagctgcatg tgatgccttg gaccagcaca acctcaagca aaatgaccag  3180
cccatggata tcctgcagat tattaattgt ttgaccacta tttatgaccg cctggagcaa  3240
gagcacaaca atttggtcaa cgtccctctc tgcgtggata tgtgtctgaa ctggctgctg  3300
aatgtttatg atacgggacg aacagggagg atccgtgtcc tgtcttttaa aactggcatc  3360
atttccctgt gtaaagcaca tttggaagac aagtacagat accttttcaa gcaagtggca  3420
agttcaacag gattttgtga ccagcgcagg ctgggcctcc ttctgcatga ttctatccaa  3480
attccaagac agttgggtga agttgcatcc tttgggggca gtaacattga gccaagtgtc  3540
cggagctgct tccaatttgc taataataag ccagagatcg aagcggccct cttcctagac  3600
tggatgagac tggaacccca gtccatggtg tggctgcccg tcctgcacag agtggctgct  3660
gcagaaactg ccaagcatca ggccaaatgt aacatctgca aagagtgtcc aatcattgga  3720
ttcaggtaca ggagtctaaa gcactttaat tatgacatct gccaaagctg ctttttttct  3780
ggtcgagttg caaaaggcca taaaatgcac tatcccatgg tggaatattg cactccgact  3840
acatcaggag aagatgttcg agactttgcc aaggtactaa aaaacaaatt tcgaaccaaa  3900
aggtattttg cgaagcatcc ccgaatgggc tacctgccag tgcagactgt cttagagggg  3960
gacaacatgg aaacttag                                                 3978

SEQ ID NO: 27          moltype = AA  length = 1329
FEATURE                Location/Qualifiers
source                 1..1329
                       mol_type = protein
```

```
                        organism = synthetic construct
SEQUENCE: 27
MVWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDQPDL APGLTTIGAS PTQTVTLVTQ PVVTKETAIS KLEMPSSLML  600
EVPTHRLLQQ FPLDLEKFLA WLTEAETTAN VLQDATRKER LLEDSKGVKE LMKQWQDLQG  660
EIEAHTDVYH NLDENSQKIL RSLEGSDDAV LLQRRLDNMN FKWSELRKKS LNIRSHLEAS  720
SDQWKRLHLS LQELLVWLQL KDDELSRQAP IGGDFPAVQK QNDVHRAFKR ELKTKEPVIM  780
STLETVRIFL TEQPLEGLEK LYQEPRELPP EERAQNVTRL LRKQAEEVNT EWEKLNLHSA  840
DWQRKIDETL ERLQELQEAT DELDLKLRQA EVIKGSWQPV GDLLIDSLQD HLEKVKALRG  900
EIAPLKENVS HVNDLARQLT TLGIQLSPYN LSTLEDLNTR WKLLQVAVED RVRQLHEAHR  960
DFGPASQHFL STSVQGPWER AISPNKVPYY INHETQTTCW DHPKMTELYQ SLADLNNVRF  1020
SAYRTAMKLR RLQKALCLDL LSLSAACDAL DQHNLKQNDQ PMDILQIINC LTTIYDRLEQ  1080
EHNNLVNVPL CVDMCLNWLL NVYDTGRTGR IRVLSFKTGI ISLCKAHLED KYRYLFKQVA  1140
SSTGFCDQRR LGLLLHDSIQ IPRQLGEVAS FGGSNIEPSV RSCFQFANNK PEIEAALFLD  1200
WMRLEPQSMV WLPVLHRVAA AETAKHQAKC NICKECPIIG FRYRSLKHFN YDICQSCFFS  1260
GRVAKGHKMH YPMVEYCTPT TSGEDVRDFA KVLKNKFRTK RYFAKHPRMG YLPVQTVLEG  1320
DNMETPDTM                                                         1329

SEQ ID NO: 28           moltype = DNA  length = 3990
FEATURE                 Location/Qualifiers
source                  1..3990
                        mol_type = other DNA
                        organism = synthetic construct
SEQUENCE: 28
atggtttggt gggaagaagt agaggactgt tatgaaagag aagatgttca aaagaaaaca  60
ttcacaaaat gggtaaatgc acaattttct aagtttggga agcagcatat tgagaacctc  120
ttcagtgacc tacaggatgg gaggcgcctc ctagacctcc tcgaaggcct gacagggcaa  180
aaactgccaa aagaaaaagg atccacaaga gttcatgccc tgaacaatgt caacaaggca  240
ctgcgggttt tgcagaacaa taatgttgat ttagtgaata ttggaagtac tgacatcgta  300
gatggaaatc ataaactgac tcttggtttg atttggaata taatcctcca ctggcaggtc  360
aaaaatgtaa tgaaaaatat catggctgga ttgcaacaaa ccaacagtga aaagattctc  420
ctgagctggg tccgacaatc aactcgtaat tatccacagg ttaatgtaat caacttcacc  480
accagctggt ctgatggcct ggctttgaat gctctcatcc atagtcatag gccagaccta  540
tttgactgga atagtgtggt ttgccagcag tcagccacac aacgactgga acatgcattc  600
aacatcgcca gatatcaatt aggcatagag aaactactcg atcctgaaga tgttgatacc  660
acctatccag ataagaagtc catcttaatg tacatcacat cactcttcca agttttgcct  720
caacaagtga gcattgaagc catccaggaa gtggaaatgt tgccaaggcc acctaaagtg  780
actaaagaag aacattttca gttacatcat caaatgcact attctcaaca gatcacggtc  840
agtctagcac agggatatga gagaacttct tcccctaagc ctcgattcaa gagctatgcc  900
tacacacagg ctgcttatgt caccacctct gaccctacac ggagcccatt tccttcacag  960
catttggaag ctcctgaaga caagtcattt ggcagttcat tgatggagag tgaagtaaac  1020
ctggaccgtt atcaaacagc tttagaagaa gtattatcgt ggcttctttc tgctgaggac  1080
acattgcaag cacaaggaga gatttctaat gatgtggaag tggtgaaaga ccagtttcat  1140
actcatgagg ggtacatgat ggatttgaca gcccatcagg gccgggttgg taatattcta  1200
caattgggaa gtaagctgat tggaacagga aaattatcag aagatgaaga aactgaagta  1260
caagagcaga tgaatctcct aaattcaaga tgggaatgcc tcagggtagc tagcatggaa  1320
aaacaaagca atttacatag agttttaatg gatctccaga atcagaaact gaaagagttg  1380
aatgactggc taacaaaaac agaagaaaga acaaggaaaa tggaggaaga gcctcttgga  1440
cctgatcttg aagacctaaa acgccaagta caacaacata aggtgcttca agaagatcta  1500
gaacaagaac aagtcagggt caattctctc actcacatgg tggtggtagt tgatgaatct  1560
agtggagatc acgcaactgc tgctttggaa gaacaactta aggtattggg agatcgatgg  1620
gcaaacatct gtagatggac agaagaccgc tgggttcttt tacaagacca gcctgaccta  1680
gctcctggac tgaccactat tggagcctct cctactcaga ctgttactct ggtgacacaa  1740
cctgtggtta ctaaggaaac tgccatctcc aaactagaaa tgccatcttc cttgatgttg  1800
gaggtaccta ctcatagatt actgcaacag ttcccccctgg acctggaaaa gtttcttgcc  1860
tggcttacag aagctgaaac aactgccaat gtcctacagg atgctacccg taaggaaagg  1920
ctcctagaag actccaaggg agtaaaagag ctgatgaaac aatggcaaga cctccaaggt  1980
gaaattgaag ctcacacaga tgtttatcac aacctggatg aaaacagcca aaaaatcctg  2040
agatccctgg aaggttccga tgatgcagtc ctgttacaaa gacgtttgga taacatgaac  2100
ttcaagtgga gtgaacttcg gaaaaagtct ctcaacatta ggtcccattt ggaagccagt  2160
tctgaccagt ggaagcgtct gcacctttct ctgcaggaac ttctggtgtg gctacagctg  2220
aaagatgatg aattaagccg gcaggcacct attggaggcg actttccagc agttcagaag  2280
cagaacgatg tacatagggc cttcaagagg gaattgaaaa ctaaagaacc tgtaatcatg  2340
agtactcttg agactgtacg aatatttctg acagagcagc ctttggaagg actagagaaa  2400
ctctaccagg agcccagaga gctgcctcct gaggagagag cccagaatgt cactcggctt  2460
ctacgaaagc aggctgagga ggtcaatact gagtgggaaa aattgaacct gcactccgct  2520
gactggcaga gaaaaataga tgagaccctt gaaagactcc aggaacttca agaggccacg  2580
gatgagctgg acctcaagct gcgccaagct gaggtgatca agggatcctg gcagcccgtg  2640
ggcgatctcc tcattgactc tctccaagat cacctcgaga aagtcaaggc acttcgagga  2700
gaaattgcgc ctctgaaaga gaacgtgagc cacgtcaatg accttgctcg ccagcttacc  2760
actttgggca ttcagctctc accgtataac ctcagcactc tggaagacct gaacaccaga  2820
```

-continued

```
tggaagcttc tgcaggtggc cgtcgaggac cgagtcaggc agctgcatga agcccacagg  2880
gactttggtc cagcatctca gcactttctt tccacgtctg tccagggtcc ctgggagaga  2940
gccatctcgc caaacaaagt gccctactat atcaaccacg agactcaaac aacttgctgg  3000
gaccatccca aaatgacaga gctctaccag tctttagctg acctgaataa tgtcagattc  3060
tcagcttata ggactgccat gaaactccga agactgcaga aggccctttg cttggatctc  3120
ttgagcctgt cagctgcatg tgatgccttg gaccagcaca acctcaagca aaatgaccag  3180
cccatggata tcctgcagat tattaattgt ttgaccacta tttatgaccg cctggagcaa  3240
gagcacaaca atttggtcaa cgtccctctc tgcgtggata tgtgtctgaa ctggctgctg  3300
aatgtttatg atacgggacg aacagggagg atccgtgtcc tgtcttttaa aactggcatc  3360
atttccctgt gtaaagcaca tttggaagac aagtacagat acctttttcaa gcaagtggca  3420
agttcaacag gattttgtga ccagcgcagg ctgggcctcc ttctgcatga ttctatccaa  3480
attccaagac agttgggtga agttgcatcc tttgggggca gtaacattga gccaagtgtc  3540
cggagctgct tccaatttgc taataataag ccagagatcg aagcggccct cttcctagac  3600
tggatgagac tggaacccca gtccatggtg tggctgcccg tcctgcacag agtggctgct  3660
gcagaaactg ccaagcatca ggccaaatgt aacatctgca aagagtgtcc aatcattgga  3720
ttcaggtaca ggagtctaaa gcactttaat tatgacatct gccaaagctg cttttttttct  3780
ggtcgagttg caaaaggcca taaaatgcac tatcccatgg tggaatattg cactccgact  3840
acatcaggag aagatgttcg agactttgcc aaggtactaa aaaacaaatt tcgaaccaaa  3900
aggtattttg cgaagcatcc ccgaatgggc tacctgccag tgcagactgt cttagagggg  3960
gacaacatgg aaactcccga cacaatgtag                                  3990
```